US006739006B2

(12) United States Patent
Borders et al.

(10) Patent No.: US 6,739,006 B2
(45) Date of Patent: May 25, 2004

(54) HEAD SECTION SUPPORT FOR A SURGICAL TABLE APPARATUS

(75) Inventors: Richard L. Borders, Cincinnati, OH (US); Mark Graham, Batesville, IN (US); David C. Newkirk, Lawrenceburg, IN (US); Christian H. Reinke, Bellbrook, OH (US); Gary S. Siegle, Cincinnati, OH (US); Stephen R. Hamberg, Cincinnati, OH (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 10/056,959

(22) Filed: Jan. 25, 2002

(65) Prior Publication Data

US 2002/0170116 A1 Nov. 21, 2002

Related U.S. Application Data

(63) Continuation-in-part of application No. 09/934,226, filed on Aug. 21, 2001, now Pat. No. 6,446,287, which is a continuation of application No. 09/734,487, filed on Dec. 11, 2001, now Pat. No. 6,276,012, which is a division of application No. 09/187,990, filed on Nov. 6, 1998, now Pat. No. 6,202,230, application No. 10/056,959, which is a continuation-in-part of application No. 09/874,710, filed on Jun. 5, 2001, now Pat. No. 6,615,429.
(60) Provisional application No. 60/326,866, filed on Oct. 3, 2001, provisional application No. 60/300,625, filed on Jun. 25, 2001, provisional application No. 60/264,214, filed on Jan. 25, 2001, provisional application No. 60/264,090, filed on Jan. 25, 2001, provisional application No. 60/083,673, filed on Apr. 30, 1998, and provisional application No. 60/064,709, filed on Nov. 7, 1997.

(51) Int. Cl.[7] ................................................. A61G 7/07
(52) U.S. Cl. ............................................. 5/622; 5/638
(58) Field of Search ........................... 5/622, 637, 640, 5/638; 128/845

(56) References Cited

U.S. PATENT DOCUMENTS

| 12,944 A | 5/1855 | Daniels |
| 238,799 A | 3/1881 | Morgan |
| 964,170 A | 7/1910 | Leonard |

(List continued on next page.)

FOREIGN PATENT DOCUMENTS

| DE | 1 258 021 | 1/1968 |
| DE | 2 324 486 | 12/1973 |
| DE | 35 38 887 A1 | 5/1986 |

(List continued on next page.)

OTHER PUBLICATIONS

ProneView from Dupaco, copyright 2000 (2 pages).
Reliance M–701 Surgical Stretcher—Mobile Surgical Stretcher from Reliance Products.
"Products for Head and Neck Surgery" from Hausted. Models 878, 678 & 675 Uni–Care Mobile Surgical Stretchers.
"547 SLS" from Midmark Corporation; copyright 1998.
"A report to the Department of Trade and Industry—The Operating Room of the Year 2010" complied and edited by R. David Rosin and Chris R. Kemp; Jan. 1999.
"Head/Neck Surgery Stretcher—Model 1067"; Stryker Patient Handling; Renaissance Series.

Primary Examiner—Michael F. Trettel
(74) Attorney, Agent, or Firm—Bose McKinney & Evans LLP

(57) ABSTRACT

A surgical table apparatus is provided for supporting a patient before, during, or after a surgical procedure. The surgical table apparatus includes a base and a table top. The table top includes a body support section adapted to support the body of a patient and a head support section adapted to support the head of a patient.

70 Claims, 72 Drawing Sheets

U.S. PATENT DOCUMENTS

| | | |
|---|---|---|
| 1,437,568 A | 12/1922 | Taplin |
| 1,626,091 A | 4/1927 | Macklin |
| 1,775,547 A | 9/1930 | Bayer |
| 2,042,399 A | 5/1936 | Holme |
| 2,067,871 A | 1/1937 | Comper |
| 2,120,732 A | 6/1938 | Comper et al. |
| 2,257,491 A | 9/1941 | Armstrong |
| 2,258,782 A | 10/1941 | Mckean |
| 2,306,031 A | 12/1942 | Anderson et al. |
| 2,452,366 A | 10/1948 | Freund |
| 2,463,410 A | 3/1949 | Morris |
| 2,556,591 A | 6/1951 | Loxley |
| 2,564,323 A | 8/1951 | Brown |
| 2,579,783 A | 12/1951 | Branto |
| 2,605,151 A | 7/1952 | Shampaine |
| 2,658,211 A | 11/1953 | Bendersky |
| 2,766,463 A | 10/1956 | Bendersky |
| 2,832,655 A | 4/1958 | Adolphson et al. |
| 2,872,259 A | 2/1959 | Thorpe |
| 2,972,505 A | 2/1961 | Weickgenannt |
| 3,041,121 A | 6/1962 | Comper |
| 3,041,122 A | 6/1962 | Weickgenannt et al. |
| 3,053,568 A | 9/1962 | Miller |
| 3,099,441 A | 7/1963 | Ries |
| 3,100,129 A | 8/1963 | Adolphson |
| 3,124,328 A | 3/1964 | Kortsch |
| 3,159,426 A | 12/1964 | Kerr |
| 3,188,079 A | 6/1965 | Boetcker et al. |
| 3,220,021 A | 11/1965 | Nelson |
| 3,220,022 A | 11/1965 | Nelson |
| 3,226,105 A | 12/1965 | Weickgenannt et al. |
| 3,226,106 A | 12/1965 | Johnson et al. |
| 3,227,439 A | 1/1966 | Carlson |
| 3,227,440 A | 1/1966 | Scott |
| 3,233,255 A | 2/1966 | Propst |
| 3,281,141 A | 10/1966 | Smiley et al. |
| 3,318,596 A | 5/1967 | Herzog |
| 3,411,766 A | 11/1968 | Lanigan |
| 3,428,307 A | 2/1969 | Hunter et al. |
| 3,477,761 A * | 11/1969 | Krantz ..................... 297/409 |
| 3,572,835 A | 3/1971 | Kees et al. |
| 3,635,461 A | 1/1972 | Bellucci et al. |
| 3,754,749 A | 8/1973 | Lyon et al. |
| 3,806,110 A | 4/1974 | Glasser et al. |
| 3,813,091 A | 5/1974 | Metzger |
| 3,814,414 A | 6/1974 | Chapa |
| 3,817,512 A | 6/1974 | Torrey |
| 3,845,945 A | 11/1974 | Lawley et al. |
| 3,845,947 A | 11/1974 | Lee |
| 3,868,103 A | 2/1975 | Pageot et al. |
| 3,893,197 A | 7/1975 | Ricke |
| 3,897,973 A | 8/1975 | Long et al. |
| 3,902,204 A | 9/1975 | Lee |
| 3,929,309 A | 12/1975 | De Vore |
| 3,967,128 A | 6/1976 | Smulewicz |
| 3,980,288 A | 9/1976 | Mitchell et al. |
| 3,993,051 A | 11/1976 | Maruyama |
| 4,058,112 A | 11/1977 | Johnson |
| 4,061,324 A | 12/1977 | Kvaerna et al. |
| 4,076,230 A | 2/1978 | Pike |
| 4,101,120 A | 7/1978 | Seshima |
| 4,103,170 A | 7/1978 | Spradlin |
| 4,139,917 A | 2/1979 | Fenwick |
| 4,148,472 A | 4/1979 | Rais et al. |
| 4,168,099 A | 9/1979 | Jacobs et al. |
| 4,183,109 A | 1/1980 | Howell |
| 4,212,454 A | 7/1980 | Lee |
| 4,221,213 A | 9/1980 | Gregory et al. |
| 4,225,126 A | 9/1980 | Lee |
| 4,225,127 A | 9/1980 | Strutton |
| 4,247,091 A | 1/1981 | Glowacki et al. |
| 4,258,445 A | 3/1981 | Zur |
| 4,266,760 A | 5/1981 | Matsui et al. |
| 4,323,060 A | 4/1982 | Pecheux |
| 4,327,596 A | 5/1982 | Simon |
| 4,333,638 A | 6/1982 | Gillotti |
| 4,336,965 A | 6/1982 | Lipp |
| D268,802 S | 5/1983 | Fenwick |
| 4,387,888 A | 6/1983 | Marinakis |
| 4,390,011 A | 6/1983 | Evans |
| 4,411,035 A | 10/1983 | Fenwick |
| 4,426,071 A | 1/1984 | Klevstad |
| 4,457,502 A | 7/1984 | Beach |
| 4,504,050 A | 3/1985 | Osborne |
| 4,552,346 A | 11/1985 | Schnelle et al. |
| 4,552,348 A | 11/1985 | Forssmann et al. |
| 4,558,857 A | 12/1985 | Heller |
| 4,559,656 A | 12/1985 | Foster |
| 4,564,164 A | 1/1986 | Allen et al. |
| 4,592,104 A | 6/1986 | Foster et al. |
| 4,615,058 A | 10/1986 | Feldt |
| 4,620,697 A * | 11/1986 | Pithon ......................... 5/640 |
| 4,660,549 A | 4/1987 | Kowalski et al. |
| 4,682,376 A | 7/1987 | Feldt |
| 4,688,780 A | 8/1987 | Hanz |
| 4,698,837 A | 10/1987 | Van Steenburg |
| 4,700,691 A | 10/1987 | Tari et al. |
| 4,710,991 A | 12/1987 | Wilmore et al. |
| 4,724,555 A | 2/1988 | Poehner et al. |
| 4,751,754 A | 6/1988 | Bailey et al. |
| 4,752,064 A | 6/1988 | Voss |
| D298,992 S | 12/1988 | Voss |
| 4,805,249 A | 2/1989 | Usman et al. |
| 4,807,618 A | 2/1989 | Auchinleck et al. |
| 4,809,687 A | 3/1989 | Allen |
| D300,657 S | 4/1989 | Simpkins et al. |
| 4,856,128 A | 8/1989 | Alsip et al. |
| 4,862,529 A | 9/1989 | Peck |
| 4,865,303 A | 9/1989 | Hall |
| 4,872,656 A | 10/1989 | Brendgord et al. |
| 4,881,728 A | 11/1989 | Hunter |
| 4,882,797 A | 11/1989 | Failor et al. |
| 4,886,258 A | 12/1989 | Scott |
| 4,894,876 A | 1/1990 | Fenwick |
| 4,898,491 A | 2/1990 | Van Steenburg |
| 4,940,218 A | 7/1990 | Akcelrod |
| 4,956,592 A | 9/1990 | Schulte et al. |
| 4,958,816 A | 9/1990 | Chaney et al. |
| 4,968,013 A | 11/1990 | Kuck |
| 4,989,848 A | 2/1991 | Monroe |
| 5,022,388 A | 6/1991 | Harter |
| 5,039,167 A | 8/1991 | Sweet |
| 5,060,327 A | 10/1991 | Celestina et al. |
| 5,104,363 A | 4/1992 | Shi |
| 5,116,008 A | 5/1992 | Allen |
| 5,129,117 A | 7/1992 | Celestina et al. |
| 5,134,737 A | 8/1992 | Wyman |
| 5,134,739 A | 8/1992 | Gaffe et al. |
| 5,135,210 A | 8/1992 | Michelson |
| 5,147,287 A | 9/1992 | Jewell et al. |
| 5,148,562 A | 9/1992 | Borders et al. |
| 5,157,800 A | 10/1992 | Borders |
| 5,177,823 A * | 1/1993 | Riach ......................... 5/636 |
| 5,201,087 A | 4/1993 | Wickham et al. |
| 5,214,812 A | 6/1993 | Bartow et al. |
| 5,214,815 A | 6/1993 | Agbodoe et al. |
| 5,226,187 A | 7/1993 | Borders et al. |
| D337,914 S | 8/1993 | McDonald |
| 5,231,719 A | 8/1993 | Schnelle |
| 5,233,713 A | 8/1993 | Murphy et al. |
| 5,276,927 A | 1/1994 | Day |

| | | | | | | |
|---|---|---|---|---|---|---|
| D344,802 S | 3/1994 | Kuck et al. | | 6,240,582 B1 | 6/2001 | Reinke |
| 5,317,771 A | 6/1994 | Cook | | 6,276,012 B2 * | 8/2001 | Borders .................. 5/622 |
| 5,335,384 A | 8/1994 | Foster et al. | | 6,282,738 B1 | 9/2001 | Heimbrock et al. |
| 5,347,668 A | 9/1994 | Manning | | 6,374,439 B2 * | 4/2002 | Heimbrock et al. ......... 5/622 |

| | | |
|---|---|---|
| 5,362,302 A | 11/1994 | Jensen et al. |
| 5,369,825 A | 12/1994 | Reesby |
| 5,369,827 A | 12/1994 | Parke et al. |
| 5,408,713 A | 4/1995 | Stratton et al. |
| 5,427,436 A * | 6/1995 | Lloyd .................. 297/408 |
| 5,469,588 A | 11/1995 | DiMatteo et al. |
| 5,479,666 A | 1/1996 | Foster et al. |
| 5,520,623 A | 5/1996 | Williams |
| 5,560,577 A | 10/1996 | Keselman |
| 5,575,026 A | 11/1996 | Way et al. |
| 5,582,379 A | 12/1996 | Keselman et al. |
| 5,645,079 A | 7/1997 | Zahiri et al. |
| 5,655,238 A | 8/1997 | Stickley et al. |
| 5,661,859 A | 9/1997 | Schaefer |
| D385,040 S | 10/1997 | Keselman |
| 5,678,894 A | 10/1997 | Eley |
| 5,692,255 A | 12/1997 | Canfield |
| 5,715,548 A | 2/1998 | Weismiller et al. |
| 5,740,571 A | 4/1998 | Tyra et al. |
| 5,740,572 A | 4/1998 | Hannant |
| 5,745,937 A | 5/1998 | Weismiller et al. |
| 5,754,997 A | 5/1998 | Lüssi et al. |
| 5,774,914 A | 7/1998 | Johnson et al. |
| 5,774,915 A | 7/1998 | Scott et al. |
| 5,778,467 A | 7/1998 | Scott et al. |
| 5,784,734 A | 7/1998 | Scott et al. |
| 5,802,636 A | 9/1998 | Corbin et al. |
| 5,802,641 A | 9/1998 | Van Steenburg |
| 5,862,549 A | 1/1999 | Morton et al. |
| 5,865,505 A | 2/1999 | Eley |
| 5,878,748 A | 3/1999 | Garth et al. |
| 5,890,765 A | 4/1999 | LaPointe et al. |
| 5,900,997 A | 5/1999 | Shapiro |
| 5,918,330 A | 7/1999 | Navarro et al. |
| 5,926,002 A | 7/1999 | Cavanaugh et al. |
| 5,926,878 A | 7/1999 | Morton et al. |
| 5,941,175 A | 8/1999 | Bannister |
| 5,961,085 A | 10/1999 | Navarro et al. |
| 6,038,718 A | 3/2000 | Pennington et al. |
| 6,058,534 A | 5/2000 | Navarro et al. |
| 6,076,208 A | 6/2000 | Heimbrock et al. |
| 6,081,947 A | 7/2000 | Disher |
| 6,089,593 A | 7/2000 | Hanson et al. |
| 6,108,840 A | 8/2000 | Heimbrock et al. |
| 6,141,806 A | 11/2000 | Bobey et al. |
| 6,170,103 B1 | 1/2001 | Wang et al. |
| 6,202,230 B1 | 3/2001 | Borders |
| 6,212,714 B1 | 4/2001 | Allen et al. |
| 6,226,821 B1 | 5/2001 | Heimbrock et al. |

FOREIGN PATENT DOCUMENTS

| | | |
|---|---|---|
| EP | 0 673 633 | 3/1995 |
| FR | 1.518.724 | 2/1968 |
| FR | 2 547 195 | 12/1984 |
| FR | 2 666 013 | 2/1992 |
| GB | 1058787 | 2/1967 |
| GB | 2 225 228 A | 11/1988 |
| GB | 2 248 016 | 3/1992 |
| GB | 2313303 | 11/1997 |
| JP | 35-19293 | 8/1960 |
| JP | 35-28580 | 10/1960 |
| JP | 39-32275 | 10/1964 |
| JP | 40-23833 | 10/1965 |
| JP | 42-1715 | 1/1967 |
| JP | 42-11267 | 6/1967 |
| JP | 46-21835 | 7/1971 |
| JP | 49-21396 | 2/1974 |
| JP | 52-7276 | 3/1977 |
| JP | 53-74190 | 6/1978 |
| JP | 53-74191 | 6/1978 |
| JP | 55-50357 | 4/1980 |
| JP | 56-109663 | 8/1981 |
| JP | 58-127648 | 7/1983 |
| JP | 58-143753 | 8/1983 |
| JP | 60-85749 | 5/1985 |
| JP | 60-145138 | 7/1985 |
| JP | 60-195018 | 12/1985 |
| JP | 61-22577 | 6/1986 |
| JP | 61-119257 | 6/1986 |
| JP | 61-168351 | 7/1986 |
| JP | 61-44019 | 10/1986 |
| JP | 61-226043 | 10/1986 |
| JP | 61-50626 | 11/1986 |
| JP | 2-147120 | 12/1990 |
| JP | 2-297366 | 12/1990 |
| JP | 2-297367 | 12/1990 |
| JP | 2-297368 | 12/1990 |
| JP | 3-4808 | 1/1991 |
| JP | 3-4809 | 1/1991 |
| JP | 5-31145 | 2/1993 |
| JP | 6-12755 | 4/1994 |
| JP | 7-112012 | 5/1995 |
| WO | 92/18082 | 10/1992 |
| WO | 99/15126 | 4/1999 |
| WO | 99/23991 | 5/1999 |

* cited by examiner

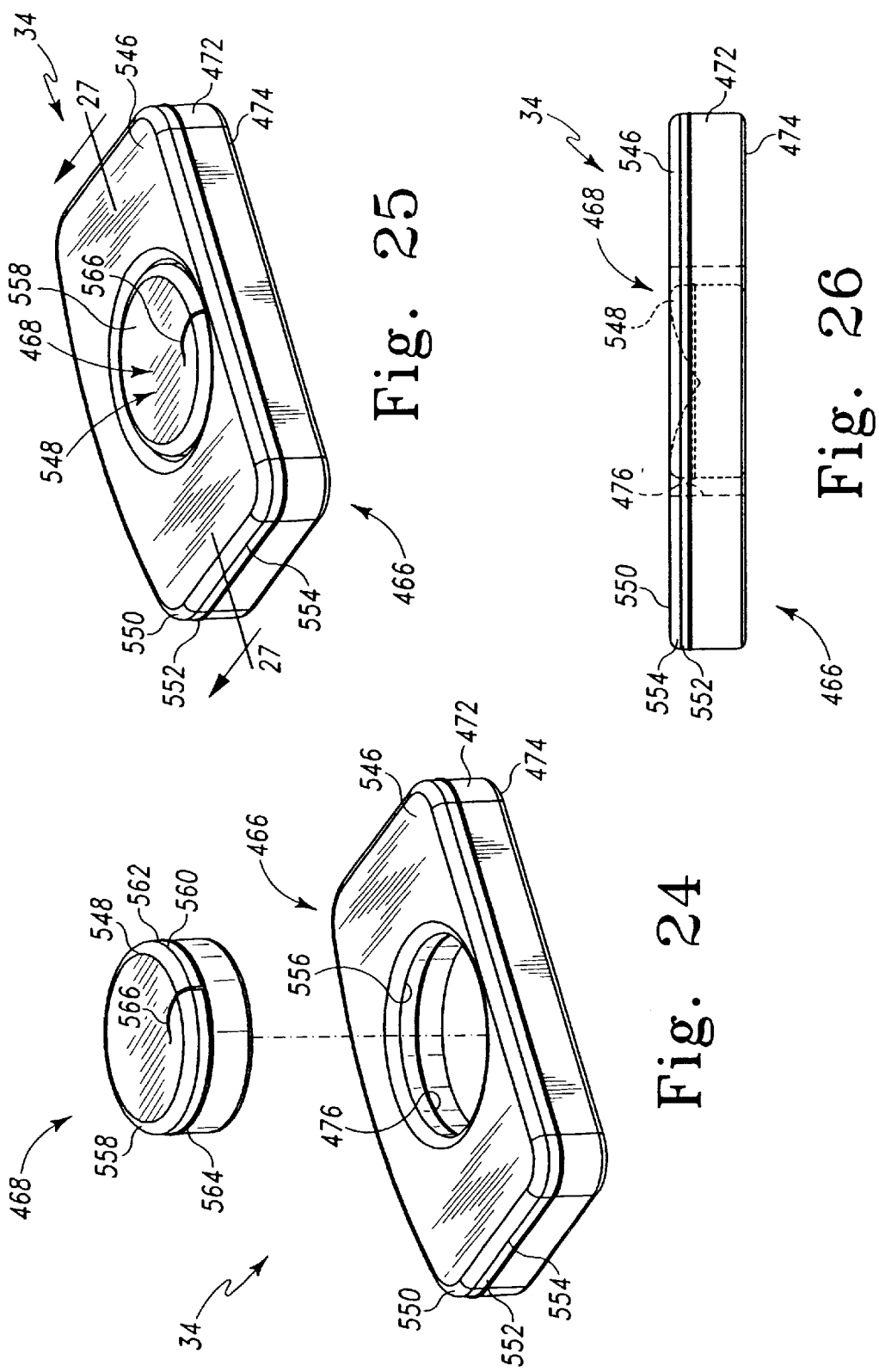

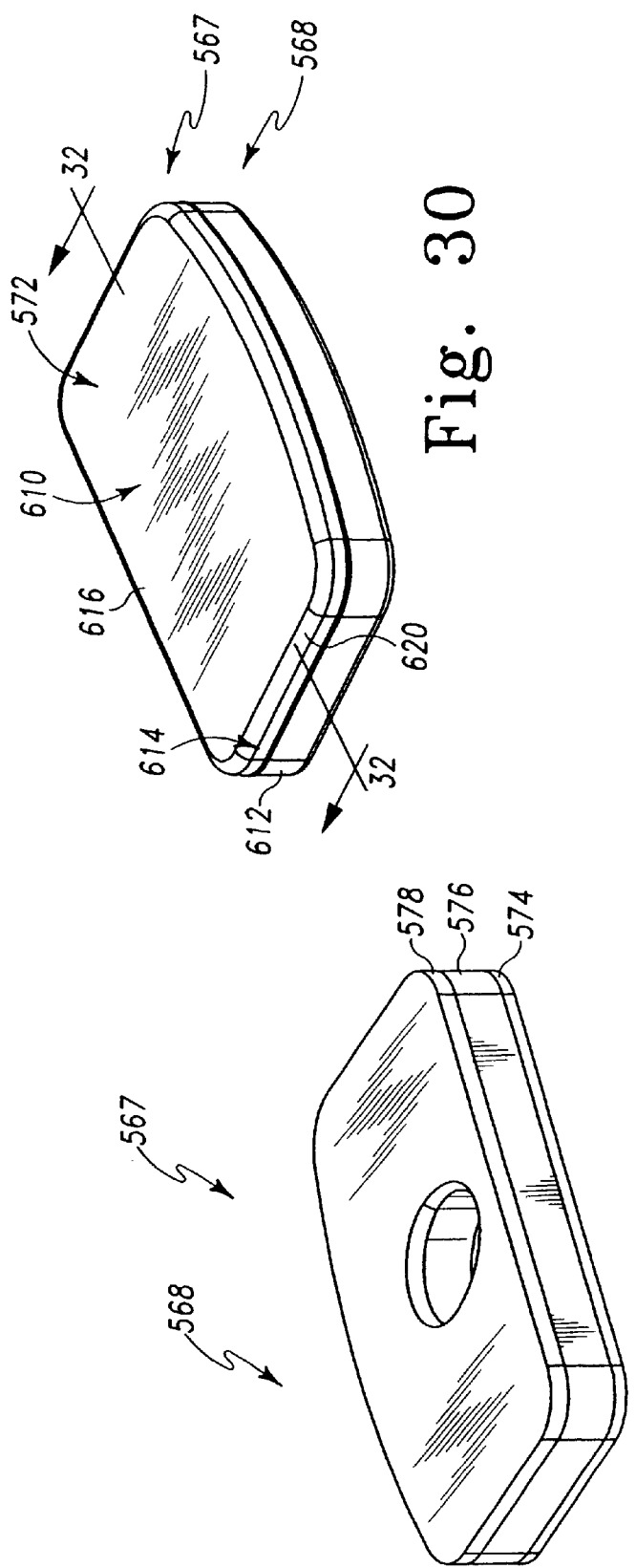

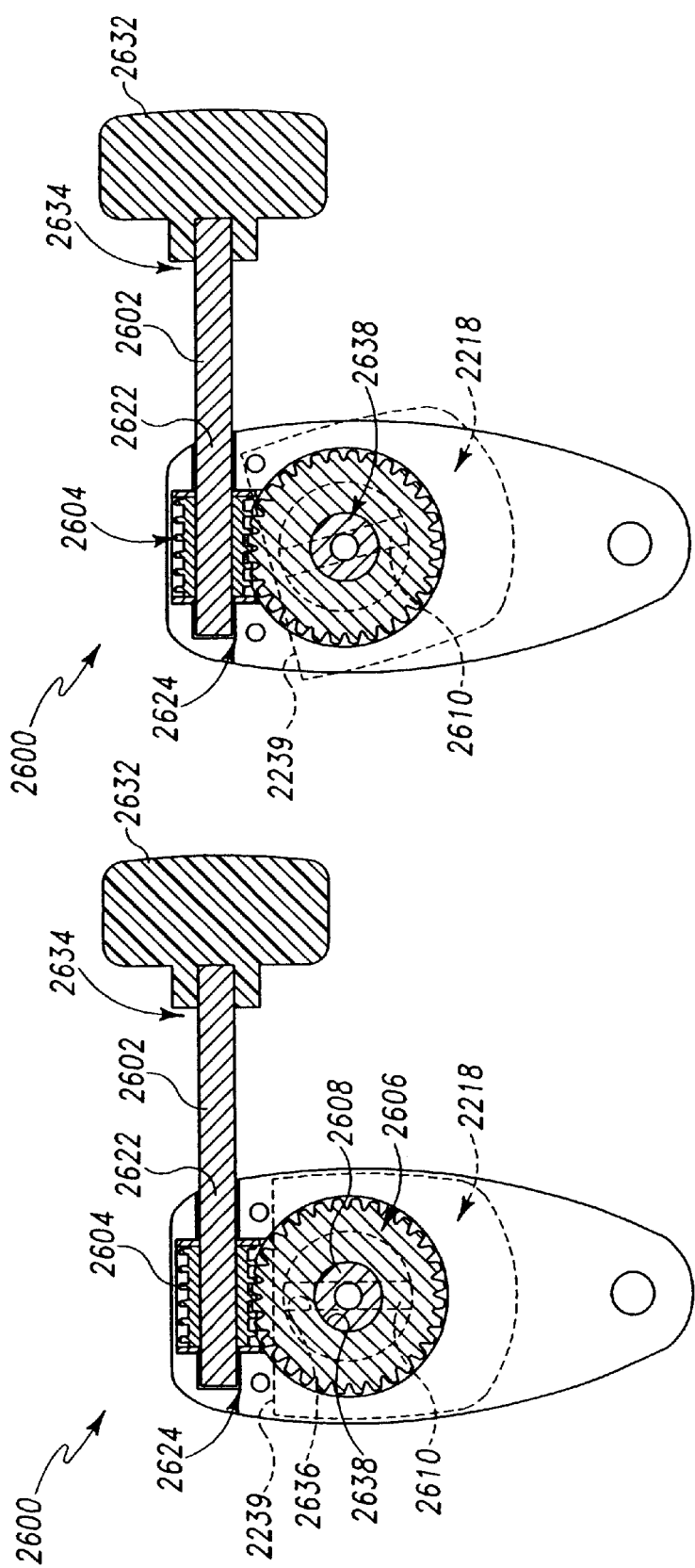

HEAD SECTION SUPPORT FOR A SURGICAL TABLE APPARATUS

RELATED PROCEEDINGS

This application is a continuation-in-part of U.S. patent application Ser. No. 09/874,710, to Weil et al., filed Jun. 5, 2001 now U.S. Pat. No. 6,615,429; and a continuation-in-part of U.S. patent application Ser. No. 09/934,226, to Borders, filed Aug. 21, 2001, now U.S Pat. No. 6,446,287; which is a continuation of U.S. patent application Ser. No. 09/734,487, to Borders, filed Dec. 11, 2001, now U.S. Pat. No. 6,276,012, which is a divisional of U.S. patent application Ser. No. 09/187,990, to Borders, filed Nov. 6, 1998, now U.S. Pat. No. 6,202,230; which claims benefit to U.S. Provisional Patent Application Nos. 60/064,709 filed Nov. 7, 1997, and 60/083,673 filed Apr. 30, 1998. This application claims the benefit of U.S. Provisional Patents Application Nos. 60/264,090, to Borders et al., filed on Jan. 25, 2001; U.S. Provisional Patent Application No. 60/264,214, to Blyshak et al., filed Jan. 25, 2001; U.S. Provisional Patent Application No. 60/300,625, to Borders et al., filed on Jun. 25, 2001 to Borders et al.; and U.S. Provisional Patent Application No. 60/326,866, to Borders et al., filed Oct. 3, 2001. The disclosures of all the above-referenced patent applications are expressly incorporated by reference herein.

BACKGROUND OF THE INVENTION

The present invention relates to surgical tables. More specifically, the present invention relates to the structures and mechanisms associated with the support surface of surgical tables.

Surgical tables are know that provide a plurality of sections for supporting different sections of a patient's body, such as the head, torso, arms, and legs of a patient. Is it also known to provide joints between such sections of a surgical table to permit movement of one section of the surgical table relative to another section of the surgical table. For example, U.S. Pat. No. 2,872,259 discloses an operating table that has head and foot sections that are moveable relative to upper and lower trunk sections.

According to a first aspect of the invention, a surgical table apparatus is provided that is configured to support the head and body of a patient. The surgical table apparatus includes a base, a body support section adapted to support the body of the patient, and a head support section. The head support section includes a head support member defining a head support surface configured to support the head of the patient and a first pair of parallel links configured to support the head support member. The links includes first and second ends. The first ends are pivotally supported to permit movement of the head support section relative to the body support section. The head support member is pivotally supported by the second ends of the links to permit movement of the head support member relative to the links. The head support member extends from the second ends of the links toward the body support section.

According to an another aspect of the invention, a surgical table apparatus is provided to support the head and body of a patient. The surgical table apparatus includes a base, a body support section, and a head support section. The body support section is adapted to support the body of the patient and has a longitudinal axis. The head support section includes a head support member defining a head support surface configured to support the head of the patient and a first link extending away from the body support section. The link includes a link body and first and second ends and defines a space lateral of the link body. The head support member is movably coupled to the second end of the link to permit movement of the head support member in the space lateral of the link body.

According to an another aspect of the invention, a surgical table apparatus is provided to support the head and body of a patient. The surgical table apparatus includes a base, a body support section adapted to support the body of the patient, and a head support section. The head support section includes a head support surface and a first four-bar linkage configured to permit lowering of the head support surface below the level of the body support surface.

According to another aspect of the invention, a surgical table apparatus is provided that is configured to support the appendages and body of a patient. The surgical table apparatus includes a base, a body support section adapted to support the body of the patient, and an appendage support section coupled to the body support section. The appendage support section includes an appendage support surface and a linkage configured to permit movement of the appendage support surface through first and second ranges of elevations relative to the body support section. The appendage support surface is substantially parallel to the body support section though the first range of elevations and substantially non-parallel to the body support section through the second range of elevations.

According to an another aspect of the invention, a surgical table apparatus is provided to support the head and body of a patient. The surgical table apparatus includes a base, a body support section including a body support surface adapted to support the body of a patient, and a head support section. The head support section includes a head support member defining a head support surface adapted to support the head of a patient and a member support configured to support the head support member. The member support is configured to permit movement of the head support surface of the head support member between a first use position and a storage position with the head support surface and the body support surface cooperating to define an angle of greater than 270° therebetween.

According to an another aspect of the invention, a surgical table apparatus is provided to support the head and body of a patient. The surgical table apparatus includes a base, a body support section including a body support surface adapted to support the body of a patient, and a head support section including a head support member. The head support member includes a head support surface adapted to support the head of a patient. The head support surface and the body support surface cooperate to define an angle therebetween. The head support section further includes a first position holder configured to permit adjustment of the angle. The head support member includes a first end and a second opposite end positioned between the first end and the body support section. The position holder is positioned adjacent to the first end of the head support member.

According to an another aspect of the invention, a surgical table apparatus is provided to support the head and body of a patient. The surgical table apparatus includes a base, a body support section adapted to support the body of a patient, and a head support section. The head support section including first and second head support members adapted to support the head of a patient. The first head support member is configured to move between a support position supporting a portion of the patient's head and a non-support position spaced apart from said portion of the patient's head. The second head support member is configured to move between a support position supporting another portion of the patient's head and a non-support position spaced apart from said portion of the patient's head. The first head support member is movable independently from the second head support member.

According to an another aspect of the invention, a surgical table apparatus is provided to support the head and body of a patient. The surgical table apparatus includes a base, a body support section adapted to support the body of the patient, and a head support section. The head support section includes first and second head support members adapted to support the head of a patient. The second head support member defines a recess sized to removably receive the first head support member.

According to an another aspect of the invention, a surgical table apparatus is provided to support the head and body of a patient. The surgical table apparatus includes a base, a body support section adapted to support the body of the patient, and a head support section. The head support section includes a first head support member adapted to support a first portion of a patient's head, a second head support member adapted to support a second portion of a patient's head, and a position holder configured to permit movement of the first and second head support members relative to the body support section. The position holder is configured to permit movement of the first and second members relative to one another.

According to an another aspect of the invention, a surgical table apparatus is provided to support the head and body of a patient. The surgical table apparatus includes a base, a body support section adapted to support the body of the patient, and a head support section. The head support section includes a head support member adapted to support a patient's head and a position holder configured to permit movement of the head support member relative to the body support section. The position holder includes a binding member and a bound member. The binding member includes an edge defining a void sized to receive a portion of the bound member. The binding member is movable relative to the portion of the bound member between a bound position in which a projection of the void relative to the portion of the bound member has a first area and a unbound position in which the projection of the void relative to the portion of the bound member has a second area that is greater than the first area.

According to an another aspect of the invention, a surgical table apparatus is provided to support the head and body of a patient. The surgical table apparatus includes a base, a body support section adapted to support the body of the patient, and a head support section. The head section includes a head support member including a head support surface adapted to support the head of a patient, a member support configured to support the head support member and permit movement of the head support member relative to the body support section, and a position holder supported by the member support and configured to permit movement of the head support member relative to the body support section. The position holder includes a worm gear mechanism.

According to an another aspect of the invention, a surgical table apparatus is provided to support the head and body of a patient. The surgical table apparatus includes a base, a body support section adapted to support the body of the patient, and a head support section. The head support section includes a head support member including a head support surface adapted to support the head of a patient and a position holder configured to permit movement of the head support member relative to the body support section. The position holder includes a first base supported by the body support section and a second base configured to support the head support member. The second base is movable relative to the first base to permit movement of the head support member relative to the body support section. The position holder further includes a cam configured to move relative to at least one of the first and second bases and a key configured to block movement of the second base relative to the first base when in a locked position and to permit movement of the second base relative to the first base when in an unlocked position. The cam is positioned to move the key between the locked and unlocked positions.

According to an another aspect of the invention, a surgical table apparatus is provided to support the head and body of a patient. The surgical table apparatus includes a base, a body support section adapted to support the body of the patient, and a head support section. The head support section includes a head support member including a head support surface adapted to support the head of a patient and a position holder configured to permit movement of the head support member relative to the body support section. The position holder includes a first base, a second base movable relative to the first base, and a key movable relative to the first and second bases. At least one of the bases is configured to support the head support member. At least one of the first and second bases includes a first set of complementary formations. The key includes a second set of complementary formations that interacts with the first set of complementary formations to block movement of the first base relative to the second base. Movement of the key disengages the first and second complementary formations to permit movement of the first and second bases to permit movement of the head support section relative to the body support section.

According to another aspect of the invention, a surgical table device is provided. The surgical table device includes a surgical table apparatus and an accessory apparatus. The surgical table apparatus includes a body support section adapted to support the body of a patient and an appendage support section includes an appendage support member adapted to support an appendage of the patient and a frame member configured to support the head support member relative to the body support section. The accessory apparatus is configured to removably couple to the frame member of the appendage support section.

According to an another aspect of the invention, a surgical table apparatus is provided to support the head and body of a patient. The surgical table apparatus includes a base, a body support section adapted to support the body of the patient, and a head support section. The head support section includes a cover having an interior region and a head support pad positioned in the cover and defining a void sized to receive a portion of a patient's head.

According to an another aspect of the invention, a surgical table apparatus is provided to support the head and body of a patient. The surgical table apparatus includes a base, a body support section adapted to support the body of the patient, and a head support section. The head support section includes a head support member and a member support configured to support the head support member. The head support member includes a first head support pad. The first head support pad includes a first head support surface adapted to support the head of a patient and a second head support surface adapted to support the head of a patient. The first head support pad provides a first firmness for the first head support surface and a second firmness for the second head support surface that is greater than the first firmness.

The first head support pad is movable between a first position with the first head support surface positioned to support the head of a patient and a second position with the second head support surface positioned to support the head of the patient.

According to another aspect of the invention, a patient head support section is provided that is configured to support the head of a patient when the patient is positioned in the prone position on a surgical table apparatus. The patient head support section includes a head support pad and a transparent member. The head support pad is adapted to support the head of a patient and includes an aperture through which to view a patient's face. The transparent member is configured to support the head support pad to permit viewing of the patient's face therethrough.

According to another aspect of the invention, a patient head support section is provided that is configured to support the head of a patient when the patient is positioned in the prone position on a surgical table apparatus. The patient head support section includes a head support member and a mirror. The head support member is adapted to support the head of a patient and includes an aperture through which to view a patient's face. The mirror has a first end and a second end spaced apart from the first end. The mirror is pivotably coupled to the head support section along the first end of the mirror.

According to another aspect of the invention, a surgical table apparatus is provided that is configured to support a patient. The surgical table apparatus includes a deck support and a deck. The deck includes a deck frame and a body support member supported by the deck frame and defines a patient support surface having leg, lower torso, upper torso, and head sections. The deck frame includes a leg section supported by the deck support, a lower torso section coupled to the leg section, an upper torso section pivotably coupled to the lower torso section, and a head section coupled to the upper torso section. The upper and lower torso sections is configured to move to a first position supporting the upper and lower torso sections of the patient support surface in positions defining an angle greater than 180° therebetween.

According to another aspect of the invention, a surgical table apparatus is provided that is configured to support a patient. The surgical table apparatus includes a deck support and a deck. The deck includes a deck frame supported by the deck support and a body support member supported by the deck frame that defines a patient support surface. The patient support surface has lower leg, upper leg, torso, and head sections. The deck frame includes a lower leg section, an upper leg section, a torso section, and a head section. The upper and lower leg sections are configured to move between a first position supporting the upper and lower leg sections of the patient support surface in substantially co-planar positions and in a second position supporting the upper and lower leg sections of the patient support surface in positions defining a first angle substantially greater than 180° therebetween. The deck further includes an actuator positioned to move the upper and lower leg sections of the deck frame between the first and second positions.

Additional features of the disclosure will become apparent to those skilled in the art upon consideration of the following detailed description when taken in conjunction with the accompanying drawings.

BRIEF DESCRIPTION OF THE DRAWINGS

The detailed description of the drawings particularly refers to the accompanying figures in which:

FIG. 24 is a view similar to FIG. 22 showing the main body and insert including covers;

FIG. 25 a view similar to FIG. 23 showing the main body and insert with the covers and the insert positioned in the opening formed in the main body;

FIG. 26 is a side elevation view of the head pad of FIG. 25 showing the main body and the insert (in phantom);

FIG. 29 is a perspective view of the head pad of FIG. 28;

FIG. 30 is a perspective view of the head pad of FIG. 28 showing the head pad including a cover;

FIG. 31 is a side elevation view of the head pad of FIG. 28 without the cover;

FIG. 74 is a partial, cross-sectional view of the second position holder taken along line 74—74 of FIG. 73 showing a head support plate mount in the position shown in FIG. 70;

FIG. 75 is a view similar to FIG. 74 showing the head support plate mount in the position shown in FIG. 71;

DETAILED DESCRIPTION OF THE DRAWINGS

Figure 1:
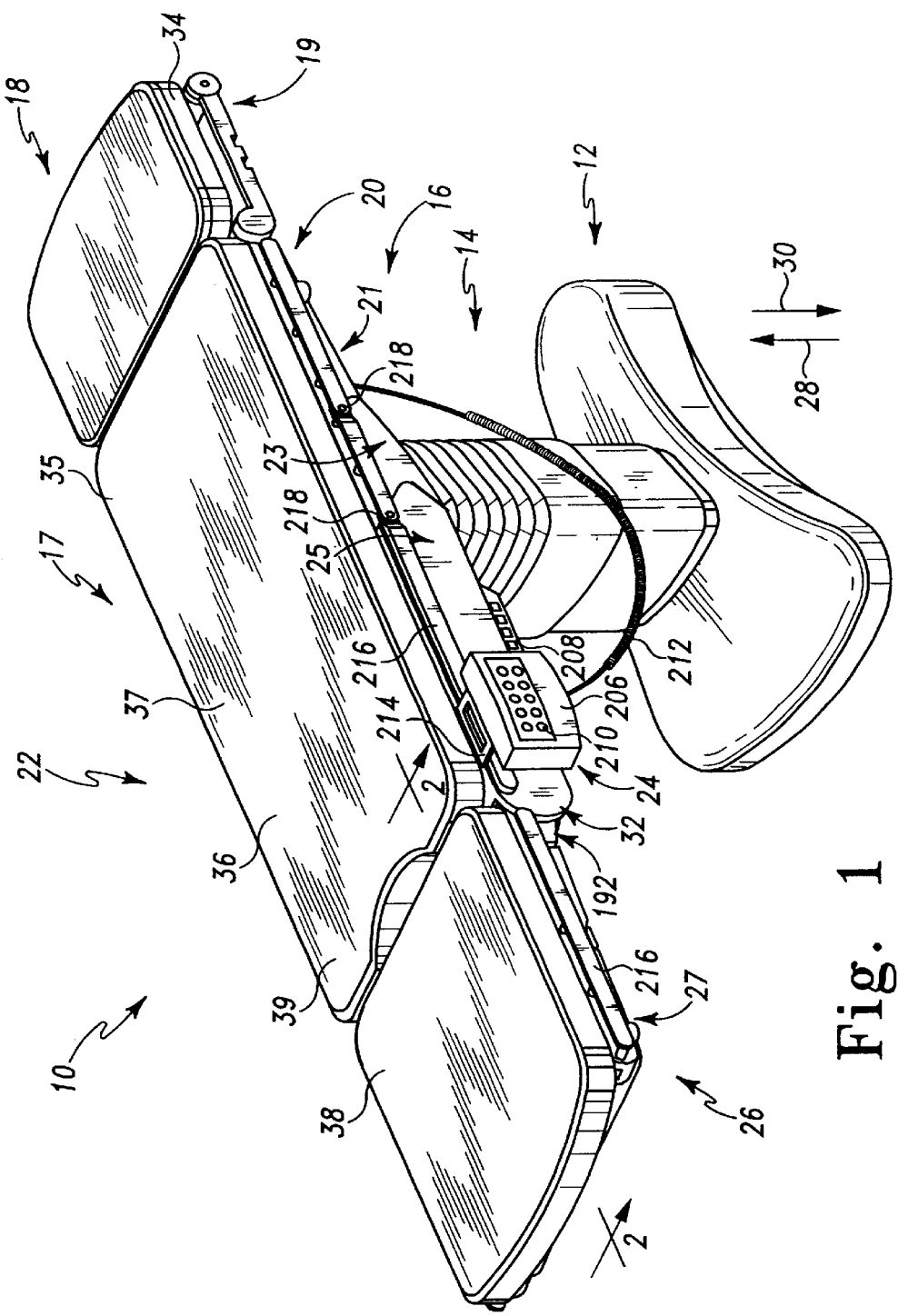
FIG. 1 is a perspective view of a first embodiment of a surgical table apparatus according to the present disclosure showing the surgical table apparatus including a base, a tabletop with head, body/upper leg, and lower leg pads.

A detailed description particularly refers to the accompanying figures in which:

A first embodiment of a surgical table apparatus or patient support 10 in accordance with the present disclosure is shown in FIG. 1. Surgical table apparatus 10 includes a base 12 including a pedestal 14 and a tabletop 16 coupled to pedestal 14.

Pedestal 14 includes a lift mechanism (not shown) for moving support surface 16 upwardly and downwardly in directions 28, 30 relative to base 12. Disclosure of a suitable lift mechanism is provided in U.S. Pat. No. unknown, entitled "Hydraulic Actuator Apparatus," filed Jan. 25, 2002, to Blyshak et al., the disclosure of which is expressly incorporated by reference herein.

Tabletop 16 includes a head support section 18, a body support section 17, and a lower leg support section 26 which generally correspond to the head, torso and lower legs of a patient positioned on surgical table apparatus 10. Body support section 17 includes an upper torso support section 20, a lower torso support section 22, and an upper leg support section 24 which generally correspond to the upper torso, lower torso, and upper legs of a patient positioned on surgical table apparatus 10. Head support section 18 includes a head support frame or member support 19 and a head pad or head support member 34 supported by head support frame 19. Upper torso, lower torso, and upper leg support sections 20, 22, 24 include upper torso, lower torso, and support frames or member supports 21, 23, 25 and upper torso, lower torso, and upper leg pads or support members 35, 37, 39 that cooperate to define a torso pad 36 supported by upper torso, lower torso, and seat support frames 21, 23, 25. Lower leg support section 26 includes a leg support frame or member support 27 and a lower leg pad 38 supported by leg support frame 27.

Support frames 19, 21, 23, 25, 27 are components of a frame or deck 32 of tabletop 16. Pads 34, 36, 38 are preferably attached to the respective support frames 19, 21, 23, 25, 27 of frame 32 by hook-and-loop type fasteners so that the head, torso, and leg pads 34, 36, 38 may easily be attached or removed from frame 32. In alternative embodiments, other types of couplers are provided to removably or otherwise attach the pads to the frame, such as snaps, ties, or other couplers known to those of ordinary skill in the art. Preferably, the couplers permit pads 34, 36, 38 to be easily removed or attached to frame 32.

According to the first embodiment of the present disclosure, head, torso, and leg pads 34, 36, 38 are filled with foam. According to alternative embodiments of the present disclosure, other materials or configurations are provided in the pads such as air, gel, liquid, air fluidized beads, or other support material known to those of ordinary skill in the art. Details of other suitable pads or supports for use on tabletop 16 are disclosed U.S. patent application Ser. No. 09/187,990, entitled SURGICAL TABLE APPARATUS, filed Nov. 6, 1998, to Richard L. Borders, the disclosure of which was expressly incorporated by reference above.

According to the first embodiment of the present disclosure, lower leg support section 26 of tabletop 16 is pivotally and removably coupled to upper leg support section 24 of tabletop 16. According to alternative embodiments of the present disclosure, leg support section is not removable and not pivotable relative to upper leg support section and is otherwise coupled to upper leg support section of frame.

Figure 2:
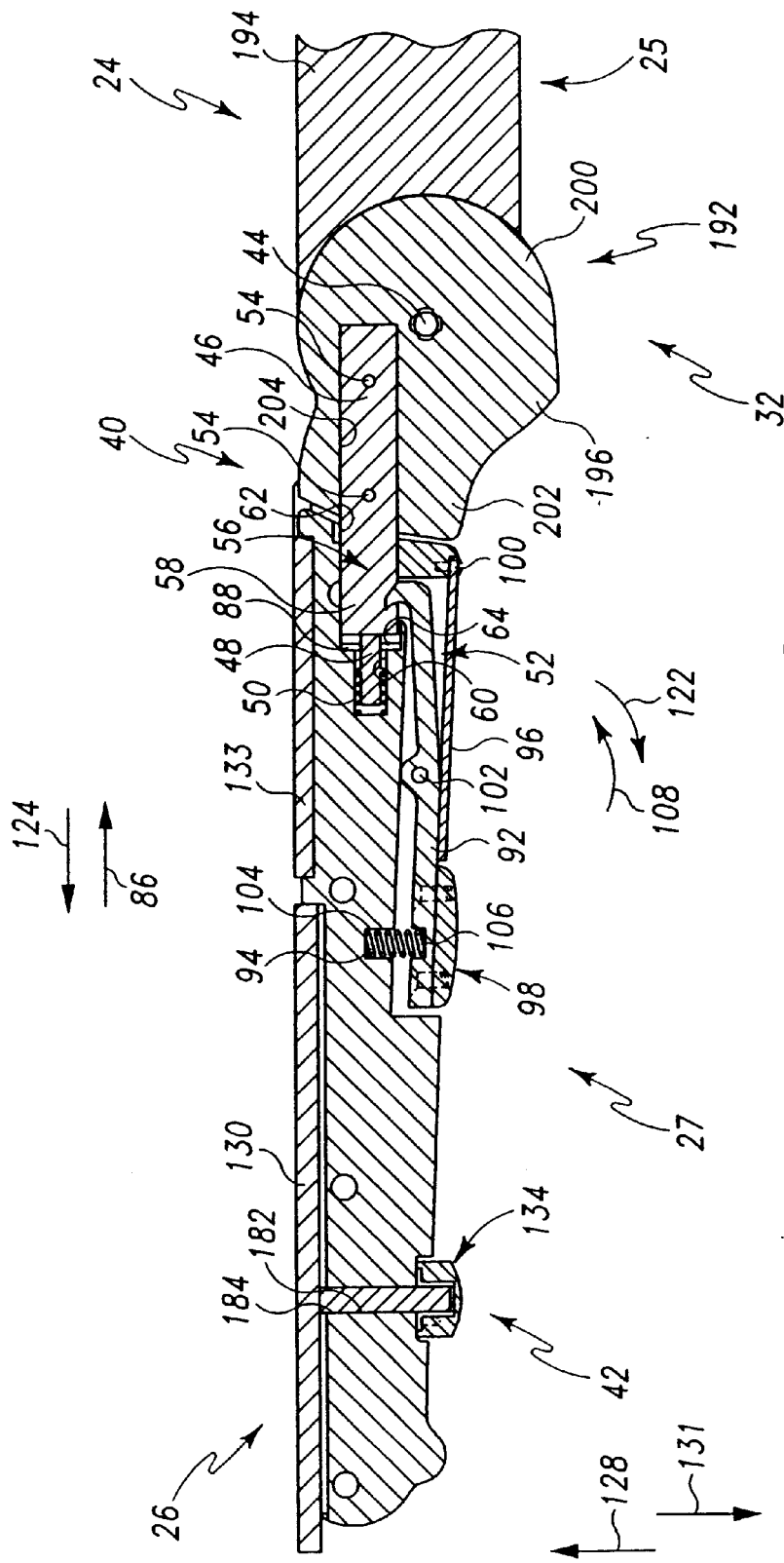
FIG. 2 is a cross-sectional view taken along line 2—2 of FIG. 1 showing a lower leg support section of the tabletop, with the lower leg pad removed, pivotally coupled to an upper leg support section, with the body/upper leg pad removed.
Figure 3:
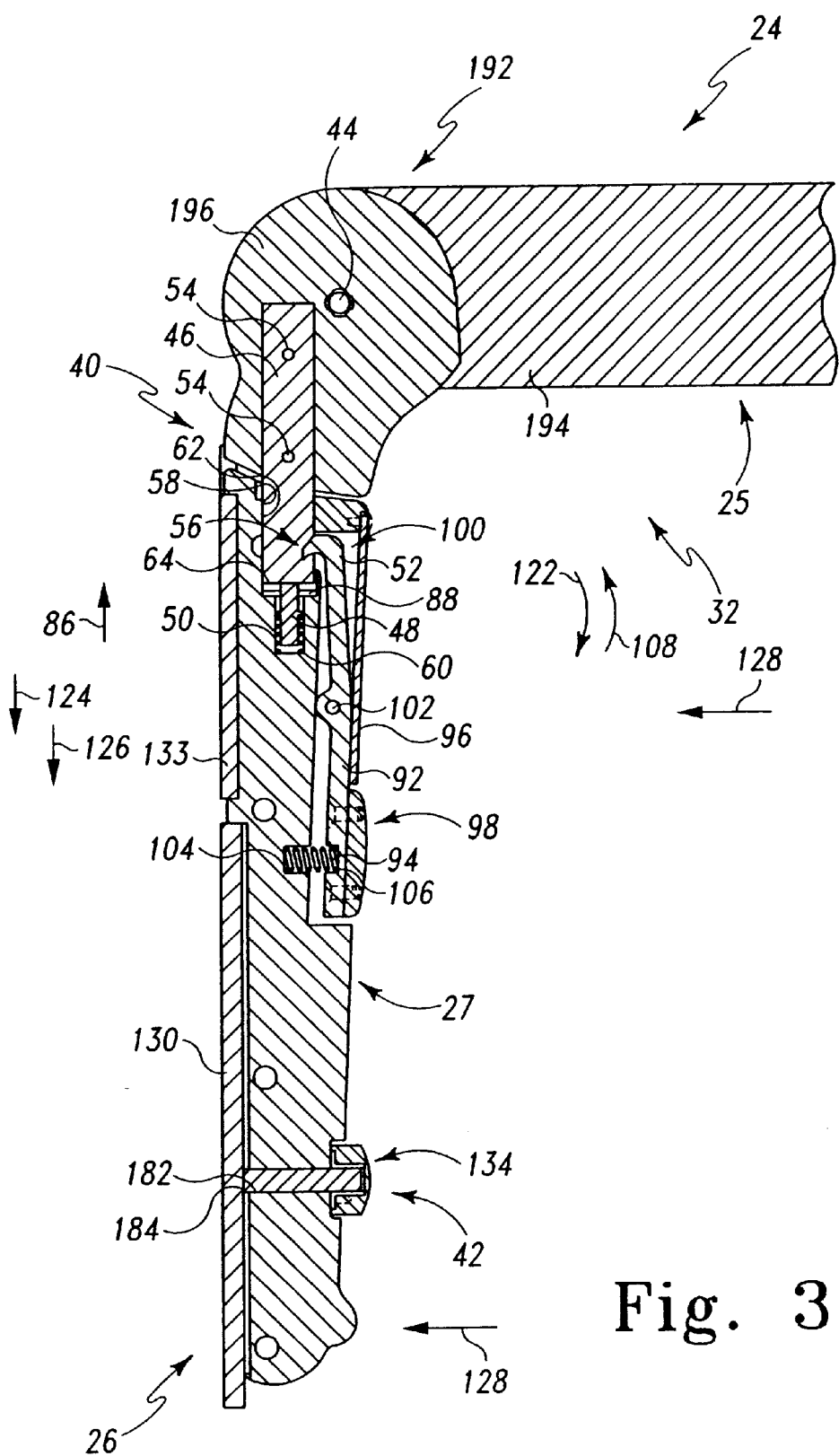
FIG. 3 is a cross-sectional view similar to FIG. 2 showing the lower leg support section of the surgical table apparatus rotated downwardly 90 degrees relative to the upper leg support section.

A lower leg section coupler 40 is provided that is configured to pivotally and removable couple lower leg support section 26 of tabletop 16 to upper leg support section 24 as shown in FIGS. 2–6. Lower leg section coupler 40 permits a user to remove lower leg support section 26 from upper leg support section 24 or rotate lower leg support section 26 relative to upper leg support section 24. As shown in FIGS. 2 and 3, lower leg support section 26 is pivotable between a first or substantially coplanar position relative to the upper leg support section 24 to a second position at a 90-degree angle to upper leg support section 24.

As shown in FIGS. 2–6, leg section coupler 40 includes a hinge 192 that pivotally couples lower leg support section 26 to upper leg support section 24. Hinge 192 includes first and second sockets 194 formed in upper leg support section 24 of frame 32 and first and second pivot members 196 pivotally received by respective sockets 194. Hinge 192 further includes a pair of axles 44 configured to rotatably couple pivot members 196 to sockets 194. According to the first embodiment of the present disclosure, a hydraulic actuator (not shown) is provided to provide the power to move pivot members 196 relative to sockets 194 between the first and second positions and any position therebetween.

Figure 6:
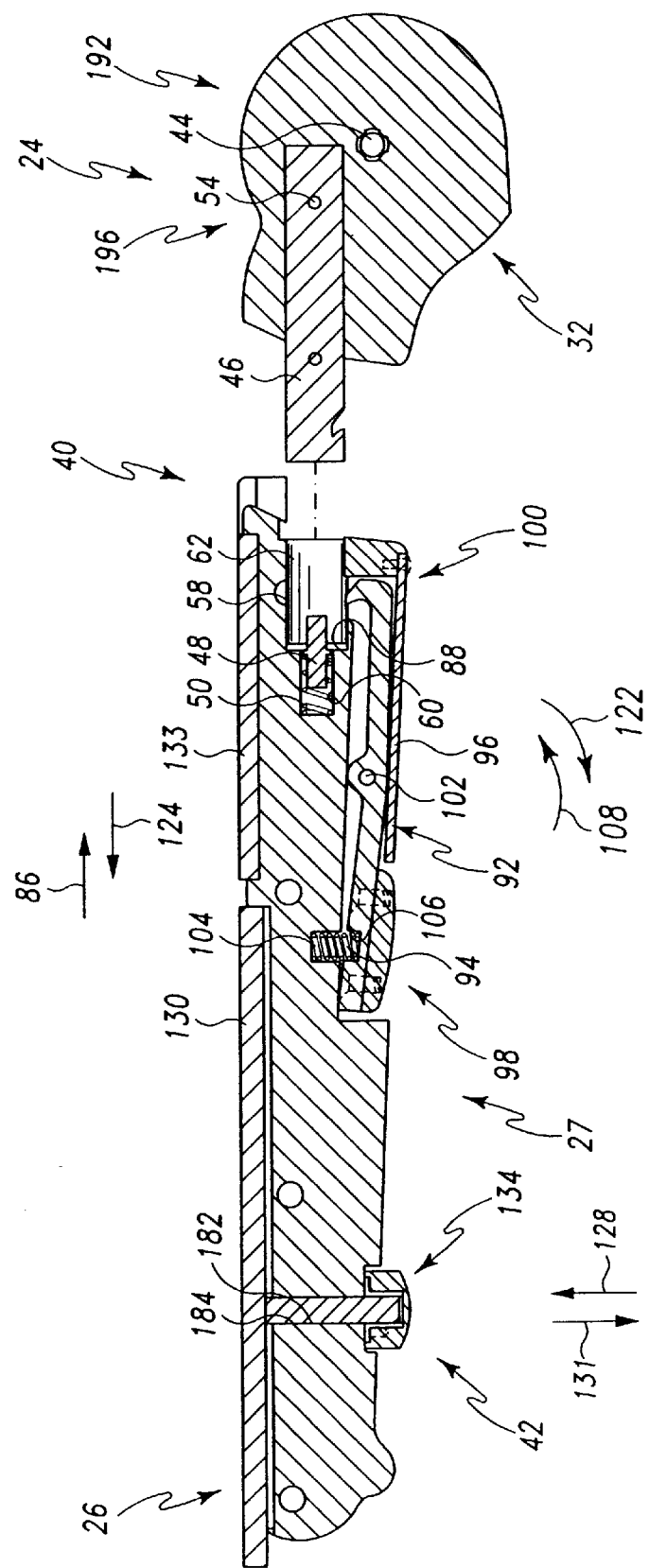
FIG. 6 is a cross-sectional view similar to FIG. 2 taken along line 6—6 of FIG. 5 showing the lower leg support section removed from the upper leg support section.

Leg section coupler 40 further includes a pair of cylindrical posts 46 fixedly coupled to pivot members 196 by pins 54 and a first set of bores 58 formed in lower leg support section 26 and sized to removably receive posts 46. When lower leg support section 26 is coupled to upper leg support section 24, posts 46 are positioned in bores 58 as shown in FIG. 2. When lower leg support section 26 is removed from upper leg support section 24, posts 46 are spaced apart from bores 58 as shown in FIG. 6. Each of bores 58 is defined by a side wall 62 and a shoulder 64 that abuts side wall 62. Side walls 62 define a circular aperture that is slightly larger than the diameter of posts 46.

Figure 4:
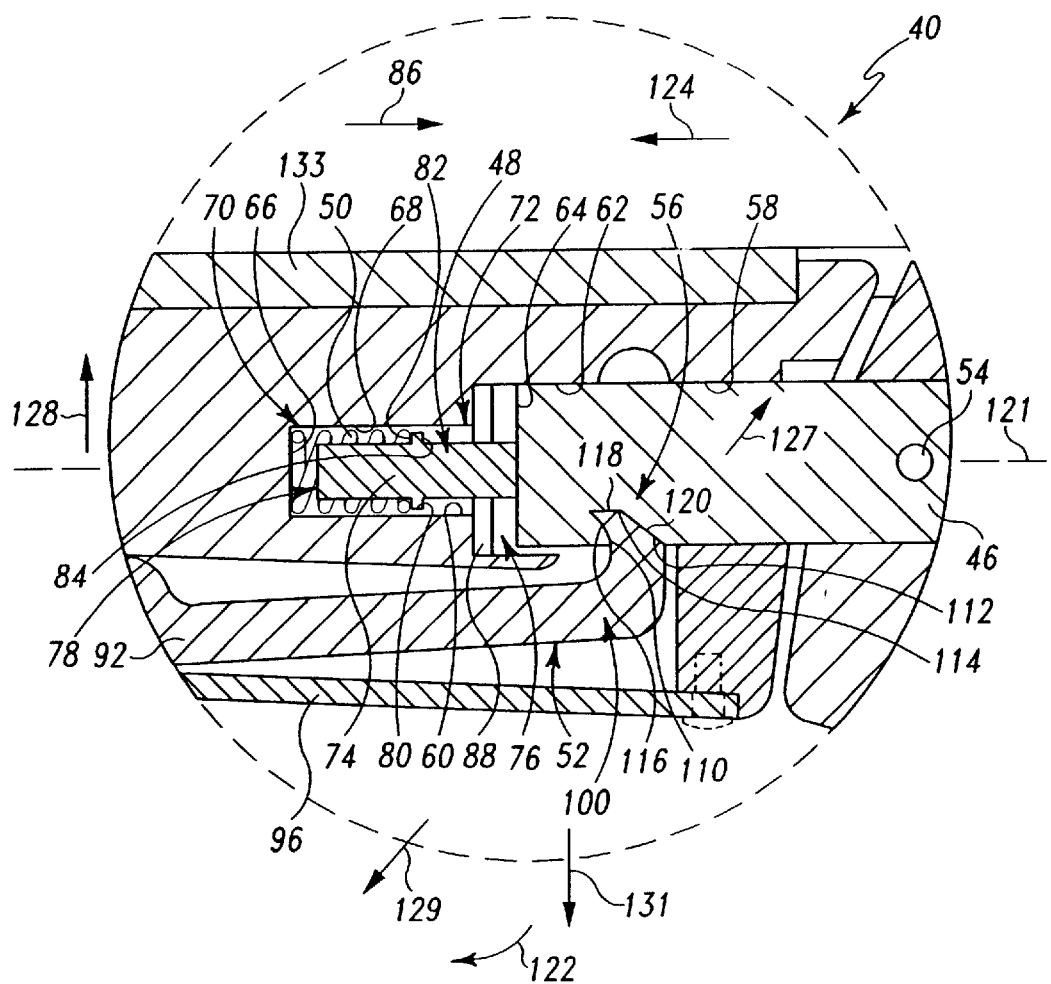
FIG. 4 is an enlarged view of a portion of FIG. 3 showing a portion of a mechanism that couples the lower leg support section of the tabletop to the upper leg support section.

Leg section coupler 40 also includes a second set of bores 60 formed in the lower leg support section 26, pins 48 positioned in bores 60, springs 50 positioned in bores 60, and limiting plates 88 coupled to the respective shoulders 64 as illustrated in FIG. 4. The second set of bores 60 are positioned adjacent to and in communication with the first set of bores 58 as shown in FIGS. 2–4. Each of bores 60 are defined by a bottom wall 66 and a side wall 68 having a first end 70 that abuts bottom wall 66 and a second end 72 that abuts shoulder 64. Side walls 68 define a circular cross section with each side walls 68 of the second set of bores 60 defining a diameter that is about half the diameter defined by side walls 62 of the first set of bores 58.

When lower leg support section 26 is coupled to upper leg support section 24, posts 46 are positioned in bores 58 and abut pins 48 as shown in FIGS. 2–4 so that pins 48 are pushed in direction 124 and compress springs 50. When lower leg support section 26 is removed, posts 46 are removed from bores 58 and springs 50 push pins 48 in direction 86 until pins 48 abut position limiting plate 88 as shown in FIG. 6.

Each of pins 48 includes a body 74 having first and second ends 76, 78 and an annular flange 80 coupled to body 74 midway between ends 76, 78. Annular flange 80 includes a first side 82 facing toward bottom wall 66 and a second side 84 facing away from bottom wall 66. First side 82 of annular flange 80 engages spring 50 so that spring 50 biases pin 52 in direction 86 away from bottom wall 66 and second side 84 engages position limiting plate 88 when posts 46 are removed from bores 58 as shown in FIG. 4.

To attach lower leg support section 26 to upper leg support section 24, locking posts 46 are aligned with bores 58 and then inserted into bores 58. When lock posts 46 are positioned in the first set of bores 58, lower leg support section 26 is moved in direction 86 so that posts 46 abut pins 48 and cause pins 48 to compress springs 50. Pins 48 compress springs 50 through the abutment of flanges 80 of pins 48 and springs 50.

As shown in FIG. 2, in the first embodiment coupler 40 further includes a pair of retainers 52 (only one shown) coupled to lower leg support section 26. Retainers 52 are configured to couple to locking posts 46 to retain lower leg support section 26 on upper leg support section 24. According to alternative embodiments of the present disclosure other retainers such as latches, hooks, fasteners, straps, and other retainers known to those of ordinary skill in the art are provided to couple the leg support section to the upper leg support section.

Retainer 52 cooperates with posts 46 to couple lower leg support section 26 to upper leg support section 24 and permit lower leg support section 26 to be removed from upper leg support section 24. Retainer 52 includes a latch or lever 92, a lever spring 94, and a housing 96 as shown in FIGS. 2–4 and 6. Lever 92 includes a handle end 98, a latch end 100, and a fulcrum 102 positioned between handle end 98 and latch end 100. Lower leg support section 26 and handle end 98 of lever 92 include bores 104, 106 that each receive a portion of lever spring 94. Lever spring 94 biases lever 92 in direction 108 about fulcrum 102 as shown in FIGS. 2 and 3.

Latch ends 100 of levers 92 interact with posts 46 to couple and uncouple seat and leg support sections 24, 26. Posts 46 includes voids or notches 56 that open downwardly toward retainer 52. Each notch 56 is defined across posts 46 such that the cross sections of posts 46 at the point of notch 56 is a circle with a chorded section removed. According to alternative embodiments of the present disclosure, other voids or interactive configurations are provided.

Notch 56 in posts 46 and latch ends 100 of levers 92 have complementary shapes as shown best in FIG. 4. Notch 56 is defined by first, second, and third surfaces 110, 112, 114 and latch ends 100 of levers 92 include complementary first, second, and third surfaces 116, 118, 120. First surfaces 110, 116 are slightly curved. Second surfaces 112, 118 are substantially flat and parallel to a longitudinal axis 121 of the posts 46. Third surfaces 114, 120 are substantially flat.

As lower leg support section 26 is coupled to upper leg support section 24, locking posts 46 move into the first sets of bores 58 and contact third surfaces 120 of levers 92. Third surfaces 120 of levers 92 are oriented to act as cam followers that are driven downwardly by posts 46. When posts 46 contact third surfaces 120 of levers 92, posts 46 rotate levers 92 in direction 122 about fulcrums 102 of levers 92 so that latch ends 100 of levers 92 move downwardly away from posts 46. This rotation causes handle ends 76 of levers 92 to rise and compress lever springs 94.

When posts 46 are moved far enough into bores 58 of lower leg support section 26 so that tips of latch ends 100 reach notches 56, latch ends 100 of levers 92 are biased into notches 56 in direction 108 by lever springs 94. Because latch ends 100 are positioned in notches 56, latch ends 100 and lower leg support section 26 are blocked from being removed from upper leg support section 24 of frame 32.

As previously mentioned, during insertion of posts 46 into bores 58, springs 50 are compressed. When the user releases lower leg support section 26, springs 50 slightly decompress and push biasing pins 48 in direction 86 into posts 46 to move posts 46 relative to latch ends 100 of levers 92 slightly in direction 86 as shown in FIG. 4. To the extent that latch or lock ends 100 of levers 92 are not fully seated within notches 56, this slight relative movement causes latch ends 100 of lock levers 92 to fully seat within notches 56.

The curved or arched first surfaces 116, 110 of levers 92 and notches 56, respectively, in combination with pin springs 50 biasing posts 46 in direction 86 helps ensures that the latch ends 100 of levers 92 fully seat within notches 56. The forces between curved surfaces 116, 110 causes curved surface 110 of post 46 to push curved surface 116 of latch end 100 in direction 127 having components in both direction 128 and direction 86 as shown in FIG. 4. The component in direction 128 pulls and maintains latch ends 100 in notch 56. Thus, if the latch ends 100 are not fully seated within notches 56, the force provided by the compressed springs 50 introduces forces between curved surfaces 116, 110 that push latch ends 100 in direction 128 so that they are fully seated.

The compression of springs 50 continue to bias pins 48 and posts 46 in direction 86 against latch or lock ends 100 when lower leg support section 26 is rotated by upper leg support section 24. This biases latch ends 100 toward the fully seated position into notches 56 to help maintain the connection between lower leg support section 26 and upper leg support section 24 during rotation of lower leg support section 26.

The weight of lower leg support section 26 also helps maintain latch ends 100 in notches 56 when lower leg support section 26 is rotated relative to upper leg support section 24. For example, when lower leg support section 26 is rotated 90 degrees relative to upper leg support section 24, as shown in FIG. 3, gravity acts upon lower leg support section 26 in direction 126. This gravity creates additional forces between curved surfaces 110, 116 and causes latch ends 100 of levers 92 to be pushed in direction 128 relative to posts 46. The force in direction 128 caused by gravity, in addition to the force applied by springs 50 discussed above, helps maintain the positive seating relationship between curved first surfaces 110, 116 of notches 56 and of lock ends 100 of levers 92, respectively. The positive seating forces between curved surfaces 110, 116 created by pin springs 50 and gravity, respectively, help prevent a caregiver from accidentally, or unintentionally bumping into handle end 98 of lever 92 and causing lower leg support section 26 to fall in direction 126 to the floor without first lifting or pushing on lower leg support section 26 in direction 86.

As shown in FIG. 6, to remove lower leg support section 26 from upper leg support section 24, the caregiver applies pressure to lower leg support section 26 in direction 86 and presses upwardly in direction 122 on handle end 98 of lever 92. Applying enough pressure to lower leg support section 26 in direction 86 moves biasing pins 48 relative to pin springs 50 urging lower leg support section 26 and levers 92 in direction 86. Because posts 46 are stationary, third surfaces 120 of latch ends 100 pushes on third surfaces 114 of post 46 in direction 129 having components in direction 124 and direction 131. The component of the force in direction 131 moves latch ends 100 in direction 131 out of notches 56.

Figure 5:
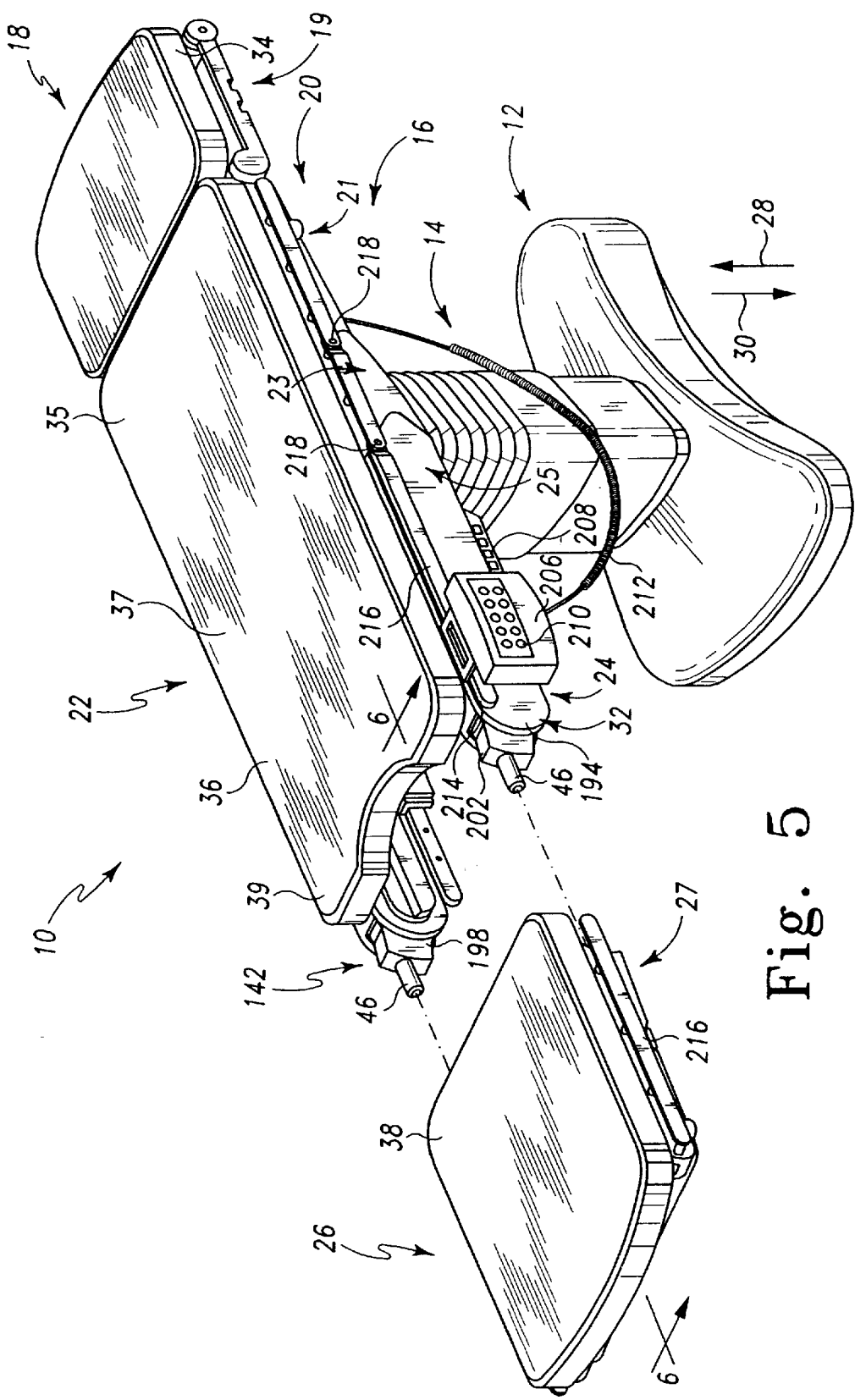
FIG. 5 is an exploded perspective view similar to FIG. 1 showing the lower leg support section of the tabletop removed from the upper leg support section.

To keep latch ends 100 from sliding back into notches 56 when lower leg support section 26 is moved in direction 124, the caregiver presses on handle ends 98 of levers 92. Otherwise, springs 94 will urge latch ends 100 back into notches 56. With latch ends 100 of levers 92 removed from notches 56 and handle ends 98 depressed, the user may pull lower leg support section 26 away from upper leg support section 24 as shown in FIGS. 5 and 6. When lower leg support section 26 is removed, the compressed pin springs 50 move biasing pins 48 in direction 86 until annular flanges 80 abut position limiting plate 88 to prevent springs 50 from falling out of the second set of bores 60.

Figure 7:
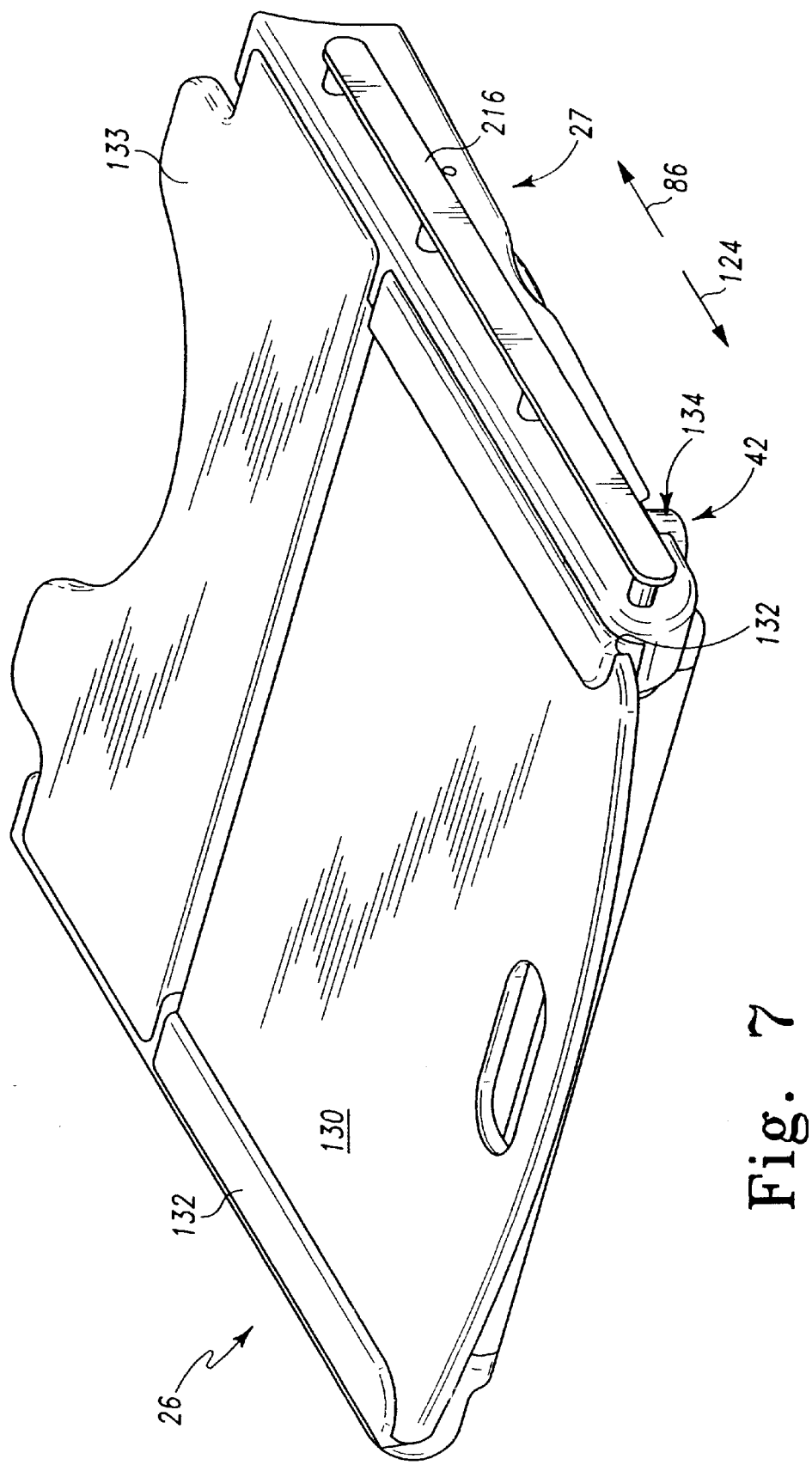
FIG. 7 is a perspective view of the lower leg support section of the tabletop of FIG. 1, with the lower leg pad removed, showing the lower leg support section including extendable and fixed leg support plates and the extendable leg support plate having a handle to assist in moving the extendable leg support plate relative to the remainder of the lower leg support section.

As shown in FIG. 7, lower leg support section 26 further includes a leg support plates 130, 133 that combine with support pads to provide leg support members, spaced-apart guide tracks or channels 132, and a leg extension coupler or position holder 42 that interacts with leg support plate 130 to fix the position of leg support plate 130. Leg support plate 130 slides on guide tracks 132 in directions 124, 86 to allow the overall length of lower leg support section 26 and surgical table apparatus 10 to be altered as desired. Leg extension coupler 42 is configured to fix the position of leg support plate 130 when it is not being moved between the various positions.

In the illustrated first embodiment in FIG. 6, leg extension coupler 42 is a torque-limited bolt 134. If too much torque is applied to a coupler when the coupler is tightened, a caregiver may not be able to loosen the coupler later. Thus, torque-limited bolt 134 is provided so that too much force or torque may not be applied that may otherwise be difficult to overcome. According to alternative embodiments of the present disclosure, non-torque-limited couplers are provided.

Figure 8:
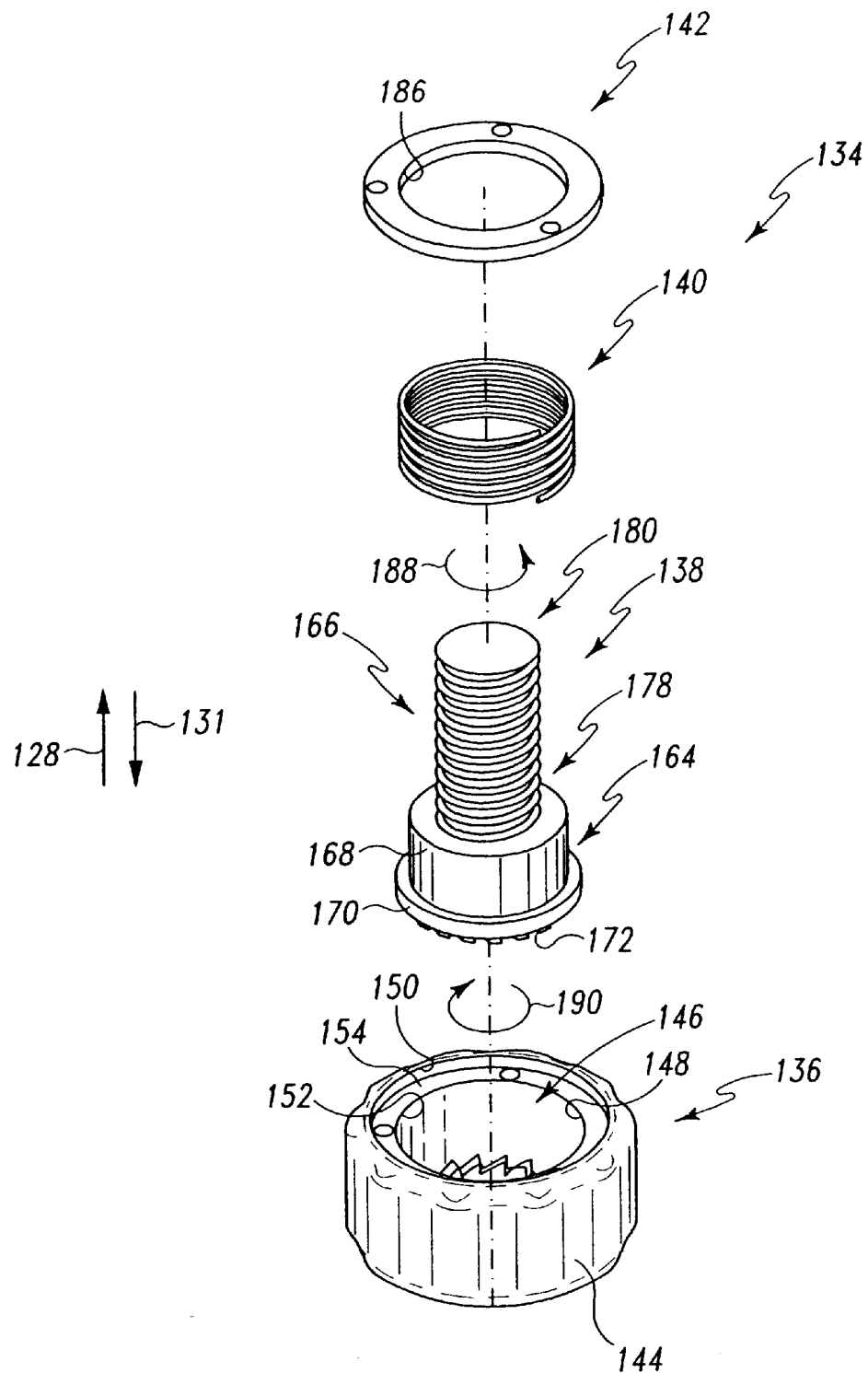
FIG. 8 is an exploded perspective view of a coupler configured to couple the extendable leg support plate to the remainder of the lower leg support section.
Figure 9:
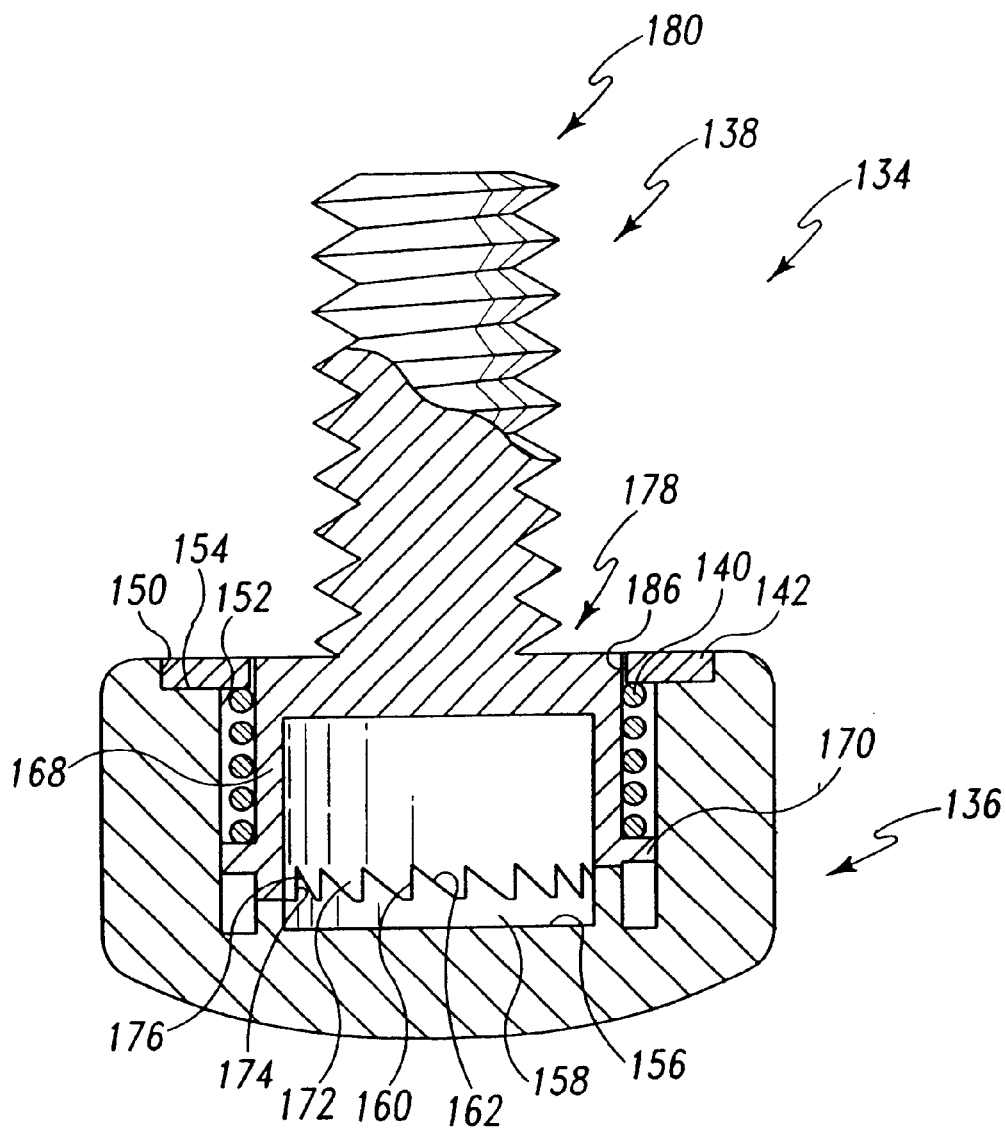
FIG. 9 is a side elevation view, with portions cut away, of the coupler of FIG. 8.

As shown in FIGS. 8 and 9, torque-limited bolt 134 includes a handle 136, a bolt or coupler member 138, a spring 140, and a ring-shaped spring retainer 142. Handle 136 is cylinder-shaped and the outer periphery of handle 136 includes a plurality of longitudinally extending undulations or ridges 144 providing an easily graspable surface. Handle 136 further includes a bore 146 that is sized to receive a portion of bolt 138. Bore 146 is defined by a cylindrical side wall 148 having first and second portions 150, 152 and a shoulder 154 that separates the first and second portions 150, 152. First portion 150 of cylindrical side wall 148 includes a larger diameter than second portion 152 of cylindrical side wall 148. Bore 146 is also defined by a bottom wall 156 and a ring of longitudinally extending teeth 158 coupled to bottom wall 156. Each of teeth 158 includes a substantially vertical, flat surface 160 and an inclined or angled surface 162 as shown in FIGS. 8 and 9.

Bolt 138 includes a head section 164 and a threaded section 166 coupled to head section 164. Threaded section 166 is cylindrical in shape and threaded and includes a first end 178 coupled to body 168 of head section 164 and a second end 180 spaced apart from first end 178. Leg support frame 27 of lower leg support section 26 includes a threaded bore 182 that is sized to receive threaded section 166 of bolt 138. Threaded bore 182 is defined by a threaded cylindrical side wall 184 that has a length less than the length of threaded section 166 of bolt 138.

Head section 164 of bolt 138 includes a body 168, an annular flange or disk shaped spring mount 170 coupled to body 168, and a plurality of teeth 172 coupled to annular flange 170. Each of teeth 172 includes a substantially vertical, flat surface 174 and an angled surface 176. The angled and flat surfaces 160, 174, 162, 176 of teeth 158, 172 of handle 136 and bolt 138 are formed to complement and fit within each other as shown in FIG. 9.

Annular flange 170 is sized to include an outer diameter that centers head section 164 of bolt 138 within second portion 152 of bore 146. Centering head section 164 aligns teeth 172 of bolt 138 relative to teeth 158 of handle 136. Body 168 of head section 164 of bolt 138 has an outer diameter that is smaller than the inner diameter of spring 140 which in turn has an outer diameter smaller than that of annular flange 170 of bolt 138 so that spring 140 rests on annular flange 170.

Spring 140 is positioned between second portion 152 of cylindrical wall 148 of handle 136 and body 168 of head section 164 of bolt 138 as shown in FIG. 9. Spring 140 has an inner diameter greater than the outer diameter of body 168 of head section 102 and an outer diameter smaller than inner diameter of second portion 152 of cylindrical wall 148 that defines bore 146 of handle 136. In the illustrated embodiment, spring 140 is a coil type spring.

Spring retainer 142 is positioned to abut shoulder 154 of handle 136 and first portion 150 of cylindrical wall 148 and compresses spring 140 against annular flange 170 of head section 164 of bolt 138 when assembled as shown in FIG. 9. Spring retainer 142 includes a bore 186 having a diameter greater than the diameter of threaded section 166 of bolt 138 to allow bolt 138 to pass through spring retainer 142. Further, the diameter of bore 186 is smaller than the outer diameter of spring 140 so that spring retainer 142 retains spring 140 within bore 146 of handle 136.

In the illustrated embodiment, the relaxed length of spring 140 is greater than the distance between spring retainer 142 and annular flange 170 of head section 164 of bolt 138 so that spring 140 is compressed to urge teeth 172 of bolt 138 against teeth 158 of handle 136. This creates normal forces and frictional forces between teeth 172 of bolt 138 and teeth 158 of handle 136.

Torque-limited bolt 134 is assembled by placing head section 164 of bolt 138 fully within bore 146 of handle 136 so that teeth 172 of bolt 138 are oriented to engage teeth 158 of handle 136. Next, spring 140 is placed over bolt 138 within bore 146 of handle 136 so that the spring rests on annular flange 170 of bolt 138. Then, spring retainer 142 is placed over bolt 138 and positioned in first section 150 of cylindrical wall 148 that defines bore 146 of handle 136. An adhesive or other fastener, such as a screw(s) or rivet(s), is applied to spring retainer 142 to secure it to handle 136 and compress spring 140 against annular flange 170 of bolt 138.

Torque-limited bolt 134 threadably engages threaded bore 182 as shown in FIGS. 2, 3, and 6. Torque-limited bolt 134 is advanced into threaded bore 182 in direction 128 by rotating torque-limited bolt 134 in direction 188 and backed out of threaded bore 182 in direction 131 by rotating torque-limited bolt 134 in direction 190 as shown in FIG. 8. Threaded section 166 is longer than the length of threaded cylindrical wall 184 that defines bore 182 so that when torque-limited bolt 134 is fully advanced into threaded bore 182, second end 180 of threaded section 166 protrudes past threaded cylindrical wall 184 and abuts leg support plate 130.

When second end 180 of threaded section 166 of bolt 138 protrudes from threaded bore 182 and abuts leg support plate 130, second end 180 of threaded section 166 fixes the position of leg support plate 130 relative to tracks 132. When second end 180 of threaded section 166 is backed out enough to relieve enough force between bolt 138 and leg support plate 130, for example, when bolt 138 is spaced apart from leg support plate 130, leg support plate 130 may slide horizontally within guide tracks 132.

To fix the position of leg support plate 130, torque-limited bolt 134 is rotated in direction 188 to apply the necessary force onto leg support plate 130. Applying torque to handle 136 in direction 188 creates additional normal forces between angled surfaces 162 of teeth 158 of handle 136 and angled surfaces 176 of teeth 172 of bolt 138. The lateral components of these forces causes bolt 138 to rotate with handle 136 as long as the torque applied to handle 136 is below a predetermined maximum torque.

If torque above the predetermined maximum torque is applied to handle 136, the longitudinal components of the normal force applied to teeth 158, 172 through handle 136 will overcome the longitudinal components of the normal force applied to teeth 158, 172 by spring 140. This imbalance in the longitudinal forces causes handle 136 to move against the bias of spring 140 so that teeth 158, 172 travel over and past each other causing teeth 158, 172 to slip so that torque above the predetermined maximum is not applied to bolt 138. By limiting the amount of torque that can be applied to bolt 138, stripping or other damage to the threads of bolt 138 is avoided and bolt 138 is not over tightened.

To move leg support plate 130 relative to the remainder of lower leg support section 26, handle 136 is rotated in direction 190 to move second end 180 of threaded section 166 away from leg support plate 130. When handle 136 is rotated in direction 190, vertical surfaces 160 of teeth 158 of handle 136 engage vertical edges 174 of teeth 172 of bolt 138. Because the engaging surfaces 160, 174 of teeth 158, 172 are vertical, the rotational force applied by the caregiver does not have any vertical component and therefore does not cause teeth 158, 172 to move over or slip relative to each other, but rather transmits the full torque applied to handle 136 to bolt 138.

According to the preferred embodiment of the first embodiment of the present disclosure, an actuator (not shown) is provided that rotates pivot member 196 of leg section coupler 40 relative to upper leg support section 24. As previously mentioned, by moving pivot member 196, lower leg support section 26 is also rotated as shown in FIGS. 2 and 3.

A pair of controllers 206, 208 are provided to control movement of the actuator. Controllers 206, 208 include a plurality of buttons 210 configured to control the actuator and other functions of surgical table apparatus 10. Buttons 210 control the hydraulics which power the articulation of upper torso, lower torso, seat, and leg support sections 20, 22, 24, 26. Buttons 210 further control the length of pedestal 14 and therefore the height of support frame 32. Details of a controller for the support surface and surgical table apparatus are disclosed in U.S. application Ser. No. 09/187,825, entitled MEDICAL EQUIPMENT CONTROLLER, filed Nov. 6, 1998, to Richard L. Borders, the disclosure of which is expressly incorporated by reference herein. According to alternative embodiments of the present disclosure, additional buttons or button configurations are provided to control other devices typically found in a patient environment.

Controller 208 is stationary and is attached to the underside of upper leg support section 24. Wires (not shown) couple stationary controller 208 to a processor (not shown). Controller 206 is removably coupled to support frame 32 and includes a coiled cord 212 that couples the remainder of controller 206 to the processor. Coiled cord 212 is comprised of a plurality of wires (not shown) suitable for transmitting electronic signals and a plastic sheath that surrounds the plurality of wires.

Controllers 206, 208 receive input as a user presses buttons 210. The input received by controller 206 is transferred through wires, in coiled cord 212 or otherwise, to the processor which controls the hydraulics of surgical table apparatus 10.

Handheld controller 206 has a hook portion 214 that allows handheld console 206 to be mounted upon side rails 216. Side rails 216 are attached to the sides of upper torso, lower torso, seat, and leg support sections 20, 22, 24, 26 as shown in FIG. 1. Side rails 216 of upper torso, lower torso, and upper leg support sections 20, 22, 24 are connected to side rail 216 of the adjacent support section by hinges 218 which allow side rails 216 to articulate as their associated support sections 20, 22, 24 also articulate. Handheld controller 206 can be hung on side rails 216 when controller 206 is not in use. When controller 206 is in use, the user may press buttons 210 while controller 206 is hung on side rails 216, or the user may remove controller 206 from side rails 216 and thereafter manipulate buttons 210.

As previously stated, buttons 210 control the hydraulics which control the articulation of upper torso, lower torso, seat, and leg support sections 20, 22, 24. Each support section 20, 22, 24, is pivotally coupled to its neighboring support sections 20, 22, 24. Pivot members and sockets defined by the respective upper torso, lower torso, and upper leg support sections 20, 22, 24 are provided at each interface that are similar to pivot members 196 and sockets 94 that permit lower leg support section 26 to pivot relative to upper leg support section 24 as previously described.

In addition to being pivotally coupled to lower torso support section 22, upper leg support section 24 is also coupled to an upper end of pedestal 14. Therefore, elongation or contraction of pedestal 14 will translate into an adjustment of the height of upper leg support section 24. The length of pedestal 14, and therefore height of support frame 32, is adjusted by use of either of controllers 206, 208.

One adjustment that is not controlled by controllers 206, 208 is the articulation of head support section 18. A user manually articulates head support section 18 between several positions as shown, for example, in FIGS. 10–14. According to alternative embodiments of the present disclosure, hydraulics are provided to articulate the head support section.

Head support section 18 includes a head support plate 220 configured to support head pad 34, first and second links 222, 224 supporting head support plate 220, a first set of couplers 226 that couple head support plate 220 to first and second links 222, 224, first and second attachment rods or couplers 228, 230, a second set of couplers 232 that couple first and second links 222, 224 to attachment rods 228, 230, and a third set of couplers 234 that couple attachment rods 228, 230 to upper torso support section 20 as shown in FIGS. 10–14.

A caregiver uses first, second, and third sets of couplers 226, 232, 234 to manually adjust the position of head support section 18 to a variety of positions as shown in FIGS. 10–13. In the illustrated embodiment, first and second sets of couplers 226, 232 include position holders or button joints 226, 232 that permit rotation of the respective head support plate 220 with head pad 34 relative to first and second links 222, 224 and first and second links 222, 224 relative to attachment rods 228, 230 when pressed. Third set of coupler 234 include position holder such as torque-limited bolts that are substantially similar to torque-limited bolts 134 discussed above and shown in FIGS. 8 and 9.

Figure 10:
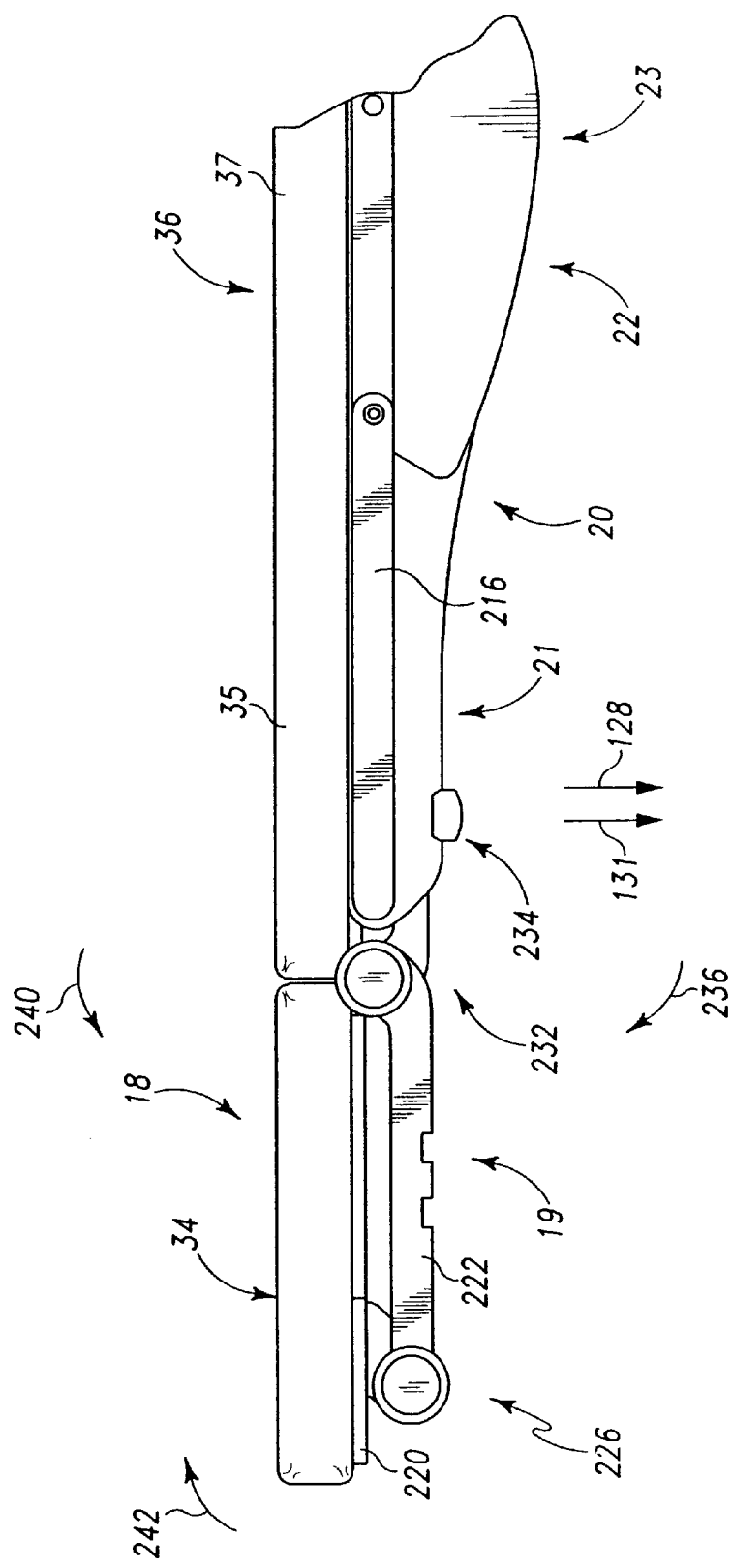
FIG. 10 is a side elevation view of the head support section, an upper torso support section, and a portion of a lower torso support section of the tabletop of FIG. 1 showing the head support section pivotally coupled to the upper torso support section with a head support surface of the head support section substantially coplanar with a body support surface of the upper torso support section.
Figure 11:
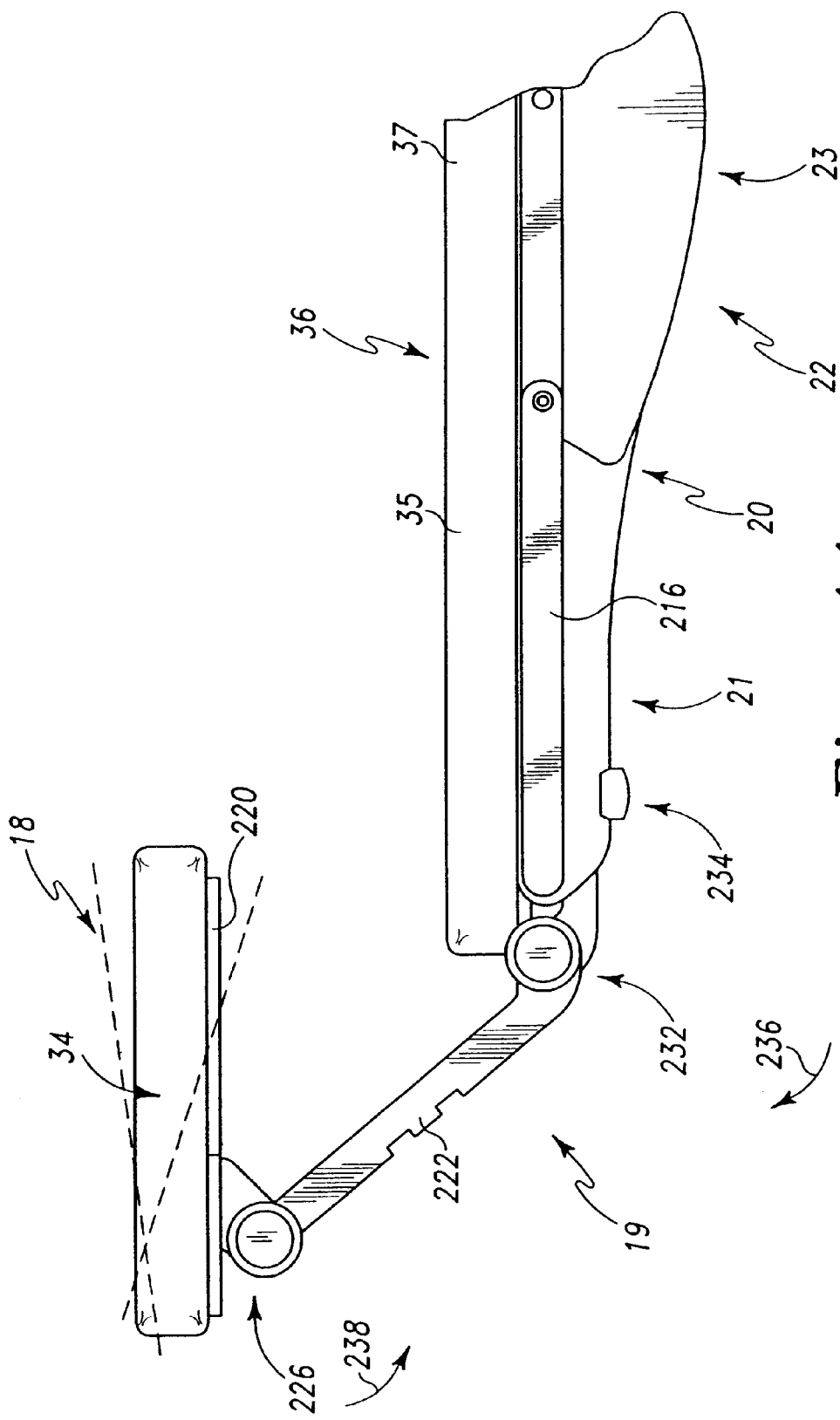
FIG. 11 is a view similar to FIG. 10 showing the head support section rotated relative to the upper torso support section and a head support surface of the head support section being parallel and raised relative to body support surface of the upper torso support section.

As shown in FIG. 10, head support section 18 is positioned in a first horizontal position with head pad 34 supported in a substantially coplanar position with torso pad 36. When a caregiver wants to support a patient's head in an elevated position, head pad 34 is moved to a second horizontal position parallel and elevated relative to torso pad 36 as shown in FIG. 11. To move head pad 34 to a second horizontal position, a caregiver presses on first set of button joint 226 and rotates head support 220 upwardly in direction 238 relative to links 222, 224 and presses on second set of button joints 232 and rotates first and second links 222, 224 upwardly in direction 236 relative to attachment rods 228, 230 as shown in FIG. 11. Head pad 34 may also be rotated using button joint 226 so that head pad 34 is not horizontal as shown in phantom lines in FIG. 11.

Figure 12:
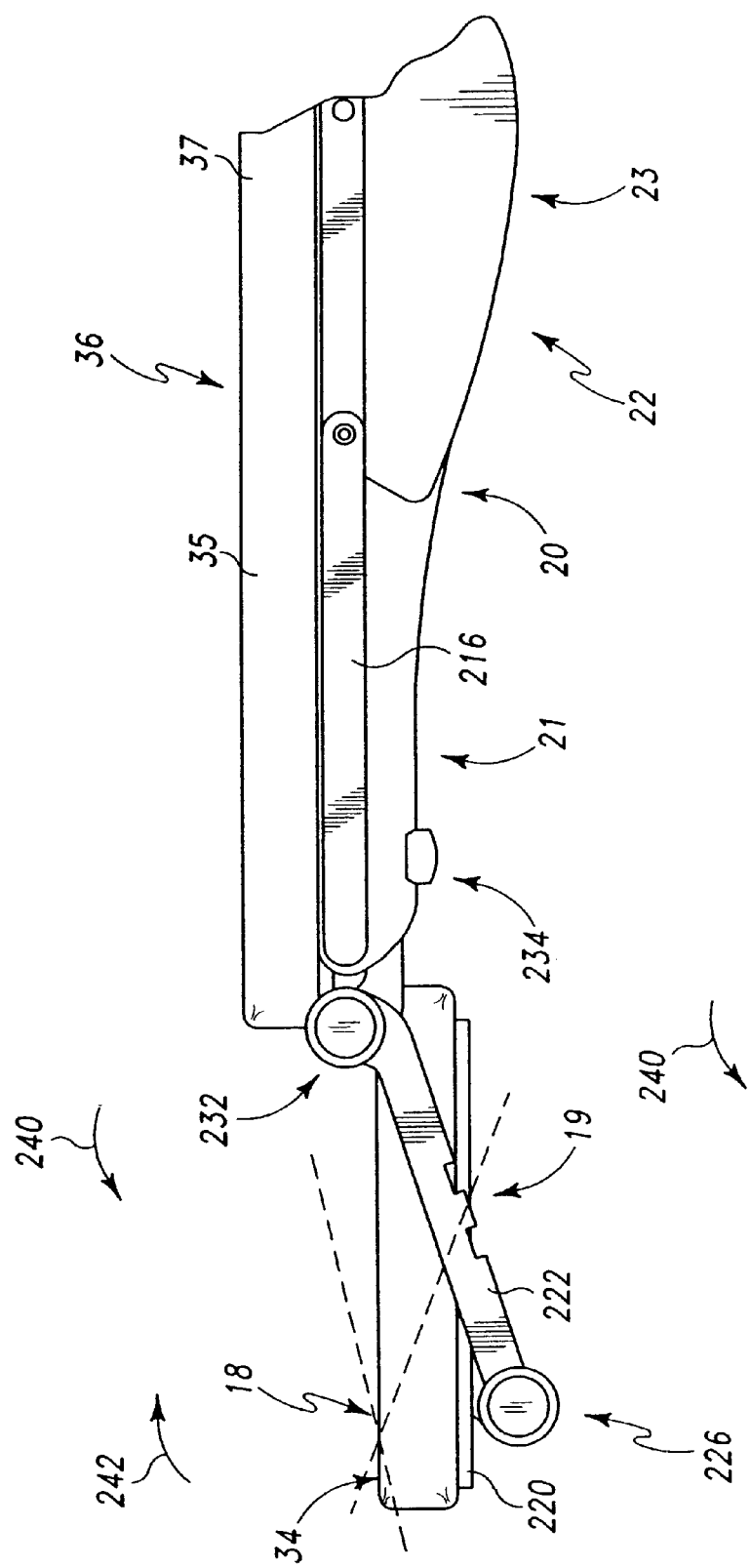
FIG. 12 is a view similar to FIG. 10 showing the head support section rotated relative to the upper torso support section and the head support surface of the head support section being parallel and lowered relative to the body support surface of the upper torso support section.

When a caregiver wants to support a patient's head in a lowered position, the head pad 34 is moved to a third horizontal position parallel and lowered relative to the torso pad 36 as shown in FIG. 12. To move the head pad 34 to the third horizontal position, a caregiver presses the first set of button joints 226 and rotates the head support 220 downwardly in direction 242 relative to links 222, 224 and presses second set of button joints 232 and rotates the links 222, 224 downwardly in direction 240 relative to the attachment rods 228, 230 as shown in FIG. 12. Head pad 34 may also be rotated using button joints 226 so that head pad 34 is not horizontal as shown in phantom lines in FIG. 12.

Figure 13:
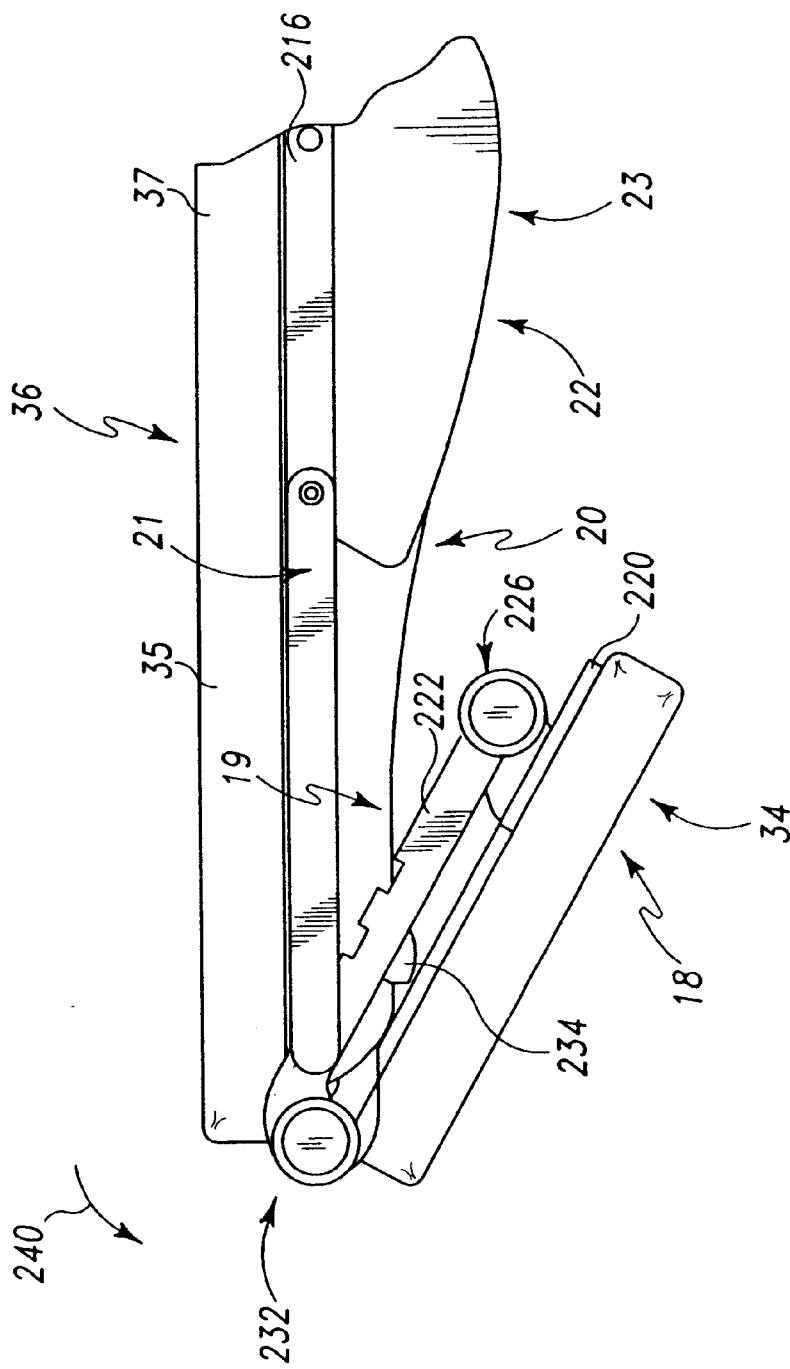
FIG. 13 is a side elevation view similar to FIG. 10 showing the head support section rotated relative to the upper torso support section with the head support surface of the head support section tucked under the upper torso support section.
Figure 14:
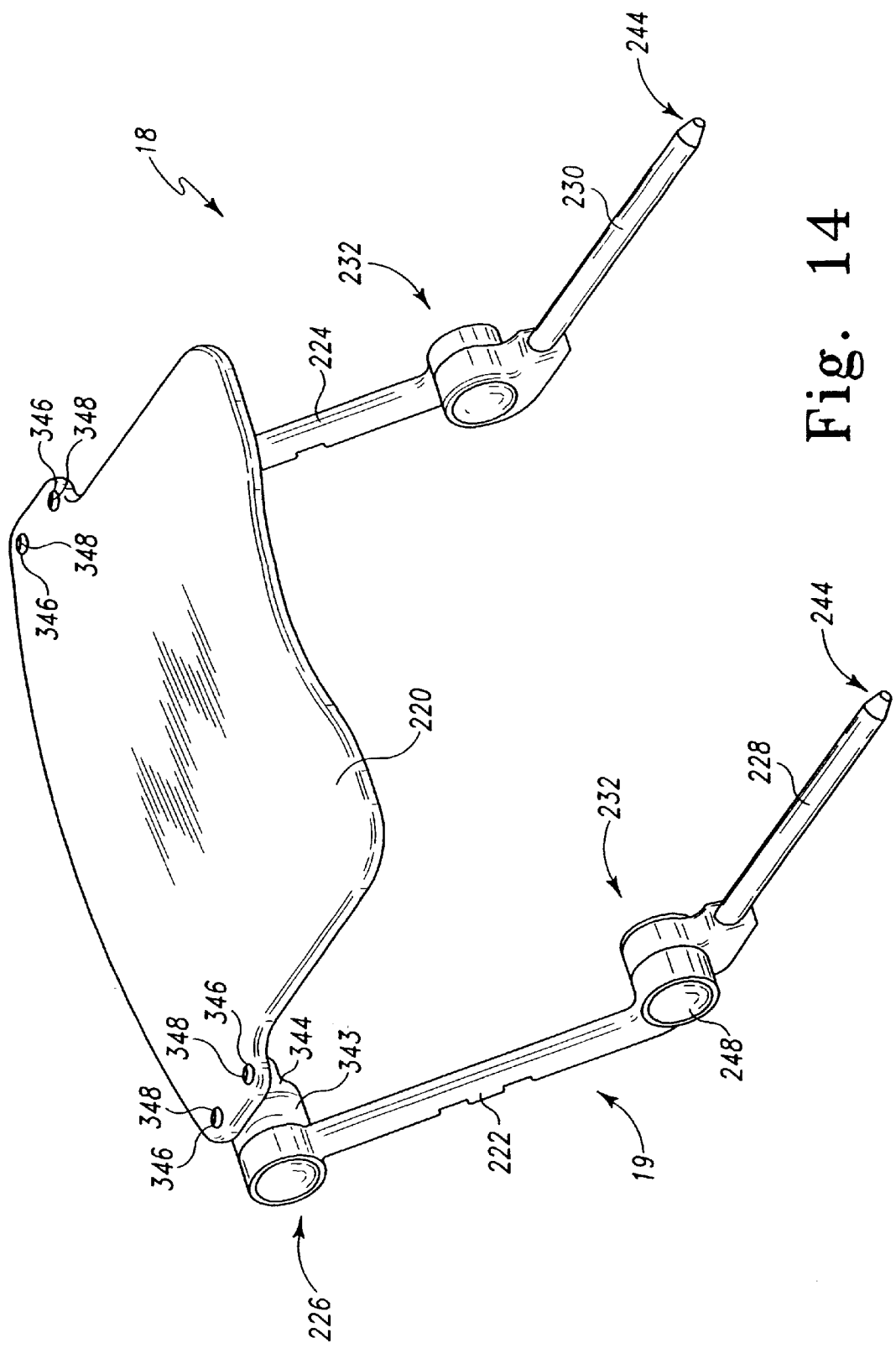
FIG. 14 is a perspective view of the head support section of the tabletop, with the head support pad removed, showing the head support section including a head support plate, a pair of links supporting the head support plate, a first pair of couplers or position holders pivotally coupling the head support plate to the pair of links, a pair of attachment posts or rods, and a second pair of couplers or position holders pivotally coupling the pair of links to the attachment rods.

If the caregiver wants to store head pad 34, head pad 34 is moved to a fourth or tucked position under upper torso support section 20 of frame 32 as shown in FIG. 13. To move head pad 34 to the tucked position, the caregiver presses second set of button joints 232 and rotates links 222, 224 downwardly in direction 240 relative to attachment rods 228, 230. The positions of head support section 18 in FIGS. 10–13 are merely examples of the many positions that head support section 18 can assume relative to upper torso support section 20.

As discussed above, button joints or position holders 226, 232 either allow head support plate 220 to rotate relative to links 222, 224 and links 222, 224 to rotate relative to attachment rods 228, 230 or fix the relative positions of head support plate 220 and links 222, 224. Rotation of bolts 234 either allows attachment rods 228, 230 to move longitudinally in directions 86, 124 relative to upper torso support section 20 of support frame 32 or fixes the position of attachment rods 228, 230 relative to upper torso support section 20.

Each of attachment rods 228, 230 have first and second ends 244, 246. First ends 244 are tapered and second ends 246 support couplers 232. Tapered ends 244 are received within bores (not shown) defined in upper torso support frame 21 of upper torso support section 20. Tapered ends 244 of attachment rods 228, 230 decrease in cross section to create a slope that guides insertion of rods 228, 230 into the bores. The bores include a depth equal to or greater than the length of attachment rods 228, 230. Support frame 21 of upper torso support section 20 also includes threaded bores (not shown) sized to receive torque-limited bolts 234. Bolts 234 are operated as discussed above with reference to bolts 134 to permit movement of attachment rods 228, 230 in directions 131, 128 or to fix the position of attachment rods 228, 230 relative to upper torso support section 20.

Figure 15:
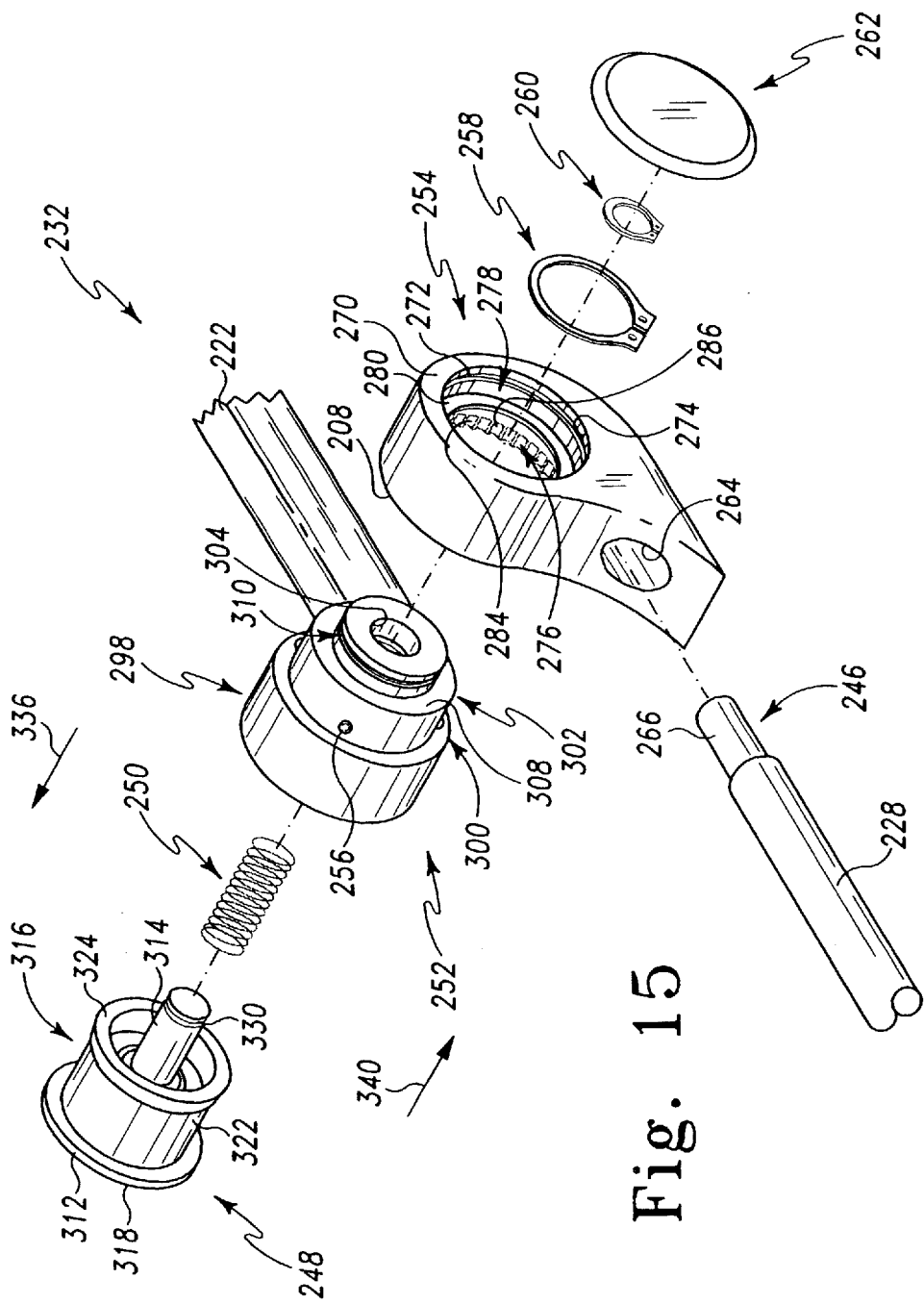
FIG. 15 is an exploded perspective view of one of the second pair of couplers of the head support section of FIG. 14.

As shown in FIG. 15, each of second set of button joints 232 includes a button 248, a spring 250, first and second housings or bases 252, 254, bearings or keys 256, first and second C-clips or snap rings 258, 260, and a cover 262. Each of first housings 252 are coupled to one of first and second links 222, 224 and each of second housings 254 are coupled to one of attachments rods 228, 230. As shown in FIG. 15, second housing 254 includes an aperture or void 264 sized to receive second end 246 of attachment rod 228. Second end 246 of attachment rod 228 includes a section 266 of reduced radius that is positioned in aperture 264 of second housing 254.

Button joint 232 operates to fix the positions of housings 252, 254 relative to each other and thus fix the positions of links 222, 224 and attachment rods 228 relative to each other. When buttons 248 are pressed by a caregiver, housings 252, 254 are permitted to rotate relative to each other and thus links 222, 224 and attachment rods 228 are permitted to rotate relative to each other.

Figure 16:
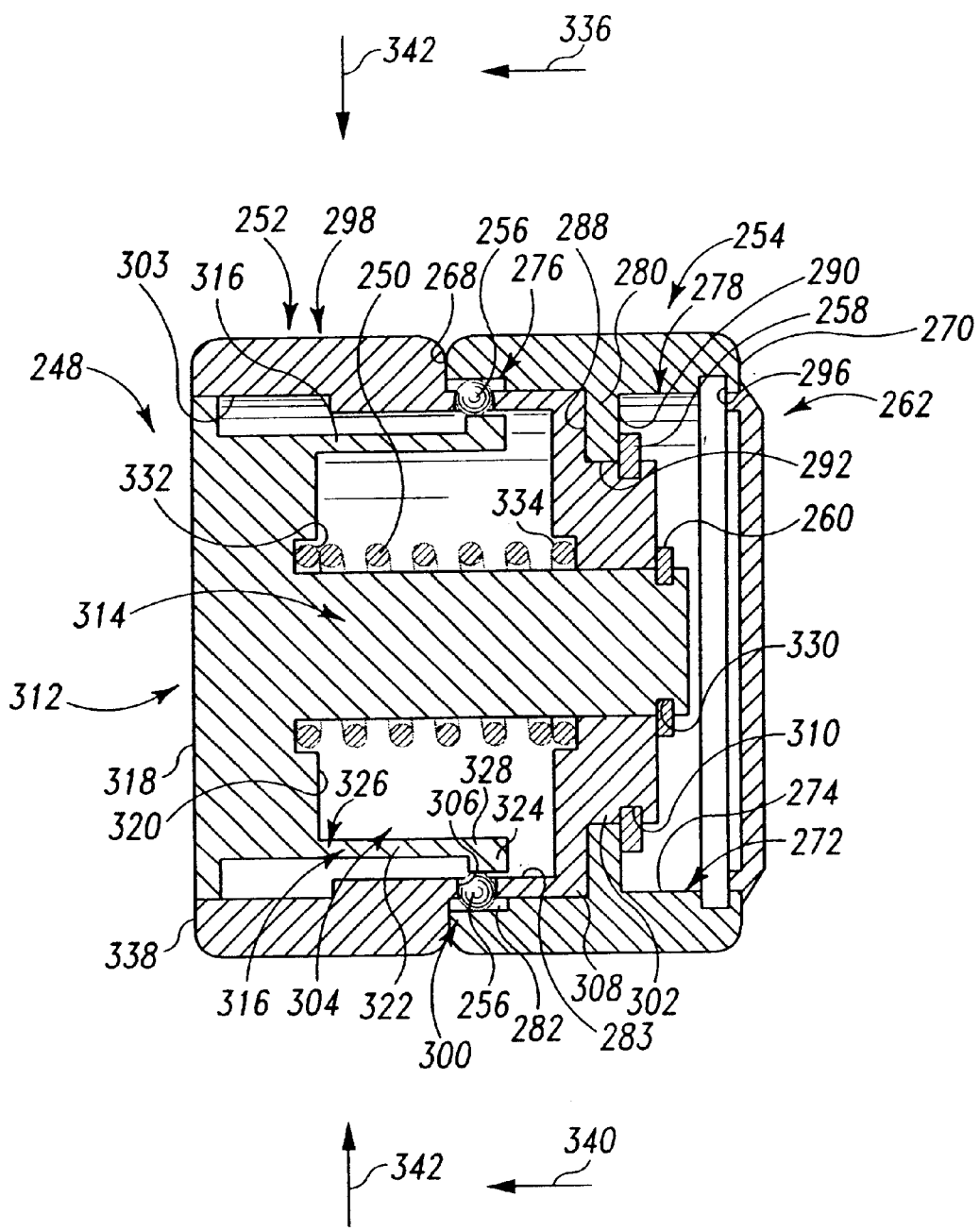
FIG. 16 is a cross-sectional view of the coupler of FIG. 15 showing the coupler in a first position fixedly coupling the respective link to the respective attachment rod.

As shown in FIG. 16, each second housing 254 includes a first side 268 facing toward first housing 252, a second side 270 facing away from first housing 252, and an inner surface 274 having a plurality of diameters that define a substantially circular void or passage 272 extending between first and second sides 268, 270 as shown in FIG. 15. Inner surface 274 has a lock portion 276, a fastening portion 278, and an annular ring or stop 280 separating lock and fastening portions 276, 278. Lock portion 276 is positioned between annular stop 280 and first side 268 of second housing 254 and fastening portion 278 is positioned between annular stop 280 and second side 270 of second housing 254.

Lock portion 276 includes lock groove section 282 positioned adjacent to first side 268 of second housing 254 and a substantially annular section 283 positioned between lock groove section 282 and stop 280. Lock groove section 282 includes a plurality of semi-circular recesses 284 that are separated from each other by a plurality of ridges or formations 286 as shown in FIG. 15. Lock groove section 282 is spaced apart from annular stop 280. In alternative embodiments, the lock groove section extends to the annular stop and there is no substantially annular section.

Annular stop 280 is ring-shaped and extends into void 272. Annular stop 280 includes opposed first and second side surfaces 288, 290 and an end surface 292 that extends between side surfaces 288, 290. Annular stop 280 is sized so that the end surface 292 defines an inner diameter that is smaller than an outer diameter of first housing 252 to prevent first housing 252 from passing completely through void 272 of second housing 254.

Fastening portion 278 includes a groove 296 defined by inner surface 274 that is spaced apart from annular stop 280.

Figure 17:
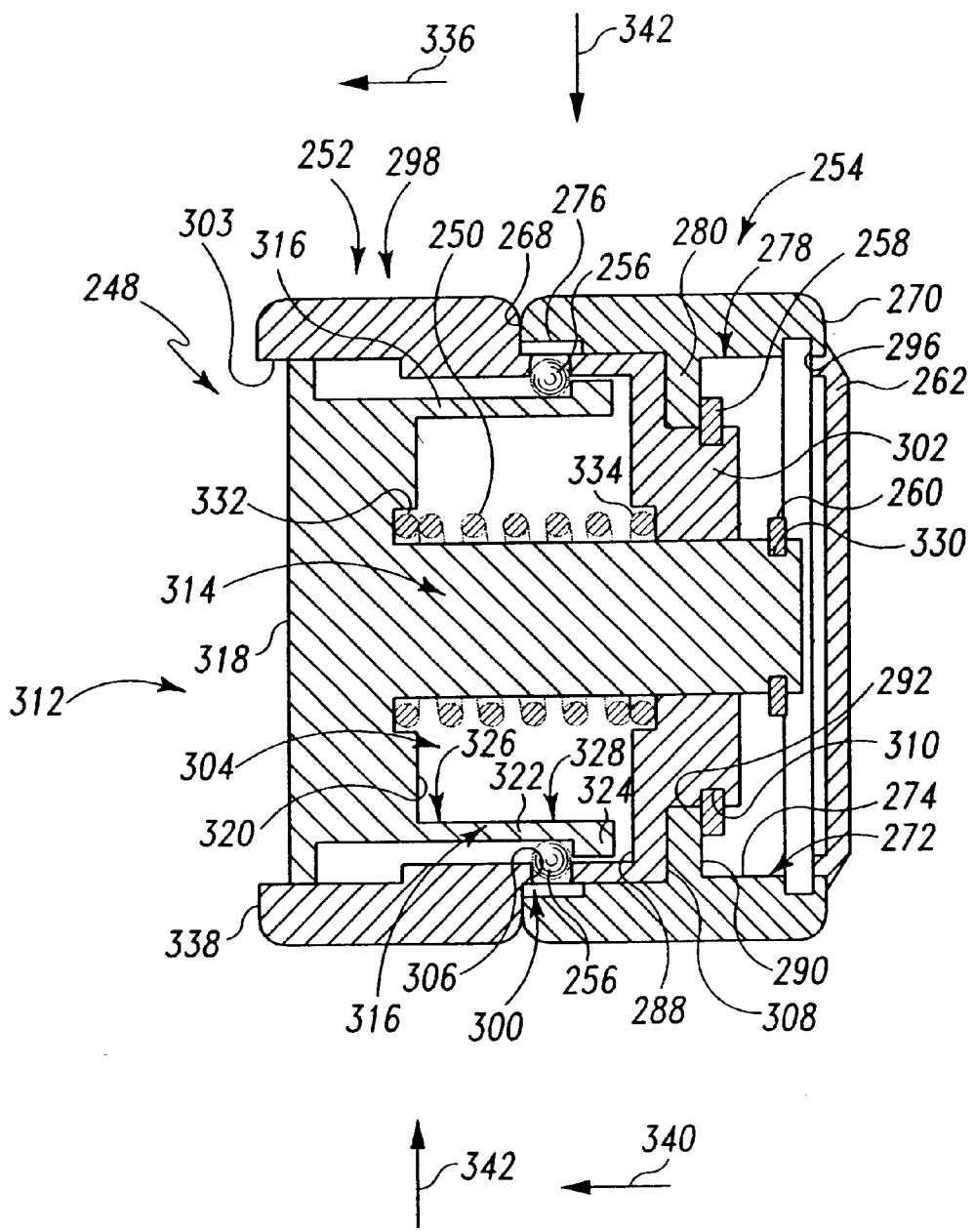
FIG. 17 is a view similar to FIG. 16 showing the coupler in a second position permitting rotation of the respective link relative to the respective attachment rod.

Groove 296 is sized to receive a portion of cover 262 as shown in FIGS. 16 and 17 so that voids 264 are covered.

First housing 252 includes an exposed portion 298, a lock portion 300, a fastening portion 302, and an inner surface 303 that defines a void or passage 304 that extends through the portions 298, 300, 302. When assembled lock and fastening portions 300, 302 are positioned in void 272 of second housing 254 as shown in FIGS. 16 and 17. The exposed portion 298 is positioned out of void 272 and abuts first side 268 of second housing 254.

Each fastening portion 302 of first housings 252 includes a shoulder 308 that abuts first side 288 of annular stop 280 of the respective second housings 254 and an annular groove 310 that is sized to receive first snap ring 258. First snap ring 258 and shoulder 308 of fastening portion 302 trap annular stop 280 of second housing 254 therebetween to couple first and second housings 252, 254 together. While housings 252, 254 are coupled together, first snap ring 258 permits housings 252, 254 to rotate relativ 1060e to one another and thus permits links 222, 224 and rods 228, 230 coupled to housings 252, 254 to rotate relative to each other.

First snap ring 258 includes an outer diameter which is greater than the inner diameter of annular stop 280 of second housing 254 and an inner diameter which is approximately equal to the diameter of annular groove 310. First snap ring 258 is expandable so that it fits over and into groove 310 of fastening portion 302. Once first snap ring 258 is placed within annular groove 310, it contracts so that the inner diameter is approximately equal to the diameter of annular groove 310.

Lock portion 300 of first housing 252 is positioned adjacent to lock portion 276 of second housing 254 and includes a plurality of bores 306 that are adjacent to and axially aligned with the plurality of recesses 284 and ridges 286 in second housing 254. In the illustrated embodiment, bores 306 are cylindrical and have a depth which is about equal to their radius. In addition, in the illustrated embodiment, the radius of each cylindrical bore 306 is substantially equal to the radius of each semi-circular recess 284.

Bearings 256 have a radius that is slightly smaller than that of circular bores 306 and are positioned within circular bores 306 so that bearings 256 are able to move within bores 306. Ball bearings 256 are movable within bores 306 between a first position, shown in FIG. 16, wherein bearings 256 are positioned in semi-circular recesses 284 of locking portion 276 of second housing 254 and a second position, shown in FIG. 17, wherein bearings 256 are positioned outside of semi-circular recesses 284 of locking portion 276 of second housing 254.

When ball bearings 256 are positioned in recesses 284, ball bearings 256 fix the position of and prevent rotation between first and second housings 252, 254 and links 222, 224 and rods 228, 230 coupled to housings 252, 254. When ball bearings 256 are not positioned in recesses 284 of lock portion 276 of second housing 254, first and second housings 252, 254 and links 222, 224 and rods 228, 230 coupled to housings 252, 254 are able to move relative to each other.

Ball bearings 256 are moved between their first and second positions shown in FIGS. 16 and 17 by buttons 248. Buttons 248 are positioned within the voids 304, 272 of first and second housings 252, 254 as shown in FIGS. 16 and 17. Buttons 248 include a caregiver interaction portion 312, a fastening post 314 coupled to interaction portion 312, and a bearing position member 316 coupled to interaction portion 312. Interaction portion 312 includes opposed first and second sides 318, 320. The caregiver pushes on first side 318 of interaction portion 312 to move bearings 256. Post 314 and bearing position member 316 are coupled to second side 320 of interaction portion 312.

To assemble button 248 and spring 520 on to first and second housing 252, 254, spring 250 is placed over fastening post 314 of button 248 and fastening post 314 is positioned in voids 304, 272 of first and second housings 252, 254 as shown in FIGS. 16 and 17. Button 248 and first housing 252 each include a spring seat 332, 334, respectively, and the ends of spring 250 are positioned in spring seats 332, 334. Each of springs 250 includes an inner radius greater than the outer radius of fastening posts 314. Springs 250 urge buttons 248 in direction 336 away from second housing 254.

Second snap ring 260 is provided to secure fastening post 314 and the remainder of button 248 on first housing 252. Fastening post 314 includes an annular groove 330 sized to receive second snap ring 260. Second snap ring 260 engages annular groove 330 in the same manner as first snap ring 258 engages annular groove 310 of first housing 252. When positioned in annular groove 330, second snap ring 260 prevents buttons 248 from separating from first housing 252 and keeps spring 250 in a compressed state so that button 248 is urged outward.

Bearing position member 316 of button 248 is configured to move ball bearings 256 between the locked and unlocked positions shown in FIGS. 16 and 17. Bearing position member 316 includes an arm 322 and a lip or cam 324 coupled to arm 322. Arm 322 includes a proximal end 326 coupled to second side 320 of interaction portion 312 and a distal end 328 on which lip 324 is coupled. Lip 324 includes a greater thickness and a greater outer radius than arm 322.

When the caregiver is not pressing button 248, first side 318 of caregiver interaction portion 312 of button 248 is substantially coplanar with an outer surface 338 of first housing 252 as shown in FIG. 16. When the button is in this position, ball bearings 256 are abutted by lips 324 of bearing position member 316 of button 248. Lip 324 maintain ball bearings 256 in a position within semi-circular recesses 284 of locking portion 276. In this position, bearings 256 prevent first 252 and second 254 housings and thus rods 228, 230 and links 222, 224 from rotating relative to each other.

Pressing on button 248 in a direction 340 with a force greater than the force generated by spring 250 compresses spring 250 as shown in FIG. 17. When button 248 is depressed, lip 228 is no longer axially aligned with ball bearings 256. Rather, ball bearings 256 are axially aligned with a portion of the bearing engaging wall that has a smaller outer radius and permits ball bearings 256 to retreat inward radially in direction 342 to disengage from semi-circular recesses 284 of locking portion 276. Because ball bearings 256 are disengaged from locking portion 276 of second housing 254, first housing 168 and links 222, 224 can rotate relative to second housing 254 and attachment rods 228, 230 so that the angle and position of links 222, 224 and rods 228, 230 can then be adjusted as desired.

When links 222, 224 and rods 228, 230 are in their desired positions, the caregiver releases button 248. Spring 250 then biases button 248 to its initial position shown in FIG. 16, and ball bearings 256 are forced back into recesses 284 to fix the relative position of housings 252, 254.

The first set of button joints 226 are substantially similar to the second set of button joints 232. Further, it should be appreciated that the first set of button joints 226 function the same as the previously described second set of button joints 232.

However, second housings or bases 343 of the first set of couplers 226 are coupled to head support brackets 344 that support head support plate 220. Head support brackets 344 are coupled to grooves 296 formed in second housing 343 to cover the voids 272. Each bracket 344 includes a pair of apertures that align with a pair of apertures 346 formed in head support plate 220. Fasteners 348, such as a rivet, bolt, screw, or other fastener, are positioned in apertures 346 to secure head support plate 220 to brackets 344.

According to alternative embodiments of the present disclosure, only one button joint is provided at the junctions of the head support plates and the links and the links and the attachment rods. The other joints are free to pivot without a positive lock. According to one alternative embodiment of the present disclosure, the joints that are free to pivot are relatively tight so that the caregiver must apply enough torque or force to overcome a preload or friction fit that resists pivoting, but does not positively lock the housings. According to an alternative embodiment of the present disclosure, a strut is provided that extends between and couples the second housing of the first set of couplers together.

First and second links or frame members 222, 224 are configured to function as accessory or side rails. Each of the first and second links 222, 224 has a rectangular cross section similar to side rails 216. Accessories (not shown) known to those of ordinary skill in the art are provided that couple to the first and second links. These accessories have clamps or other mechanisms configured to couple to links 222, 224.

Figure 18:
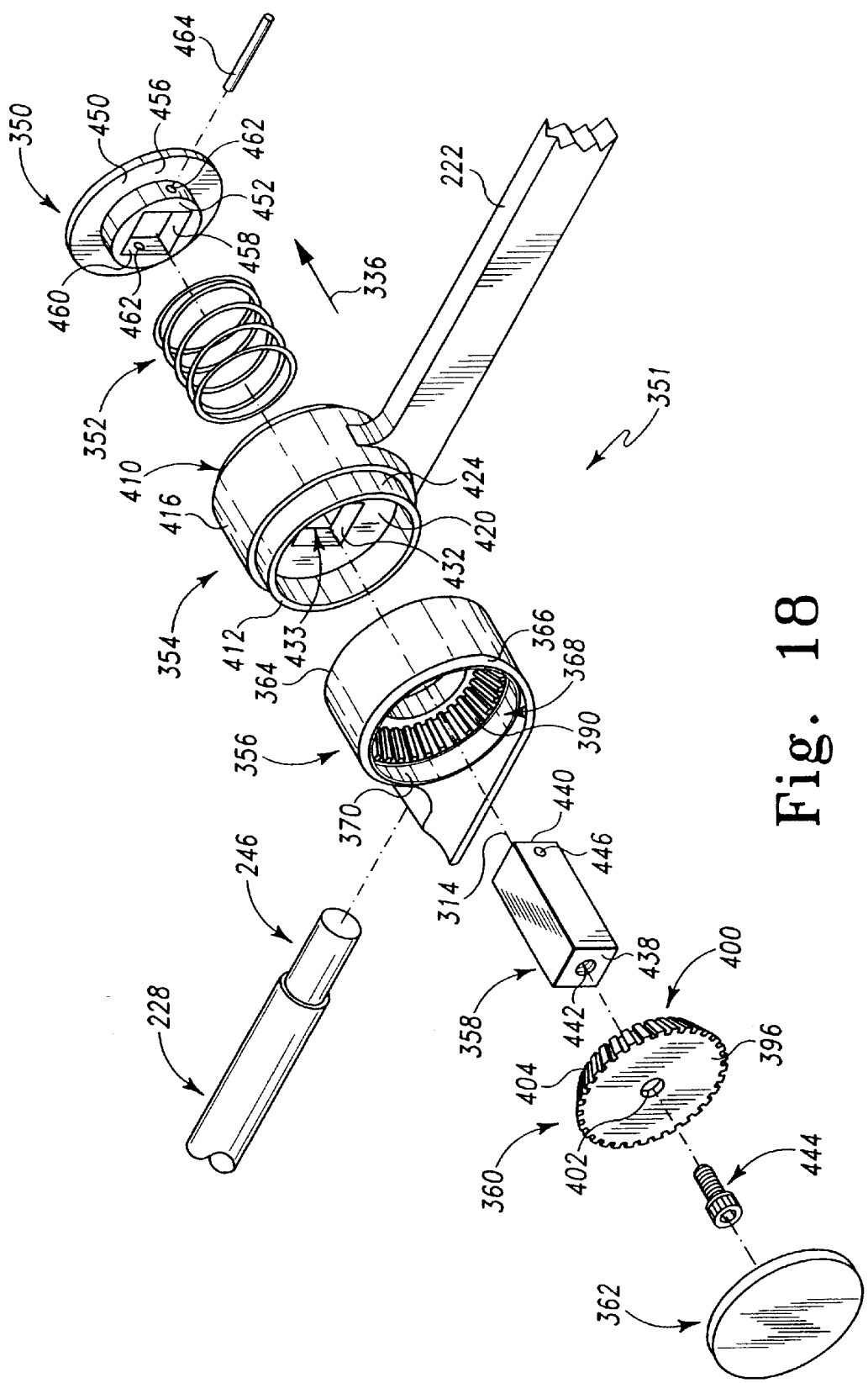
FIG. 18 is a exploded perspective view of an alternative embodiment coupler or position holder configured to pivotally couple the links to the attachment rods.
Figure 19:
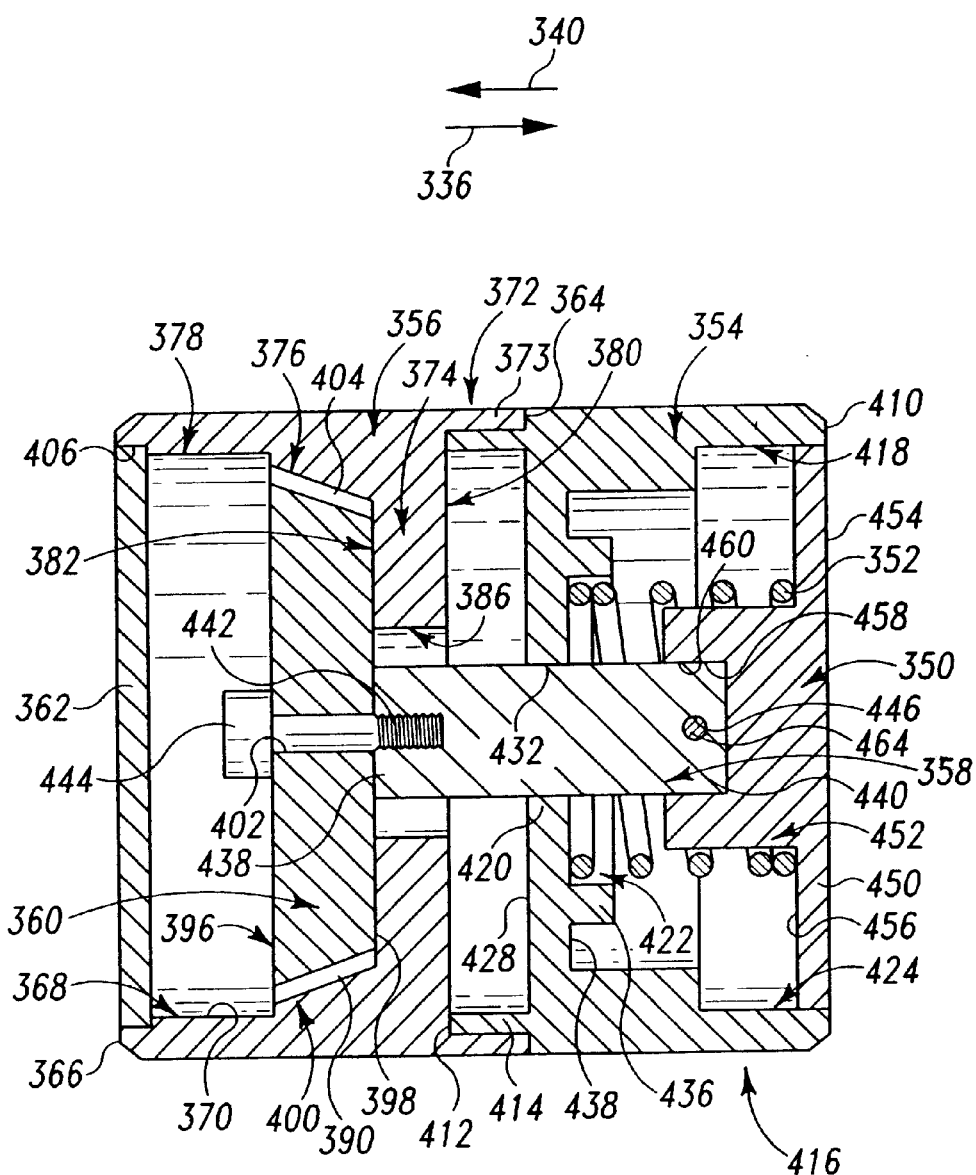
FIG. 19 is a cross-sectional view of the coupler of FIG. 18 showing the coupler in a first position fixedly coupling the respective link to the respective attachment rod.
Figure 20:
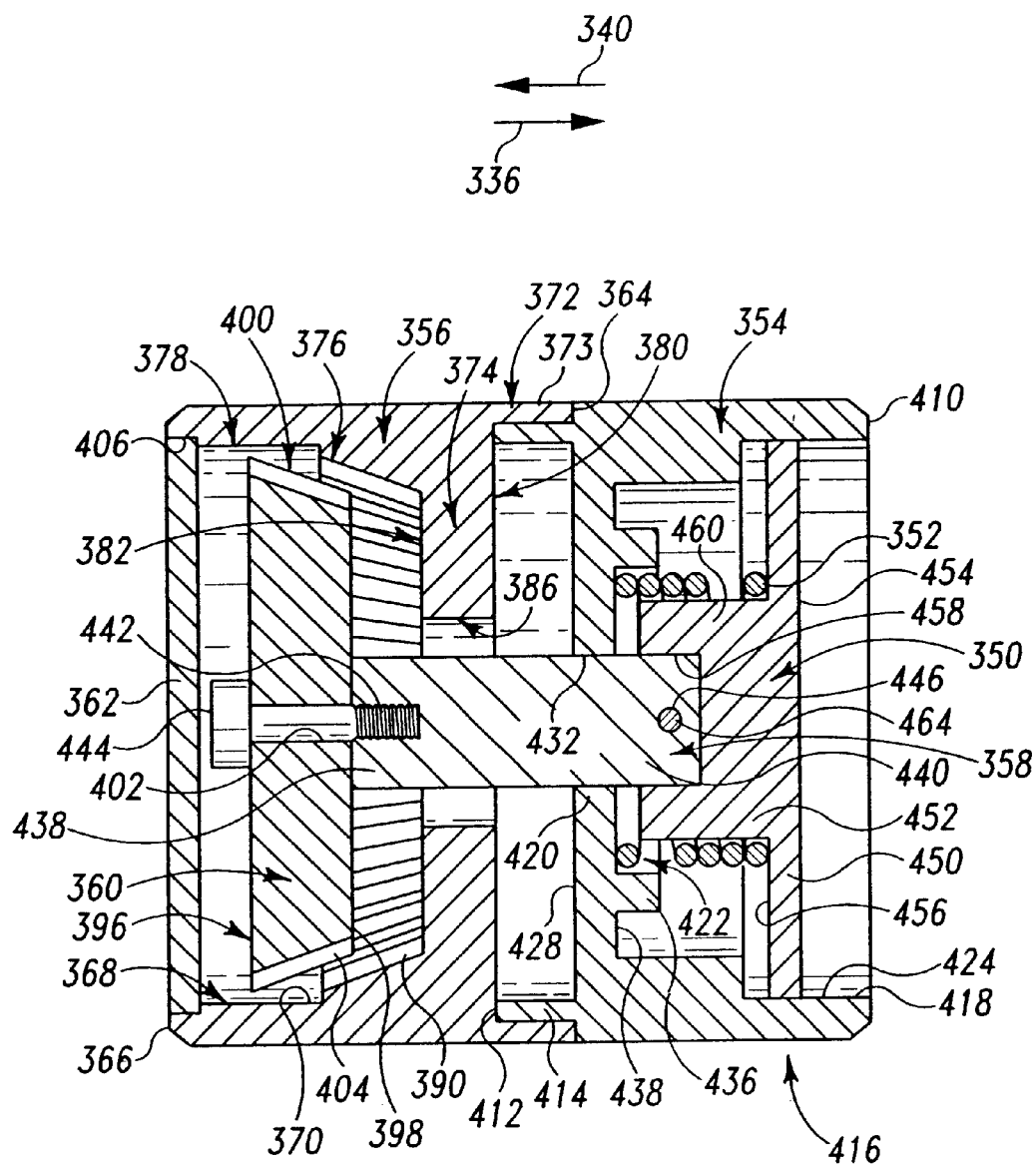
FIG. 20 is a view similar to FIG. 19 showing the coupler in a second position permitting rotation of the respective link relative to the respective attachment rod.

An alternative set of button joints or position holders 351 (only one shown) is provided to couple first and second links 222, 224 to attachment rods 228, 230 and head support plate 220 to first and second links 222, 224 as shown in FIGS. 18–20. Button joints 351 include a button 350, a spring 352, a first housing or base 354, a second housing or base 356, a connection post or shaft 358, a lock wheel or key 360, and a cover 362. Button joints 351 permit head support plate to be positioned in the same configurations as the other button joints 226, 232 shown in FIGS. 10–13.

Each second housings 356 is rigidly coupled a respective attachment rod 228, 230 and includes a first side 364 facing toward first housing 354, a second side 366 facing away from first housing 354, and an inner surface 370 that has a plurality of diameters and defines a substantially circular void or passage 368 extending between first and second sides 364, 366 as shown in FIG. 18. Second housing has a first housing engagement section 372, an annular stop section 374, a lock section 376, and a disengagement section 378 as shown in FIGS. 18–20. First housing engagement section 372 is positioned between annular stop section 374 and first side 364 and annular stop section 374 is positioned between first housing engagement section 372 and lock section 376. Further, lock section 376 is positioned between annular stop section 374 and disengagement section 378 and disengagement section 378 is positioned between lock section 376 and the second side 366 of the second housing.

The inner surface of first housing engagement section 372 is substantially smooth and has a constant diameter. First housing engagement section 372 has a lip 373 which extends from annular stop section 374. Annular stop section 374 is ring-shaped and extends into void 368. Annular stop section 374 includes opposed first and second side surfaces 380, 382 and an end surface 386 that extends between first and second side surfaces 380, 382. Annular stop section 374 is sized so that end surface 386 defines an inner diameter that is smaller than the outer diameter of first housing 354 to prevent first housing 354 from passing completely through void 368 of second housing 356.

Lock section 376 extends from second side surface 382 of stop section 374 to disengagement section 378. Lock section 376 has a varied diameter that gets larger as the distance away from annular stop section 374 increases. Lock section 376 of inner surface 370 includes a plurality of teeth 390. Teeth 390 are formed by a plurality of spaced-apart raised substantially rectangular sections. Teeth 390 cooperate to define teeth-receiving spaces therebetween that have a width equal to the width of teeth 390.

Lock wheel 360 complements lock section 376 to lock first and second housings 356, 354 together. Lock wheel 360 is disk-shaped and has a first side 396, a second side 398, an end surface 400 extending between first and second sides 396, 398, and a void or passage 402 extending between first and second sides 396, 398. First side 396 has an outer diameter that is larger than an outer diameter of second side 398 and slightly smaller than the largest diameter of lock section 376. The diameter of second side 398 is slightly smaller than the smallest diameter of lock section 376. End surface 400 is angled relative to longitudinal axis 394 of void 368 and defines a plurality of complementary formations or teeth 404. Similar to teeth 390 of lock section 376, complementary formations or teeth 404 of the lock wheel are formed by a plurality of spaced-apart raised substantially rectangular sections. Teeth 404 cooperate to define teeth-receiving spaces therebetween that have a width equal to the width of teeth 404.

The pattern of raised teeth 404 and the spaces therebetween of the lock wheel 360 complement teeth 390 and spaces therebetween of lock section 376. Therefore, when lock wheel 360 is positioned within lock section 376, teeth 390 of lock section 376 are positioned within the spaces defined between teeth 404 of lock wheel 360 and teeth 404 of lock wheel 360 are positioned in the spaces defined between teeth 404 of the lock section 376 to prevent relative rotation between lock wheel 360 and second housing 356.

Disengagement section 378 has a substantially smooth cylindrical inner surface of a constant diameter. The diameter of the inner surface of disengagement section 378 is larger than the largest diameter of lock section 376. Disengagement section 378 includes a groove 406 defined by the inner surface that is sized to receive a portion of cover 362 as shown in FIGS. 19 and 20. Groove 406 is spaced apart from lock section 376 and end cover 408 is positioned in groove 406 to cover voids 368.

First housing 354 includes a first side 410 facing away from second housing 356, a second side 412 facing toward second housing 356, a lip portion 414, an exposed portion 416, and a void or passage 418 that extends through portions 414, 416. Exposed portion 416 includes a square lock portion 420, a spring-receiving portion 422, and a button portion 424.

Lip portion 414 is coupled to exposed portion 416 and is sized to fit within lip 373 of first housing engagement section 372 of second housing 356 as shown in FIGS. 19 and 20. Lip portion 414 is ring-shaped and includes an outer surface that is circle-shaped and of a constant diameter such that lip portion 414 of first housing 354 rotates within lip 373 of second housing 356.

Square lock portion 420 of exposed portion 416 is positioned between lip portion 414 and spring-receiving portion 422 and extends into void 418. Square lock portion 420 includes opposed first and second side surfaces 428, 430 and an end surface 432. End surface 432 defines a substantially square aperture 433 extending through square lock portion 420.

Square-shaped connection post 358 is sized to fit snugly within the substantially square aperture 433. Therefore, connection post 358, when positioned in substantially square aperture 433 is blocked from rotating relative to first housing 354.

Spring-receiving portion 422 is located between square lock portion 420 of first housing 354 and button portion 424. Spring-receiving portion 422 includes a spring seat or annular rib 436 that extends from second side 430 of square lock portion 420 into void 418. Rib 436 is substantially circle-shaped and has an inner diameter greater than an outer diameter of spring 352.

Button portion 424 of exposed portion 416 is positioned adjacent to spring-receiving portion 422 and extends to first side 410 of first housing 354. Button portion 424 has a larger inner diameter than spring-receiving portion 422 and is sized to receive button 350 therein.

Connection post 358 is positioned in portions of first and second housings 354, 356 as shown in FIG. 19. Connection post 358 includes first and second ends 438, 440 having substantially square cross sections. First end 438 has a threaded bore 442 that extends along longitudinal axis 394 of connection post 358 and receives a threaded bolt 444 or other fastener. Bolt 444 passes through void 402 of lock wheel 360 and into threaded bore 442 to secure lock wheel 360 to first end 438 of connection post 358. Second end 440 has a transverse void 446 defined therein that extends perpendicular to the longitudinal axis 394 of connection post 358.

Button 350 includes a disk section 450 and an attachment section 452. Disk section 450 includes a first side 454 and a second side 456. Attachment section 452 extends from second side 456 of disk section 450 toward connection post 358. Attachment section 452 is substantially circular and has an outer diameter that is less than an inner diameter of spring 352. Attachment section 452 includes an inner surface 460 that defines a square bore or aperture 458 therein sized to receive second end 440 of connection post 358. Attachment section 452 includes a pair of voids 462 defined therein that align with the transverse void 446 of connection post 358 when second end 440 of connection post 358 is positioned within square bore 516 as shown in FIGS. 19 and 20. A locking pin 464 is positioned in the voids 462 of attachment section 452 and transverse void 446 of connection post 358 to couple button 350 to connection post 358.

As shown in FIGS. 19 and 20, spring 352 is positioned around connection post 358. Spring 352 is a coil type spring and includes an inner radius that is greater than the outer diameter of connection post 358. Spring 352 is compressed between square lock portion 420 and second side 456 of button 350 to urge button 350 in direction 336 away from second housing 356. As shown in FIG. 19, the abutment of lock wheel 360 on annular stop section 374 limits the travel of connection post 358 and button 350.

When button 350 is not being pressed by a caregiver, first side 454 of disk section 450 of button 350 is substantially coplanar with first side 410 of first housing 354 as shown in FIG. 19. When button 350 is in this position, teeth 390 of lock section 376 are positioned between teeth 404 of lock wheel 360. In this position, teeth 390, 404 prevent first 354 and second 356 housings and thus rods 228, 230 and links 222, 224 from rotating relative to each other.

Pressing on button 350 in the direction 340 with a force greater than the force of spring 352 further compresses spring 352 as shown in FIG. 20. When button 350 is depressed, lock wheel 360 is pushed into disengagement section 378, and teeth 390, 404 are no longer engaged with each other. The disengagement of lock wheel 360 and lock section 376 of second housing 356 allows first housings 354 and links 222, 224 to rotate relative to second housings 356 and attachment rods 228, 230 so that the angle and position of links 222, 224 and rods 228, 230 can be adjusted as desired.

When links 222, 224 and rods 228, 230 are in their desired positions, button 350 is released to permit spring 352 to urge button 350 and lock wheel 360 to the initial position shown in FIG. 19 to fix the position of housings 354, 356 relative to each other.

As shown in FIGS. 21–27, head pad 34 includes a first pad or main body 466, a second pad or insert 468, and main and insert covers 546, 548. Main body 466 includes upper and lower portions 472, 474, respectively. In preferred embodiments, upper portion 472 is a relatively soft foam material and lower portion 474 is a relatively stiff foam material. Both of upper and lower portions 472, 474 include apertures 476, 478, respectively, that are in communication with each other, as shown, for example, in FIGS. 22, 24, 26, and 27. In preferred embodiments, upper and lower portions 472, 474 of main body 466 are glued together.

Figure 21:
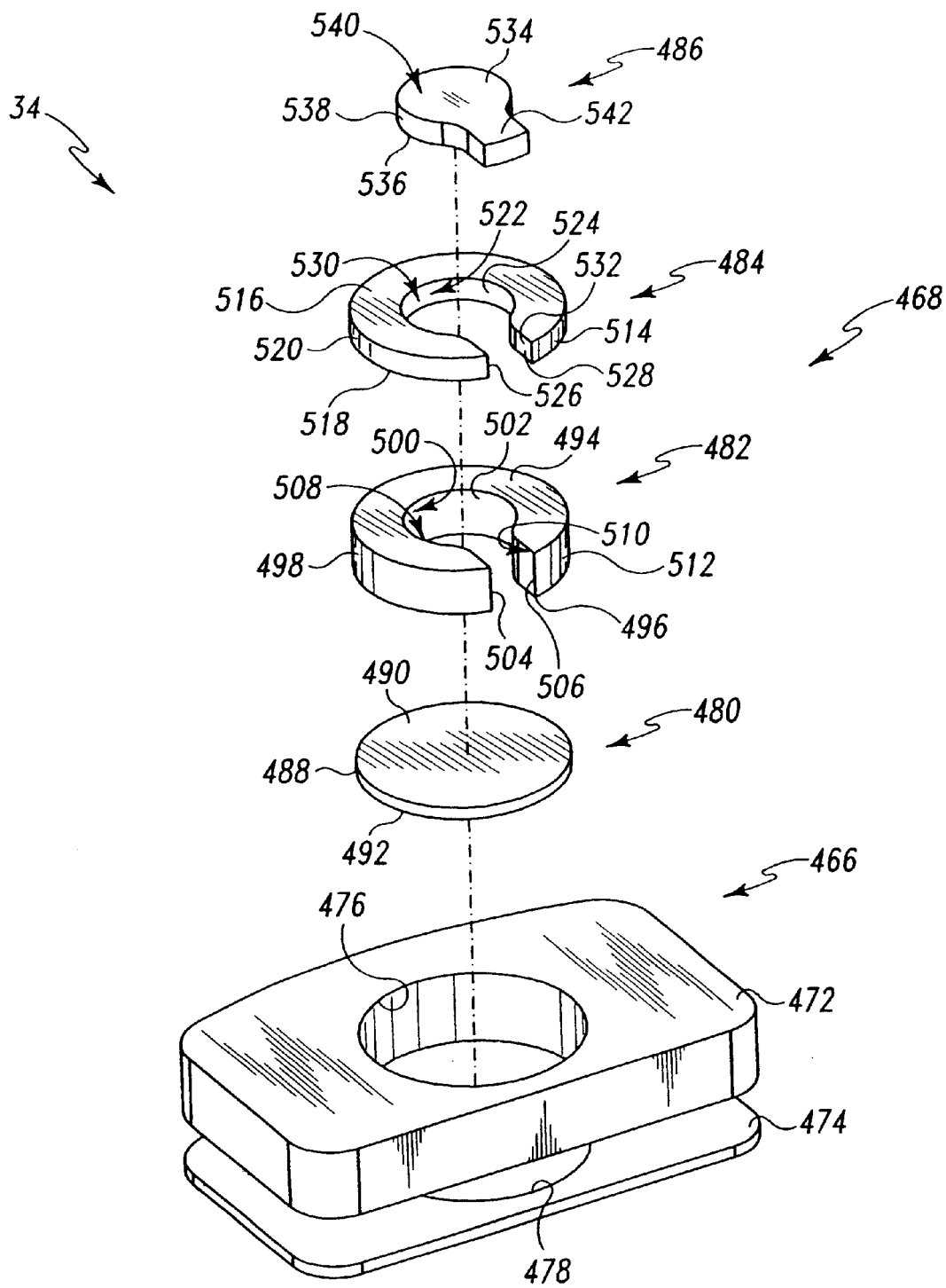
FIG. 21 is an exploded perspective view of the head pad.
Figure 23:
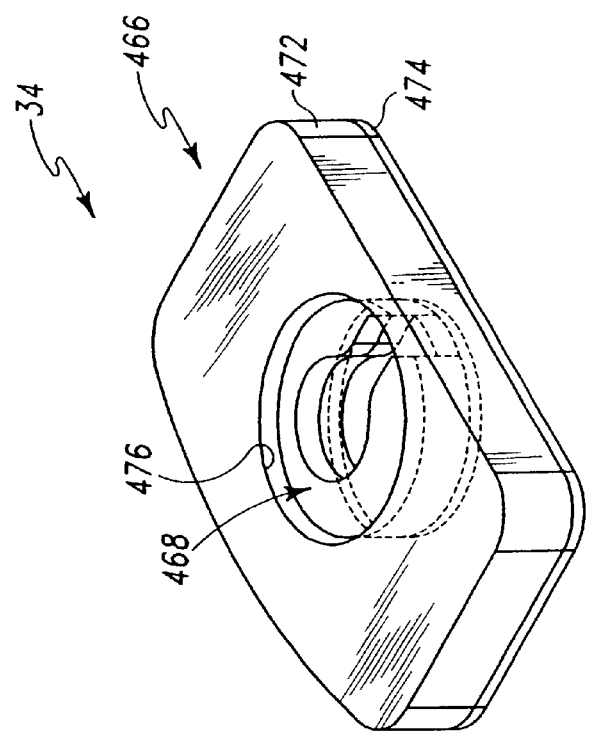
FIG. 23 is a view similar to FIG. 22 showing the insert positioned in an opening formed in the main body.
Figure 22:
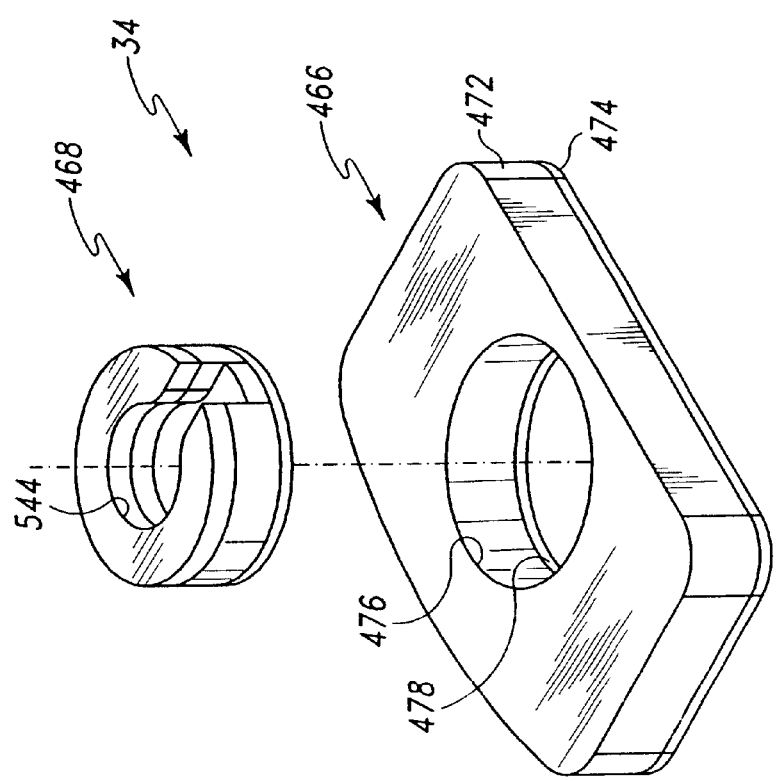
FIG. 22 is a perspective view of the head pad of FIG. 21 showing the head pad including a first pad or main body and a second pad or circular insert.

Insert 468 includes first, second, third, and fourth portions 480, 482, 484, 486, as shown, for example, in FIG. 21. These portions 480, 482, 484, 486 are coupled together as shown in FIG. 22 to define insert 468. In preferred embodiments, portions 480, 482, 484, 486 are coupled together by an adhesive. Insert 468 has an outer diameter that is slightly less than the diameter of apertures 476, 478 of upper and lower portions 472, 474, respectively, of main body 466 so that insert 468 may be positioned in apertures 476, 478 as shown in FIG. 23. First portion 480 of insert 468 is a substantially flat disk having an upper surface 490, a lower surface 492, and an outer surface 488 as shown in FIG. 21. Second portion 482 of insert 468 is substantially C-shaped and includes an upper surface 494, a lower surface 496, an outer surface 498, and an inner surface 500, as shown, for example, in FIG. 21. Inner surface 500 includes a substantially circular portion 502 and spaced-apart substantially planar portions 504, 506 that extend between outer surface 498 and circular portion 502, as shown, for example, in FIG. 21. Circular portion 502 defines a substantially circular aperture 508 and the spaced-apart planar portions 504, 506 define a channel 510 that is in communication with circular aperture 508.

Third portion 484 is shaped similarly to second portion 482 as shown in FIG. 21. Second portion 482 includes a thickness 512 that is greater than a thickness 514 of third portion 484. Third portion 484 is substantially C-shaped and includes an upper surface 516, a lower surface 518, an outer surface 520, and an inner surface 522, as shown, for example, in FIG. 21. Inner surface 522 includes a substantially circular portion 524 and spaced-apart substantially planar portions 526, 528 that extend between outer surface 520 and circular portion 524, as shown, for example, in FIG. 21. Circular portion 524 defines a substantially circular aperture 530 and the spaced-apart planar portions 526, 528 define a channel 532 that is in communication with circular aperture 530.

Fourth portion 486 is configured to be positioned in circular aperture 508 and channel 510 of second portion 482 and circular aperture 530 and channel 532 of third portion 484, as shown, for example, in FIG. 22. Fourth portion 486 includes an upper surface 534, a lower surface 536, and an outer surface 538, as shown, for example, in FIGS. 21 and 27. Fourth portion 486 includes a circular portion 540 configured to fit within circular apertures 508, 530 of second and third portions 482, 484, respectively, and a channel portion 542 that is connected to circular portion 540.

In preferred embodiments of the first embodiment, first, second, third, and fourth portions 480, 482, 484, 486 are coupled together using an adhesive. Lower surface 496 of second portion 482 is adhered to upper surface 490 of first portion 480. Lower surface 518 of third portion 484 is adhered to upper surface 494 of second portion 482 in a manner so that inner surfaces 500, 522 and outer surfaces 498, 520 of second and third portions 482, 484, respectively, are aligned. Lower surface 536 of fourth portion 486 is adhered to upper surface 490 of first portion 480 and positioned in circular aperture 508 and channel 510 of second portion 482. In the preferred embodiment of the first embodiment, first, second, third, and fourth portions 480, 482, 484, 486 have decreasing stiffness so that fourth portion 486 is less stiff than first portion 480.

Insert 468 includes a recess or void 544 defined by second, third, and fourth portions 482, 484, 486 as shown in FIG. 22. Recess 544 provides an opening into which a portion of a patient's head may extend to provide relief for the patient. For example, a patient's ear may be more comfortable if positioned over recess 544. Insert 468 can be rotated within main body 466 to position recess 544 in a plurality of positions. For example, the channels may be aligned to provide relief for a patient's eye socket.

Figure 27:
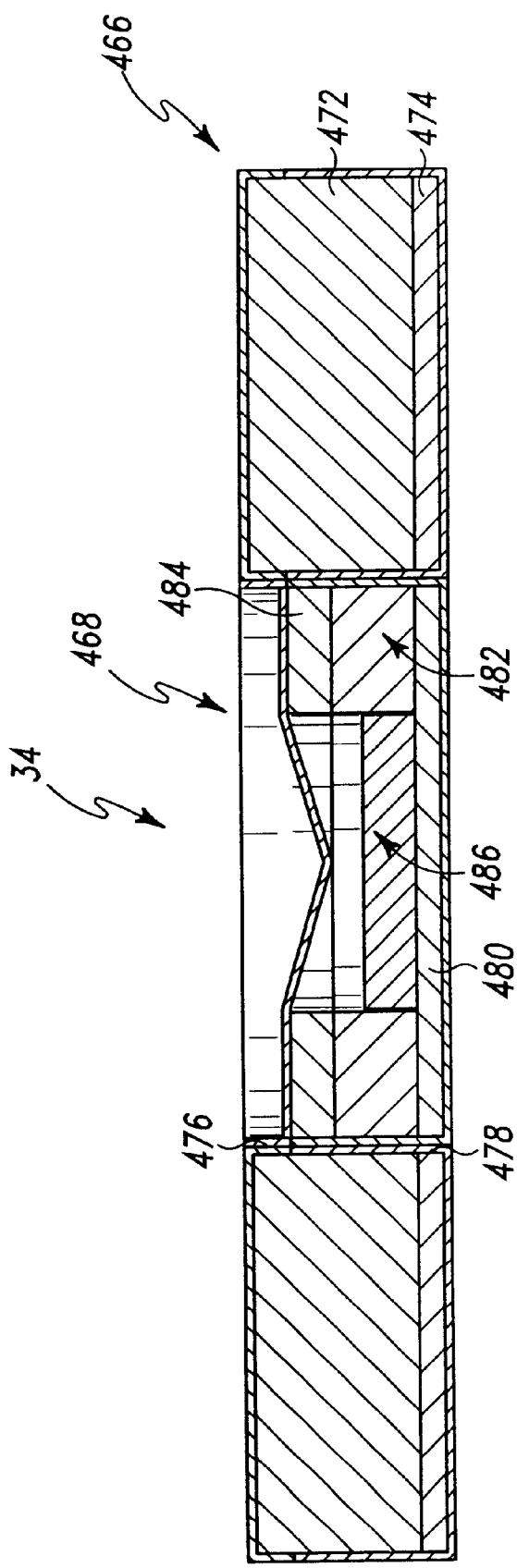
FIG. 27 is a cross-sectional view taken long line 27—27 of FIG. 25 showing the insert of the head pad positioned in the main body.
Figure 28:
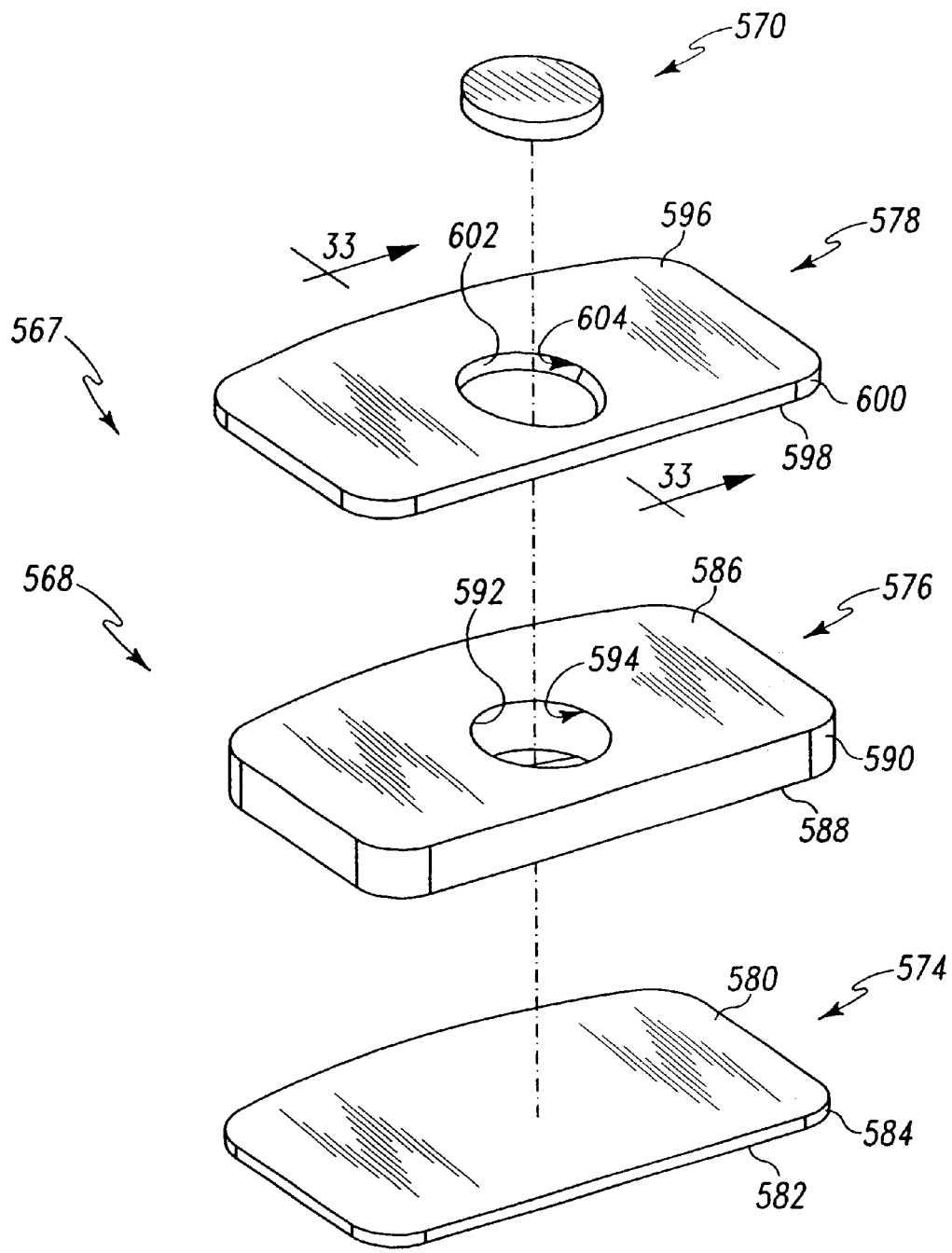
FIG. 28 is an exploded perspective view of an alternative embodiment head pad.

Main body cover 546 includes upper and lower portions 550, 552 that are coupled together at outer and inner seams 554, 556, as shown, for example, in FIGS. 24–26. In preferred embodiments, upper and lower portions 550, 552 of main body cover 546 are made of a stretch fabric material, such as neoprene, and Herculite-10®, respectively. Insert cover 548 similarly includes upper and lower portions 558, 560 that are coupled together at a seam 562. Upper portion 558 is conical and dips down into recess 544 as shown in FIG. 27. Seam 562 includes an annular portion 564 and a spur portion 566 coupled to annular portion 564. In preferred embodiments of the first embodiment, insert cover 548 is oriented relative to insert 468 so that spur portion 566 of seam 562 lies above recess 544 of insert 468. In preferred embodiments of the first embodiment, insert cover 548 is made of a four-way stretch fabric material, such as neoprene.

Insert 468 is removable from main pad 466 and configured to be flipped so that a user has a choice of selecting the less firm support provided by void 544 or the more firm support provided by fourth portion 480. For example, if a patient felt that the relative lack of support provided by void 544 was uncomfortable, the nurse could remove, flip, and replace insert 468 in main pad 466 to provide the patient with the firmer support of the opposite side of insert 468.

An alternative embodiment of head pad 567 is shown in FIGS. 28–32. Head pad 567 includes a main body 568, an insert 570, and a cover 572, as shown in FIGS. 28–32. Main body 568 includes first, second, and third portions 574, 576, 578, as shown, for example, in FIG. 28. First portion 574 includes an upper surface 580, a lower surface 582, and an outer surface 584. First portion 574 is a flat piece of foam that, in preferred embodiments, is firm. Second portion 576 includes an upper surface 586, a lower surface 588, an outer surface 590, and an inner surface 592. Inner surface 592 defines an aperture 594 which is sized to receive insert 570. Second portion 576 is made of a foam material that is less stiff than first portion 574.

Third portion 578 includes an upper surface 596, a lower surface 598, an outer surface 600, and an inner surface 602. Inner surface 602 defines an aperture 604, through which insert 570 may be moved. In preferred embodiments, upper surface 596 of third portion 578 has a relatively low coefficient friction and is referred to as an anti-sheer layer. In preferred embodiments, third portion 578 is made of a visco-elastic foam that is less stiff than second portion 576.

Figure 33:
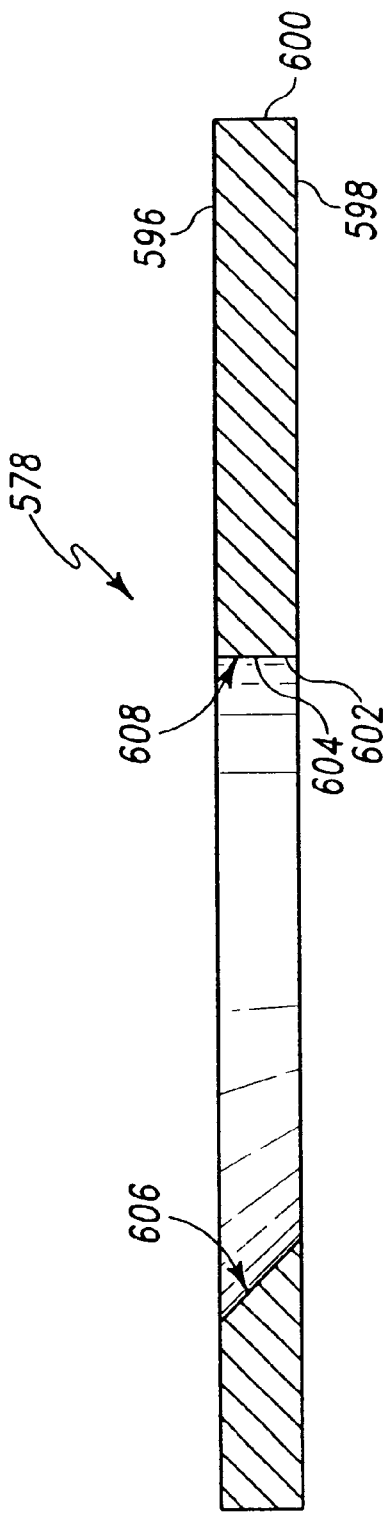
FIG. 33 is a cross-sectional view of a portion of the head pad of FIG. 28 taken along line 33—33 of FIGS. 28 and 34.
Figure 34:
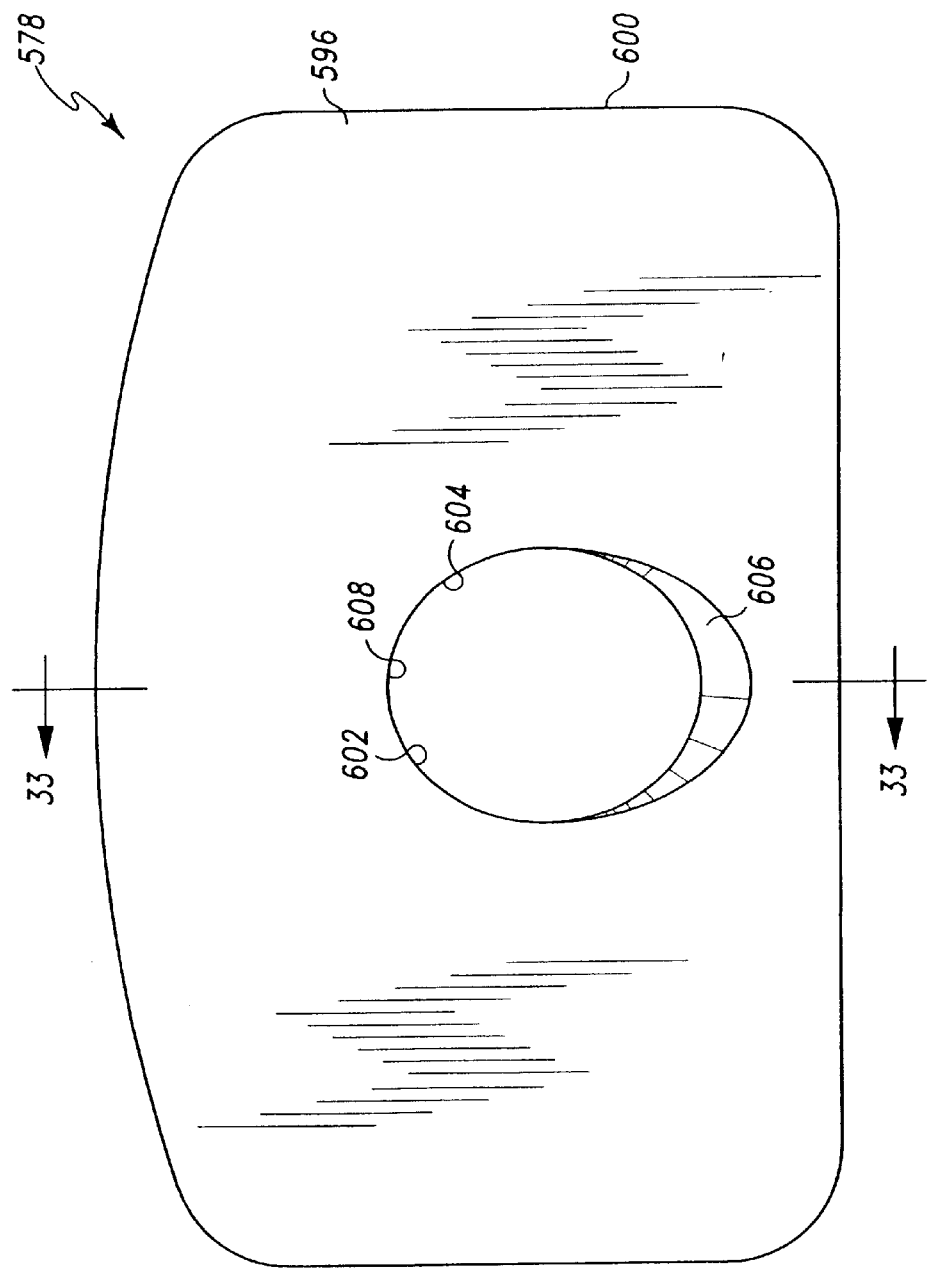
FIG. 34 is a top plan view of the portion of the head pad shown in FIG. 33.

Inner surface 602 of third portion 578 includes beveled and non-beveled portions 606, 608 as shown, for example, in FIG. 33. In beveled portion 606, aperture 604 is larger at upper surface 596 of third portion 578 than at lower surface 598. Beveled and non-beveled portions 606, 608 of inner surface 602 are sized and shaped at lower surface 598 to match the size and shape of aperture 594 of second portion 576. However, beveled portion 606 increases the size of aperture 604 of third portion 578 as the inner surface 602 extends from lower surface 598 to upper surface 596. Beveled portion 606 is used, for example, to conform to the back of a patient's neck and head when a patient is lying on head pad 567.

First, second, and third portions 574, 576, 578 of main body 568 and insert 570 are coupled together as shown in FIG. 26. In preferred embodiments of the first embodiment, these components are coupled together using an adhesive. Upper surface 580 of first portion 574 is adhered to lower surface 588 of second portion 576 so that outer surfaces 584, 590 of first and second portions 574, 576 are aligned. Second and third portions 576, 578 are adhered at their upper and lower surfaces 586, 598, respectively, so that their inner surfaces 592, 602, respectively, and outer surfaces 590, 600, respectively, are aligned. Insert 570 is adhered to upper surface 580 of first portion 574 of main body 568. In preferred embodiments of the first embodiment, the insert is made of a soft foam material.

Figure 32:
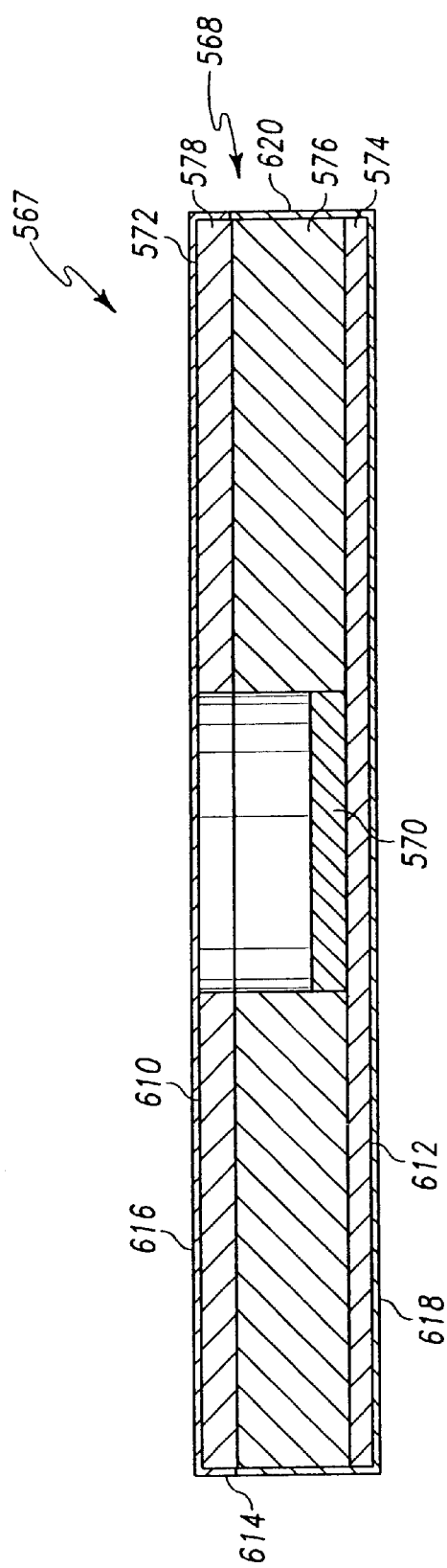
FIG. 32 is a cross-sectional view of the head pad of FIG. 28 taken along line 32—32 of FIG. 30.

Cover 572 includes upper and lower portions 610, 612 that are coupled at a seam 614 as shown, for example, in FIGS. 30 and 32. Cover 572 further includes an upper surface 616 defined by upper portion 610, a lower surface 618 defined by lower portion 612, and a side wall 620 defined by upper and lower portions 610, 612 as shown in FIG. 32. Seam 614 is positioned on side wall 620 at a position closer to upper surface 616 than lower surface 618. In preferred embodiments of the first embodiment, upper portion 610 of cover 572 is made from a stretch fabric, such as neoprene, and lower portion 612 of cover 572 is made from Herculite-10®. Entire pad 567 is also reversible to permit the user to select the desired firmness provided by the opposite sides of pad 567.

A second embodiment of a surgical table 622 in shown in FIGS. 35–45. Surgical table 622 includes a tabletop 624, a base 626, and a lift mechanism 628 that moves tabletop 624 in directions 630, 632 relative to base 626. Tabletop 624 includes several portions that are movable relative to each other by mechanical couplers and hydraulic cylinders to place the support surface in a plurality of positions as shown, for example, in FIG. 36. Tabletop 624 can be configured to place a patient 634 on tabletop 624 in a position most convenient for the caregiver.

Tabletop 624 includes a head support section 636, a body support section 638, and a leg support section 640. Head support section 636 is a two-piece head support that includes first and second portions 642, 644 and a coupler or position holder 646 that permits head support section 636 to be moved relative to body support section 638. More specifically, coupler 646 permits movement of head support section 636 relative to body support section 638 in directions 648, 649 about an axis 652 and permits axial movement of the head support section 636 relative to the body support section 638 in directions 650, 651.

Figure 35:
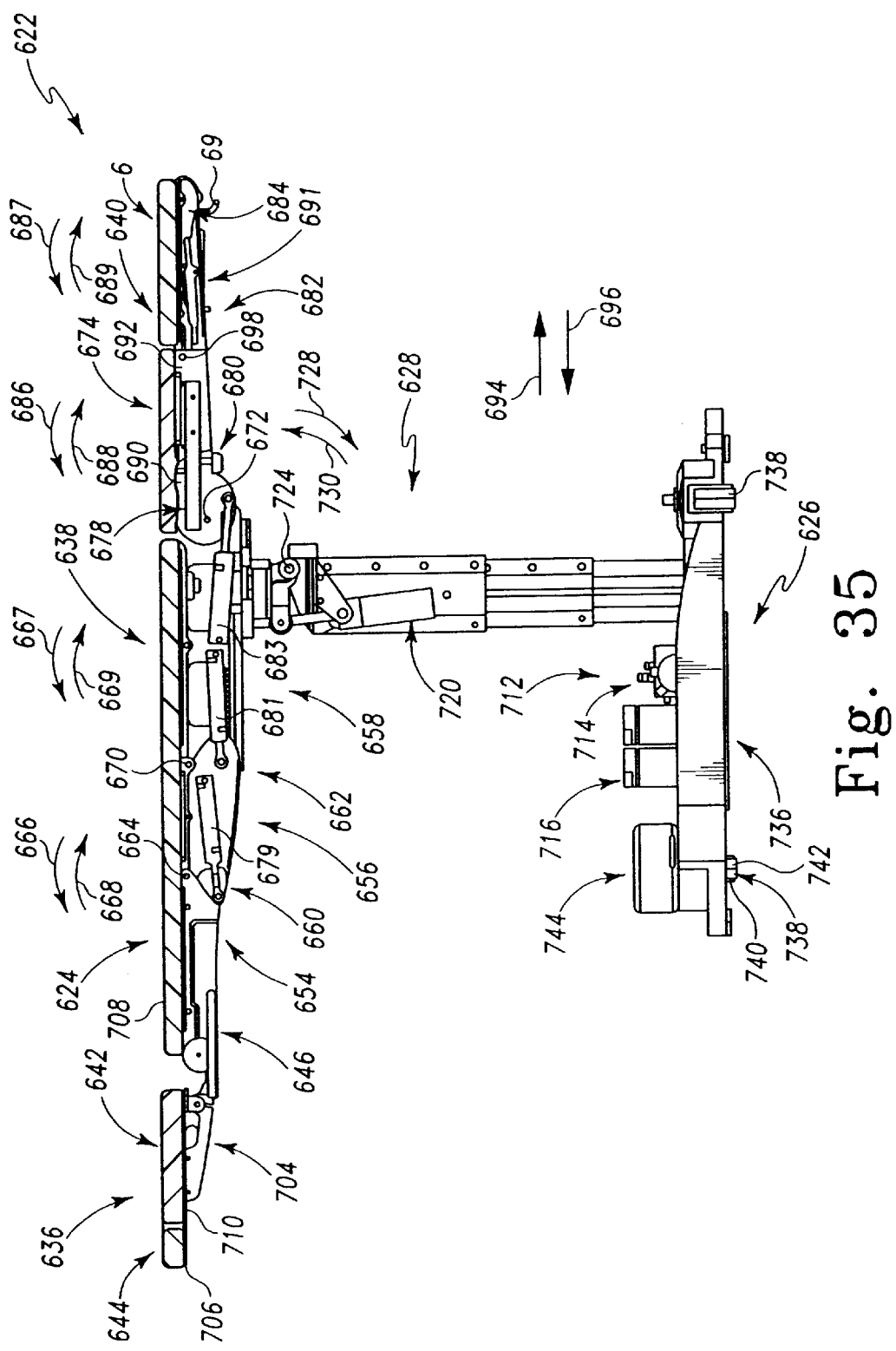
FIG. 35 is a side elevation view, with portions cut away, of a second embodiment of a surgical table apparatus.
Figure 36:
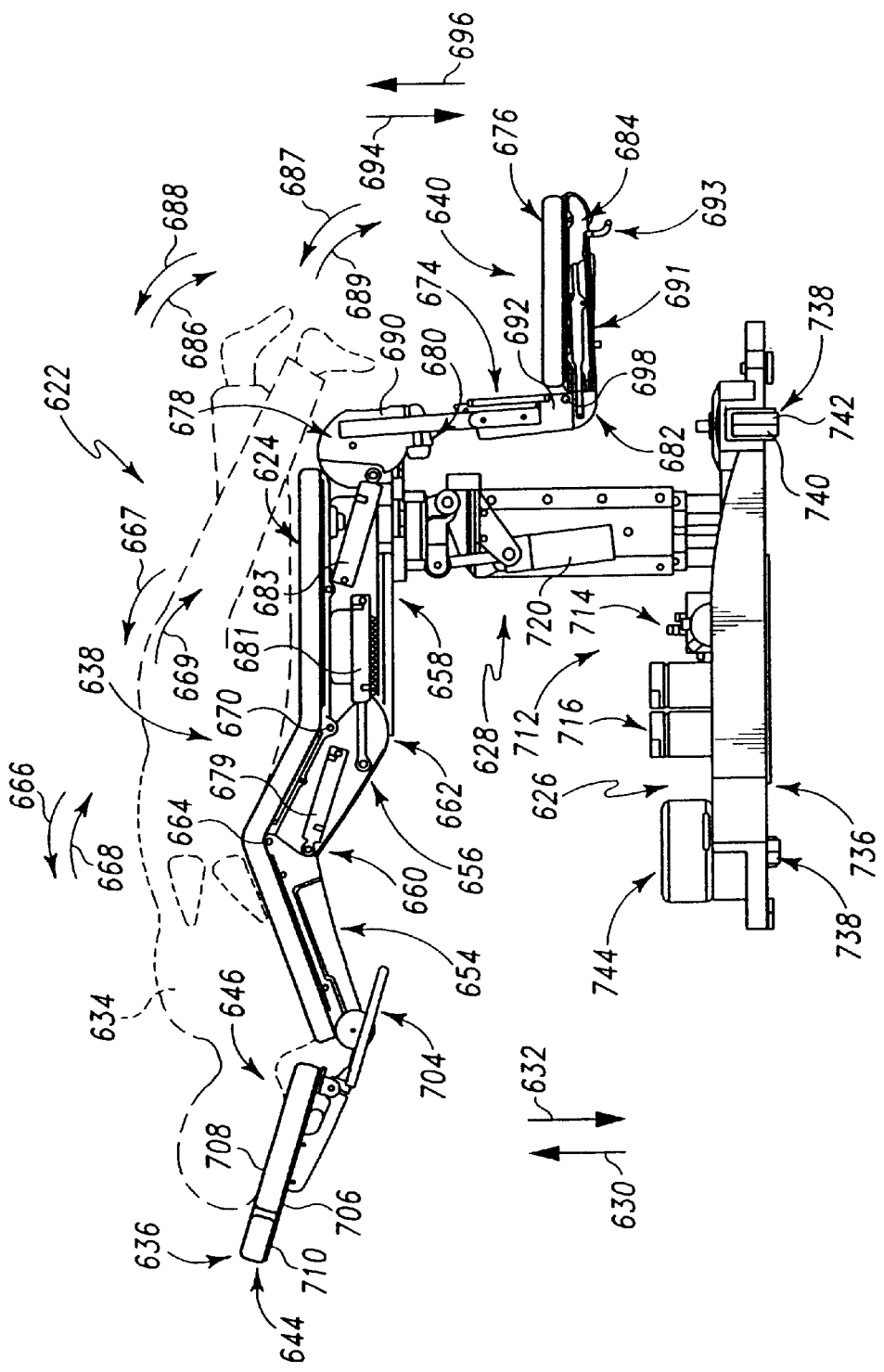
FIG. 36 is a side elevation view of the surgical table apparatus of FIG. 35 showing support sections of the surgical table apparatus moved to conform to a patient's body (shown in phantom)

Body support section 638 includes first or upper torso, second or lower torso, and third or upper leg support portions 654, 656, 658 and first and second couplers 660, 662. First coupler 660 permits rotational movement of first support portion 654 relative to second support portion 656 about axis 664 in directions 666, 668 as shown in FIGS. 35 and 36. Similarly, second coupler 662 permits movement of second support portion 656 relative to third support portion 658 about axis 670 in directions 667, 669.

Leg support section 640 includes first and second support portions 674, 676 and first, second, third, and fourth couplers 678, 680, 682, 684 that permit relative movement of first and second support portions 674, 676. More specifically, first coupler 678 permits rotation of first support portion 674 of lower leg support section 640 about axis 672 relative to body support section 638 in directions 686, 688. First support portion 674 of lower leg support section 640 includes first and second support sections 690, 692 and second coupler 680 permits axial movement of second support section 692 relative to first support section 690 in directions 694, 696. Third coupler 682 permits second support portion 676 to rotate relative to first support portion 674 about axis 698 in directions 687, 689.

Tabletop 624 includes a frame 704 and a plurality of pads or supports 706 coupled to and lying above frame 704 as shown, for example, in FIGS. 31–32. Supports 706 include an upper surface 708 which define the support surface on which patient 634 lies and a lower surface 710 facing toward frame 704.

Table 622 further includes first, second, and third actuators 679, 681, 683, configured to move the supports 706 relative to one another. Actuators 679, 681, 683 of tabletop 624 are all coupled to frame 704 as shown, for example, in FIGS. 35 and 36.

In the illustrated embodiment, actuators 679, 681, 683 are hydraulic cylinders. To drive hydraulic cylinders 679, 681, 683, the patient support further includes a hydraulic actuation system 712 that comprises a hydraulic pump and motor 714, batteries 716, and a plurality of valves 718 as shown, for example, in FIGS. 35–37. The hydraulic pump and motor 714 and batteries 716 are positioned on base 626 while the valves 718 are positioned on the lift mechanism 628. Hydraulic lines (not shown) extend from hydraulic pump and motor 714 to valves 718 as disclosed in U.S. Patent Provisional Application Ser. No. 60/264,214, entitled "Hydraulic Actuator Apparatus," filed Jan. 25, 2001, to Blyshak et al., the disclosure of which is expressly incorporated by reference herein. Additional hydraulic lines (not shown) then extend from valves 718 to hydraulic cylinders 679, 681, 683. The valves 718 control the flow of hydraulic fluid to hydraulic cylinders 679, 681, 683 to move the various support portions of tabletop 624 as desired.

As shown in FIGS. 35 and 36, first and second actuators 679, 681 are configured to move tabletop 624 to a kidney lift position (lower leg support section 640 is normally substantially horizontal when tabletop 624 is in the kidney lift position, but is shown in a knee-shelf position for illustrative purposes). Second actuator 681 is configured to move second support portion 656 of body support section 638 about the axis of rotation 670. To move second support portion 656 to the kidney lift position, second actuator 681 is extended to rotate second support portion 656 in direction 669.

First actuator 679 is configured to move first support portion 654 of body support section 638 about the axis of rotation 664. To move first support portion 654 to the kidney lift position, first actuator 679 is retracted to rotate first support portion 654 in direction 666. Preferably, first and second actuators 679, 681 move first and second supports portions 654, 656 simultaneously. To return tabletop 624 to the substantially flat position, first actuator 679 is extended and second actuator 681 is retracted.

Third actuator 683 is configured to assist in moving support surface 642 to a knee-shelf position as shown in FIG. 36 with first portion 674 of the leg support section 640 in a substantially vertical position and second portion 676 of leg support section 640 in a substantially horizontal position. Third actuator 683 is configured to move first portion 674 of leg support section 640 about the axis of rotation 672. To move first portion 674 to the vertical position, third actuator 683 is retracted to rotate first portion 674 in direction 688.

Second portion 676 is then rotated in direction 687 about axis of rotation 698. A lock or clutch 691 is coupled to first and second portions 674, 676 to lock and unlock the relative positions thereof. To release clutch 691, a caregiver moves a handle 693 so that second portion 676 can be rotated. Once the caregiver lets go of handle 693, clutch 691 locks the position of second portion 676 relative to first portion 674. Additional description of clutch 691 is provided in U.S. Provisional Application Ser. No. 60/209,053, entitled "Foot Support Apparatus for a Birthing Bed," to Ruehl et al., filed Jun. 2, 2000 the disclosure of which is expressly incorporated by reference herein and in application Ser. No. 09/872, 594, entitled "Foot Support Apparatus for a Birthing Bed," to Ruehl et al., filed Jun. 2, 2001 the disclosure of which is expressly incorporated by reference herein. To return support surface 642 to the substantially flat position, third actuator 683 is extended to rotate first portion 674 of leg support section 640 in direction 688, and second portion 676 is rotated in direction 689.

Figure 37:
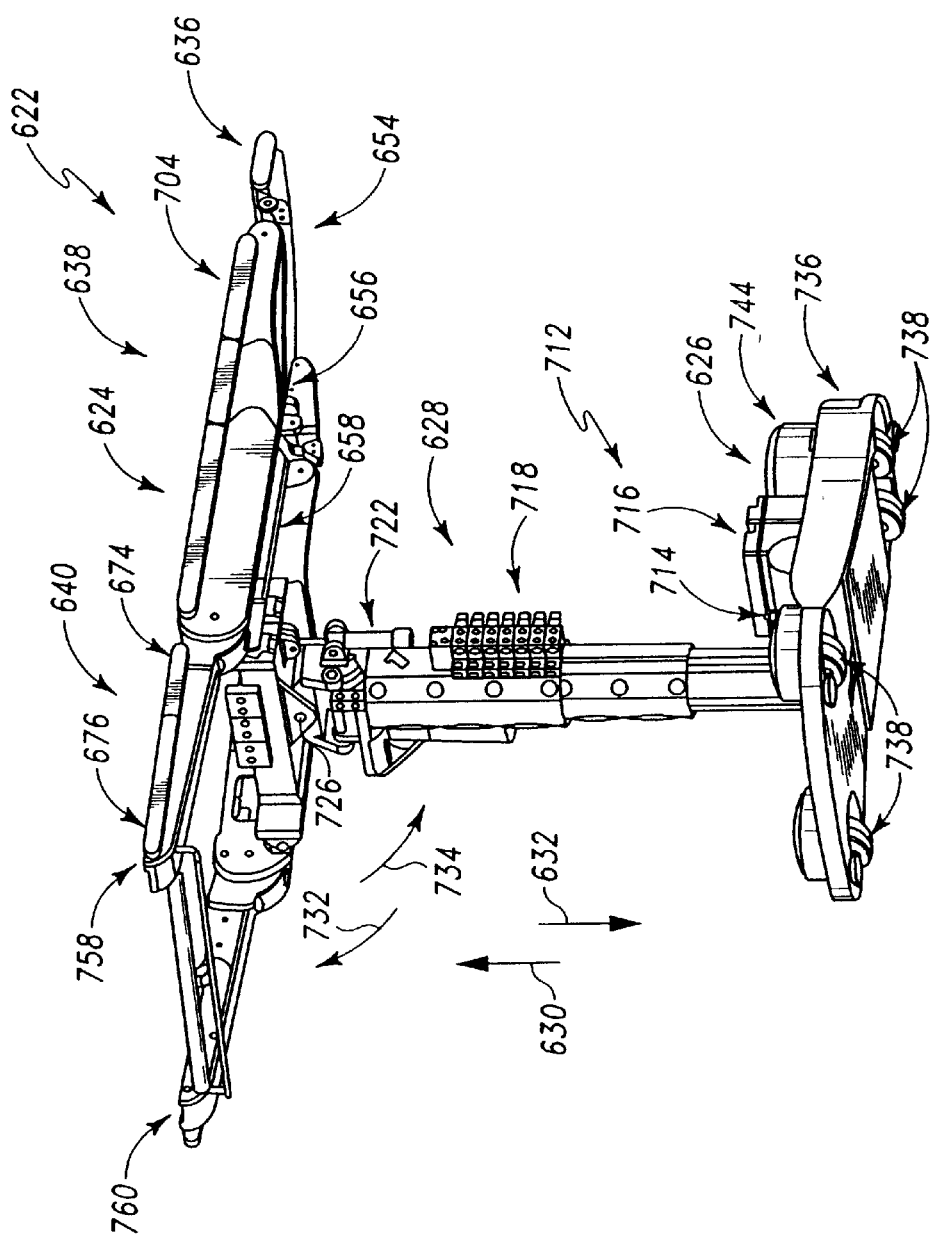
FIG. 37 is a perspective view of the surgical table apparatus of FIG. 35 showing a lower leg support section of the surgical table apparatus removed.

Surgical table apparatus 622 further includes a Trendelenburg actuator 720 and a tilt actuator 722 that move tabletop 624 about horizontal axes 724, 726, respectively, as shown in FIGS. 35 and 37. Trendelenburg actuator 720 rotates tabletop 624 in direction 728 about axis 724 to place patient 634 lying on surgical table apparatus 622 in a Trendelenburg position or in direction 730 to place patient 634 in a Reverse Trendelenburg position. Tilt actuator 722 rotates tabletop 624 about horizontal axis 726 in directions 732, 734. Both of these actuators 720, 722 receive hydraulic fluid from hydraulic actuation system 712.

Base 626 includes a housing 736 and four sets of dual-caster wheels 738 coupled to housing 736. Wheels 738 each include separate first and second wheels 740, 742. Battery 716 may be recharged through a power cord (not shown) which is housed within a power cord retractor 744.

Figure 38:
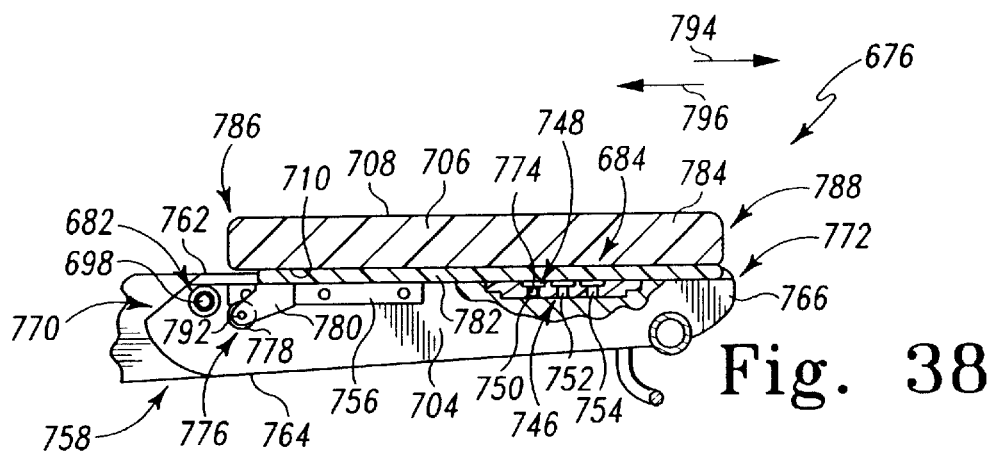
FIG. 38 is a side elevation view, with portions cut away, of a foot support section of the lower leg support section of the surgical table apparatus showing the foot support section including a frame and foot pad in a first position relative to the frame.
Figure 39:
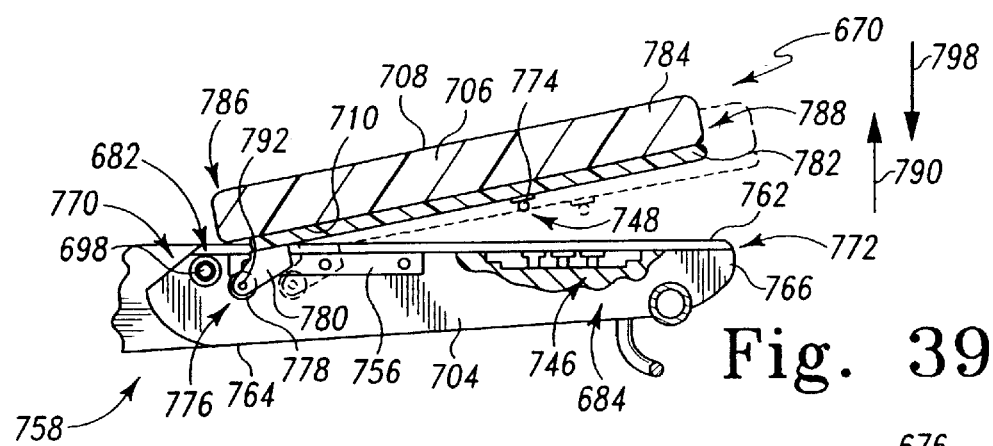
FIG. 39 is a view similar to FIG. 38 showing the foot pad rotated upwardly relative to the frame of the foot support section.
Figure 40:
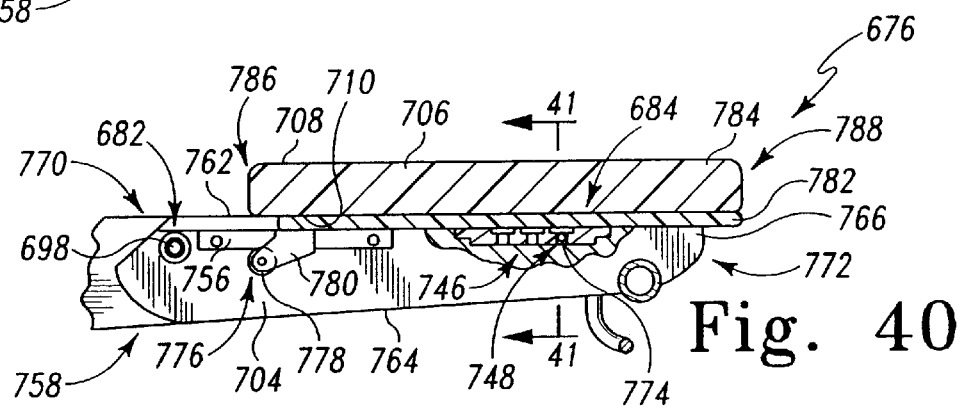
FIG. 40 is a view similar to FIG. 38 showing the foot pad moved to the right relative to the frame.

As shown in FIGS. 38–40, lower leg support section 640 is configured to have an adjustable length to permit the overall length of tabletop 624 to be adjusted for different length patients. In the second support portion 676 of leg support section 640 of tabletop 624, the support 706 may be moved relative to the frame 704. Fourth coupler or position holder 684 of leg support section 640 includes interactive portions 746, 748 on frame 704 and support 706, respectively, that permit the support to be positioned relative to the frame 704 in a plurality of positions, as shown in FIGS. 38–41.

Interactive portions 746 of frame 704 of second support portion 676 include first, second and third recesses or pockets 750, 752, 754 and a track 756. The portion of the frame 704 positioned in leg support section 640 includes spaced-apart arms 758, 760 that each have an upper surface 762, a lower surface 764, an inner surface 766, an outer surface 768, a first end 770 facing toward first support portion 674 of leg support section 640, and a second end 772 spaced apart from the first end 770, as shown in FIGS. 38–41. First, second, and third recesses 750, 752, 754 are formed in the upper surface 762 of each of arms 758, 760 and tracks 756 are coupled to inner surface 766 of each arm 758, 760. Tracks 756 are coupled to each of first and second arms 758, 760 at a position between first, second, and third recesses 750, 752, 754, and first end 770 of arms 758, 760. In alternative embodiments, fewer and more recesses are provided on the interactive portion.

Interactive portion 748 of second support portion 676 includes a detent 774 and a roller assembly 776. Detent 774 is configured to be positioned in one of the recesses 750, 752, 754. When detent 774 is positioned in one of recesses 750, 752, 754, support 706 is blocked from moving. When detent 774 is not positioned in one of recesses 750, 752, 754, as shown in FIG. 39, the support is permitted to move to adjust the overall length of tabletop 624. In alternative embodiments, different types of interactive portions such as button snaps, hook-and-loop type fasteners, magnets, and other types of interactive portions known to those of ordinary skill in the art are provided instead of interactive portions 746, 748.

Roller assembly 776 is provided to assist a caregiver in moving detent 774 between recesses 750, 752, 754. Roller assembly 776 includes a roller 778 and a bracket 780 that couples roller 778 to a backing 782 as shown, for example, in FIGS. 38–41.

Support 706 of second support portion 676 of leg support section 640 includes a mat or pad 784 and backing 782 coupled to pad 784 and positioned between pad 784 and frame 704. Detent 774 is coupled to backing 782 in a location so that detent 774 may be positioned in any of recesses 750, 752, 754. Support 706 further includes a first end 786 facing toward first support portion 674 of leg support section 640 and a second end 788 spaced apart from first end 786.

Figure 41:
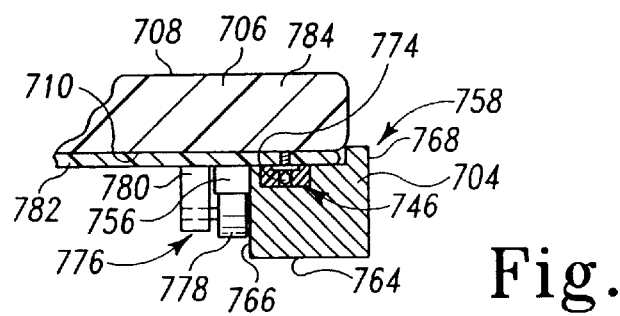
FIG. 41 is a sectional view taken along line 41—41 of FIG. 40.
Figure 42:
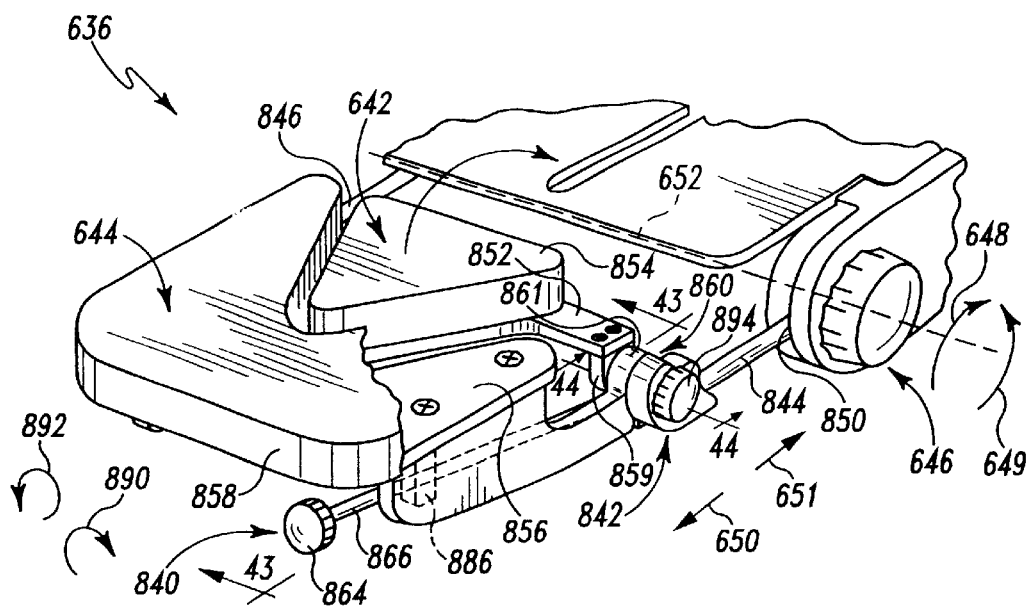
FIG. 42 is a perspective view of a head support section of the surgical table apparatus of FIG. 38 pivotally coupled to an upper torso support section, with portions cut away, of the surgical table apparatus.

As shown in FIG. 39, support 706 of second support portion 676 may be moved relative to frame 704 of second support portion 676. To move support 706 in this manner, support 706 is lifted up in direction 790 about an axis 792 defined by roller 778 until detents 774 are no longer positioned in a recess 750, 752, 754. Then, support 706 is moved in either direction 794, 796. During this movement, roller 778 rolls along track 756 to provide a smooth path. When support 706 is in the desired position, it is lowered in direction 798 about axis 792 until detents 774 are positioned in a desired recess 750, 752, 754 as shown in FIGS. 40 and 41.

Figure 44:
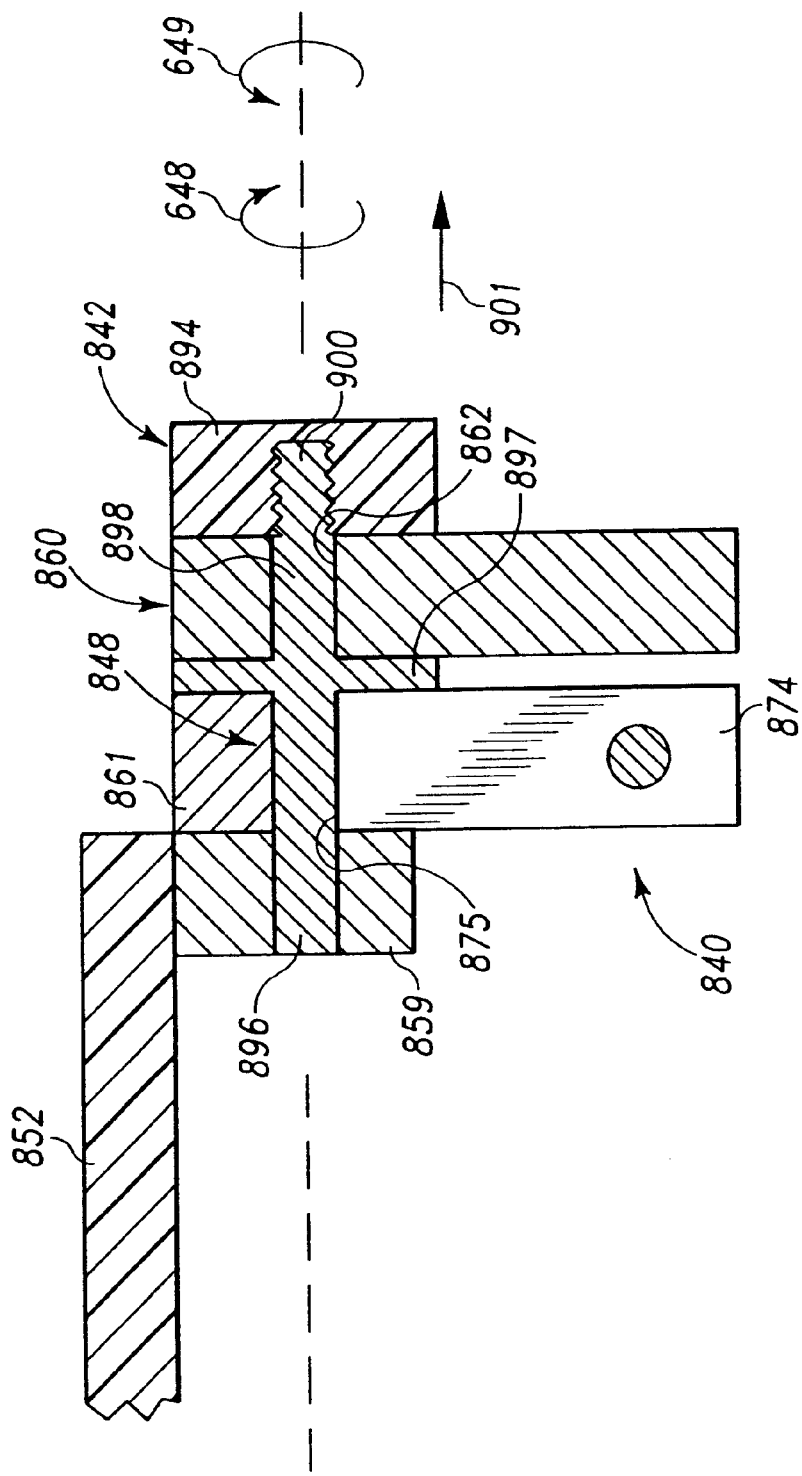
FIG. 44 is a cross-sectional view taken along line 44—44 of FIG. 42.
Figure 46:
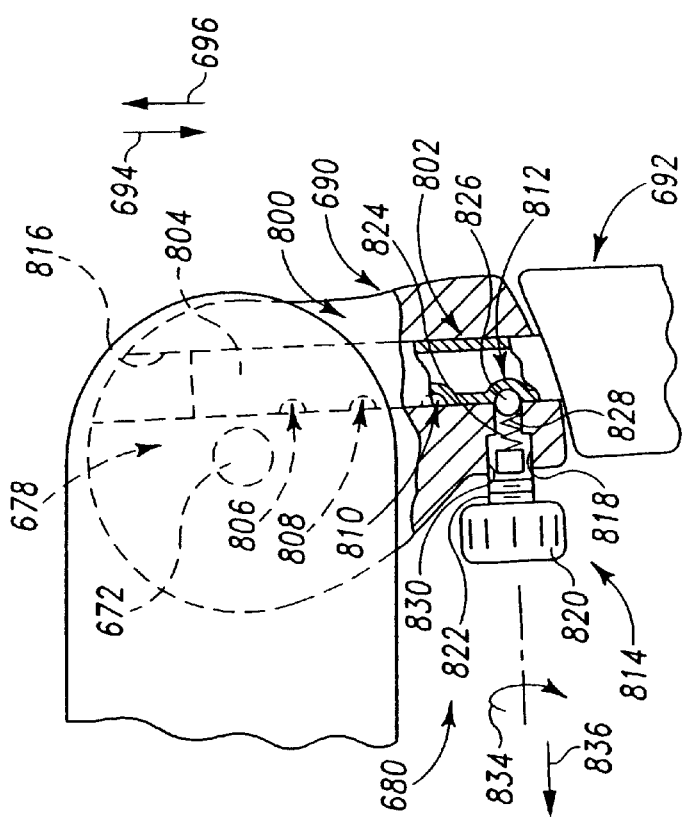
FIG. 46 is view similar to FIG. 45 showing the lower leg support section slid closer to the upper leg support section of the tabletop.
Figure 45:
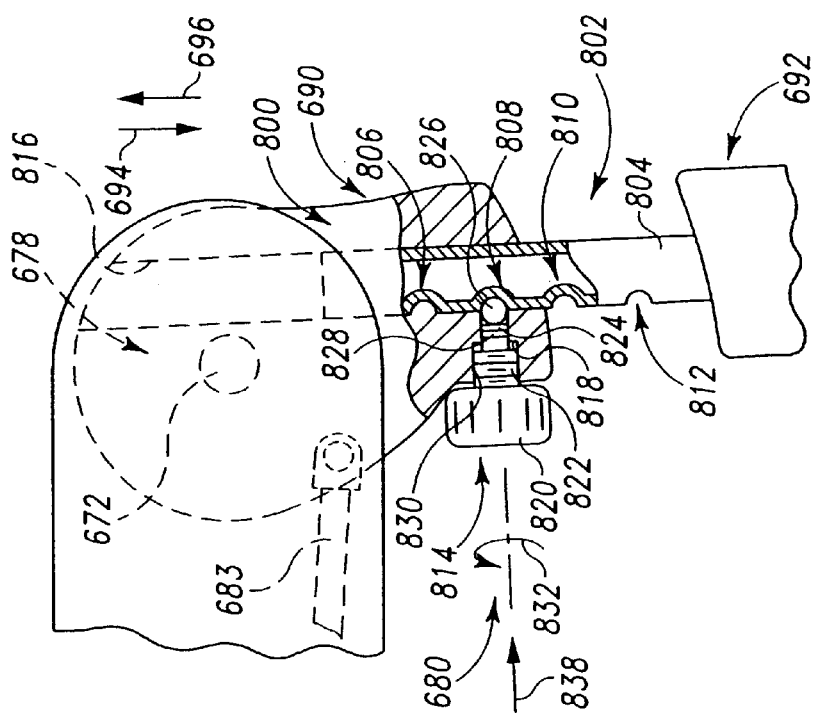
FIG. 45 is side elevation view of a coupler or position holder, with portions cut away, configured to pivotally and slidably couple a lower leg support section to an upper section of the tabletop.

As shown in FIGS. 44 and 45, second coupler or position holder 680 of leg support section 640 permits relative axial movement between first and second or support sections 690, 692 of first support portion 674 in directions 694, 696. Second coupler 680 includes interactive portions 800, 802 on each of first and second support sections 690, 692 that cooperate to fix the position of first and second support sections 690, 692 in one of a plurality of positions.

Interactive portion 802 of second support section 692 includes a rod 804 with recesses 806, 808, 810, 812. Interactive portion 800 of first support section 690 includes a spring-loaded detent 814, an aperture 816 sized to receive rod 804, and a threaded aperture 818 sized to receive the spring-loaded detent 814 as shown, for example, in FIGS. 44 and 45. Spring-loaded detent 814 includes a handle 820, a threaded stud 822 that is coupled to handle 820, a spring 824, and a ball 826. Aperture 818 is formed in first support section 690 of first support portion 674 and includes a first portion 828 that is slightly wider than ball 826 and a second portion 830 that is threaded to receive threaded stud 822. Ball 826 is positioned in second portion 830 of aperture 818. Threaded stud 822 is configured to thread in and out of the threaded first portion 828 of aperture 818 and spring 824 extends between threaded stud 822 and ball 826 in both first and second portions 828 and 830 of aperture 818.

A caregiver rotates handle 820 of spring-loaded detent 814 in direction 832 to press ball 826 into one of recesses 806, 808, 810, 812 to fix the position of first and second sections 690, 692. A caregiver rotates handle 820 in the opposite direction 834 to permit ball 826 to move inward in direction 836 against the bias of spring 824 so that first and second sections 582, 584 may be moved relative to each other in directions 694, 696.

During rotation of handle 820 in direction 834, threaded stud 822 moves in direction 836 away from rod 804 as shown in FIG. 45. When handle 820 and threaded stud 822 are moved away from rod 804, spring 824 still maintains the position of ball 826 in a recess 806, 808, 810, 812 of rod 804. However, the ball may be moved against the bias of spring 824 in direction 836 when a caregiver moves rod 804 in either direction 694, 696.

When the caregiver positions second section 692 relative to first section 690 in a desired position and ball 826 is positioned in one of recesses 806, 808, 810, 812, the caregiver rotates handle 820 in direction 832 to move handle 820 and threaded stud 822 in direction 838 so that ball 826 is pressed into one of recesses 806, 808, 810, 812 to fix the position of first and second sections 690, 692. In the illustrated embodiment, interactive portion 802 of second section 690 includes four recesses 806, 808, 810, 812. In alternative embodiments, fewer or more recesses are included on the rod. In addition, different types of interactive portions such as the torque-limited bolt described above, pins, latches, or other interactive portions known to those of ordinary skill in the art are provided instead of interactive portions 800, 802.

As discussed above, head support section 636 includes first and second portions 642, 644 and coupler or position holder 646. Coupler 646 is configured to permit head support section 636 to be moved relative to body support section 638. In addition, head support section 636 includes two additional couplers or position holders 840, 842, first and second attachment rods 844, 846, and an axle or shaft 848 that is coupled to the first and second portions 642, 644 and one of attachment rods 844 of head support section 636. Attachment rods 844, 846 are positioned in apertures 850 formed in coupler 646 and, when permitted by coupler 646, are configured to be slid through apertures 850 in directions 650, 651. The two additional couplers 840, 842 permit movement of head support section 636 relative to body support section 638 and movement of first and second head support members 642, 644 of head support section 636 relative to each other.

First head support member 642 of head support section 636 includes a support plate or frame 852 and a support or pad 854 coupled to support plate or frame 852. Similarly, second head support member 644 of head support section 636 includes a support plate or frame 856 and a support or pad 858 coupled to support plate or frame 856. First and second portions 642, 644 include axle supports 859, 861 and attachment rod 844 includes an axle support 860 and an aperture 862 in support 860 that is sized to receive axle 848 as shown in FIG. 44. Axle 848 is rigidly coupled to axle support 859 of first portion 642 of head support section 636.

Figure 43:
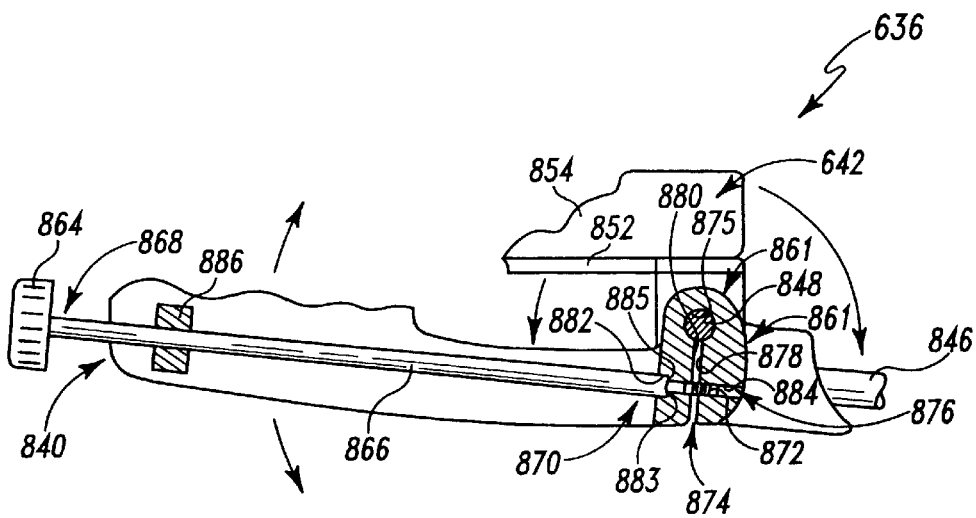
FIG. 43 is a cross-sectional view taken along line 43—43 of FIG. 42 showing a coupler or position holder configured to permit movement of a first head support member of the head support section relative to a second head support member of the head support section.

First coupler or clamp 840 includes a handle 864, a rod 866 having a first end 868 coupled to handle 864 and a second end 870 spaced apart from the first end 868, and a threaded tip 872 coupled to second end 870 of rod 866. Axle support 861 of second portion 644 includes an aperture 875 and a slot 874 in communication with the aperture 875 and an aperture 876 that is substantially perpendicular to the slot 874 as shown in FIG. 43. Slot 874 and aperture 875 are defined by opposing first 878 and second 880 surfaces. Aperture 876 includes first and second portions 882, 884. First portion 882 is not threaded and is slightly larger than threaded tip 872 of rod 866 of first coupler 840. Furthermore, first portion 882 includes a shoulder 883 positioned to abut a shoulder 885 of rod 886 as shown in FIG. 43. Second portion 884 is threaded and is sized so that threaded tip 872 of first coupler 840 can threadingly engages second portion 884.

Second portion 644 further includes a rod support 886 having an aperture 888 sized to receive rod 866 of first coupler 840. Rod 866 of first coupler 840 is positioned to extend through rod support 886 and into second aperture 876 in axle support 861 of second portion 644.

First coupler or clamp 840 permits second portion 644 of head support section 636 to move relative to first portion 642 of head support section 636. Slot 874 in axle support 861 permits axle support 861 to operate as a clamp 861 that either fixes second portion 644 to axle 848 or permits second portion 644 to move or rotate about axle 848 relative to first portion 642 of head support section 636. Rotation of handle 864 in direction 890 causes the opposing surfaces 878, 880 that define the aperture 862 and slot 874 to move together and thus clamp axle 848. Because second portion 844 of aperture 876 is threaded and rod 886 abuts shoulder 883 of first portion 842 of aperture 876, rotation of handle 864 and rod 886 draws second portion 844 toward first portion 844 and narrows slot 874. When axle 848 is clamped, axle support 861 and thus second portion 644 are fixed to first axle 848.

Rotation of handle 864 in the opposite direction 892 causes the opposing surfaces 878, 880 to move away from each other to unclamp axle 848. When axle 848 is not clamped, axle support 861 and thus second portion 644 may rotate about axle 848 relative to first portion 642 and attachment rods 844, 864.

Second coupler 842 permits movement of first and second portions 642, 644 of head support section 636 relative to attachment rods 844, 846. Second coupler 842 includes a handle 894 that interact with axle 848 and axle support 860 of attachment rod 844. Second coupler 842 is tightened to prevent movement of first and second portions 642, 644 of head support section 636 relative to attachment rods 844, 846 and is loosened to permit movement of first and second portions 642, 644 relative to attachment rods 844, 846.

Axle 848 includes a first end 896, a second end 898 spaced apart from first end 896, a washer or shoulder 897, and a threaded portion 900 extending from second end 898. First end 896 is rigidly coupled to axle support 85a of first portion 642 of head support section 636. Threaded portion 900 extends through and protrudes from axle support 860 of the attachment rod 844. Handle 894 threadably engages threaded portion 900 of axle 848.

Rotation of handle 894 in a first direction 648, causes handle 894 to pull axle 848 in direction 901 and traps axle supports 860 between shoulder 897 and handle 894 to fix the position of both portions 642, 644 of head support section 636 relative to attachment rods 844, 846. Rotation of handle 894 in the opposite direction 649 causes handle 894 to release the grip on axle support 860 to permit both portions 642, 644 of head support section 636 to move relative to attachment rods 844, 846.

Portion 642 can be rotated upwardly or downwardly relative to portion 644 so that an opening exists to permit a patient to face downwardly through portion 644. To rotate portion 642 downwardly and leave the opening, handle 894 is loosened and both portions 642, 644 are rotated downwardly in direction 649. Handle 894 is then tightened and handle 864 is loosened so that portion 644 can be rotated in direction 648 until portion 644 is substantially horizontal. After handle 894 is tightened, a person's face can be positioned in the opening once occupied by portion 642. Portion 642 can be rotated upwardly relative to portion 644 in a similar manner.

Figure 47:
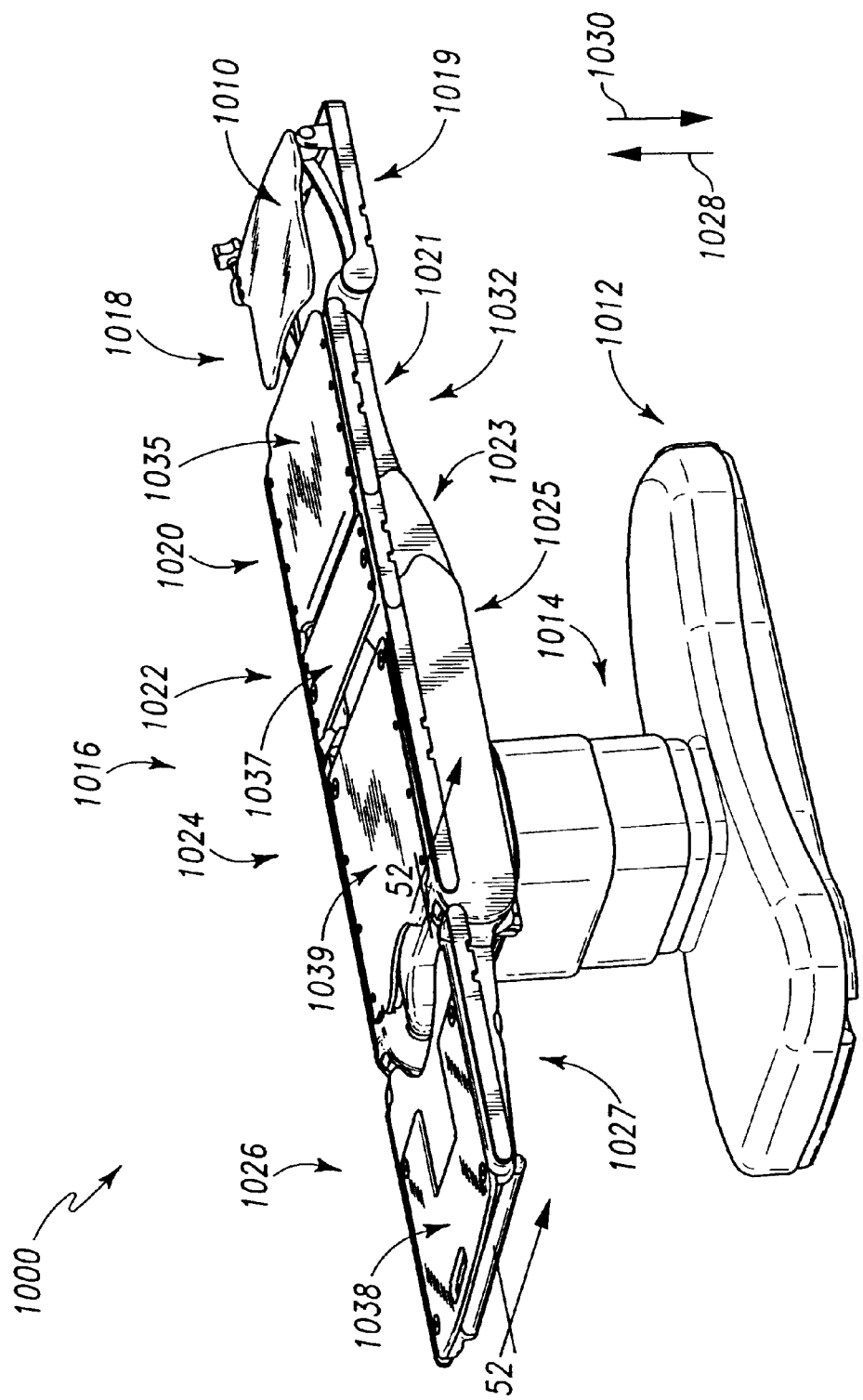
FIG. 47 is a perspective view of a third embodiment of a surgical table apparatus according to the present disclosure showing the surgical table apparatus including a base including a pedestal and a tabletop having head, upper torso, lower torso, seat and leg support sections with head, torso, and lower leg pads removed to show the frame of the head, upper torso, lower torso, upper, and lower leg support sections.
Figure 48:
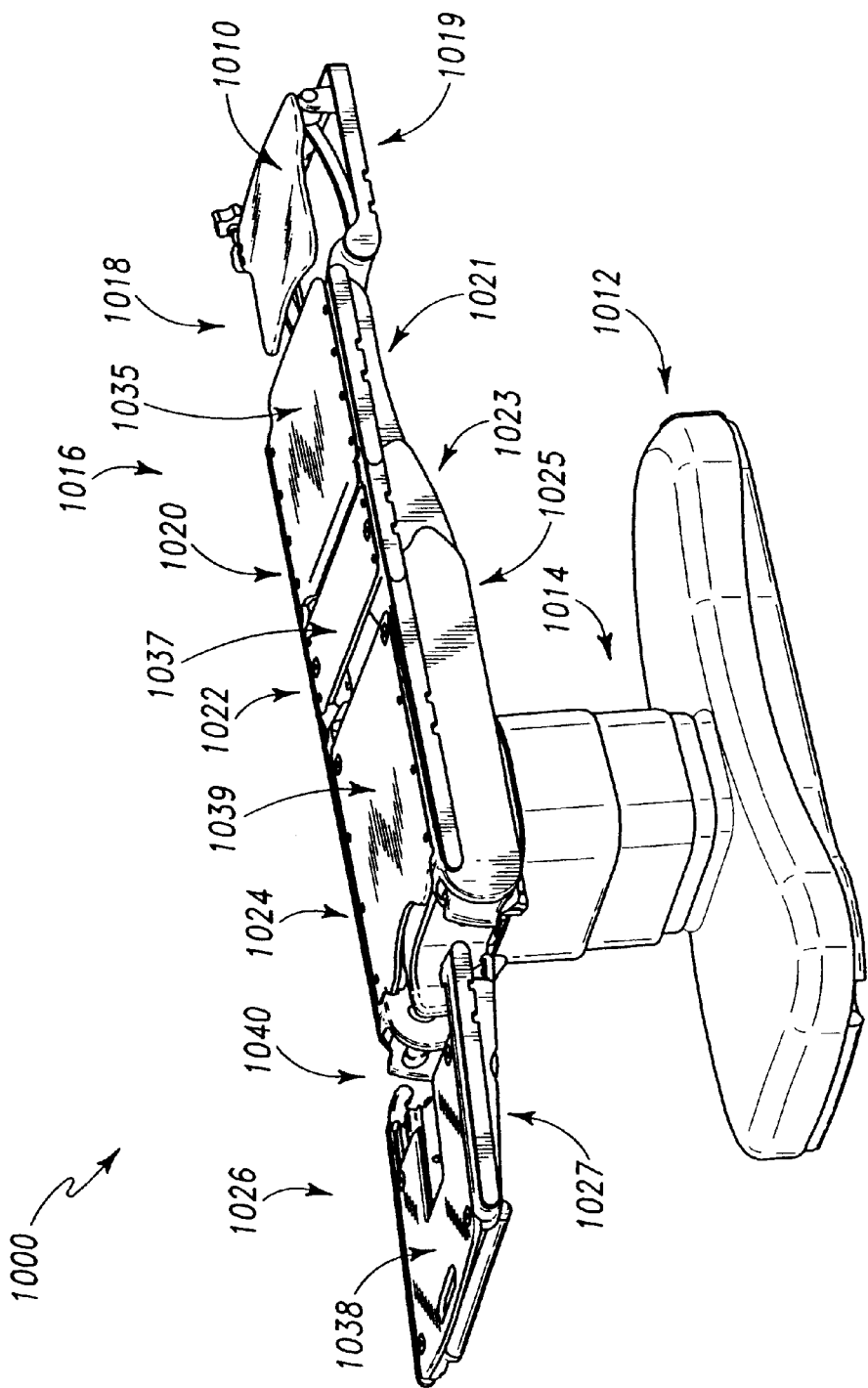
FIG. 48 is a perspective view similar to FIG. 47 showing the lower leg support section uncoupled from the upper leg support section.

A third embodiment of a surgical table apparatus or patient support 1000 in accordance with the present disclosure is shown in FIGS. 47–79. Referring to FIG. 47, surgical table apparatus 1000 includes a base 1012 including a pedestal 1014, and a tabletop 1016 coupled to pedestal 1014.

Pedestal 1014 includes a lift mechanism (not shown) for moving tabletop 1016 upwardly and downwardly in directions 1028, 1030 relative to base 1012. Disclosure of a suitable lift mechanism is provided in U.S. Patent Provisional Application Ser. No. 60/264,214, entitled "Hydraulic Actuator Apparatus," filed Jan. 25, 2001, to Blyshak et al., the disclosure of which is expressly incorporated by reference herein.

Tabletop 1016 includes a head support section 1018, an upper torso support section 1020, a lower torso support section 1022, a upper leg support section 1024, and a lower leg support section 1026 which generally correspond to the head, upper torso, lower torso, upper leg, and lower legs of a patient positioned on surgical table apparatus 1000. Head support section 1018 includes a head support frame 1019 and a head support plate 1010 supported by head support frame 1019. A head pad or support (not shown) is supported by head support plate 1010. Upper torso, lower torso, and upper leg support sections 1020, 1022, 1024 include upper torso, lower torso, and upper leg support frames 1021, 1023, 1025 and upper torso, lower torso and upper leg support plates 1035, 1037, 1039. Upper torso, lower torso and upper leg pads (not shown) are supported by upper torso, lower torso and upper leg support plates 1035, 1037, 1039, respectively. The upper torso, lower torso, and upper leg pad portions cooperate to define a torso pad (not shown) supported by upper torso, lower torso, and upper leg support plates 1035, 1037, 1039. Lowe lower leg support section 1026 includes a lower leg support frame 1027 and a lower leg support plate 1038 supported by lower leg support frame 1027. A lower leg support pad (not shown) is supported by lower leg support plate 1038.

Support frames 1019, 1021, 1023, 1025, 1027 are components of a deck or frame 1032 of tabletop 1016. The head, torso and leg pads are preferably attached to the respective support frames 1019, 1021, 1023, 1025, 1027 of frame 1032 by hook-and-loop type fasteners so that the head, torso, and leg pads may easily be attached or removed from frame 1032. In alternative embodiments, other types of couplers are provided to removably or otherwise attach the pads to the frame, such as snaps, ties, or other couplers known to those of ordinary skill in the art. Preferably, the couplers permit the pads to be easily removed or attached to the frame.

According to the third embodiment of the present disclosure, the head, torso, and leg pads are filled with foam. According to alternative embodiments of the present disclosure, other materials or configurations are provided in the pads such as air, gel, liquid, air fluidized beads, or other support material known to those of ordinary skill in the art. Details of other suitable pads or supports for use on tabletop 1016 are disclosed U.S. application Ser. No. 09/187,990, entitled SURGICAL TABLE APPARATUS, filed Nov. 6, 1998, to Richard L. Borders, the disclosure of which is expressly incorporated by reference herein.

According to the illustrative embodiment shown in FIGS. 47–55, lower leg support section 1026 of tabletop 1016 is pivotally and removably coupled to upper leg support section 1024 of tabletop 1016. Furthermore, leg support plate 1038 of lower leg support section 1026 is an extendable support which allows the overall length of lower leg support section 1026 and tabletop 1016 to be extended or retracted. According to alternative embodiments of the present disclosure, the leg support section is not removable and not pivotable relative to the upper leg support section and is otherwise coupled to the upper leg support section of the frame. According to other alternative embodiments, the leg support plate is not extendable.

Figure 50:
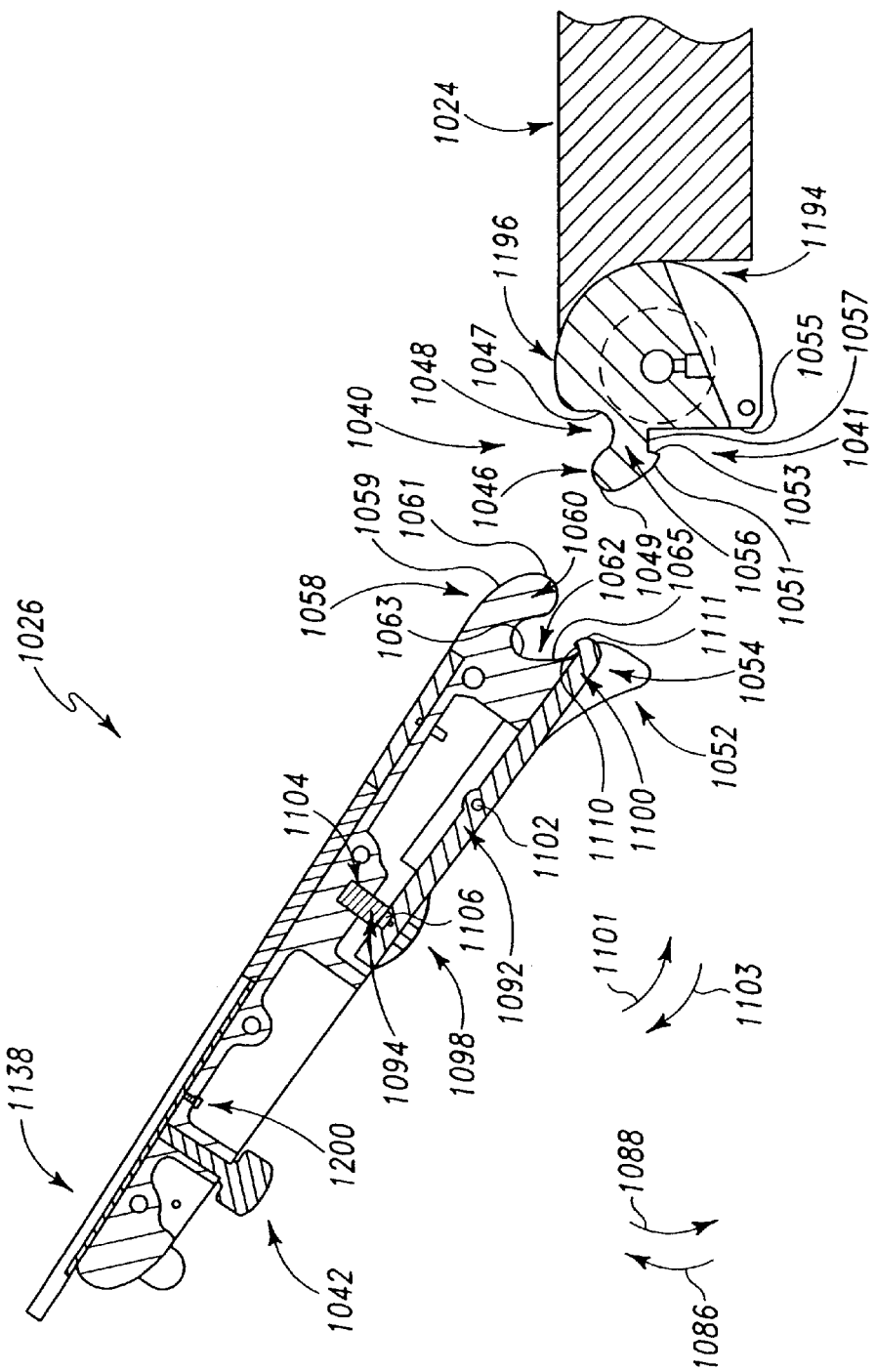
FIG. 50 is a cross-sectional view showing the lower leg support section angled upward and spaced apart from the upper leg support section and positioned so that the lower leg support section can be coupled to the upper leg support section.
Figure 51:
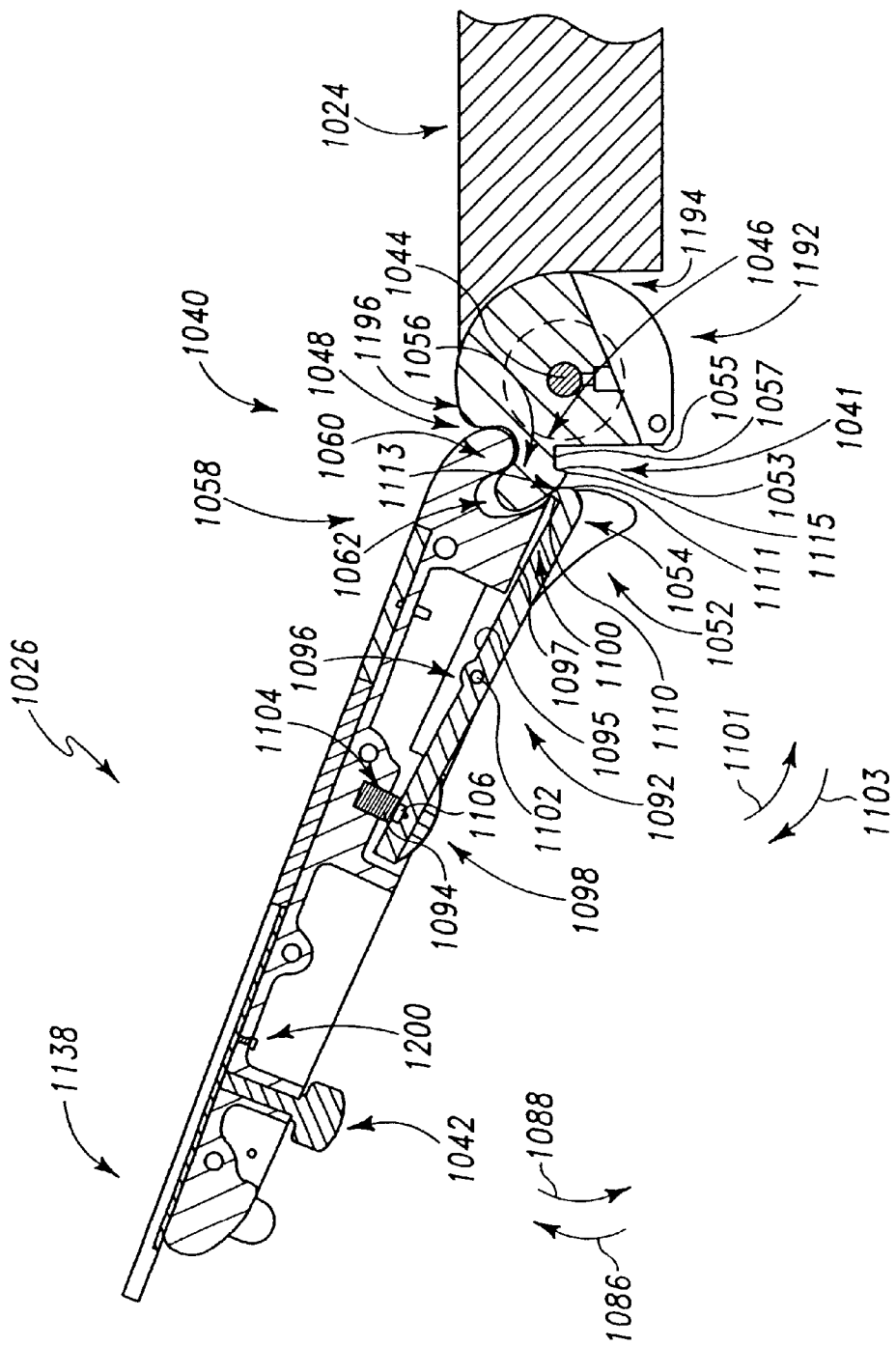
FIG. 51 is a cross-sectional view similar to FIG. 50 showing the lower leg support section aligned with the upper leg support section so that an upper lobe of the lower leg support section is received by a pocket in the upper leg support section.

Lower leg support section 1026 is pivotally and removably coupled to upper leg support section 1024 by a leg coupler 1040. As shown in FIG. 50, leg coupler 1040 includes a pair of first couplers or interactive members 1046 coupled to upper leg support section 1024 and a pair of second couplers or interactive members 1058 formed in lower leg support section 1026. Lower leg support section 1026 is coupled to upper leg support section 1024 by angling lower leg support section 1026 upward relative to upper leg support section 1024 and aligning second couplers 1058 with first couplers 1046, as shown in FIGS. 50 and 51. Second couplers 1058 are funneled into alignment with first couplers 1046 by the rounded configurations of first couplers 1046 and second couplers 1058. This configuration facilitates the alignment of second couplers 1058 and first couplers 1046.

Figure 52:
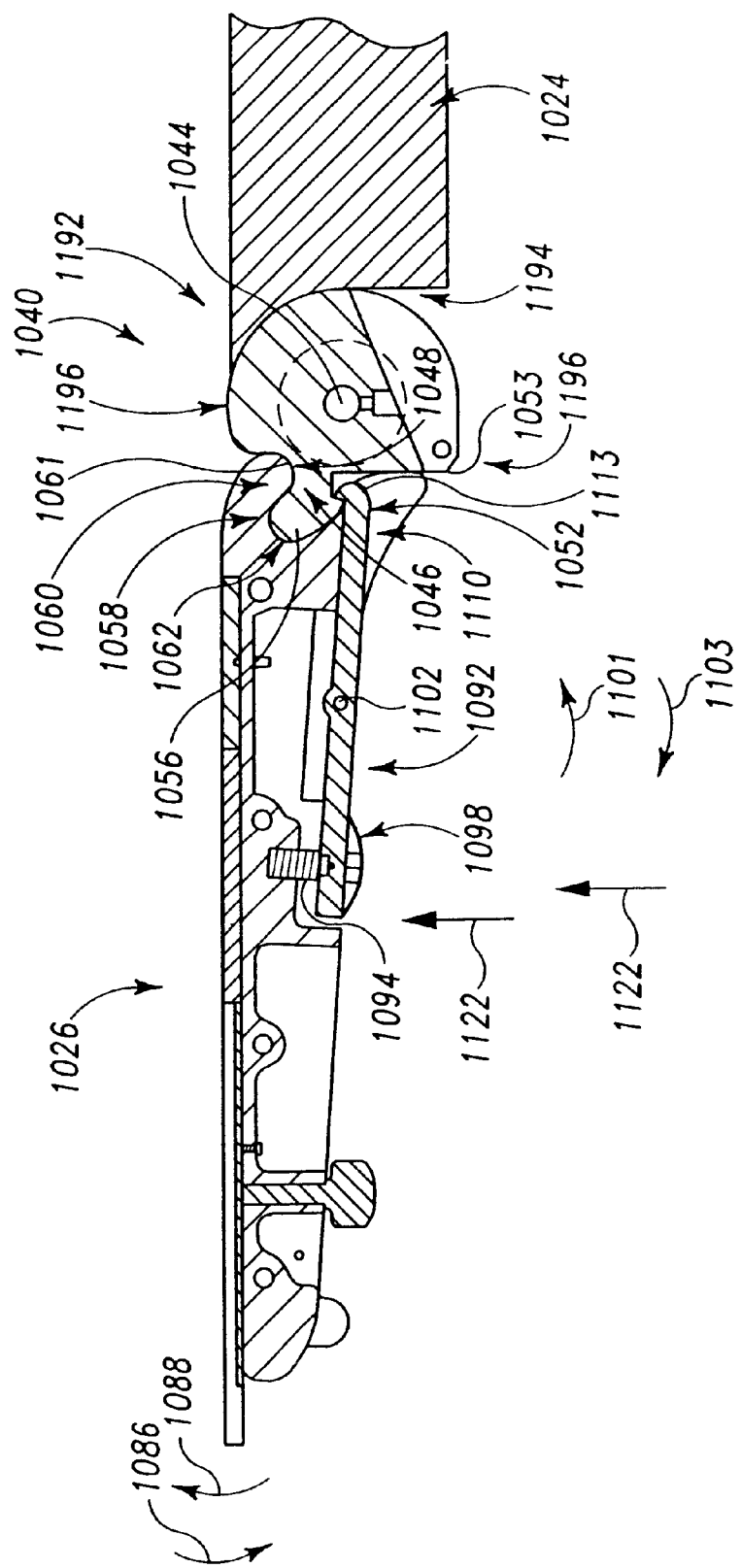
FIG. 52 is a cross-sectional view taken along line 52—52 of FIG. 47 showing the lower leg support section pivotally coupled to the upper leg support section of the surgical table apparatus.

After first and second couplers 1046, 1058 are aligned, lower leg support section 1026 is rotated relative to upper leg support section 1024 so that first coupler 1046 and second couplers 1058 interlock together, as shown in FIG. 52. Leg coupler 1040 further includes retainers or latches 1052 which lock lower leg support section 1026 to upper leg support section 1024. Retainers 1052 and second couplers 1058 capture first couplers 1046 therebetween in a locked position, as shown in FIG. 52.

Lower leg support section 1026 is uncoupled from upper leg support section 1024 by releasing latch 1052 and rotating lower leg support section 1026 upward relative to upper leg support section 1024. As lower leg support section 1026 is rotated upward second coupler 1058 is uncoupled from first coupler 1046. Once second coupler 1058 and first coupler 1046 are uncoupled lower leg support section 1026 can be pulled away from upper leg support section 1024 such that second couplers 1058 are no longer positioned in alignment pockets 1048.

As shown in FIGS. 48–52, lower leg support section 1026 is pivotally coupled to upper leg support section 1024 through a pair of joints 1192 of leg coupler 1040. Joints 1192 include a pair of pivot members 1196 and a portion of upper leg support section 1024 that provides a pair of sockets 1194 configured to pivotally receive the respective pivot members 1192. Joints 1192 further include a pair of axles 1044 configured to rotatably couple pivot members 1196 to sockets 1194. According to the preferred embodiment of the present disclosure, a hydraulic actuator (not shown) is provided to provide the power to move pivot members 1196 relative to sockets 1194 between the first and second positions illustrated in FIGS. 52 and 53 and any position therebetween.

Figure 49:
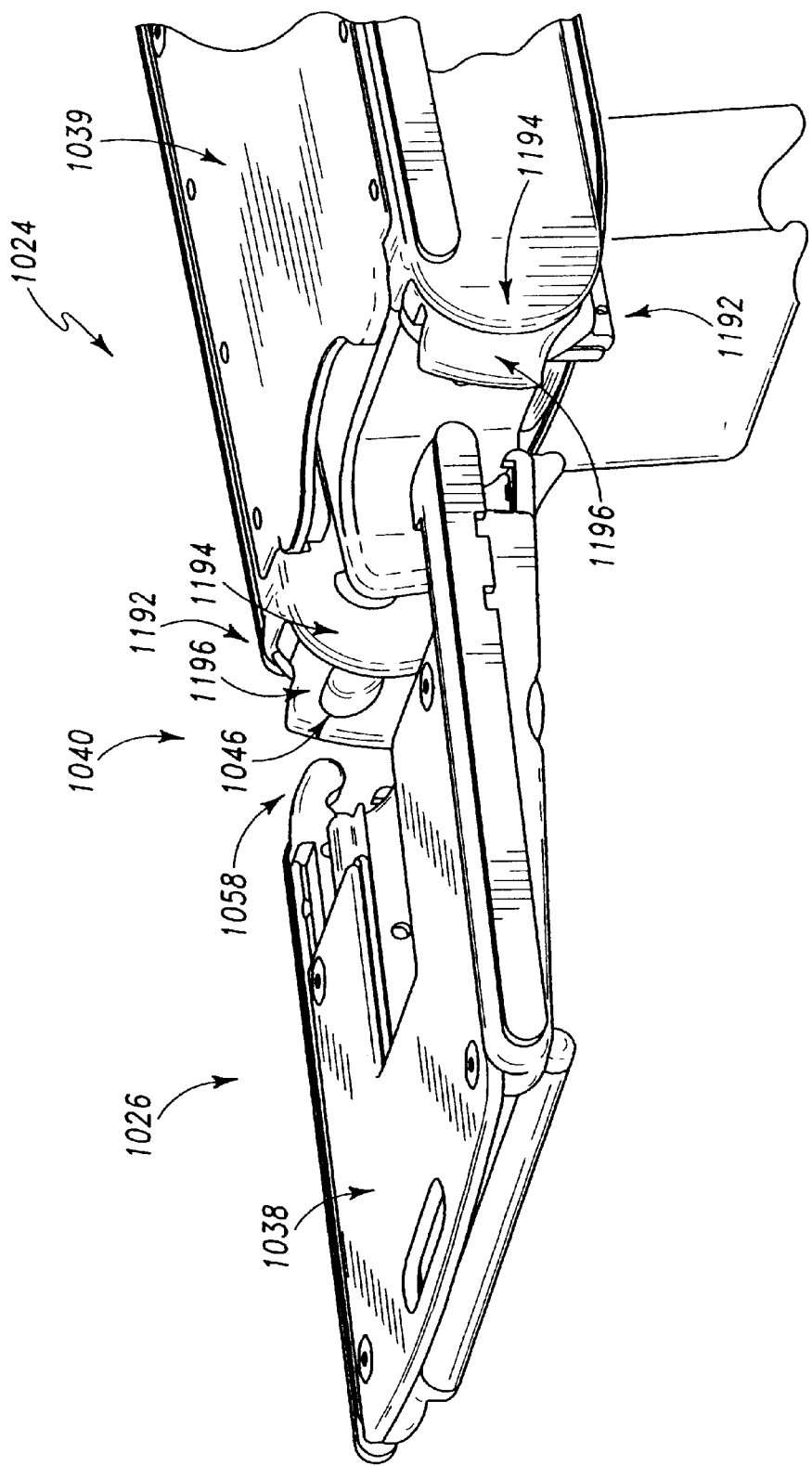
FIG. 49 is an enlarged view of a portion of FIG. 48 showing a lower leg coupler which couples the lower leg support section to the upper leg support section.

Referring to FIGS. 49 and 50, first couplers or interactive members 1046 of leg section coupler 1040 protrude from pivot members 1196. Second couplers or interactive members 1058 are formed in lower leg support section 1026. First couplers 1046 and second couplers 1058 have complementary configurations which facilitate the coupling of lower leg support section 1026 to upper leg support section 1024 and which interlock when lower leg support section 1026 and upper leg support section 1024 are coupled together. When lower leg support section 1026 is coupled to upper leg support section 1024, first couplers 1046 interlock with second couplers 1058, as shown in FIG. 52. When lower leg support section 1026 is removed from upper leg support section 1024, second couplers 1058 are spaced apart from first couplers 1046 as shown in FIGS. 49 and 50.

As mentioned above, the complementary configurations of first couplers 1046 and second couplers 1058 facilitate the coupling of lower leg support section 1026 and upper leg support section 1024. Both first couplers 1046 and second couplers 1058 have rounded configurations which ease the coupling of first couplers 1046 and second couplers 1058 because the respective portions of first couplers 1046 and second couplers 1058 slide easily over and around each other. The rounded configuration of first couplers 1046 provide a slide which funnels second couplers 1058 into alignment pockets 1048 and hence align lower leg support section 1026 with the remaining support sections of surgical table apparatus 1000.

As shown in FIG. 50, first coupler or interactive member 1046 includes a protrusion or interactive portion 1056 extending from pivot member 1196. Interactive portion 1056 includes a rounded configuration including an first arcuate surface 1047, defining an alignment pocket 1048, a second arcuate surface 1049 adjacent to first arcuate surface 1047, and a third slightly arcuate surface 1051 adjacent to second arcuate surface 1049.

Second coupler or interactive member 1058 includes a lobe or interactive portion 1060 configured to interlock with a lobe or interactive portion 1056 of first coupler 1046 and a recessed or interactive portion 1062 configured to interlock with interactive portion 1056 of first couplers 1046. Interactive portions 1060, 1062 of second coupler 1058 include a first arcuate surface 1059, a second arcuate surface 1061, a third arcuate surface 1063, and a fourth arcuate surface 1065. Arcuate surfaces 1061, 1063, 1065 of second coupler 1058 are complementary to arcuate surfaces 1047, 1049, 1051 of first coupler 1046.

Lower leg support section 1026 is coupled to upper leg support section 1024 by angling lower leg support section 1026 upward relative to upper leg support section 1024 in a direction 1088 and moving lower leg support section 1026 toward upper leg support section 1024 so that arcuate surfaces 1061 of interactive portions 1060 of second couplers 1058 are positioned in alignment pockets 1048 of interactive portions 1056 of first couplers 1046, as shown in FIG. 51. Arcuate surfaces 1061 of interactive members 1058 are funneled into alignment pockets 1048 of interactive members 1046 by contacting arcuate surfaces 1049 of interactive members 1046 and sliding down arcuate surfaces 1049 into pockets 1048 formed by arcuate surfaces 1047. When arcuate surfaces 1061 are positioned in pockets 1048, as shown in FIG. 51, lower leg support section 1026 is aligned with upper leg support section 1024.

After aligning interactive members 1046, 1058, lower leg support section 1026 is rotated in a direction 1086 so that interactive portions 1056 of first couplers 1046 are received by the recessed or interactive portions 1062 of second couplers 1058. When lower leg support section 1026 is rotated to a substantially coplanar position relative to upper leg support section 1024 the interactive portions 1056 of first couplers 1046 and interactive portions 1060, 1062 of second couplers 1058 are coupled together. Lower leg support section 1026 is maintained in the substantially coplanar position relative to upper leg support section 1024 due to the abutment of a stop 1054 of leg coupler 1040 on lower leg support section 1026 against an abutment surface 1055 of pivot members 1196.

Referring to FIGS. 50 and 52, when interactive portions 1056 of first couplers 1046 and interactive portions 1060, 1062 of second couplers 1058 are coupled together surfaces 1047, 1049, 1051 of first couplers 1046 are adjacent the complementary surfaces 1061, 1063, 1065 of second couplers 1058. Lobes 1060 and recessed portions 1062 of second couplers 1058 interlock with lobes 1056 of first couplers 1046.

As mentioned above, retainers 1052 lock lower leg support section 1026 to pivot members 1196, as shown in FIG. 51. Retainers 1052 are configured to interact with a recesses 1041 on first couplers 1046 that are defined by a side surface 1053, abutment surface 1055 and a bottom surface 1057. According to alternative embodiments of the present disclosure other retainers such as latches, hooks, fasteners, straps, and other retainers known to those of ordinary skill in the art are provided to couple the leg support section to the upper leg support section.

Referring to FIGS. 51 and 52, retainers 1052 cooperate with recesses 1041 on first couplers 1046 to lock lower leg support section 1026 to pivot members 1196 and hence to upper leg support section 1024. Retainers 1052 are also configured to permit lower leg support section 1026 to be removed from upper leg support section 1024.

Retainer 1052 includes a latch or lever 1092, a lever spring 1094, and a housing 1096 as shown in FIG. 51. Lever 1092 includes a handle end 1098, a latch end 1100, and a fulcrum 1102 positioned between handle end 1098 and latch end 1100. Lower leg support section 1026 and handle end 1098 of lever 1092 include bores 1104, 1106 that each receive a portion of lever spring 1094. Lever spring 1094 biases lever 1092 about fulcrum 1102 in a counter-clockwise direction 1101 such that a top surface 1095 of lever 1092 contacts a lower surface 1097 of housing 1096, as shown in FIG. 52.

Latch end 1100 of lever 1092 interacts with first coupler 1046 to lock and unlock the seat and leg support sections 1024, 1026. Latch end 1100 of lever 1092 includes a latch surface 1110 which is complementary to side surface 1053 of first couplers 1046 and an arcuate surface 1111. Latch surface 1110 is positioned adjacent to side surfaces 1053 when lower leg support section 1026 is locked to upper leg support section 1024, as shown in FIG. 52. In one embodiment, latch surface 1110 and recess side surface 1053 are vertical, substantially flat surfaces. In alternative embodiments latch surfaces and recess side surfaces are angled to provide a lead-in for the latch end into recess. In additional alternative embodiments, the latch end and recess include lead-in surfaces separate from the latch surface and the recess side surface such as a first chamfer on the lower end of recesses surface and a second chamber on the upper end of the latch.

As mentioned above, lever 1092 is biased towards the locked position shown in FIG. 52 by lever spring 1094. Lever spring 1094 biases lever 1092, in direction 1101 so that upper surface 1095 of lever 1092 normally contacts lower surface 1097 of housing 1096. Referring to FIG. 51, as lower leg support section 1026 is attached to upper leg support section 1024, arcuate surface 1111 of latch end 1100 contacts arcuate surface 1051 of first coupler 1046.

Arcuate surface 1111 of latch end 1100 acts as a cam follower to arcuate or cam surfaces 1051 of first coupler 1046. As such, when lower leg support section 1026 is rotated in direction 1086 to the substantially coplanar position relative to upper leg support section 1024, cam follower surface 1111 of latch end 1100 contacts cam surface 1051 of first coupler 1046 and causes lever 1092 to rotate about fulcrum 1102 in a clockwise direction 1103 such that lever surface 1095 is spaced apart from surface 1097 of housing 1096 and such that lever spring 1094 is further compressed.

When lower leg support section 1026 is substantially parallel to upper leg support section 1024, a first end 1113 of cam follower surface 1111 moves past a first end 1115 of cam surface 1051 such that latch end 1100 of lever 1092 snaps or moves into recess 1041 of first coupler 1046 to lock lower leg support section 1026 to upper leg support section 1204. Latch end 1100 moves into recess 1041 due to the biasing of lever 1092 by lever spring 1094 in direction 1101 about fulcrum 1102.

Figure 53:
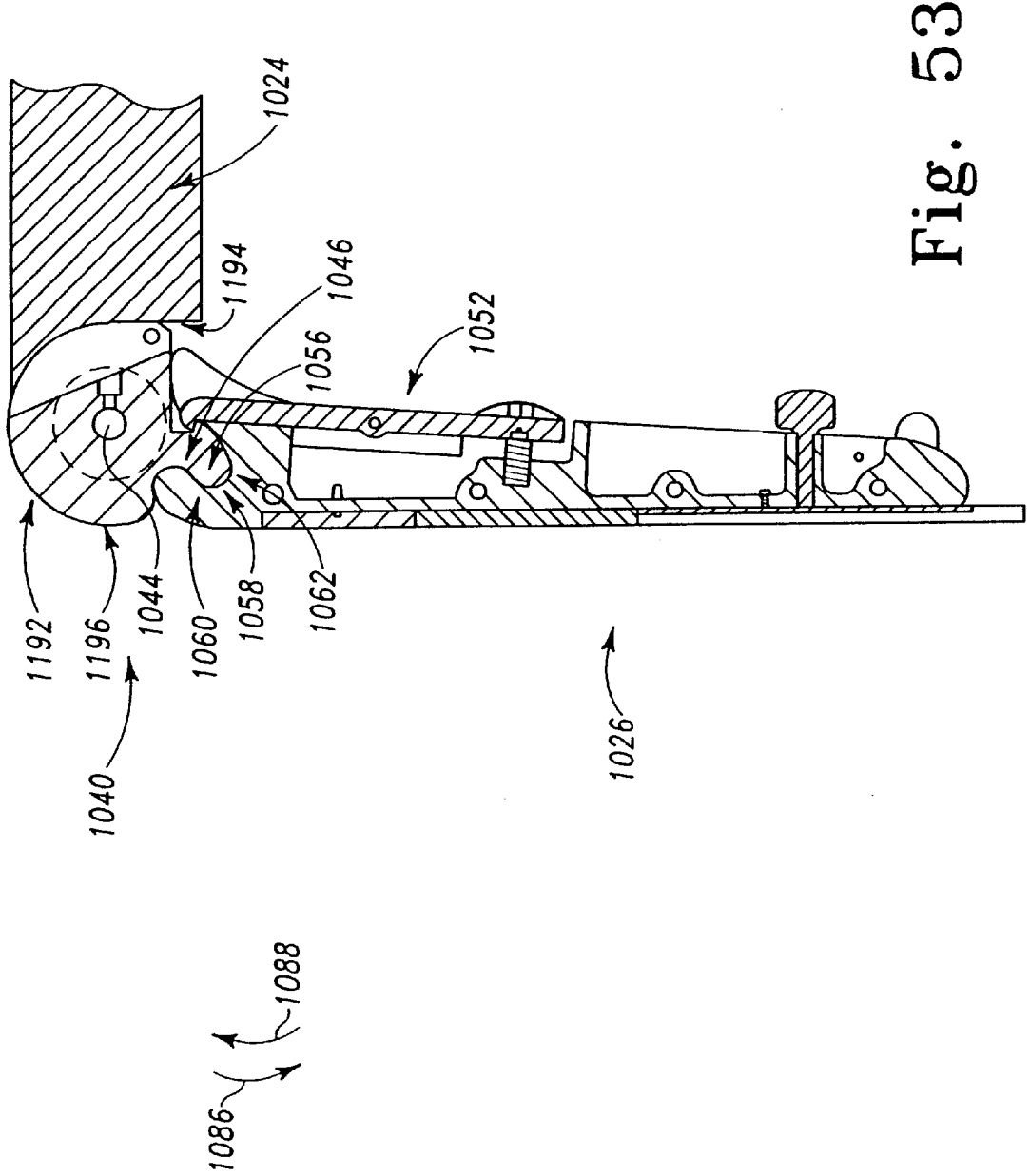
FIG. 53 is a cross-sectional view similar to FIG. 52 showing the lower leg support section of the surgical table apparatus rotated downwardly 90 degrees relative to the upper leg support section.

Leg support section coupler 1040 is also configured to permit rotation of lower leg support section 1026 of tabletop 1016 relative to upper leg support section 1024 as shown in FIGS. 52–53. Leg section coupler 1040 permits a user to pivot lower leg support section 1026 relative to upper leg support section 1024 while lower leg support section 1026 is coupled to upper leg support section 1024. Lower leg support section 1026 is pivotable between a first or substantially coplanar position relative to the upper leg support section 1024 and a second position at a 90-degree angle relative to upper leg support section 1024.

The interlocking of first couplers 1046 and second couplers 1058 and the positive locking of retainers 1052 in recesses 1041 maintain lower leg support section 1026 coupled to upper leg support section 1024 when leg support section is substantially coplanar with upper leg support section 1024, as shown in FIG. 52, when lower leg support section 1026 is rotated 90 degrees relative to upper leg support section 1024, as shown in FIG. 53, and at positions therebetween. Interactive portions 1056 of first couplers 1046 are trapped or held in recessed or interactive portions 1062 of second couplers 1058 by interactive portions or lobes 1060 of second couplers 1058 and by retainers 1052. When lower leg support section 1026 is substantially coplanar with upper leg support section 1024, the interlocking of interactive portions 1056 and interactive portions 1060, 1062 and the abutment of stops 1054 against abutment surfaces 1055 maintain the substantially coplanar position of lower leg support section 1026 relative to upper leg support section 1024 and retainer 1052 locks lower leg support section 1026 to upper leg support section 1024. When lower leg support section 1026 is rotated downward 90 degrees relative to upper leg support section 1024 due to the rotation of pivot members 1196, the holding of interactive portions 1056 by interactive portions 1060 and retainers 1052 maintain the position of lower leg support section 1026 relative to pivot member 1196.

Referring to FIG. 52, to uncouple lower leg support section 1026 from upper leg support section 1024, a caregiver presses upwardly in direction 1122 on handle end 1098 of lever 1092 to move retainer 1052 from the locked position to the unlocked position. In response to the force applied by the caregiver, lever 1092 rotates about fulcrum 1102 in clockwise direction 1103 so that latch end 1100 of lever 1092 is removed from recess 1041 of first coupler 1046. Once latch end 1100 of lever 1092 is removed from recess 1041 of first coupler 1046, the caregiver rotates lower leg support section 1026 in clockwise direction 1088 relative to upper leg support section 1024 such that the interlocking surfaces of first coupler 1046 and second coupler 1058 are spaced apart except for surface 1061 of second coupler 1058 which is positioned in pocket 1048. Once the interlocking surfaces of first coupler 1046 and second coupler 1058 are spaced apart, lower leg support section 1026 is lifted such that surface 1061 of second coupler 1058 is removed from pocket 1048. When surface 1061 of second coupler 1058 is removed from pocket 1048, the caregiver can remove lower leg support section 1026 from upper leg support section 1024.

Figure 54:
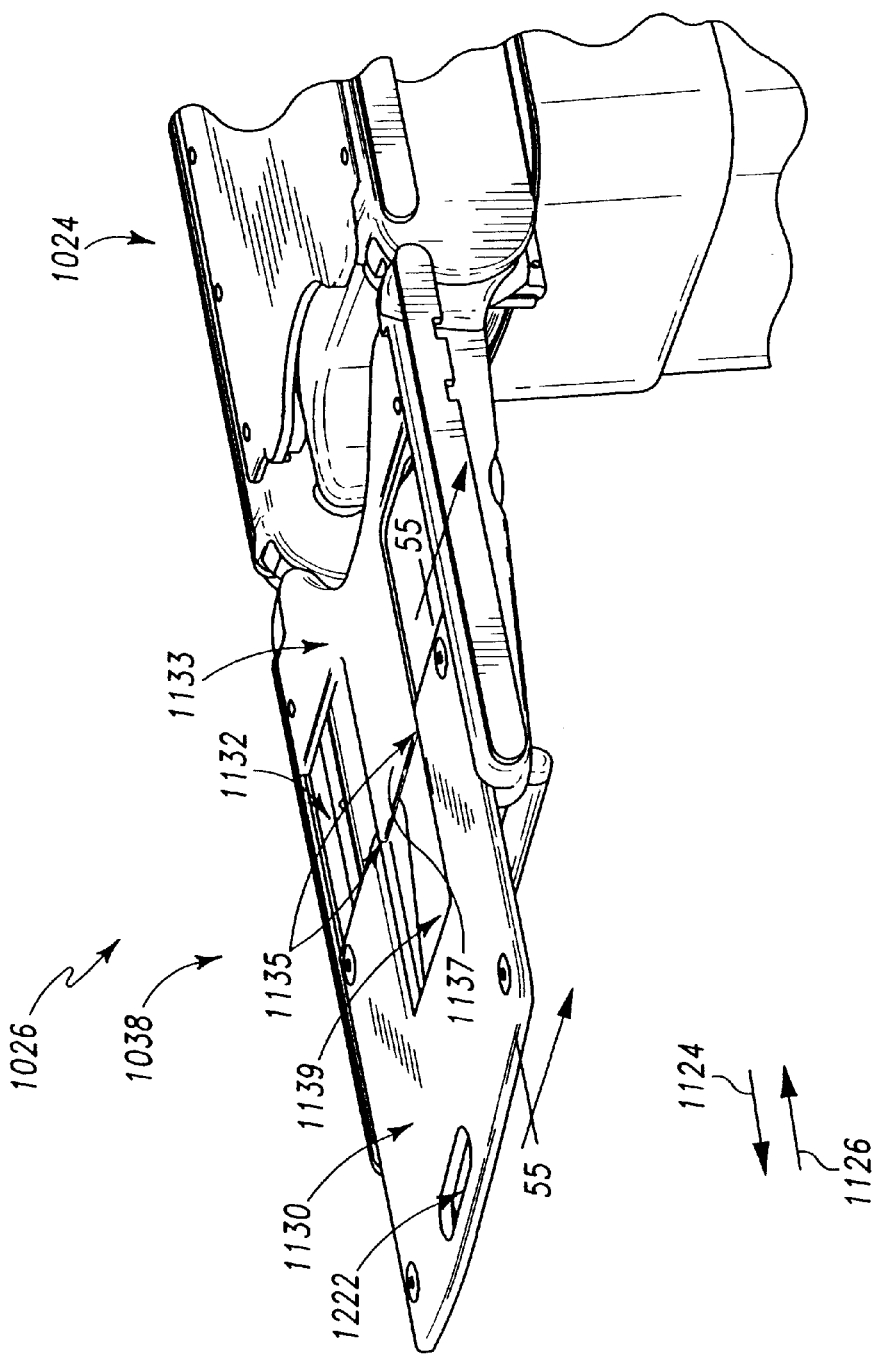
FIG. 54 is a perspective view of the lower leg support section of the tabletop of FIG. 47 showing the lower leg support section including movable and fixed leg support plates, the movable leg support plate having a handle to assist in moving the movable leg support plate relative to the remainder of the lower leg support section.

As previously mentioned and shown in FIG. 54, leg support plate 1038 of lower leg support section 1026 is an extendable support which allows the overall length of lower leg support section 1026 and tabletop 1016 to be extended or retracted. Support plate 1038 of lower leg support section 1026 includes a fixed support plate 1133 and movable leg support plate 1130. To increase the length of leg support plate 1038, movable leg support plate 1130 is pulled away from fixed support plate 1133 in direction 1124. To decrease the length of leg support plate 1038, movable leg support plate 1130 is pushed toward fixed support plate 1133 in direction 1126.

A handle 1222 is provided for a caregiver to grasp to assist in moving leg support plate 1130 relative to leg support plate 1133 in directions 1124, 1126. Movable leg support plate 1130 is configured to be received by spaced-apart guide tracks or channels 1132 formed in a portion of leg section frame 1027. Guide tracks 1132 facilitate the movement of movable leg support plate 1130 in directions 1124 and 1126. In alternative embodiments, the guide tracks may be coated with a low friction material or ball bearings may be interposed between the guide rails and the movable support plate.

The configurations of movable leg support 1130 and fixed leg support 1133 are configured so that movable leg support 1130 and fixed leg support 1133 provide a contiguous support surface as leg support 1130 is moved in directions 1124, 1126. As shown in FIG. 54, fixed support plate 1133 includes a central tab 1137 which is received in a recess 1139 formed in movable leg support 1130. Movable leg support 1130 and fixed leg support 1133 are moveably joined on tracks or joints 1135. Joints 1135, in one embodiment, are lap joints. In alternative embodiments, the joints are tongue and groove joints or additional suitable joints.

A leg extension coupler or position holder 1042 is provided to fix the position of movable leg support 1130. Leg extension coupler 1042 interacts with movable leg support plate 1130 to fix the position of leg support plate 1130. As shown in FIG. 54, leg support plate 1130 slides on guide tracks 1132 in directions 1124, 1126 to allow the overall length of lower leg support section 1026 and surgical table apparatus 1000 to be altered as desired. Leg extension coupler 1042 is configured to fix the position of leg support plate 1130 when it is not being moved between the various positions.

In the illustrated preferred embodiment, leg extension coupler 1042 is a torque-limited bolt 1134. If too much torque is applied to a coupler when the coupler is tightened, a caregiver may not be able to loosen the coupler later. Thus, torque-limited bolt 1134 is provided so that too much torque may not be applied that may otherwise be difficult to overcome. Torque-limited bolt 1134 is substantially identical to torque-limited bolt 134 of the first embodiment of the present disclosure discussed above in conjunction with FIGS. 8 and 9. According to alternative embodiments of the present disclosure, non-torque-limited couplers are provided.

Figure 55:
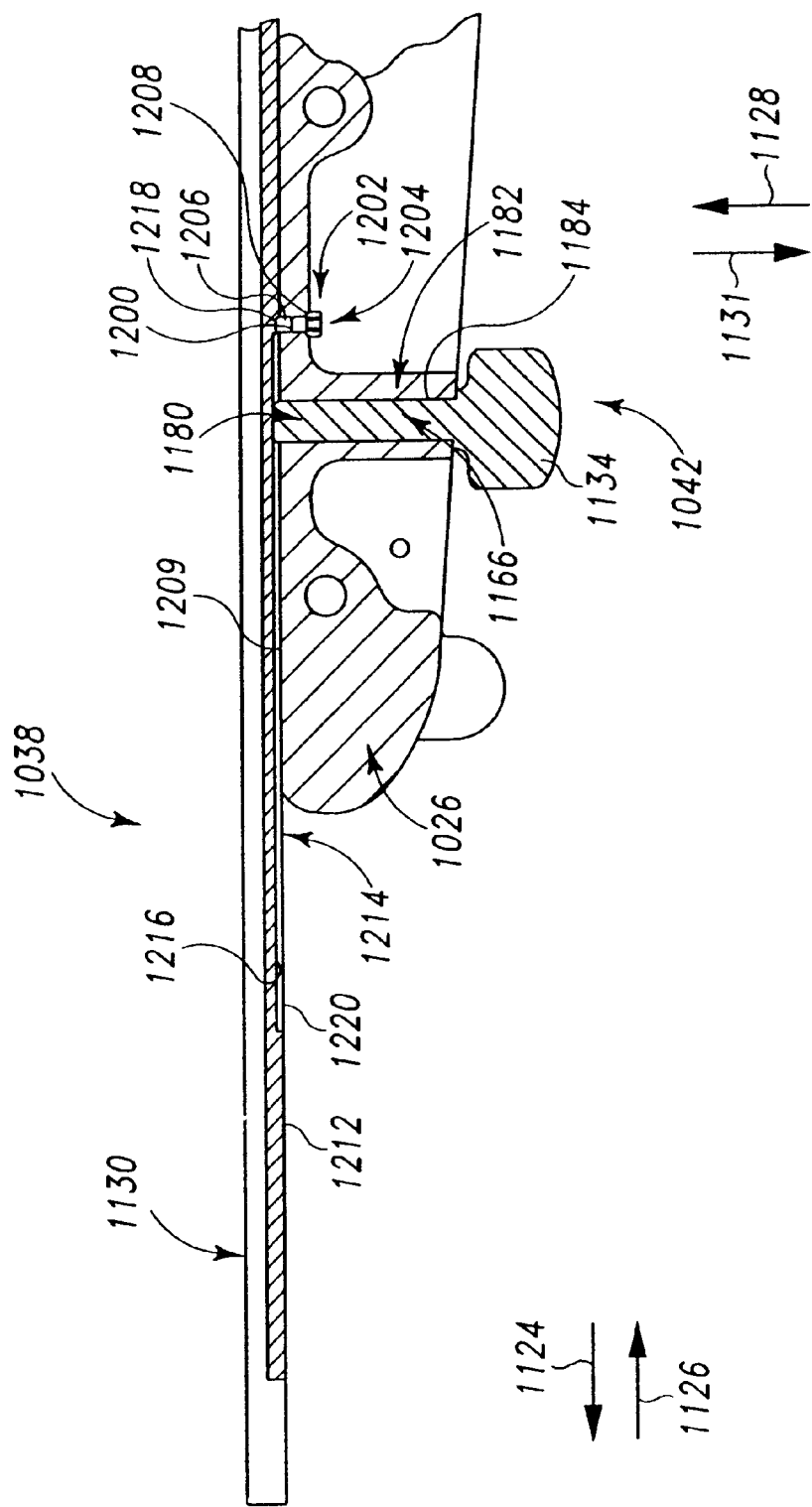
FIG. 55 is a cross-sectional view taken along line 55—55 of FIG. 54 showing a leg extension coupler or position holder which fixes the position of the movable leg support plate and a limit or stop which limits the range of movement of the movable leg support plate.

Torque-limited bolt 1134 threadably engages a threaded bore 1182 of lower leg support section 1026, as shown in FIG. 55. Torque-limited bolt 1134 includes a threaded section 1166 which is longer than the length of a threaded cylindrical wall 1184 which defines threaded bore 1182 so that when torque-limited bolt 1134 is fully advanced into threaded bore 1182 in a direction 1128, a second end 1180 of threaded section 1166 protrudes past threaded bore 1182 and abuts leg support plate 1130.

When second end 1180 of torque-limited bolt 1134 protrudes from threaded bore 1182 and abuts a lower surface 1212 of leg support plate 1130, second end 1180 of torque-limited bolt 1134 fixes the position of leg support plate 1130 relative to guide tracks 1132. When second end 1180 of torque-limited bolt 1134 is backed out in a direction 1131 enough to relieve enough force between bolt 1134 and leg support plate 1130, for example, when the bolt 1134 is spaced apart from leg support plate 1130, leg support plate 1130 may slide horizontally within the guide tracks 1132 of lower leg support section 1026 in directions 1124, 1086.

The extent that leg support plate 1130 is movable in direction 1124 is constrained by a stop 1200. Referring to FIG. 54, stop or limit 1200 is a set screw 1202 having a threaded portion 1204 and a head portion 1206. Threaded portion 1204 is threaded into a threaded opening 1208 in lower leg support section 1026 such that when screw 1202 is fully advanced in threaded opening 1208 a portion of threaded portion 1204 of screw 1202 extends above a top surface 1209 of leg support frame 1026. Screw 1202 is threaded into threaded opening 1208 by engaging a recess 1210 in head portion 1206 configured to receive a tool with a tool (not shown). In alternative embodiments, the stop is a pin received in an opening in the leg support frame or is a detent or protrusion extending above the top surface of the leg support frame.

A lower surface 1212 of leg support plate 1130 generally slides upon top surface 1209 leg support frame 1027 as leg support plate 1130 is moved relative to leg section frame 1027. A recess or channel 1214 is located in leg support plate 1130 to receive stop 1200 when stop 1200 is fully advanced in threaded opening 1208. Recess 1214 includes a bottom surface 1216 and a first stop surface 1218. As leg support plate 1130 is moved in direction 1124, the separation between stop 1200 and stop surface 1218 of recess 1214 decreases. Leg support plate 1130 is prevented from moving further in direction 1124 when stop 1200 contacts stop surface 1218. A second stop surface 1220 is also provided to limit the range of movement of leg support plate 1130 when leg support plate 1130 is moved in direction 1126.

Head support section 1018 of tabletop 1016 is removably coupled to upper torso support section 1020. According to alternate embodiments of the present disclosure, the head support section is not removable relative to the upper torso support section and is otherwise coupled to the upper torso support section of the frame.

Head support plate 1010 is positionable relative to upper torso support section 1020 through the operation of a first position holder 2200 and a second position holder 2600. As explained in more detail below, first position holder 2200 and second position holder 2600 function independently of each other and permit head support plate 1010 and hence the head of the patient to be positioned in a variety of positions.

In the illustrated embodiment, first position holder 2200 permits adjustment of the elevation of head support plate 1010 relative to upper torso support section 1020 within a first position range. Further, within a second position range, first position holder 2200 permits adjustment of both the elevation and angle of head support plate 1010 relative to upper torso support section 1020. The first and second position ranges are preferably exclusive. In the preferred embodiment, the first position range includes all positions wherein head support plate 1010 is between 3.0 inches above to 3.0 inches below upper torso support section 1020.

Second position holder 2600 adjusts the angle of head support plate 1010 relative to upper torso support section 1020 when within the first and second position ranges. In the preferred embodiment, second position holder 2600 permits adjustment of the angle of head support plate 1010 through a 30° range.

Figure 56:
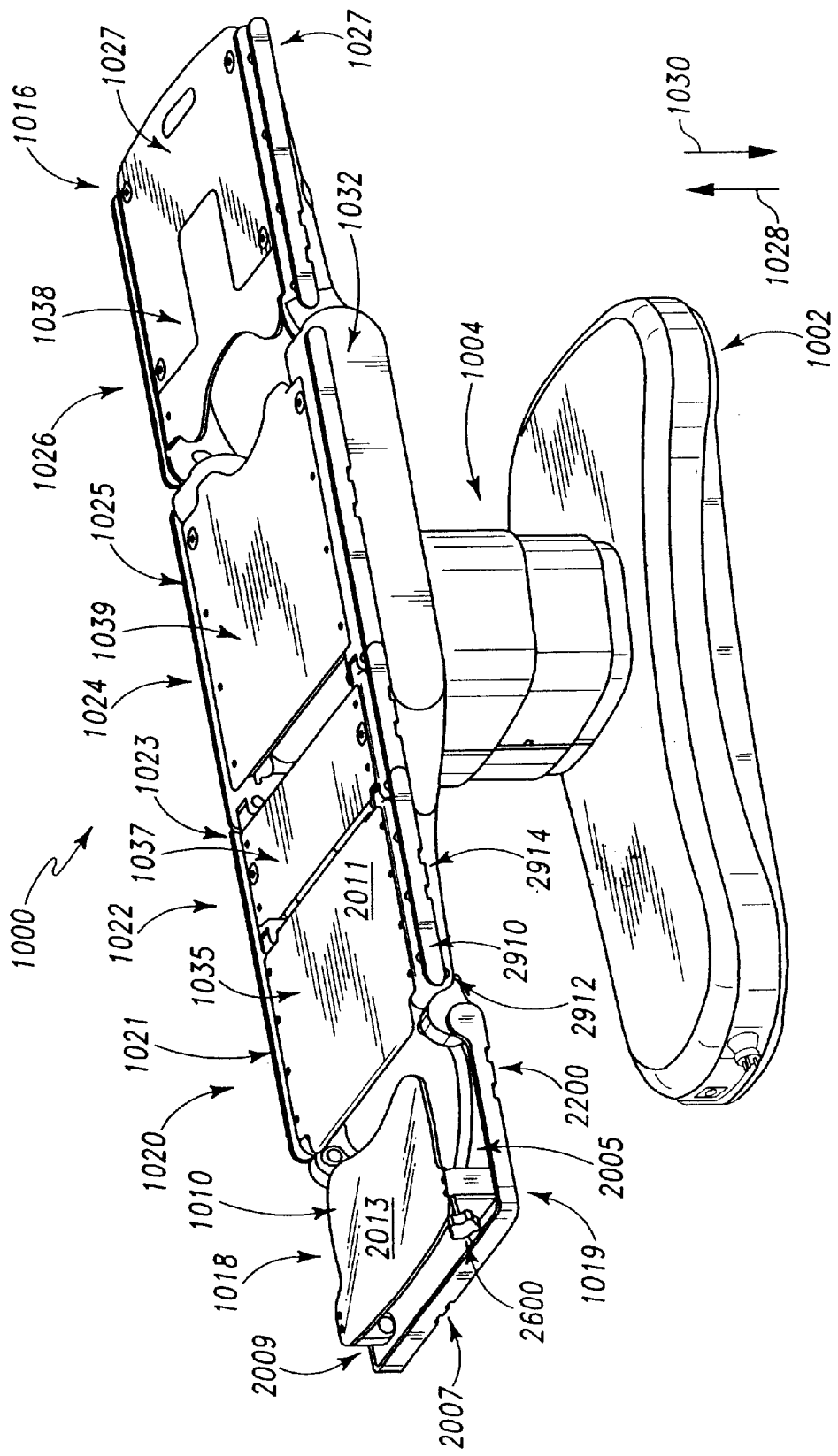
FIG. 56 is another perspective view of the surgical table apparatus of FIG. 47 showing the head support section of the surgical table apparatus.
Figure 57:
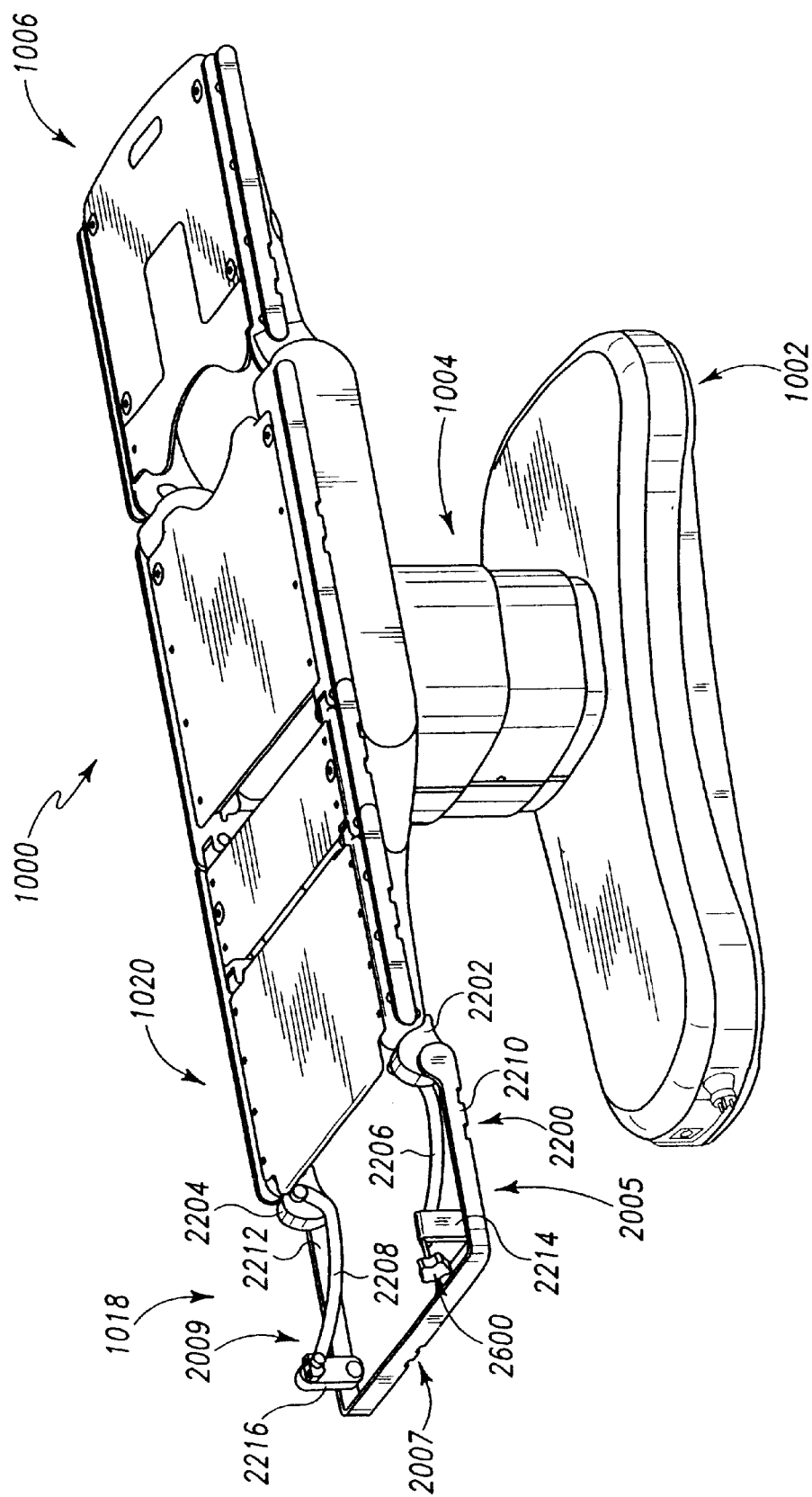
FIG. 57 is a view similar to FIG. 56, with a head support plate of the head support section removed, showing the components of a head section frame or member support.
Figure 58:
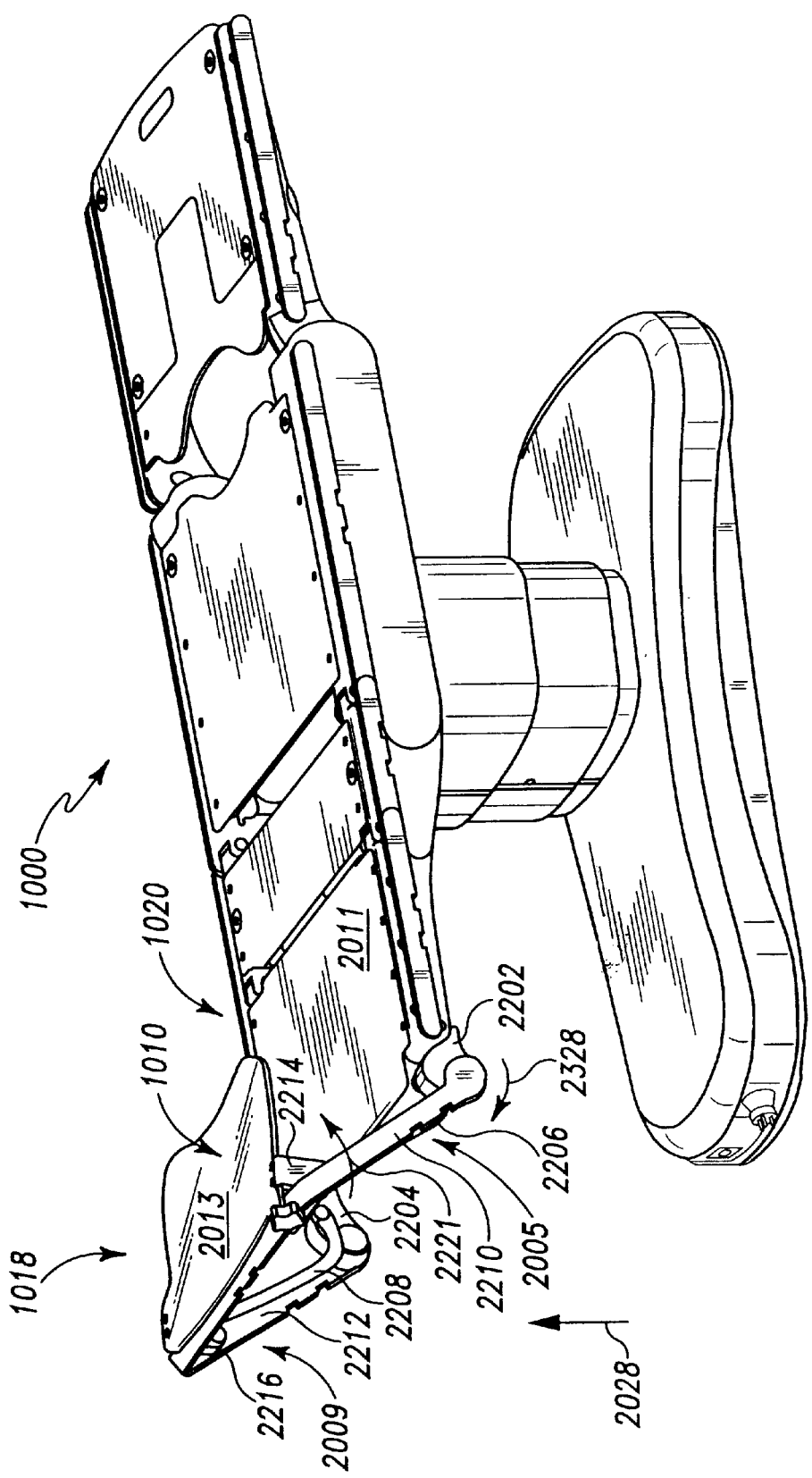
FIG. 58 is a view similar to FIG. 56 showing the head support section in an elevated position and the head support section being rotated relative to the upper torso support section with a head support surface of the head support section parallel and raised relative to a body support surface of the upper torso support section.
Figure 59:
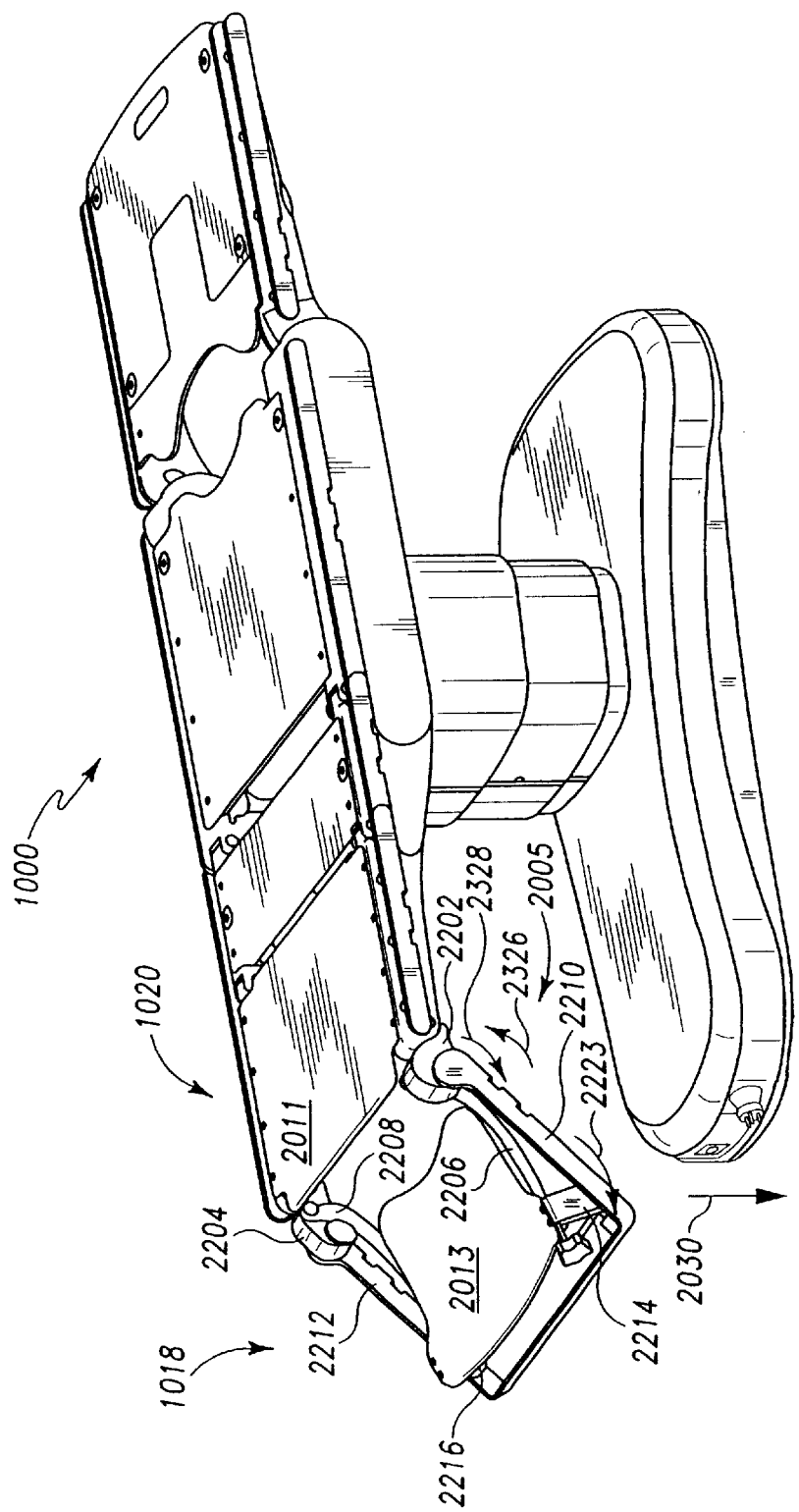
FIG. 59 is a view similar to FIG. 56 showing the head support section in a lowered position, the head support section being rotated relative to the upper torso support section, and the head support surface of the head support section being substantially parallel and lowered relative to the body support surface of the upper torso support section.
Figure 60:
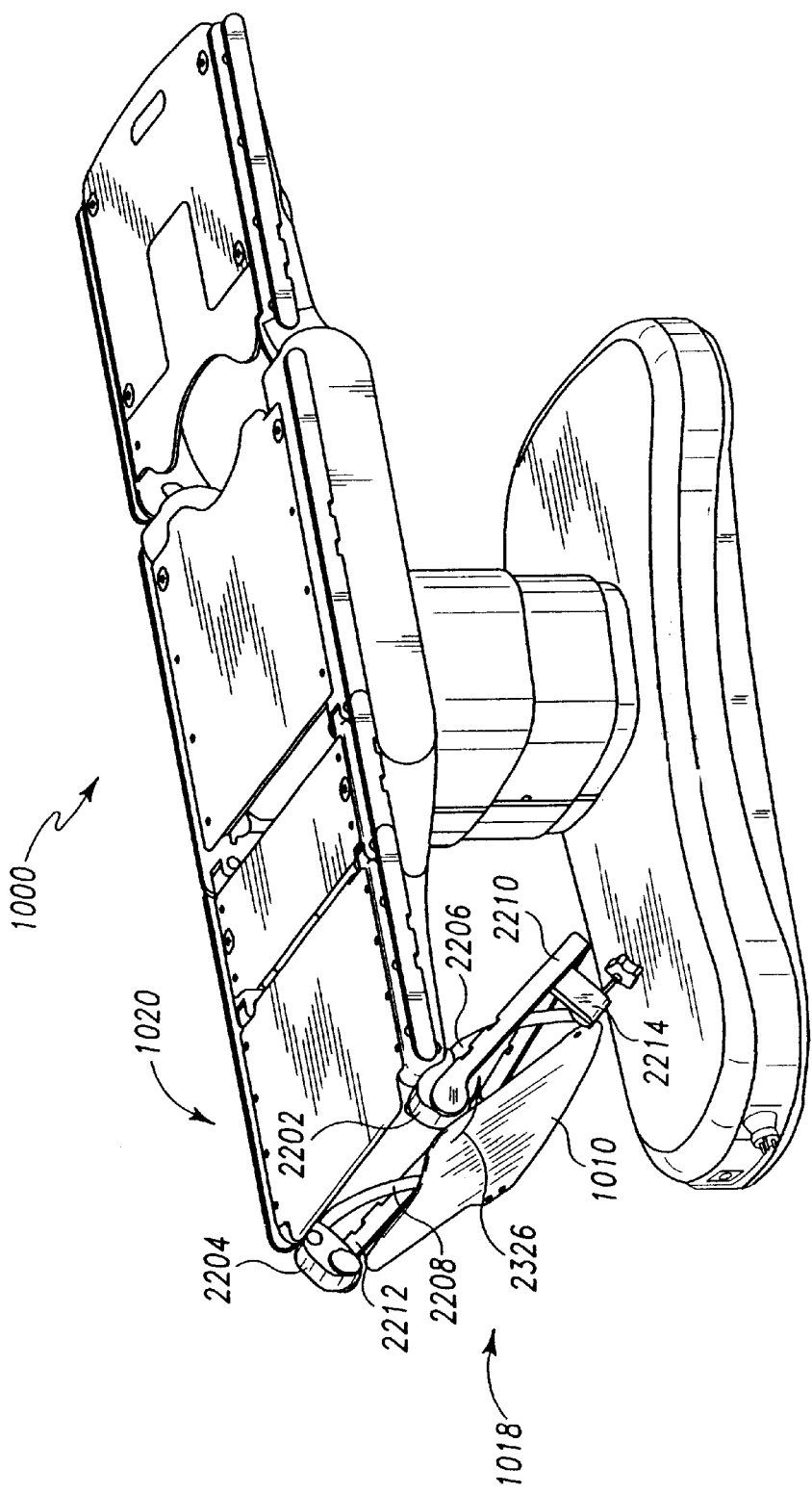
FIG. 60 is a view similar to FIG. 56 showing the head support section rotated relative to the upper torso support section and positioned in a stored or tucked position.

FIGS. 56 and 58–60 illustrate four exemplary positions of head support plate 1010 permitted by first position holder 2200. Referring to FIG. 56, a top surface 2013 of head support plate 1010 is substantially co-planar with a top surface 2011 of upper torso support section 1020. Referring to FIG. 58, top surface 2013 of head support plate 1010 is substantially parallel to top surface 2011 of upper torso support 1020 and head support plate 1010 is elevated relative to upper torso support section 1020. Referring to FIG. 59, top surface 2013 of head support plate 1010 is substantially parallel to top surface 2011 of upper torso support 1020 and head support plate 1010 is lowered relative to upper torso support section 1020. Referring to FIG. 60, head support plate 1010 is stored or tucked underneath upper torso support section 1020 for storage of head support section 1018.

The positions shown in FIGS. 56, 58, and 59 are exemplary positions within the first position range of head support plate 1010 because only the elevation of head support plate 1010 is substantially altered by first position holder 2200. The stored position shown in FIG. 60 is an exemplary position within the second position range of head support plate 1010 because both the elevation and angle of head support plate 1010 is substantially altered.

In the illustrative embodiment, a four-bar linkage 2007 is provided having a first link set 2005, and a second link set 2009. Each link set 2005, 2009 is a closed-loop linkage consisting of four links. Link sets 2005, 2009 are configured to substantially maintain a parallel relationship between head support plate 1010 and upper torso support section 1020 as head support plate 1010 is positioned at a variety of positions within the first position range, such as the exemplary positions shown in FIGS. 56, 58, and 59. Link sets 2005, 2009 are further configured to position head support plate 1010 at a variety of substantially non-parallel positions within the second position range, such as in the stored or tucked position shown in FIG. 60.

First position holder 2200 is configured to maintain the position of head support plate 1010 by maintaining the orientation of linkage 2007. First position holder 2200 is movable between a locked position and an unlocked position.

Figure 73:
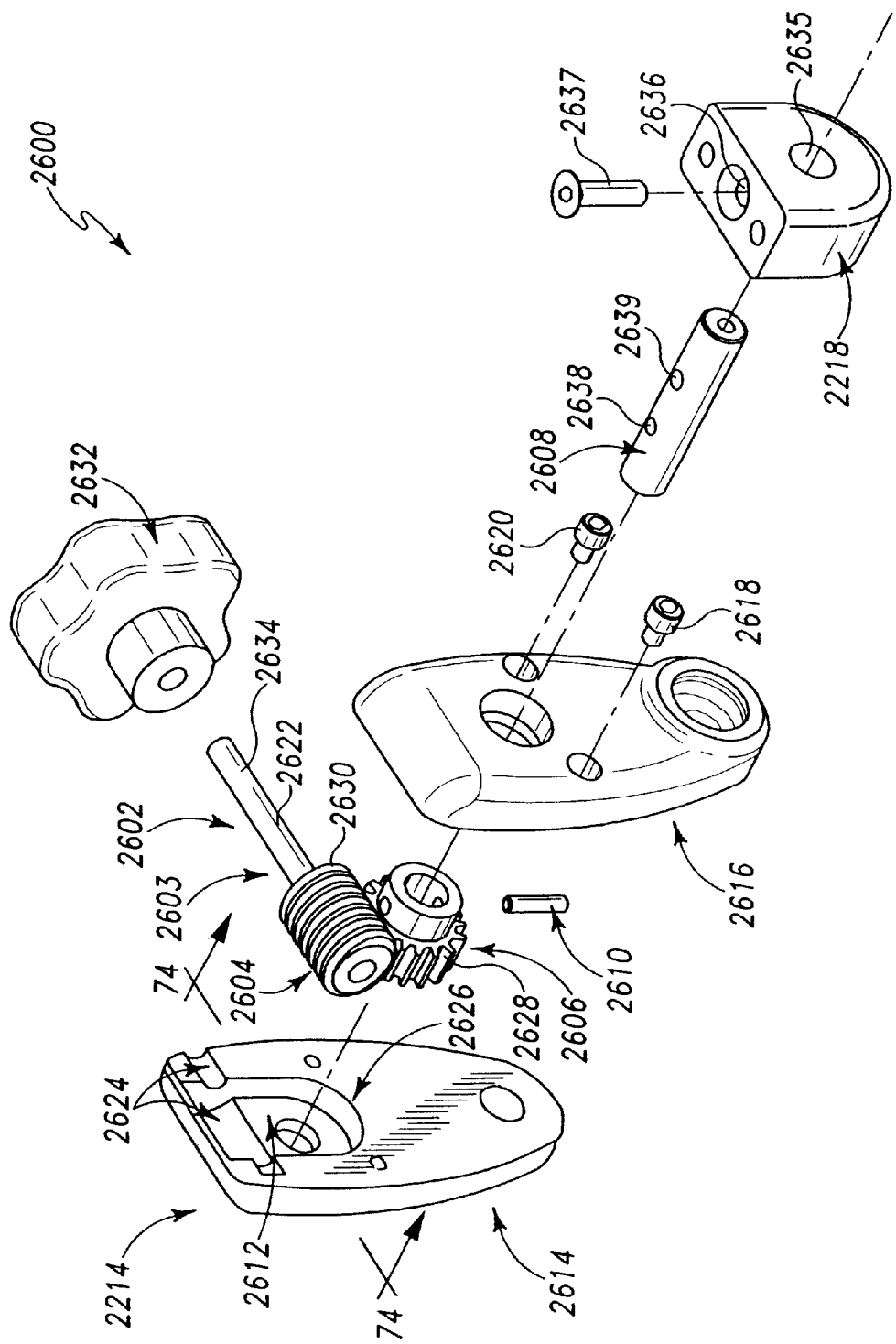
FIG. 73 is an exploded, perspective view of another position holder of the head support section.

In the illustrative embodiment, second position holder 2600 includes a gear set 2603, shown in FIGS. 73–75, which permits adjustment the angular orientation of head support plate 1010 relative to linkage 2007. Head support plate 1010 is positionable by second position holder 2600 such that head support plate 1010 is either substantially parallel to upper torso support section 1020 or tilted relative to upper torso support section 1020.

Figure 76:
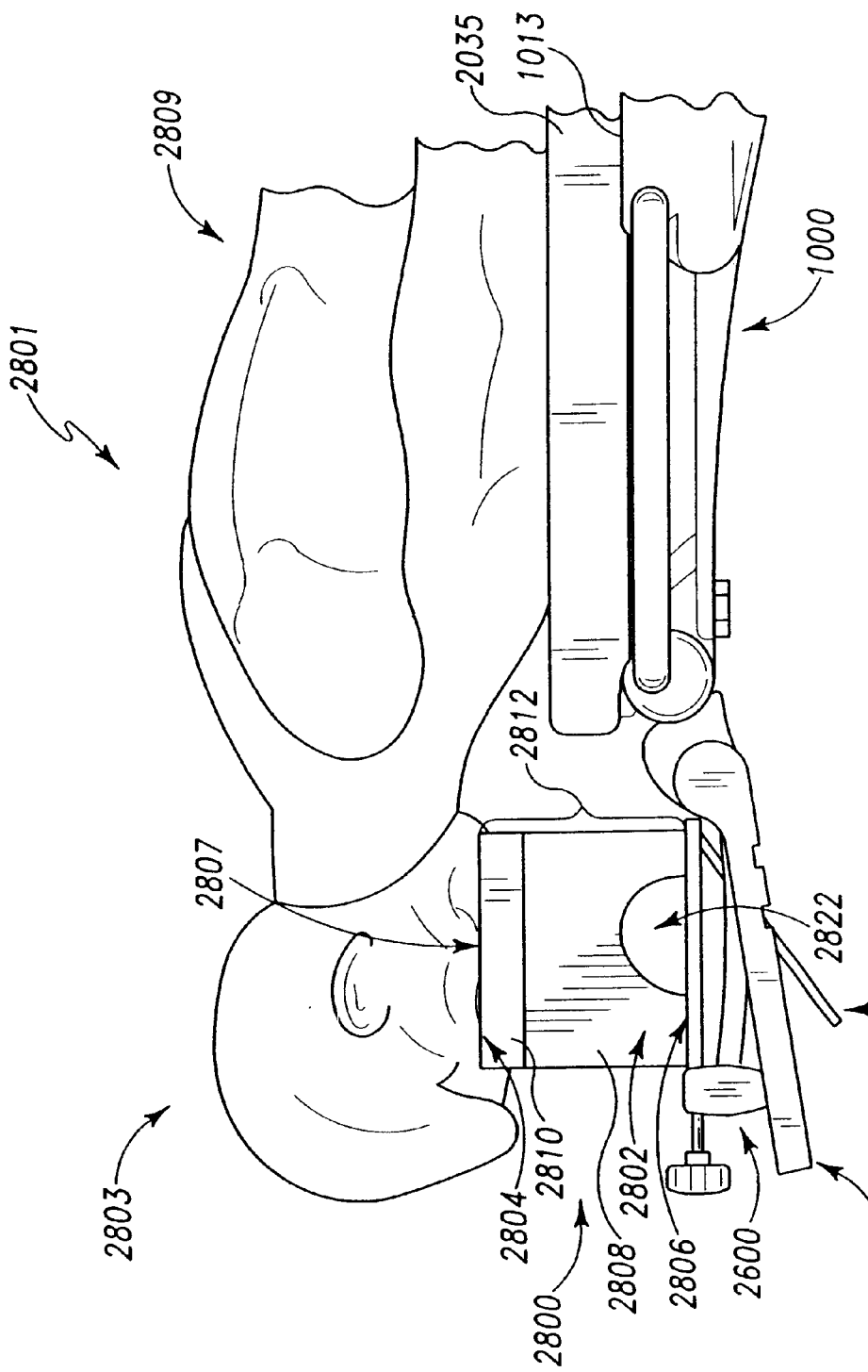
FIG. 76 is a side elevation view of a head support section of a surgical table apparatus in accordance with the present disclosure having a head support pad positioned thereon, the head support section having an at least partially transparent head support plate or member.

Head support section 1018 is further configured to work with a head support 2800, see FIG. 76. Head support 2800 is configured to receive the head of the patient when the patient is in the prone position on table apparatus 1000 and to allow access to the face of the patient.

Figure 61:
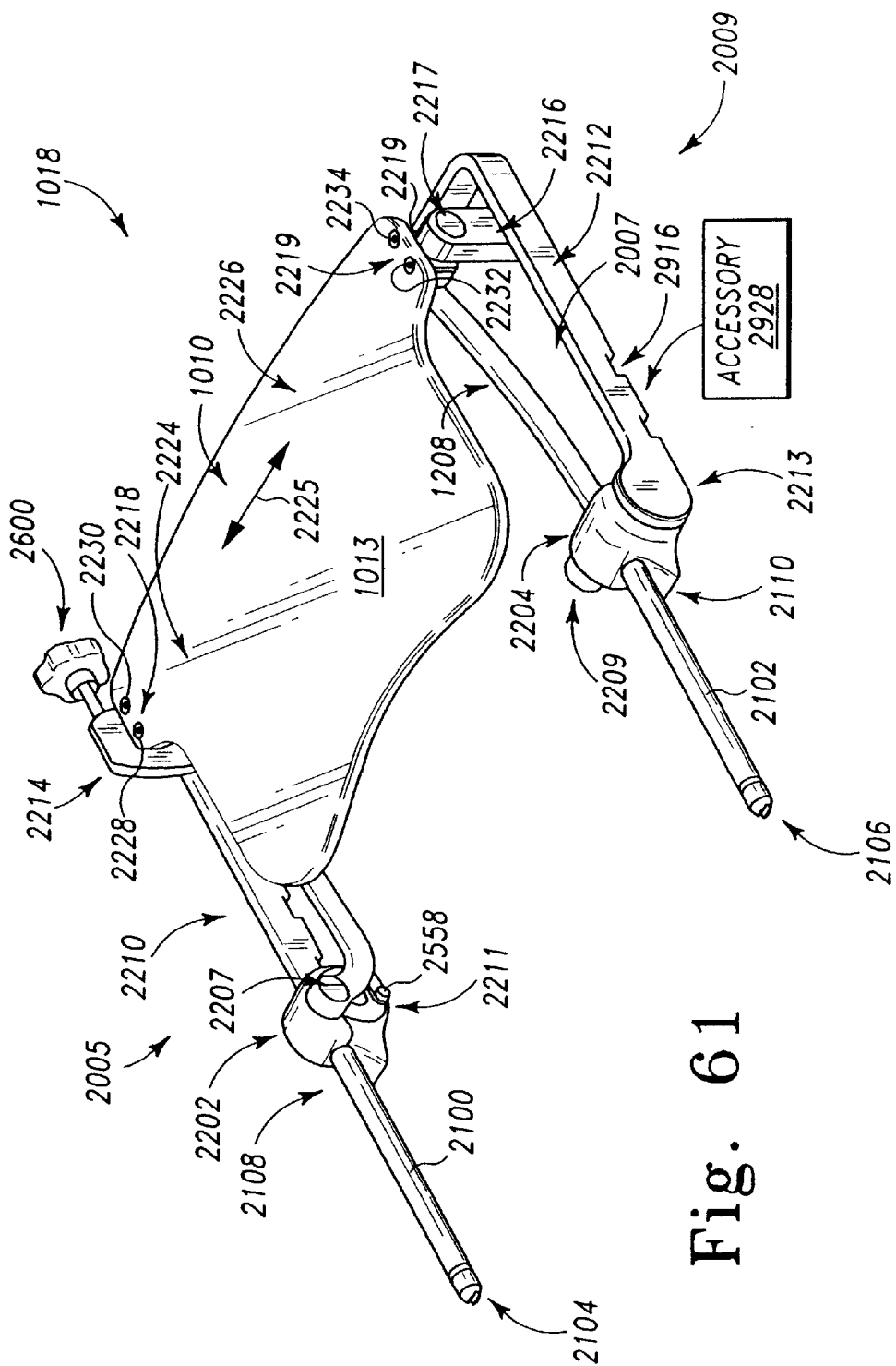
FIG. 61 is a perspective view of the head support section of the support surface of FIG. 56 showing the head support section including a set of attachment rods extending to the lower left, a four-bar linkage coupled to the attachment rods, a head support plate coupled to the four-bar linkage.
Figure 62:
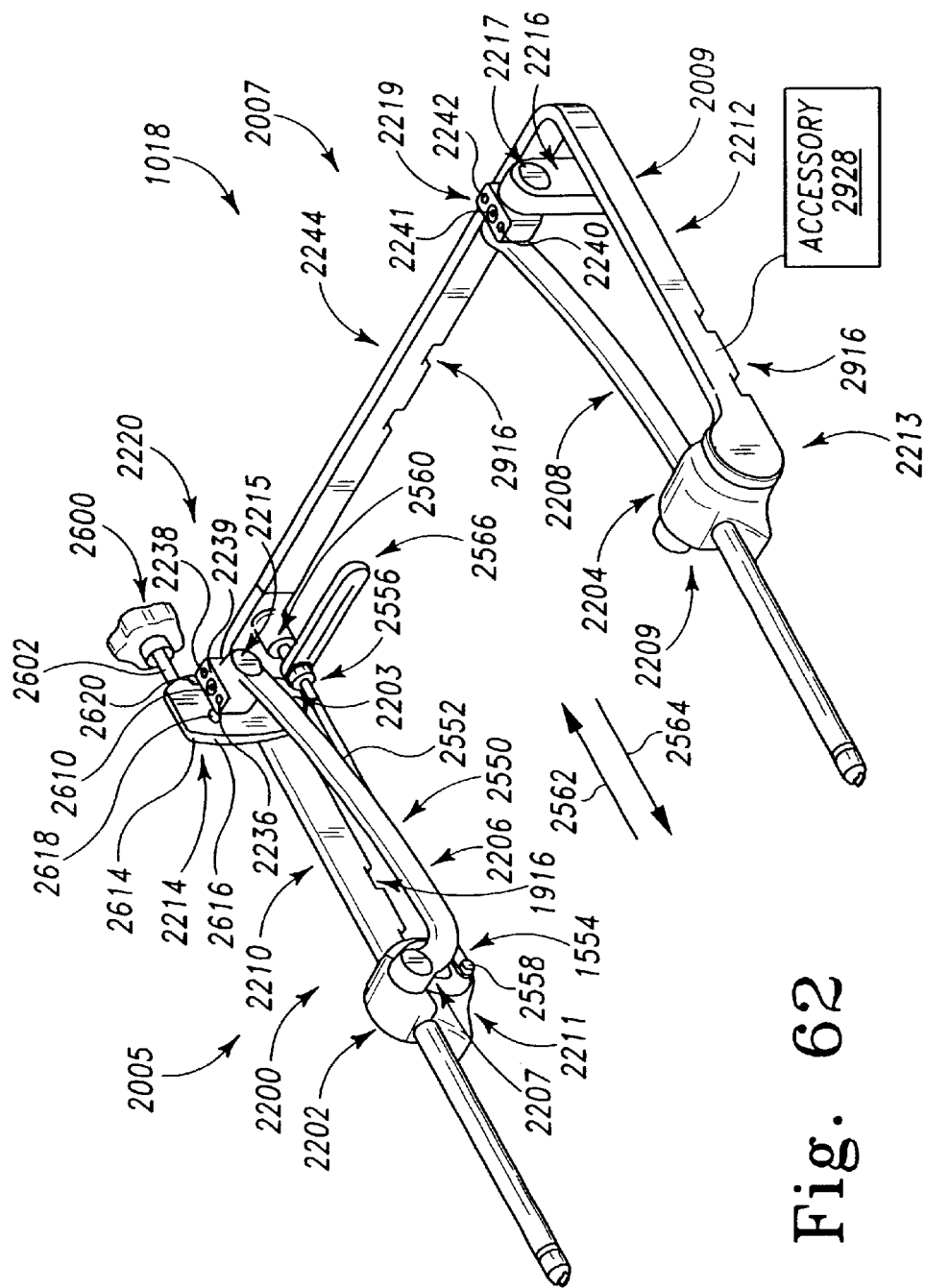
FIG. 62 is a view similar to FIG. 61, with the head support plate removed.

Referring to FIGS. 61 and 62, head support section 1018 includes first and second attachment rods or couplers 2100, 2102 that couple linkage 2007 to upper torso support frame 1021 of frame 1032. First ends 2104, 2106 of attachment rods 2100, 2102 are received by couplers (not shown) in upper torso support frame 1021 of frame 1032 of tabletop 1016 to couple head support section 1018 to upper torso support section 1020. Second ends 2108, 2110 of attachment rods 2100, 2102 are coupled to linkage 2007.

First and second link sets 2005, 2009 include first links 2202, 2204 that are coupled to second ends 2108, 2110 of attachment rods 2100, 2102, respectively. First and second link sets 2005, 2009 further include second links 2206, 2208 that are pivotally coupled to first links 2202, 2204 at joints 2207, 2209, and third links 2214, 2216 that are pivotally coupled to second links 2206, 2208 at joints 2215, 2217. First and second link sets 2005, 2009 further include fourth links 2210, 2212 that are pivotally coupled to third links 2214, 2216 at joints 2203, 2205 and to first links 2202, 2204 at joints 2211, 2213.

Head support section 1018 includes a pair of plate mounts 2218, 2219 that couple head support plate 1010 to linkage 2007 at first ends 2220, 2222 of second links 2206, 2208, respectively. In the illustrative embodiment, plate mounts 2218, 2219 include apertures 2236, 2238, 2240, 2242, which are configured to receive fasteners 2228, 2230, 2232, 2234. Fasteners 2228, 2230, 2232, 2234 couple first and second ends 2224, 2226 of head support plate 1010 to plate mounts 1218, 1219. Apertures 2236, 2238 are formed in a top surface 2239 of mount 2218 and apertures 2240, 2242 are formed in a top surface 2241 of mount 2219. In alternative embodiments, the head support plate is coupled to the mounts by welding or the use of adhesives or is integrally formed with the mounts.

To coordinate movement of first link set 2005 and second link set 2009, fourth links 2210, 2212 are coupled together by a stabilizer or cross member 2244 as shown in FIG. 62. When fourth link 2210 of first link set 2005 is moved by a caregiver, fourth link 2212 of second link set 2009 moves therewith. Cross member 2244 prevents first end 2224 of head support plate 1010 from being higher or lower than second end 2226 of head support plate 1010. As such, head support plate 1010 does not tilt along a transverse direction 2225, see FIG. 61, as head support plate 1010 is moved.

Head support plate 1010 remains substantially parallel to upper torso support section 1020 as head support plate 1010 is moved within the first position range due to the configuration of first and second link sets 2005, 2009. In the illustrative embodiment, the interconnection of links 2202, 2204, 2206, 2208, 2210, 2212, 2214, 2216 of link sets 2005, 2009 are configured such that joints 2203, 2215 of first link set 2205 are substantially vertically aligned and joints 2205, 2217 of second link set 2009 are substantially vertically aligned.

This configuration maintains third links 2214, 2216 in a substantially vertical orientation so that head support plate 1010 remains substantially horizontal. For example, as head support plate 1010 is moved to the lowered position shown in FIG. 59, fourth links 2210, 2212 rotate downward in a direction 2326 and third links 2214, 2216 rotate relative to fourth links 2210, 2212 in a direction 2223 substantially opposite direction 2326 due to the connection of third links 2214, 2216 to second links 2206, 2208. This relative movement maintains third links 2214, 2216 in the substantially vertical orientation as fourth and second links 2210, 2212, 2206, 2208 rotate down. Thus, the elevation of head support plate 2010 is lowered, while the angle of head support plate 2010 remains substantially constant.

In another example, as head support plate 1010 is moved to the elevated position shown in FIG. 58, fourth links 2210, 2212 rotate upward in a direction 2328 and third links 2212, 2214 rotate relative to fourth links 2210, 2212 in a direction 2221 opposite direction 2328 due to the connection of third links 2214, 2216 to second links 2206, 2208. As such, the interconnections of linkage 2007, counters the rotation of fourth links 2210, 2212 to maintain third links 2214, 2216 in a substantially vertical orientation, such that joints 2203, 2215 and joints 2205, 2217 remain substantially vertically aligned.

Joints 2203, 2205, 2207, 2209, 2211, 2213, 2215, 2217 of linkage 2007 are configured to permit rotation between the corresponding links 2202, 2204, 2206, 2208, 2210, 2212, 2214, 2216. The position of first position holder 2200 and hence the orientation of linkage 2007 is maintained by locking the orientation of two links selected from links 2202, 2204, 2206, 2208, 2210, 2212, 2214, 2216 to bind the remainder of linkage 2007. Because first and second link sets 2005, 2009 of linkage 2007 are each closed loop linkages coupled together by cross member 2244, the locking of one of joints 2203, 2205, 2207, 2209, 2211, 2213, 2215, 2217 binds or locks the overall linkage 2007.

Figure 63:
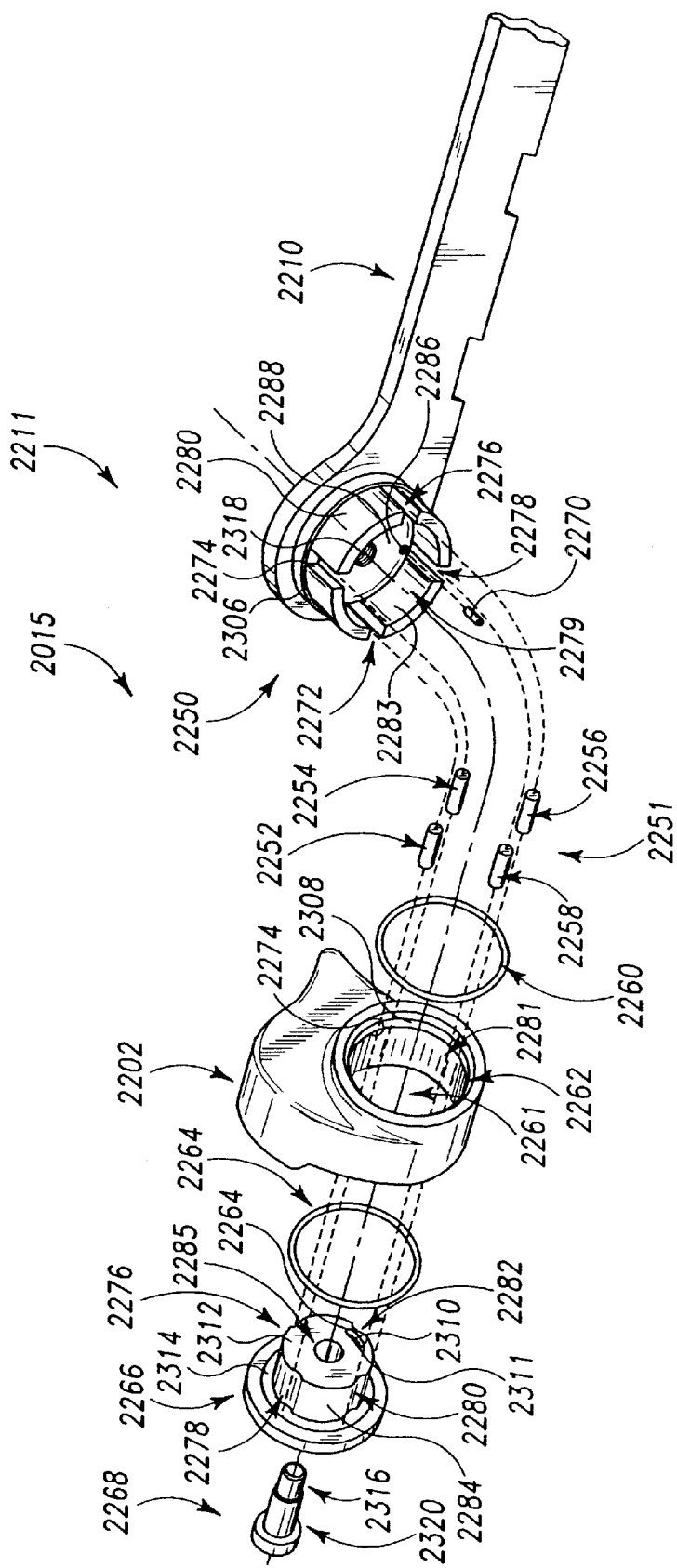
FIG. 63 is an exploded view of one of a joint of the four-bar linkage of FIGS. 61 and 62.

Referring to FIG. 63, position holder 2200 includes a support 2250 coupled to fourth link 2210, a first coupling or locking member 2251 having key members 2252, 2254, 2256, 2258, a first sealing ring 2260, second coupling or locking member 2262 defined on first link 2202, a second sealing ring 2264, a cam 2266, a fastener 2268, and a stop 2270 coupled to fourth link 2210. Support 2250 is received by an opening 2261 in first link 2202. Opening 2261 in first link 2202 is defined by surface 2281 which has a greater diameter than an outer diameter 2280 of support 2250. Further, support 2250 contains slots or openings 2272, 2274, 2276, 2278 which are sized to receive key members 2252, 2254, 2256, 2258.

Figure 64:
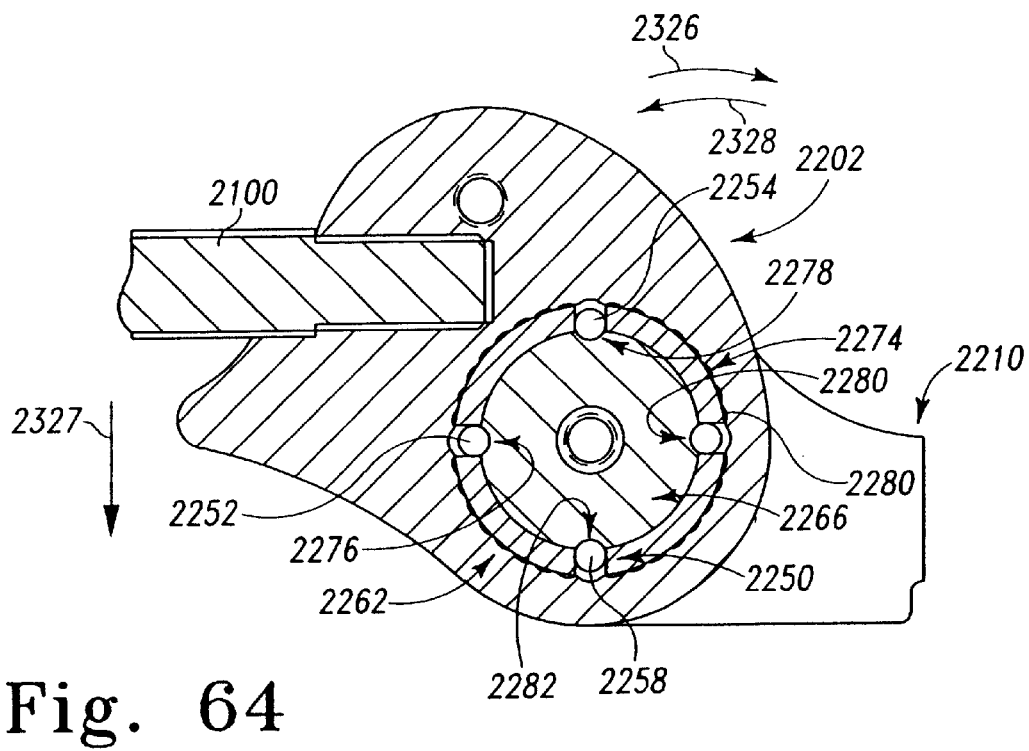
FIG. 64 is a cross-sectional view of the joint of FIG. 63 showing a position holder in an unlocked position.
Figure 65:
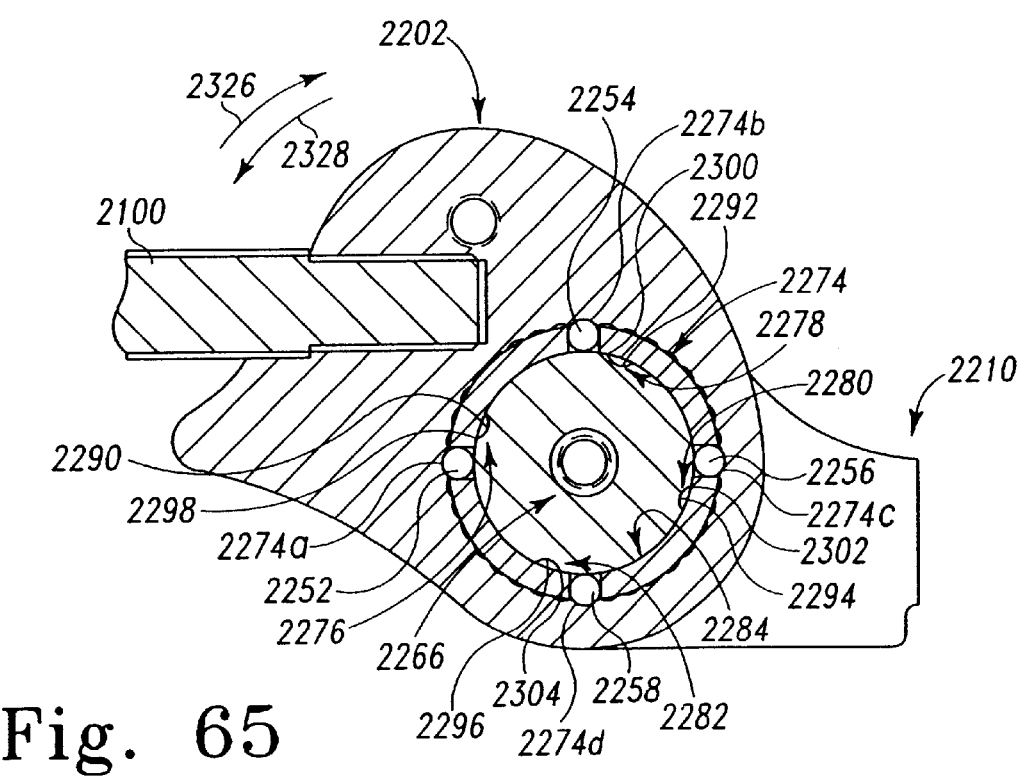
FIG. 65 is a view similar to FIG. 64 showing the position holder in a locked position.

Four key members 2252, 2254, 2256, 2258 are shown in FIGS. 63–65. According to alternative embodiments of the present disclosure, other quantities of key members are provided. For example, according to some embodiments, the locking joint contains only a single key member, two key members, three key members, or other additional numbers of key members.

Key members 2252, 2254, 2256, 2258 of first locking member 2251 interact with second locking member 2262 to lock the orientation of first link 2202 and fourth link 2210.

Second locking member 2262 is located in opening 2261 in first link 2202 and includes a plurality of indentations or keyways 2274 configured to receive first key members 2252, 2254, 2256, 2258. Keyways 2274 are equally spaced around inner diameter 2281. In a preferred embodiment, key members 2252, 2254, 2256, 2258 are cylindrical and keyways 2274 are curved such that the curvature of keyways 2274 are generally equal to the curvature of key members 2252, 2254, 2256, 2258. In alternate embodiments, the keyways are wedge-shaped or otherwise shaped and the keys have a corresponding wedge or otherwise shaped portions configured to be received by the keyways. The diameter of keys 2252, 2254, 2256, 2258 and corresponding keyways 2274 dictate the angular positions of fourth link 2210 relative to first link 2202. According to the preferred embodiment, fourth link 2210 is positionable in 10 degree increments relative to first link 2202.

First position holder 2200 is in a locked position when key members 2252, 2254, 2256, 2258 are positioned in keyways 2274, as shown in FIG. 65, and is in a unlocked position when key members 2252, 2254, 2256, 2258 are not positioned within keyways 2274 as shown in FIG. 64. Operation of cam 2266 moves key members 2252, 2254, 2256, 2258 into and out of keyways 2274.

Cam 2266 includes pockets 2276, 2278, 2280, 2282 configured to receive key members 2252, 2254, 2256, 2258, respectively. Pockets 2276, 2278, 2280, 2282, each include a first surface 2290, 2292, 2294, 2296 and a cam surface 2298, 2300, 2302, 2304, respectively. In the preferred embodiment, first surfaces 2290, 2292, 2294, 2296 are arcuate. When surfaces 2290, 2292, 2294, 2296 are aligned with slots 2272, 2274, 2276, 2278 in support 2250, pockets 2276, 2278, 2280, 2282 provide clearance for receipt of key members 2252, 2254, 2256, 2258 and position holder 2200 is in the unlocked position, see FIG. 64, so that fourth link 2210 is movable relative to first link 2202. When pockets 2276, 2278, 2280, 2282 are moved from the aligned position with slots 2272, 2274, 2276, 2278, key members 2252, 2254, 2256, 2258 are moved outward into contact with keyways 2274 and position holder 2200 is in locked position, see FIG. 65, so that fourth link 2210 is not movable relative to first link 2202.

First position holder 2200 is assembled in the following manner. Sealing ring 2260 is interposed between support 2250 and second locking member 2262. Support 2250 is inserted into opening 2261 in first link 2202 such that sealing ring 2260 contacts a surface 3306 on support 2250 and a surface 2308 on first link 2202. Sealing ring 2260 prevents the introduction of dirt and fluids into joint 2211. In the preferred embodiment, sealing ring 2260 further prevents the expulsion of lubrication (not shown) from the interior of locking joint 2211. First key members 2252, 2254, 2256, 2258 are then positioned within slots or openings 2272, 2274, 2276, 2278 of support 2250, respectively. Stop 2270 is then positioned within a recess 2286 in support 2250.

Sealing ring 2264 is interposed between first link 2202 and cam 2266 such that sealing ring 2264 contacts a surface 2314 on cam 2266 and a surface (not shown) on first link 2202. Sealing ring 2264 prevents the introduction of dirt and moisture into locking joint 2211. In the preferred embodiment, sealing ring 2264 further prevents the expulsion of lubrication (not shown) from the interior of locking joint 2211.

Cam 2266 is positioned within a recess 2279 of support 2250 defined by the surface 2283 so that stop 2270 is positioned within a recess 2310 formed in a front surface 2312 of cam 2266. Recess 2310 is elongated such that cam 2266 is rotatable relative to support 2250. However, the amount of rotation of cam 2266 relative to support 2250 is limited by the length of elongated recess 2310. As such, whenever stop 2270 contacts either a first end surface 2311 of recess 2310 or a second end surface 2313 of recess 2310, the further rotation of cam 2266 relative to support 2250 is prevented. In the preferred embodiment, recess 2310 is sized to permit the rotation of cam 2266 relative to support 2250, such that position holder 2200 is movable between the locked position, shown in FIG. 65, and the unlocked position, shown in FIG. 64.

Fastener 2268 is passed through a central bore 2285 in cam 2266 and is coupled to support 2250. Fastener 2268 is configured to permit the rotation of cam 2266 relative to support 2250.

In a preferred embodiment, fastener 2268 includes a threaded portion 2316 which is threaded into a threaded aperture 2318 formed in surface 2288 of support 2250. Fastener 2268 further includes a shoulder portion 2320 having a outer diameter generally equal to the diameter of central bore 2285 of cam 2266, such that shoulder 2320 prevents cam 2266 from moving in a radial direction relative to fastener 2268.

As stated above, position holder 2200 allows fourth link 2210 to rotate relative to first link 2202 when position holder 2200 is in unlocked position, referring to FIG. 64, and locks fourth link 2210 to first link 2202 when position holder 2200 is in locked position, referring to FIG. 65. When position holder 2200 is in unlocked position, a user may rotate fourth link 2210 in direction 2326 or direction 2328 relative to first link 2202. When position holder 2200 is in locked position, fourth link 2210 is blocked from rotating in directions 2326, 2328 relative to first link 2202 due to the ingress of key members 2252, 2254, 2256, 2258 into keyways 2274 by cam 2266.

When in the unlocked position, pockets 2276, 2278, 2280, 2282 of cam 2266 are aligned with key members 2252, 2254, 2256, 2258 as previously mentioned. Key members 2252, 2254, 2256, 2258 are capable of being received by pockets 2276, 2278, 2280, 2282, so that key members 2252, 2254, 2256, 2258 do not interfere with keyways 2274 of second locking member 2262. As shown in FIG. 64, key members 2252, 2254, 2256, 2258 are positioned inside outer diameter 2280 of support 2250 when position holder 2211 is in the unlocked position.

Due to gravity, key member 2258 will not be positioned within pocket 2282 even when pocket 2282 is aligned. However, key member 2258 is pushed up into pocket 2282 by the raised portions of key ways 2274 when fourth link 2210 is moved in direction 2326 or direction 2328 relative to first link 2202.

Referring to FIG. 65, in locked position, pockets 2276, 2278, 2280, 2282 in cam 2266 are not aligned with key members 2252, 2254, 2256, 2258. Key members 2252, 2254, 2256, 2258 are held in contact with a representative keyway 2274a, 2274b, 2274c, 2274d, respectively, by an outer diameter 2284 of cam 2266. The retention of key members 2252, 2254, 2256, 2258 in slots 2272, 2274, 2276, 2278 of support 2250 and the contact between key members 2252, 2254, 2256, 2258 and keyways 2274a, 2274b, 2274c, 2274d prevents the rotation of fourth link 2210 in directions 2326, 2328 relative to first link 2202.

Position holder is moved from the locked position to the unlocked position due to the movement of cam 2266 relative to support 2250. Key members 2252, 2254, 2256, 2258 travel up or down cam surfaces 2298, 2300, 2207, 2304, respectively, when cam 2266 is rotated.

Mover 2550, shown in FIG. 62, rotates cam 2266 relative to support 2250. In the preferred embodiment, mover 2550 includes a rod 2552 having a first end 2554 and a second end 2556. First end 2554 is coupled to cam 2266 with a fastener 2558. Second end 2556 is received into a housing 2560 coupled to fourth link 2210.

Rod 2552 is configured to move in a direction 2562 and a direction 2564. A spring (not shown) is provided to bias rod 2552 in direction 2562. The spring pushes against end 2556 of rod 2552 within housing 2560 to provide the bias. The bias exerted on rod 2552 in direction 2562 biases cam 2266 such that position holder 2200 is urged to the locked position shown in FIG. 65.

By moving rod 2552 in a direction 2564, position holder 2200 is moved from the locked position, shown in FIG. 65, to the unlocked position shown in FIG. 64. A handle, grip, or lever 2566 is attached to rod 2552 proximate to second end 2556 to aid in the movement of rod 2552 in direction 2564. A caregiver moves rod 2552 in direction 2564 by placing the palm of their hand on cross member 2244, placing their fingers on handle 2566 and pulling handle 2566 towards cross member 2244. This movement of rod 2552 rotates cam 2266 to the position shown in FIG. 64 to permit key members 2252, 2254, 2256, 2258 to move out of keyways 2274 as previously described.

In an alternative embodiment, the cam is coupled to a motor. The motor rotates the cam between the locked position and the unlocked position in response to an input signal. In one embodiment, the input signal is generated by a processor. In a further alternative embodiment, the input signal is generated by the closing of a switch or pressing of a button.

Returning to FIGS. 58 and 62, when a caregiver wants to move head support plate 1010 to an elevated position, the caregiver pulls handle 2566 of mover 2250 in direction 2564, thereby placing position holder 2200 in the unlocked position. The caregiver then rotates fourth links 2210, 2212 relative to first links 2202, 2204 in direction 2328 so that head support plate 1010 is moved upwardly in direction 2028 relative to the remaining support sections of tabletop 1016 when in the desired location, the user releases handle 24566 and position holder 2200 is moved back to the locked position. The angle of head support plate 1010 maybe adjusted using second position holder 2600. The operation of second position holder 2600 is shown generally in FIGS. 70–72 and explained in detail below.

Referring to FIGS. 59 and 62, when a caregiver wants to move head support plate 1010 to a lowered position, the caregiver pulls handle 2566 of mover 2550 in direction 2564, thereby placing position holder 2200 in the unlocked position. The caregiver rotates fourth links 2210, 2212 relative to first links 2202, 2204 in direction 2326, so that head support plate 1010 is moved downwardly in direction 2030 relative to remaining support sections of tabletop 1016. The caregiver releases handle 2566 so that position holder 2200 moves back to the locked position.

Referring to FIGS. 60 and 62, when the caregiver wants to store head support section 1018, head support section 1018 is moved to a stored or tucked position under upper torso support section 1020 of frame 1032. To move head support section 1018 to the stored or tucked position, the caregiver pulls handle 2566 of mover 2550 in direction 2564, thereby placing position holder 2200 in the unlocked position and rotates fourth links 2210, 2212 relative to first links 2202, 2204 in direction 2326 so that head support plate 1010 is tucked below upper torso support section 1020. Again, handle 2256 is released to move position holder 2200 to the locked position. The positions of head support section 1018 in FIGS. 56 and 58–60 are merely examples of the many positions that head support section 1018 can be adjusted to relative to the remaining support sections of tabletop 1016.

Figure 66:
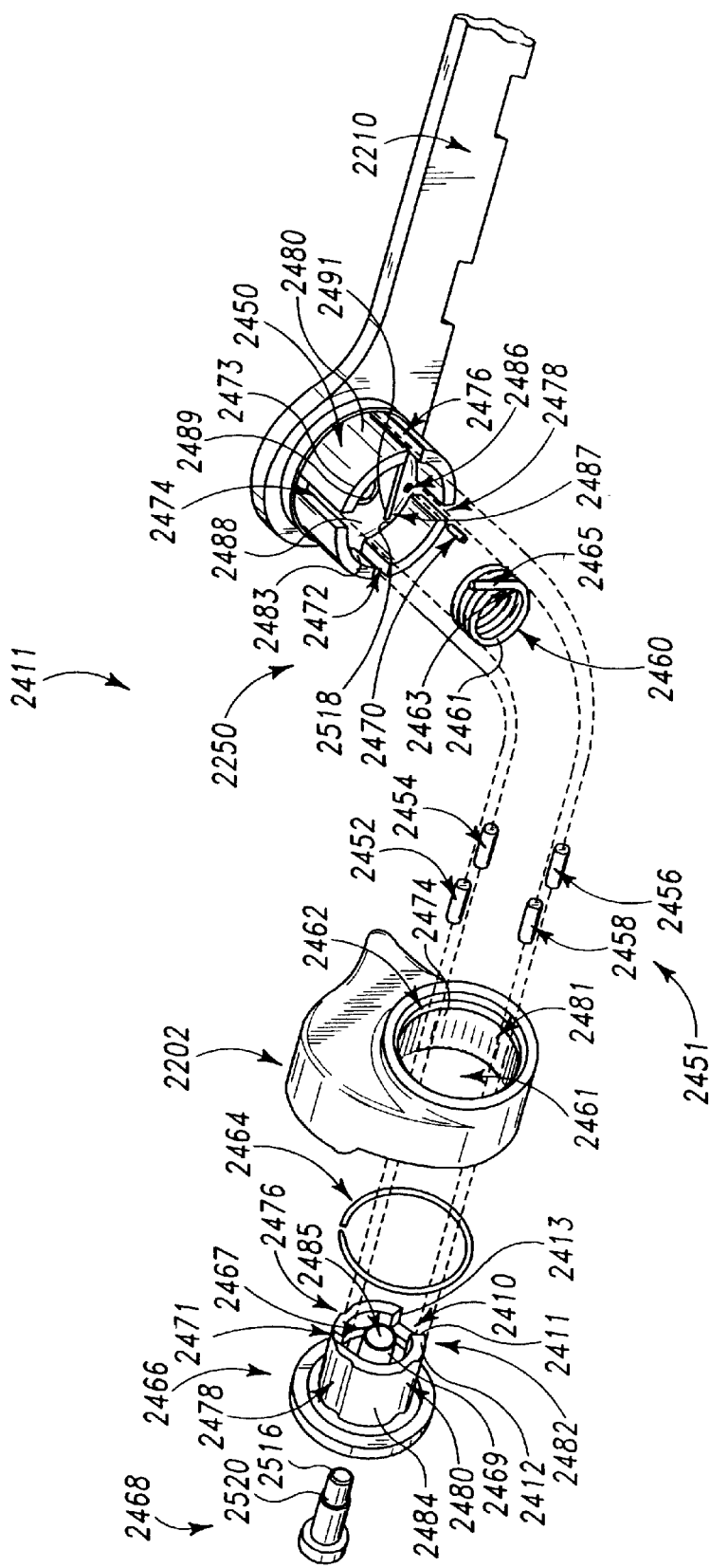
FIG. 66 is an exploded view of an alternative embodiment of the joint.

Referring to FIG. 66, an alternative embodiment position holder 2411 includes a support 2450 generally similar to support 2250 coupled to fourth link 2210, a first coupling or locking member 2451 having key members 2452, 2454, 2456, 2458 generally similar to key members 2252, 2254, 2256, 2258, a tension member or spring 2460, a second coupling or locking member 2462 generally similar to second coupling or locking member 2262 and defined in first link 2202, a retainer or snap ring 2464, a cam 2466 generally similar to cam 2266, a fastener 2468 generally similar to fastener 2268, and a stop 2470 generally similar to stop 2270.

Support 2450 is cylindrical and contains slots 2472, 2474, 2476, 2478 which are sized to receive key members 2452, 2454, 2456, 2458, respectively. Support 2450 is received by an opening 2461 in first link 2202. Opening 2461 in first link 2202 is defined by surface 2481.

Key members 2452, 2454, 2456, 2458 of first locking member 2451 interact with second locking member 2462 to lock the orientation of first link 2202 and fourth link 2210. Second locking member 2462 is located in opening 2461 in first link 2202 and includes a plurality of indentations or keyways 2474 configured to receive key members 2452, 2454, 2456, 2458.

Figure 68:
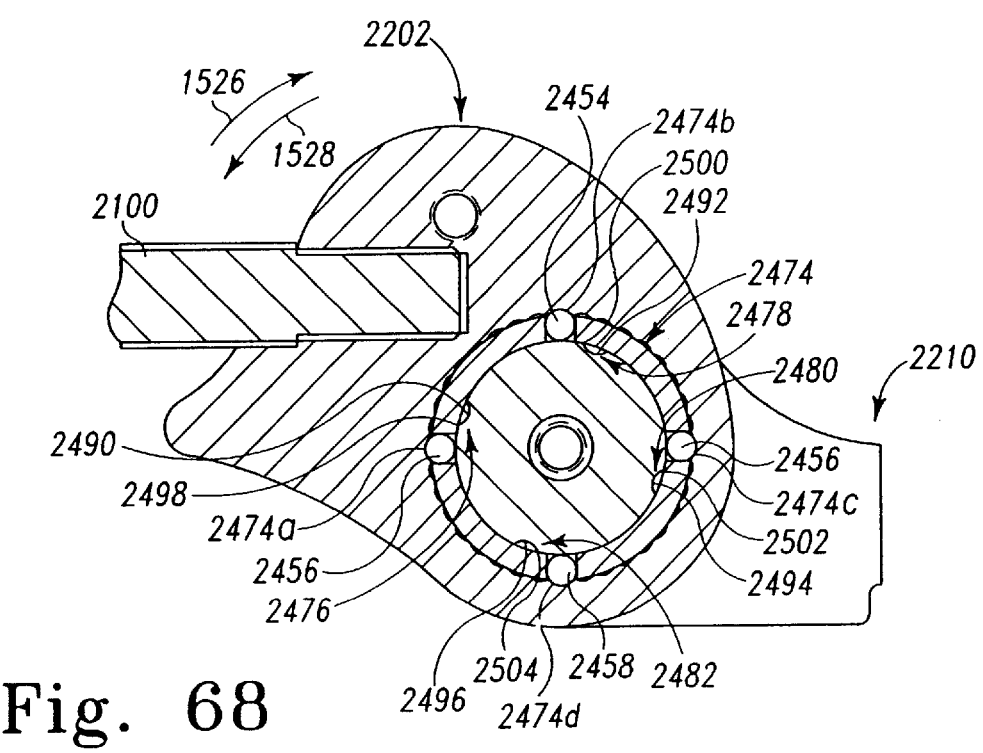
FIG. 68 is a view similar to FIG. 67 showing the position holder in a locked position.

Position holder 2411 is in a locked position shown in FIG. 68, when key members 2452, 2454, 2456, 2458 are positioned in keyways 2274. Key members 2452, 2454, 2456, 2458 are positioned in keyways 2274 by cam 2466.

Cam 2466 includes pockets 2476, 2478, 2480, 2482 configured to receive key members 2452, 2454, 2456, 2458, respectively. Cam 2466 further includes a recess 2467 sized to receive a portion of spring 2460. Recess 2467 includes a circular portion 2469 configured to receive a coil portion 2461 of spring 2460 and a channel portion 2471 configured to receive a second end 2465 of spring 2460.

Position holder 2411 is assembled in the following manner. Spring 2460 is positioned within a recess 2487 of support 2450 so that coil portion 2461 of spring 2460 is located in a circular portion 2489 of recess 2487 and first end 2463 of spring 2460 is located in a channel portion 2491 of recess 2487. Support 2450 is then inserted into opening 2461 of first link 2202. Key members 2452, 2454, 2456, 2458 are positioned within slots 2472, 2474, 2476, 2478 of support 2450, respectively. Stop 2470 is positioned within a recess 2486 in support 2450.

Support 2450 is maintained in opening 2461 in first link 2202 by snap ring or retainer 2464. A portion of snap ring 2464 is received by a circumferential recess 2473 in outer diameter 2480 of support 2450. When snap ring 2464 is positioned in recess 2473 of support 2450, support 2450 is prevented from being removed from opening 2461.

Cam 2466 is positioned within the recess of support 2450 so that stop 2470 is positioned within a recess 2410 of cam 2466 formed in a front surface 2412 of cam 2466. Recess 2410 is elongated to permit cam 2466 to rotate relative to support 2450. However, the amount of rotation of cam 2466 relative to support 2450 is limited by the size of elongated recess 2410. As such, when stop 2470 contacts either a first end surface 2411 of recess 2410 or a second end surface 2413 of recess 2410, further rotation of cam 2466 relative to support 2450 is prevented. Recess 2410 is sized to permit the rotation of cam 2466 relative to support 2450, so that position holder 2411 is movable between the locked position, shown in FIG. 78, and the unlocked position shown in FIG. 77.

Fastener 2468 permits the rotation of cam 2466 relative to support 2450. Fastener 2468 is passed through central bore 2485 in cam 2466 and is coupled to support 2450. Fastener 2468 includes a threaded portion 2516 which is threaded into a threaded aperture 2518 formed in surface 2488 of support 2450 and a shoulder portion 2520 having a outer diameter generally equal to the diameter of central bore 2485 of cam 2466. Shoulder 2520 prevents cam 2466 from moving in an axial direction.

Figure 67:
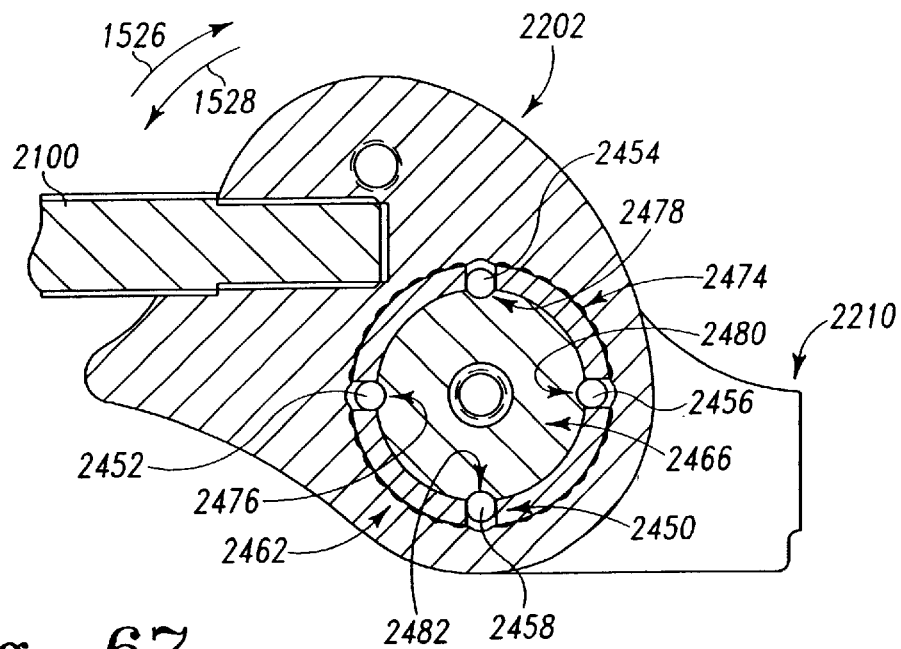
FIG. 67 is a cross-sectional view of the joint of FIG. 66 showing a position holder in an unlocked position.

As stated above, position holder 2411 allows fourth link 2210 to rotate relative to first link 2202 when position holder 2411 is in the unlocked position, referring to FIG. 67, and locks fourth link 2210 to first link 2202 when position holder 2411 is in the locked position 2524, referring to FIG. 68. When position holder 2411 is in the unlocked position, a user can rotate fourth link 2210 in direction 2526 or direction 2528 relative to first link 2202. When position holder 2411 is in the locked position, fourth link 2210 is prevented from rotating in directions 2526, 2528 relative to first link 2202 due to the positioning of key members 2452, 2454, 2456, 2458 into keyways 2474 by cam 2466.

Spring 2460 biases position holder 2411 towards the locked position. When position holder 2411 is in the locked position spring 2460 is in a relaxed state. When position holder 2411 is in the unlocked position, spring 2460 is in a wound state due to movement of second end 2465 of spring 2460 relative to first end 2463 of spring 2460. When wound, spring 2460 urges position holder 2411 towards the unlocked position which corresponds to the relaxed state of spring 2460.

In addition to locking joint 2211, preferred embodiment linkage 2007 further includes resistive joint 2213. A resistive joint is a joint having a resistance to the relative movement of its corresponding links.

Figure 69:
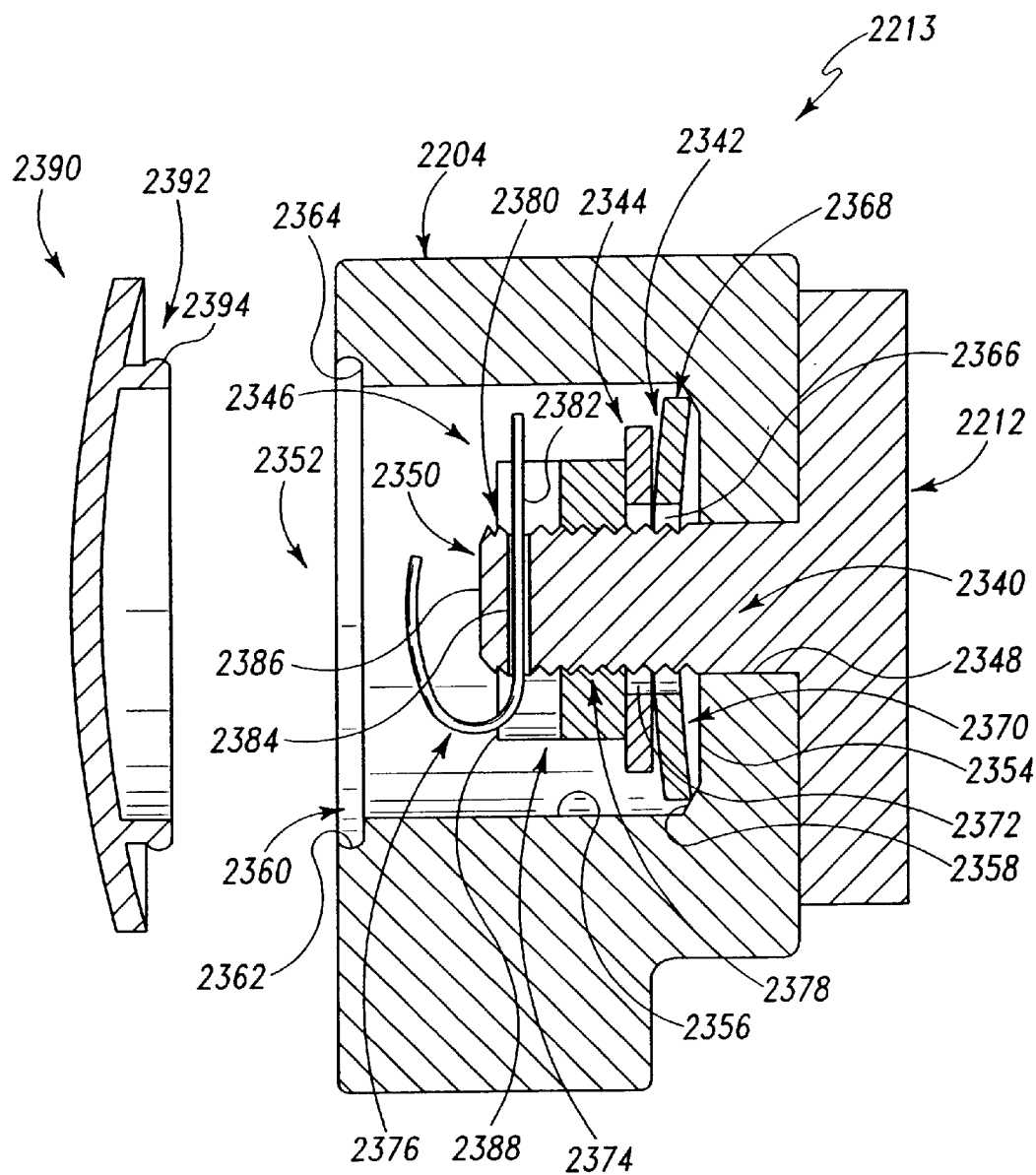
FIG. 69 is a cross-sectional view of another joint of one of the four-bar linkages of FIG. 62.

Referring to FIG. 69, in an illustrative embodiment of linkage 2007, restrictive joint 2213 includes a post or support 2340 coupled to fourth link 2212, a tension member 2342, a washer 2344, and a retainer 2346. Tension member 2342 increases the resistance to movement of fourth link 2212 relative first link 2204. Retainer 2346 and washer 2344 cooperate to set the amount of resistance exerted by tension member 2342 against movement of fourth link 2212 relative to first link 2204.

Resistive joint 2213 is assembled in the following manner. Support 2340 is received through an aperture 2348 in first link 2204. A first portion 2350 of support 2340 extends into a pocket 2352 formed in first link 2204. Pocket 2352 in first link 2204 includes a first axial surface 2354, a first radial surface 2356, and an angled surface 2358 interposed between first axial surface 2354 and first radial surface 2356.

In the preferred embodiment, tension member 2342 is a Belleville washer and is positioned in pocket 2352 with post 2340 positioned in an aperture 2366 formed in tension member 2342 so that an outer portion 2368 of tension member 2342 contacts angled surface 2358 of pocket 2352. A central portion 2370 of tension member 2342 does not contact a surface of pocket 2352.

Washer 2344 is positioned so that post 2340 is positioned in an aperture 2372 formed in washer 2344 and washer 2344 contacts tension member 2342. Retainer 2346 maintains washer 2344 in contact with tension member 2342 and maintains tension member 2342 in contact with angled surface 2358 of pocket 2352 so that first link 2204 and fourth link 2212 are effectively coupled together. Additionally, retainer 2346 controls the amount of resistance exerted by tension member 2342 on first link 2204.

In the illustrative embodiment, retainer 2346 includes a nut 2374 and a pin 2376. Nut 2374 includes a threaded aperture 2378 which is threaded onto a threaded portion 2380 of post 2340. Nut 2374 further includes a transverse channel 2382 for receiving pin 2376. Post 2340 includes a transverse channel 2384 for receiving pin 2376. The placement of pin 2376 through channel 2384 of support 2340 and channel 2382 of nut 2374 prevents rotation of nut 2374 relative to support 2340.

The amount of tension exerted by fourth link 2212 on first link 2204, associated with resistive joint 2213, is governed by the amount of force exerted by retainer 2346 on tension member 2342. To increase the resistance, retainer 2346 is threaded further onto post 2340 to further compress tension member 2342 and increase the resistance. The greater the tension exerted by fourth link 2212 on first link 2204 the greater the force required to move fourth link 2212 relative to first link 2204. In alternate embodiments, the retainer is a torque limited nut similar to torque limited bolt 134 discussed above.

Resistive joint 2213 is concealed in pocket 2352 of first link 2204 by an end cap 2390. Cap 2390 includes a coupler 2392 having a curved surface 2394. Coupler 2392 of cap 2390 is received by a coupler 2360 defined in pocket 2352 such that cap 2390 is coupled to first link 2204.

As previously mentioned, second position holder 2600 permits adjustment of the angle between head support plate mount 2218 and linkage 2007 and hence between head support plate 1010 and linkage 2007. Referring to FIGS. 70–74, the angle between third link 2214 and mount 2218 and hence head support plate 1010 is adjusted by turning a handle 2632 resulting in rotation of mount 2218 and head support plate 2218.

Figure 70:
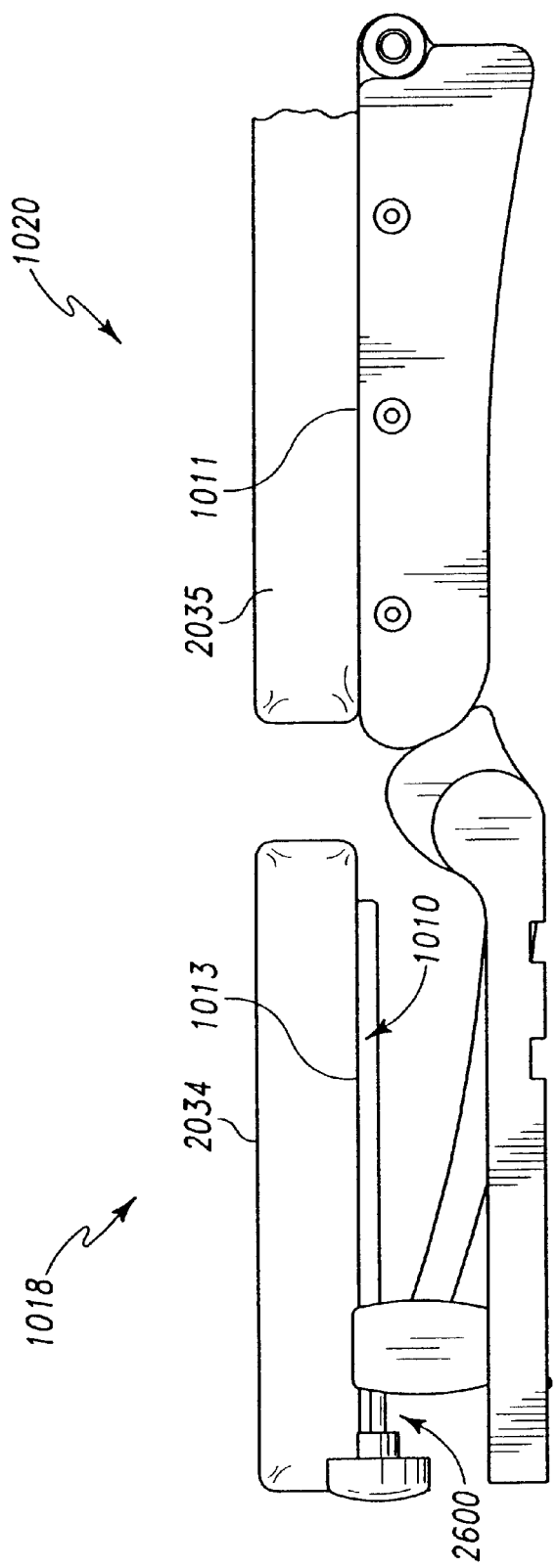
FIG. 70 is a side elevation view of the head support section of FIG. 58 showing the head support surface of the head support section substantially parallel and substantially coplanar with the body support surface of the upper torso support section.
Figure 71:
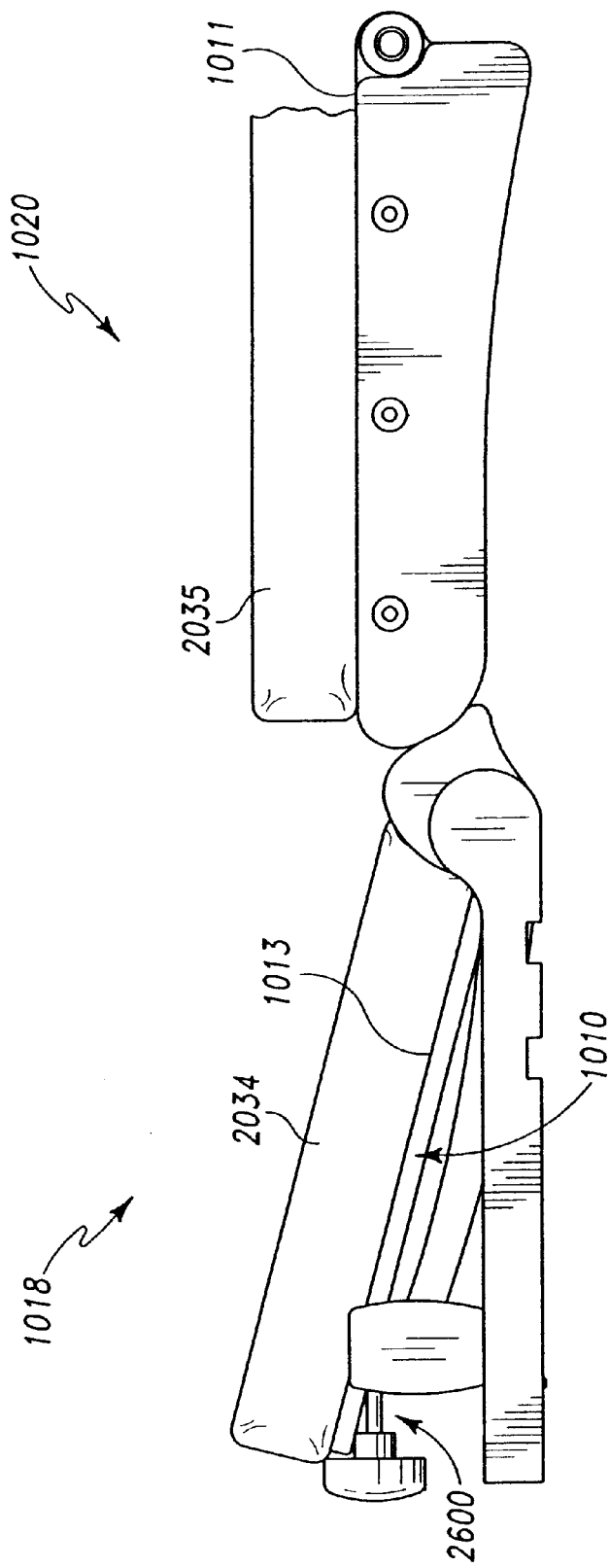
FIG. 71 is a view similar to FIG. 70 showing the head support plate angled relative to the body support surface of the upper torso support section.
Figure 72:
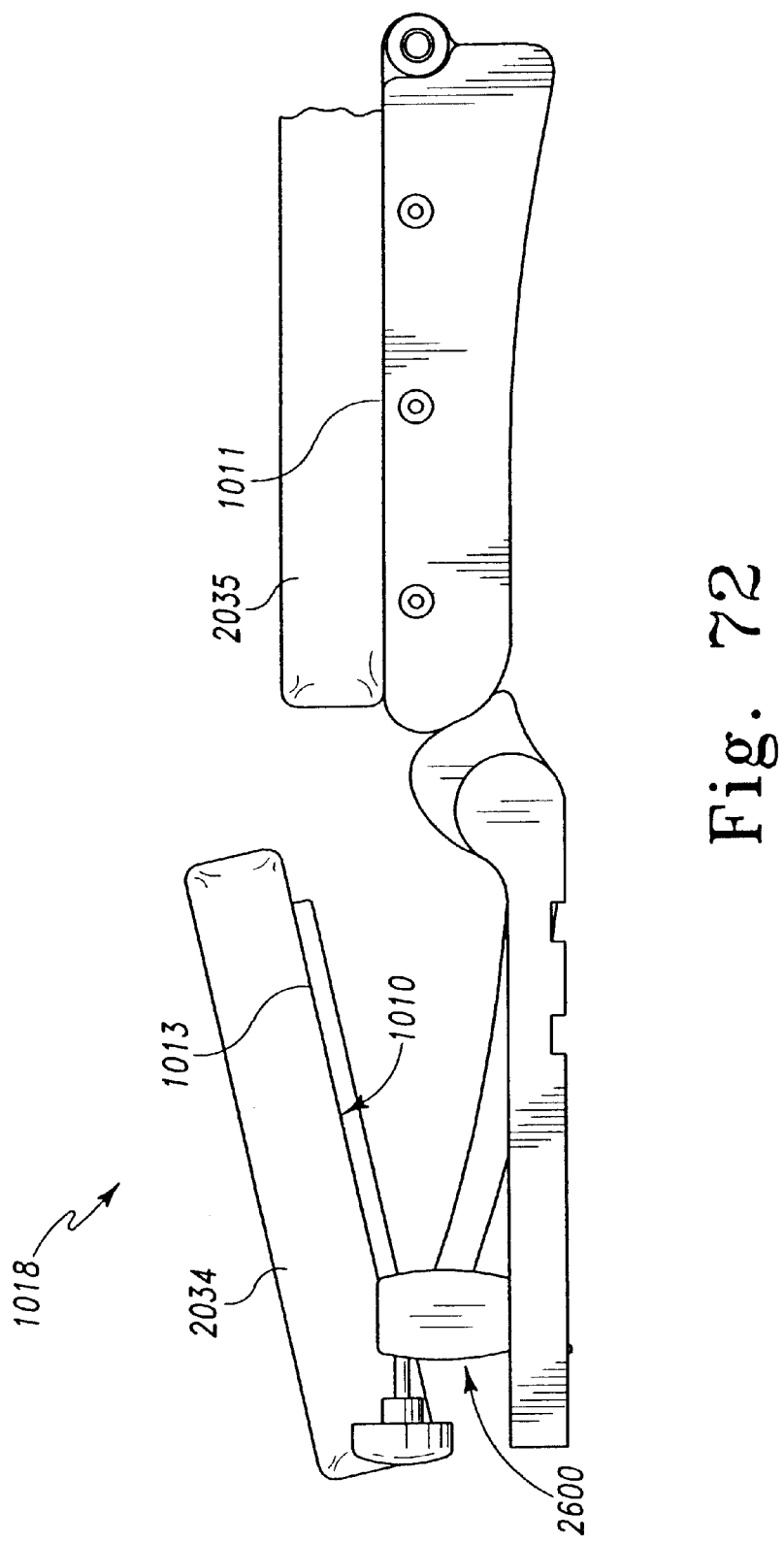
FIG. 72 is a view similar to FIG. 70 showing the head support plate angled relative to the body support surface of the upper torso support section in a direction opposite that shown in FIG. 71.

As shown in FIG. 70, head support section 1018 is positioned in a first horizontal position with a head pad 2034 supported in a substantially coplanar position relative to a torso pad 2035 positioned in part on upper torso support section 1020. Referring to FIG. 71, head support plate 1010 is positioned in a first angled position, wherein head pad 2034 is tilted towards torso pad 2035, due to an adjustment of second position holder 2600. When head support plate 1010 is positioned in the first angled position, mount 2218 is angled toward torso pad 2035. Referring to FIG. 72, head support plate 1010 is positioned in a second angled position, in which head pad 2034 is tilted away from torso pad 2035, due to an opposite adjustment of second position holder 2600.

In the preferred embodiment, second position holder 2600 includes an input shaft 2602 coupled to handle 2632, a gear set 2603 including a first gear 2604 coupled to first shaft 2602 and a second gear 2606 moveably coupled to first gear 2604, an output shaft 2608 coupled to second gear 2606 and mount 2218, and a pin 2610. First gear 2604 is preferably a worm gear. The axis of rotation of worm gear 2604 is perpendicular to the axis of rotation of second gear 2606. As such, worm gear 2604 blocks the rotation of second gear 2606 due to external force applied to output shaft 2608 from head support plate 1010. In an alternative embodiment, the input member is turned by a motor (not shown). The motor is controlled by a processor (not shown) or switch (not shown).

Referring to FIG. 73, second position holder 2600 is assembled in the following manner. Second position holder 2600 is received into a pocket 2612 in third link 2214. Third link 2214 includes a first half 2614 and a second half 2616 which are secured together by fasteners 2618, 2620. First gear 2604 and a first portion 2622 of input shaft 2602 are received by a first portion 2624 of pocket 2612. Second gear 2606 is received by a second portion 2626 of pocket 2612 and is positioned such that teeth 2628 of second gear 2606 engage thread 2630 of first gear 2604. Handle 2632 is secured to a second end 2634 of input shaft 2602 to provide a user more leverage to turn input shaft 2602.

Output shaft 2608 is received by an aperture 2635 in mount 2218. Output shaft 2608 is coupled to mount 2218 with a pin 2637 which is received in an aperture 2639 in output shaft 2608 and in an aperture 2636 of mount 2218. Output shaft 2608 further includes an aperture 2638 for receiving pin 2610. Pin 2610 prevents mount 2218 from moving relative to output shaft 2608.

When necessary or desirable, the user can use second position holder 2600 in conjunction with first position holder 2200. For example, when head support plate 1010 is lowered using first position holder 2200, second position holder 2600 can be used to position head support plate 1010 in an exactly parallel position relative to the remainder of the support surface to compensate for slight rotation of head support plate 1010 during lowering. Furthermore, second position holder 2600 can be used to position head support plate 1010 in a substantially non-parallel position when linkage 2007 moves through the first range of orientation.

Figure 77:
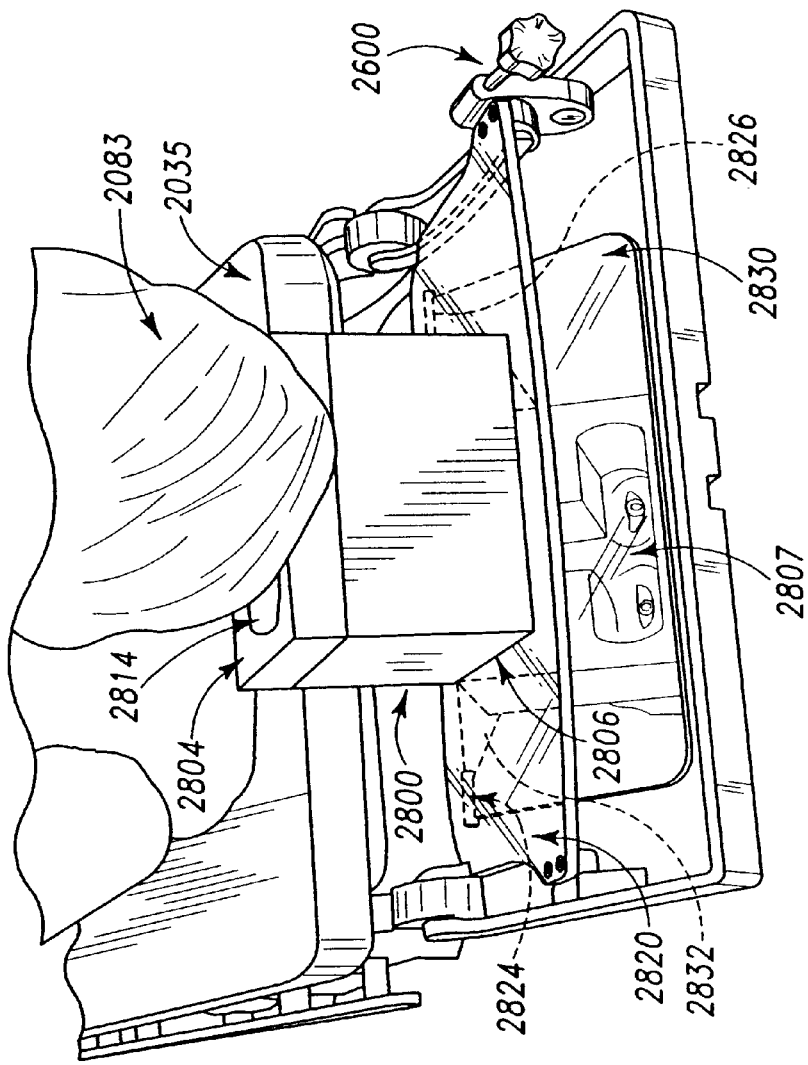
FIG. 77 is a perspective view of the head support section and head support pad of FIG. 76.

When a patient 2801 is positioned in the prone position on a surgical table apparatus, it is often desirable to be able to view the face of the patient and to have access to the face of the patient. Referring to FIGS. 76 and 77, a head support 2800 is shown in conjunction with head support section 1018. Head support 2800 is used to support a patient's head 2803, when patient 2801 is lying in the prone position on surgical table apparatus 1000. Head support 2800 includes a body 2802 having a first end 2804 and a second end 2806. First end 2804 is adapted to receive head 2803 of patient 2801. In the preferred embodiment, head support 2800 includes a first portion 2808 and a second portion 2810. First portion 2808 is made from a firm material, such as plastic or a dense foam. Second portion 2810 is made from a softer material, such as less dense foam. The firm characteristic of first portion 2808 provides a stable height 2812 of body 2802 and the soft characteristic of second portion 2810 provides a comfortable surface for patient 2801 to rest their head 2803.

Head support 2800 includes an opening 2814 which extends from first end 2804 to second end 2806. Opening 2814 is sized and shaped such that when head 2803 is received by first end 2804, a portion of a face 2807 of patient 2801 is visible from second end 2806 through opening 2814. Preferably, opening 2814 is T-shaped so that the eyes, nose and mouth of patient 2801 are visible through opening 2814. In alternate embodiments, the opening is oval or another shape.

Head support 2800 is placed on head support section 1018 such that second end 2806 is positioned on a head support plate 2820. Head support plate 2820 is generally similar to head support plate 1010, except that head support plate 2820 is at least partially transparent. The transparent characteristic of head support plate 2820 permits the portion of face 2807 of patient 2801 visible through opening 2814 to be seen through head support plate 2820. In one embodiment, head support 2800 includes a second opening 2822 in body 2802 to permit access to face 2807 of patient 2801. An exemplary use of opening 2822 is to provide an oxygen line to patient 2801. Because head support section 1018 may be lowered relative to the remaining support sections of surgical table apparatus 1000, height 2812 of head support 2800 can be increased to permit greater access to face 2807 of patient 2801.

Referring to FIG. 77, a mirror 2830 is positioned below head support plate 2820 such that an observer positioned above head support plate 2820 or to the side of head support plate 2820 may view face 2807 of patient 2801. Preferably, mirror 2830 is pivotally coupled to head support plate 2820 along a first end 2832 of mirror 2820. Couplers 2824, 2826 couple mirror 2830 to head support plate 2820. Couplers 2824, 2826 permit mirror 2830 to be rotated about first end 2832 and hold mirror 2830 in a desired viewing location. In an alternate embodiment the mirror is secured to the frame. In another alternative embodiment the mirror is coupled to a stand (not shown) placed below the head support section.

Head support 2800 is used in conjunction with head support section 1018 in the following manner. Head support 2800 is placed on head support plate 2820 and head support section 1018 is moved to a lowered position, as shown in FIG. 76. Patient 2801 is positioned on torso pad 2035 and head support 2800 such that body 2809 of patient 2801 is supported by torso pad 2035 and head 2803 of patient 2801 is supported by head support 2800. The angle of head support 2800 can be varied by adjusting the angle of head support plate 2820 with second position holder 2600. In a preferred embodiment, head support member 2800 is positioned such that head 2803 of patient 2801 is aligned with body 2809 of patient 2801 to reduce stress on the spine of patient 2801.

A caregiver adjusts mirror 2830 such that the eyes of patient 2801 are visible in mirror 2830 from the caregiver's location. By viewing the eyes of patient 2801, the caregiver can communicate with patient 2801 by having patient 2801 blink their eyes. Additionally, the caregiver can observe patient 2801 for signs of distress or pain and monitor the affects of anesthesia on patient 2801.

Figure 78:
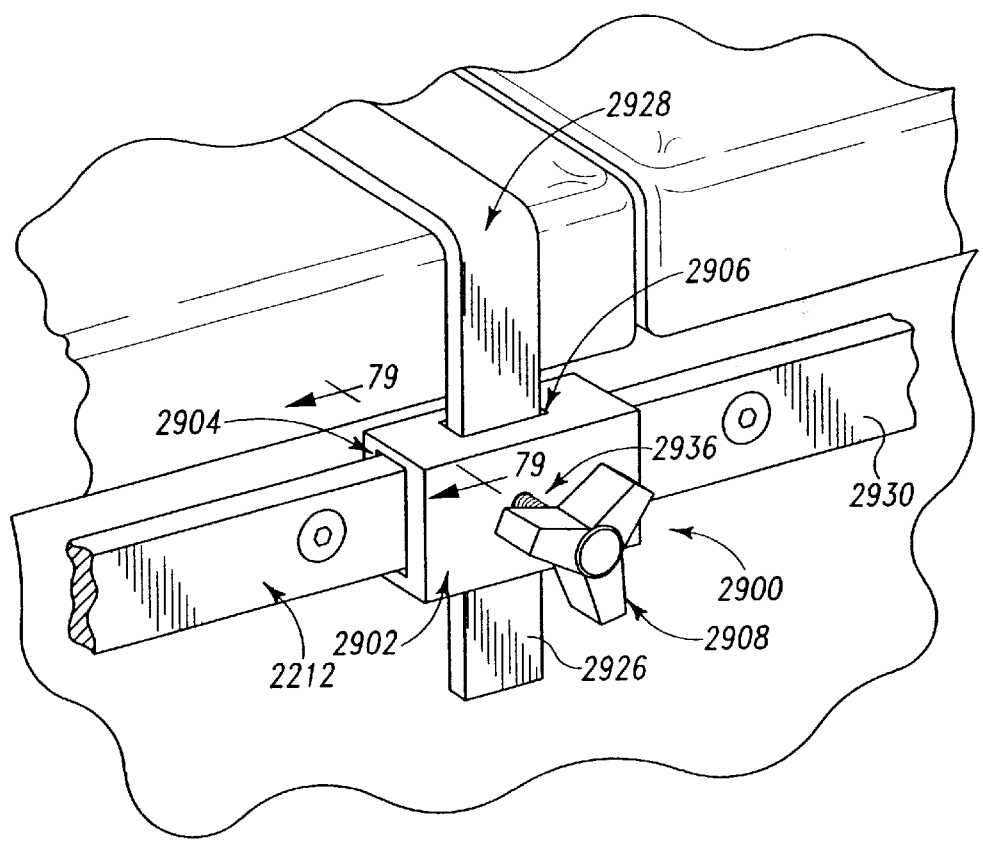
FIG. 78 is a perspective view of an accessory being coupled to a link of the linkage of FIG. 62 with an accessory clamp.
Figure 79:
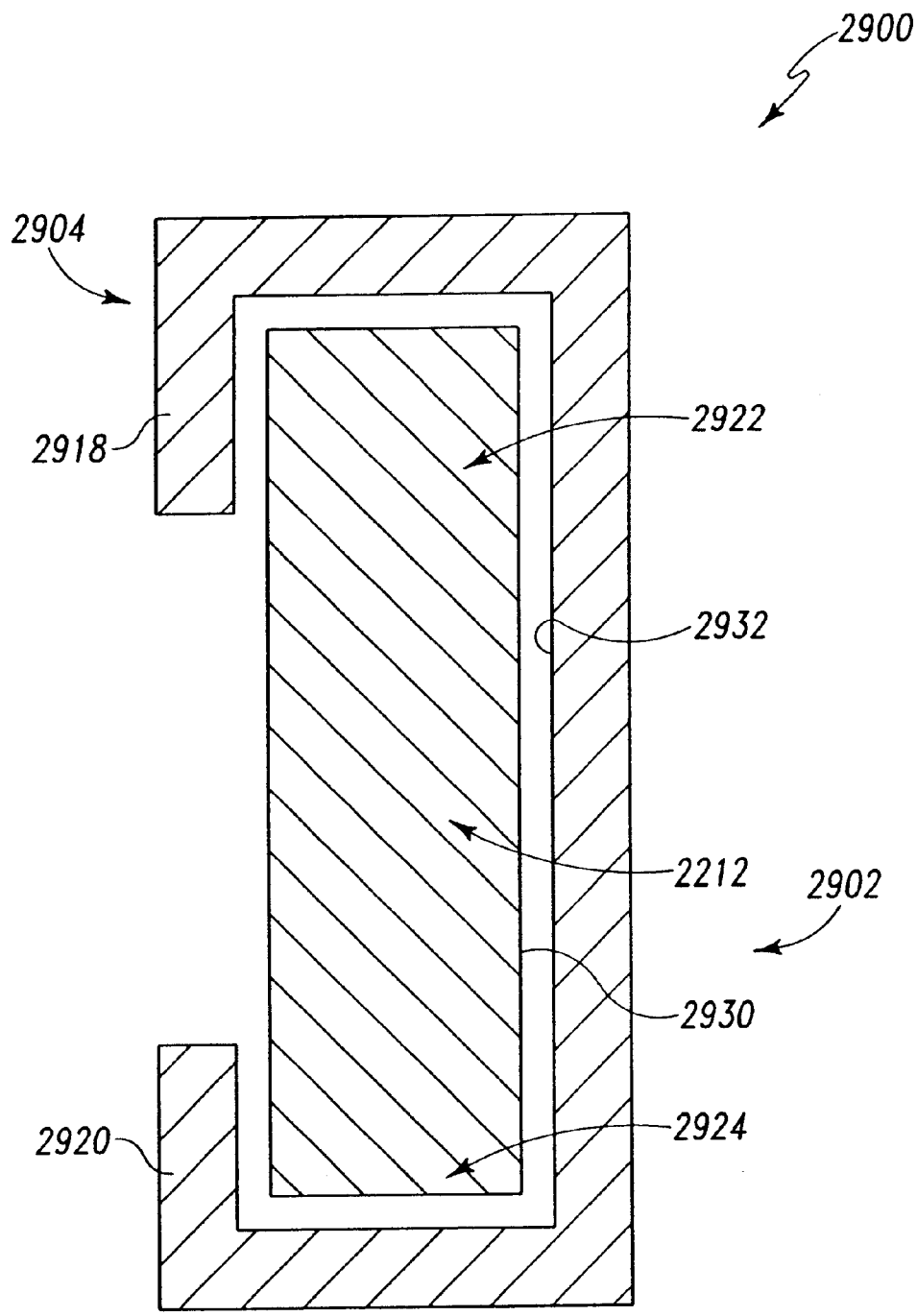
FIG. 79 is a cross-sectional view of the accessory clamp showing a rail coupler of the accessory clamp taken along line 79—79 of FIG. 78.

Referring to FIGS. 62, 78, 79 at least one of links 2210, 2212, 2244 are configured to have an accessory 2928 coupled thereto. Example accessories include leg holders, a shoulder chair, an arthroscopic stress point, a total knee stabilizer, tabletop extensions including a patient transfer extension, a narrow headrest, a foot extension, and a table width extender, an arm board, an arm board cradle, a hand or arm table, restraints including a nissen strap, shoulder braces, lateral braces, lateral supports, patient restraint straps, and an arm shield; fluid containment devices such as Uro catheter, a side catcher and a cysto table bag; an anesthesia screen; a Schure slide and a leg drape.

Referring to FIGS. 78 and 79, an accessory clamp 2900 is shown. Accessory clamp 2900 includes a body member 2902, a link coupler 2904, an accessory coupler 2906 and a tension member 2908. Accessory clamp 2900 is configured to be received by a bed rail 2910, see FIG. 56, and by links 2210, 2212, 2244, see FIGS. 61 and 62. Accessory rail 2900 is received by bed rail 2910 either at an open end 2912 of rail 2910 or through notches 2914. Accessory rail 2900 is received by links 2210, 2212, 2244 of linkage 2007 through notches 2916, see FIGS. 61 and 62.

Referring to FIG. 79, link coupler 2904 comprises a first coupler 2918 and a second coupler 2920. The first and second couplers 2918, 2920 overlap a top portion 2922 and a bottom portion 2924 of a link of linkage 2007, such as link 2212.

An accessory is attached to a link of linkage 2007 with accessory clamp 2900 in the following manner. First coupler 2918 is positioned over the top portion 2922 of link 2212 such that second coupler 2920 is proximate to notches 2916 of link 2212. Second coupler 2920 is passed through notches 2916 such that first coupler 2918 and second coupler 2920 are substantially vertically aligned. Accessory clamp 2900 is then slide along link 2212 to a desired location. A support 2926 of accessory 2928 is then positioned in accessory coupler 2906 such that support 2926 is positioned between a front surface 2930 of link 2212 and a rear surface 2932 of clamp 2900. Support 2926 of accessory 2928 and body 2902 of clamp 2900 are secured in place with tension member 2908. Tension member 2908 in one embodiment is a threaded rod 2936 which is received by a threaded aperture (not shown) in body 2902. Tension member 2908 holds first and second couplers 2918, 2920 and accessory support 2926 against link 2212.

Figure 80:
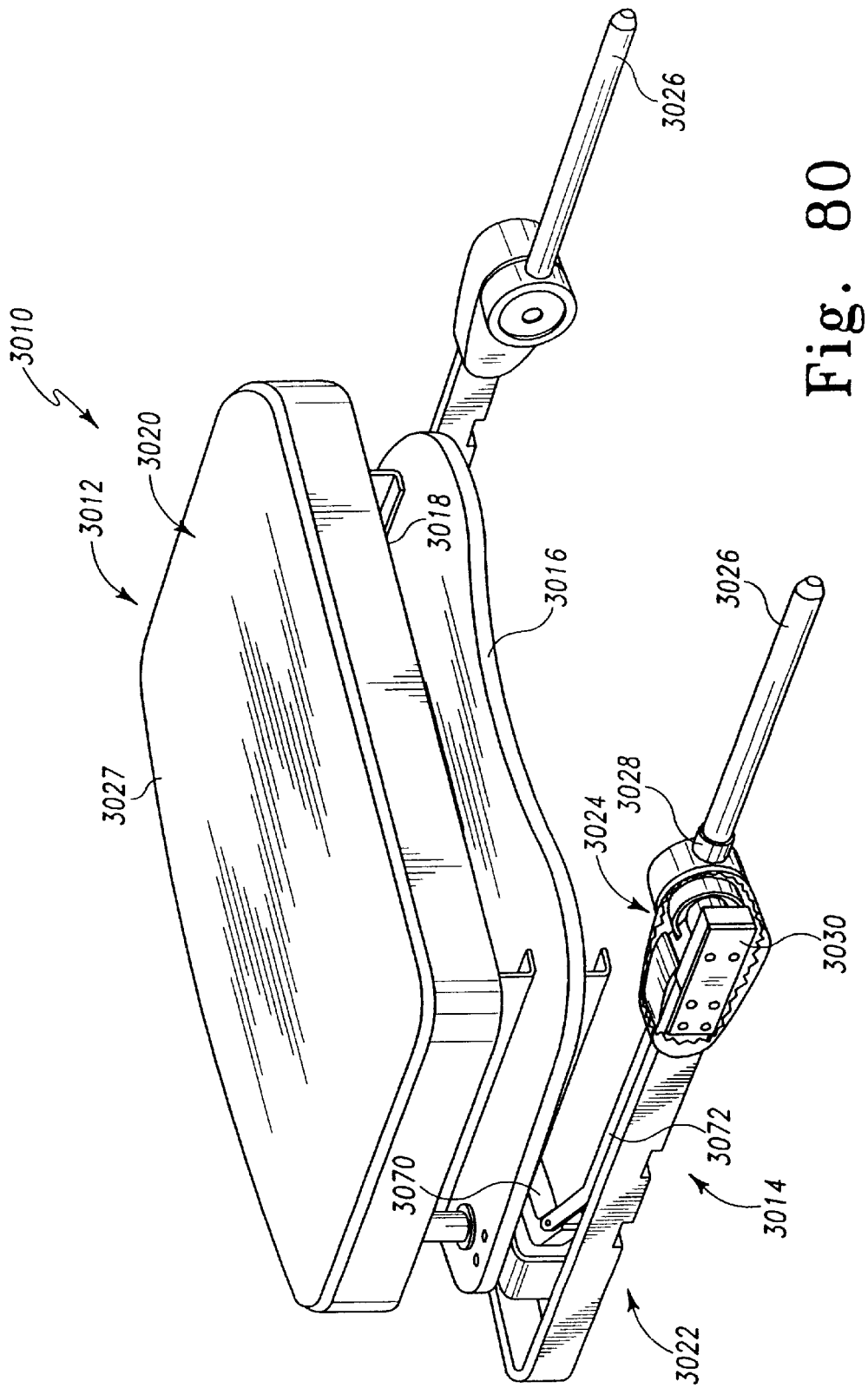
FIG. 80 is a perspective view of a head support section of a surgical table apparatus in accordance with another embodiment of the present disclosure including a head support member and a member support configured to support the head support member relative to the remainder of the surgical table apparatus.

Another alternative embodiment head support section 3010 is shown in FIG. 80. Head support section 3010 includes a head support member 3012 adapted to support the head of a patient and a member support 3014 positioned to support head support member 3012 on an adjacent upper torso support section (not shown) of a body support section (not shown). Head support member 3012 includes first and second head support plates 3016, 3018 and a head support pad 3020 supported by second head support plate 3018. Member support 3014 includes a U-shaped link 3022 coupled to a position holder 3024 supported on the upper torso support section by a pair of post 3026.

Figure 82:
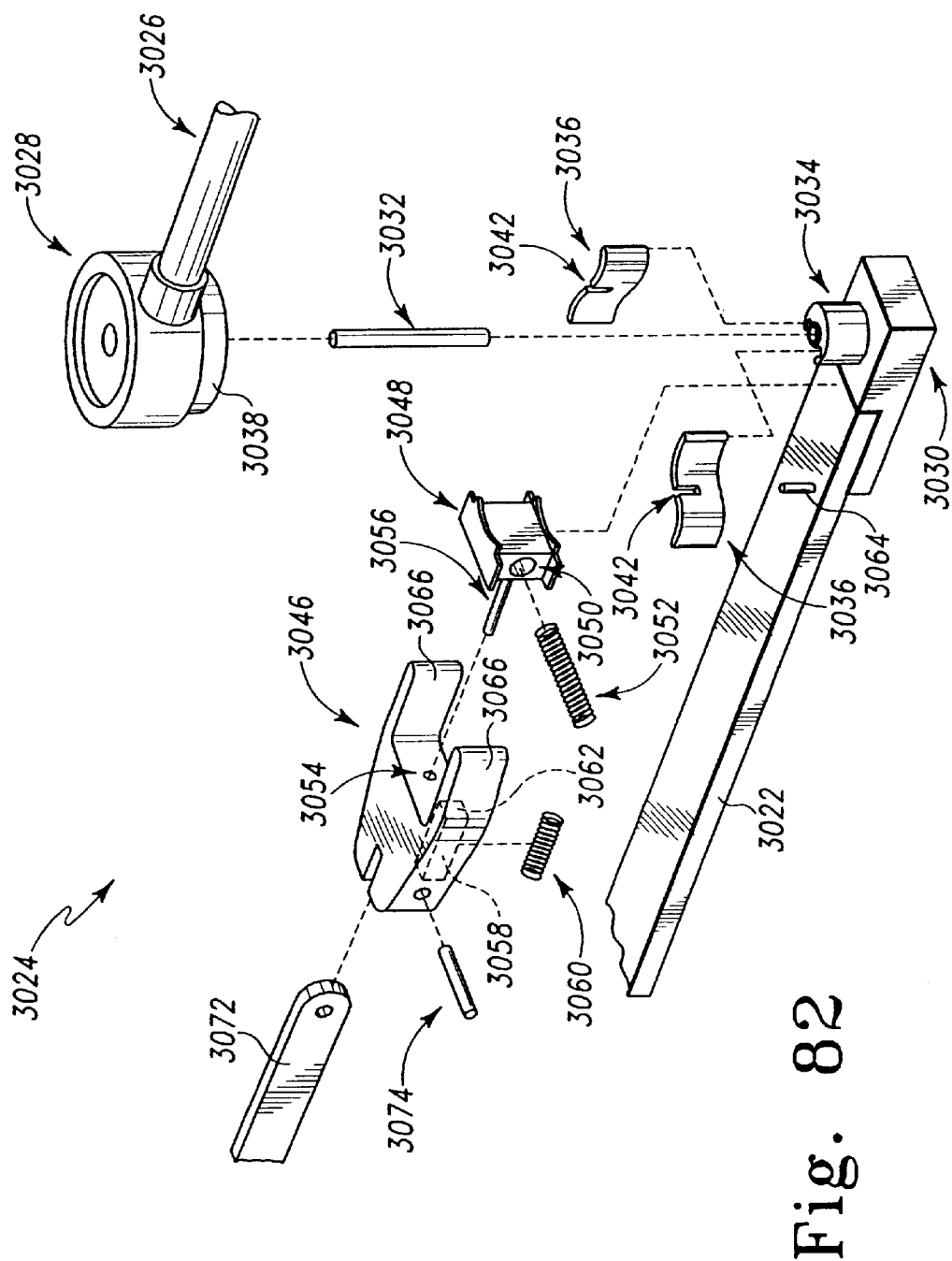
FIG. 82 is an exploded perspective view of the position holder shown in FIG. 81.

Position holder 3024 is configured to permit adjustment of the angle of a head support surface 3027 defined by head support pad 3020. As shown in FIG. 82, position holder 3024 includes a first base 3028 rigidly coupled to post 3026 and a second base 3030 coupled to rotate with link 3022. A shaft 3032 is provided on which second base 3030 rotates relative to first base 3028.

Position holder 3024 includes a cylinder-shaped support 3034 coupled to second base 3030 and a pair of binding members 3036 supported by support 3034. Position holder 3024 further includes an annular ring-shaped bound member 3038 that is rigidly coupled to first base 3028.

Figure 81:
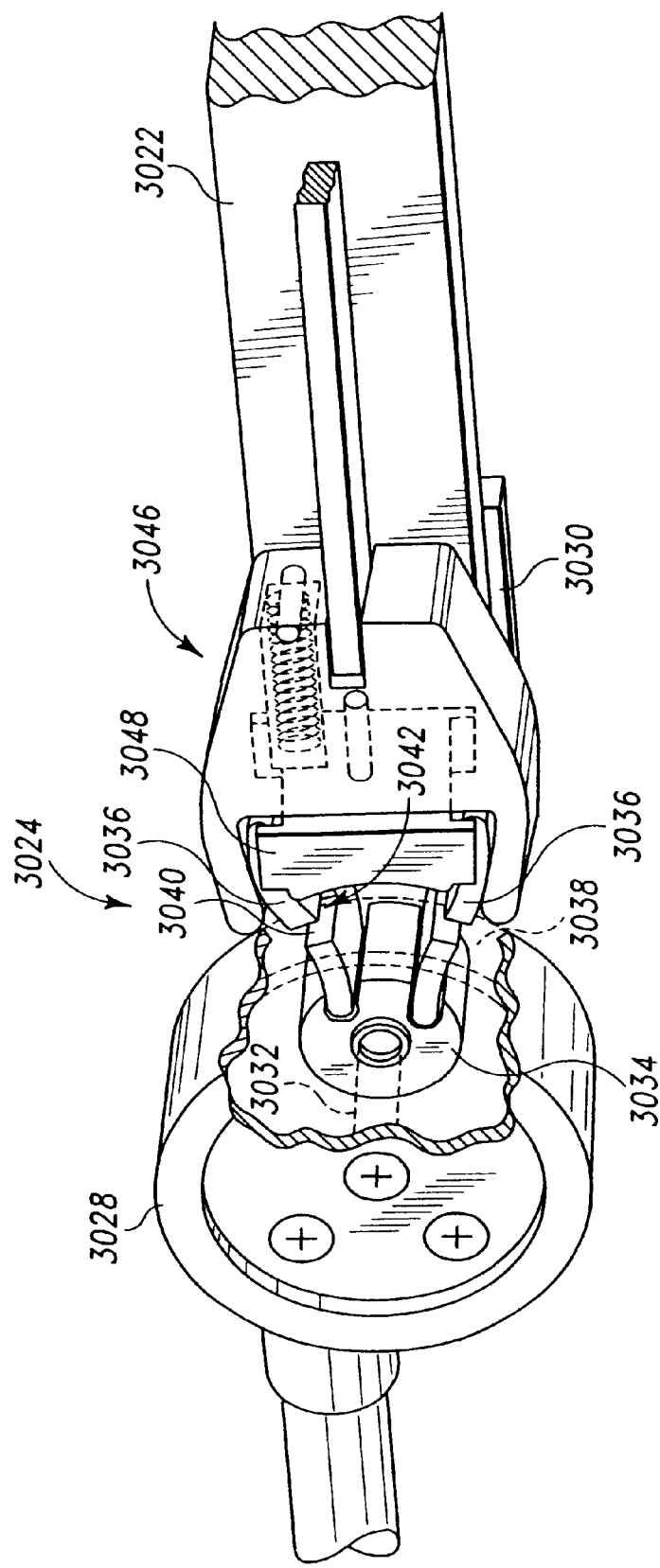
FIG. 81 is a perspective view of a position holder of the head support section of FIG. 80.
Figure 83:
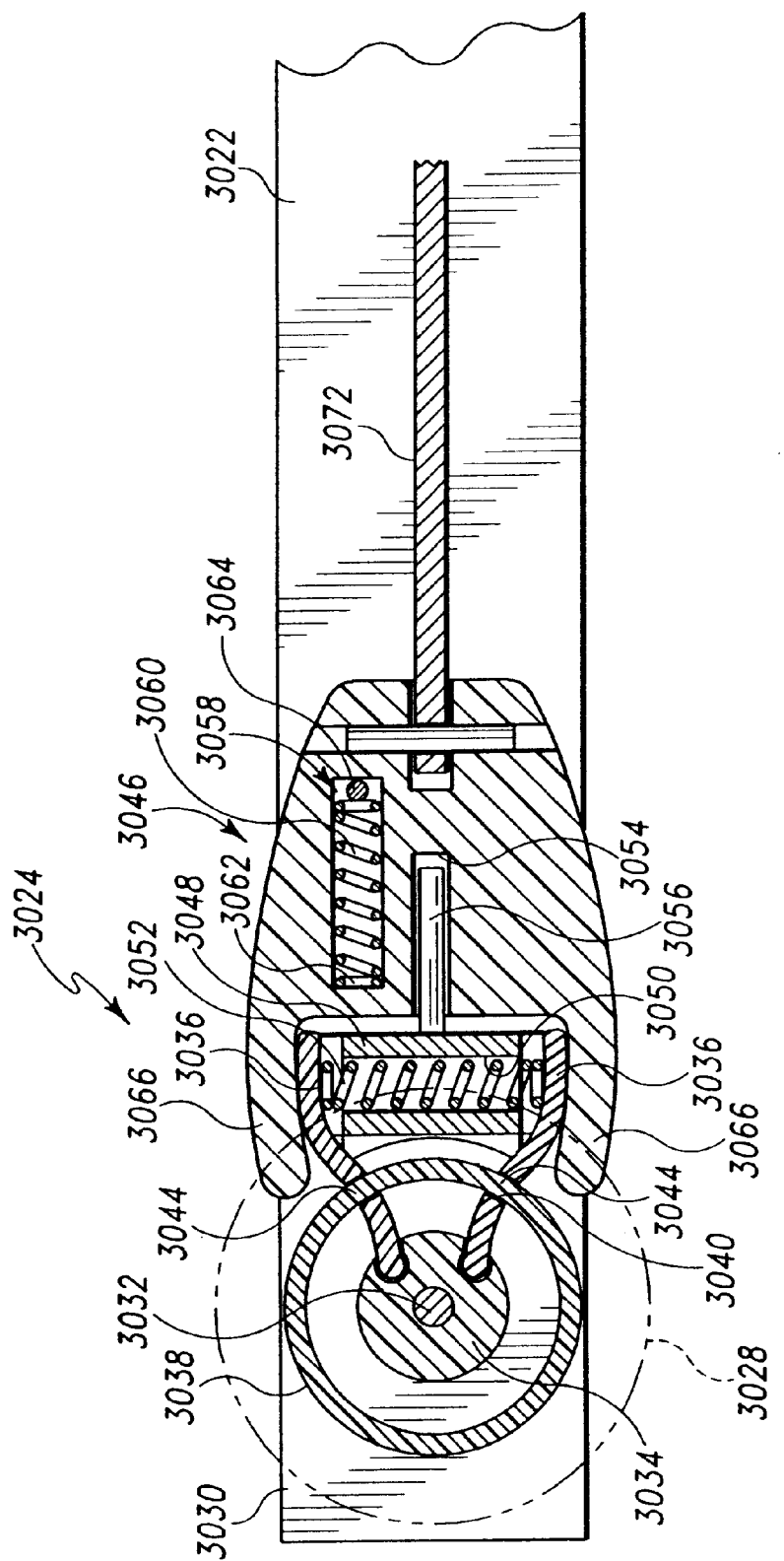
FIG. 83 is a cross-sectional view taken along line 83—83 of FIG. 81 showing the position holder in a first position blocking movement of the head support member.
Figure 84:
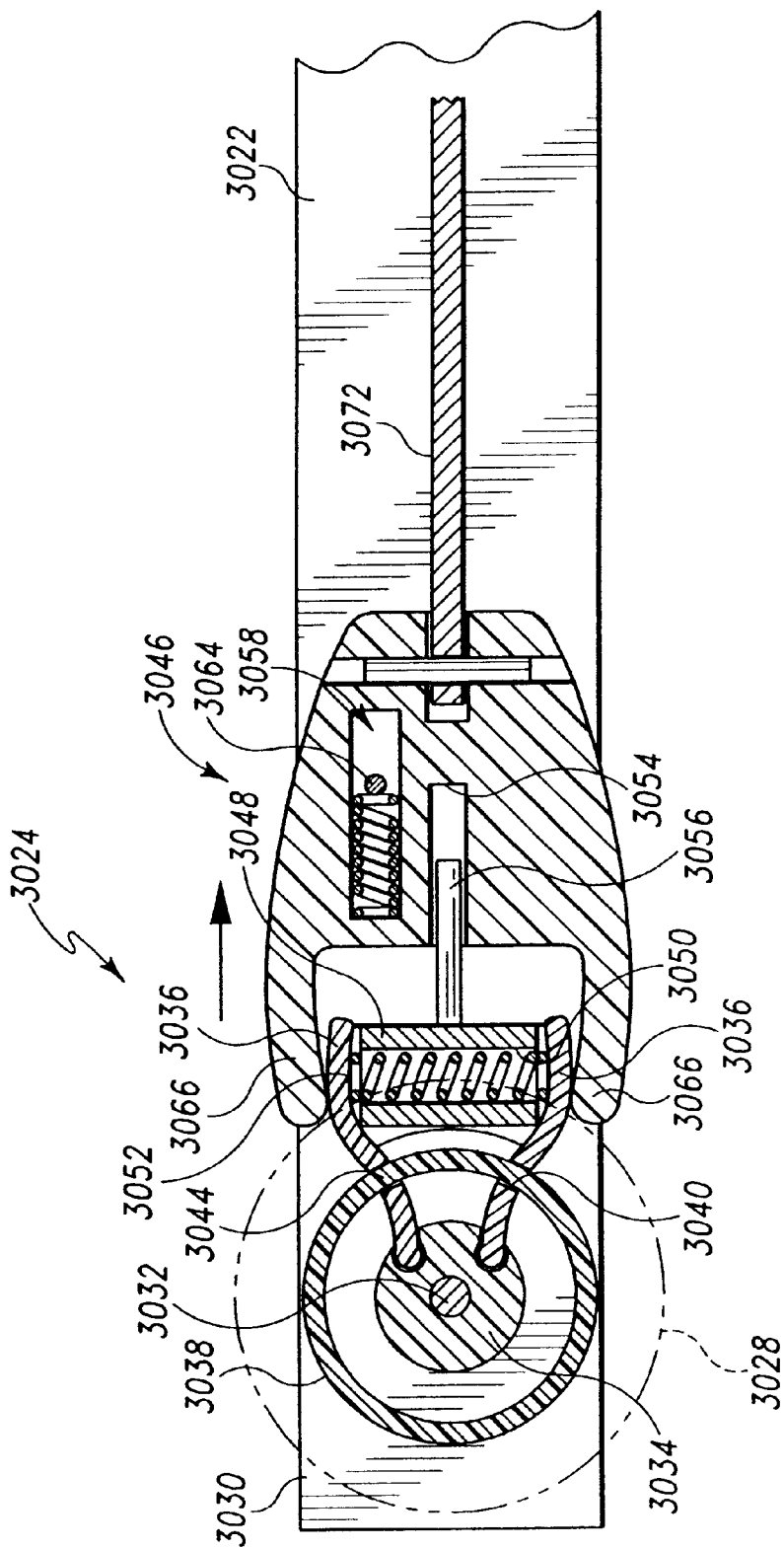
FIG. 84 is view similar to FIG. 83 showing the position holder in a second position permitting movement of the head support member.

Binding members 3036 are movable between first or binding positions, shown in FIG. 83, blocking relative movement of bound member 3038 and second or unbound position, shown in FIG. 84, permitting movement of bound member 3038. Binding members 3036 each include an edge 3040 defining a void or slot 3042 sized to receive portions 3044 of bound member 3038 as shown in FIG. 81. Slots 3042 project a first area toward portions 3044 when in the bound position and a second area toward portions 3044 when in the unbound position.

The first projected areas, when binding members 3036 are in the bound position, are the same size as portions 3044 causing binding members 3036 to grip or bind bound member 3038 blocking relative movement. However, the second projected areas, when binding members 3036 are in the unbound position, are slightly larger than portions 3044 permitting relative movement. Thus, when binding member 3036 are moved to the unbound position, link 3022 and head support pad 3020 can rotate relative to the upper torso section.

Position holder 3024 includes a C-shaped member mover 3046 configured to move binding members 3036 between the bound and unbound positions. As shown in FIG. 82, position holder 3024 further includes a spring support 3048 including a bore 3050 sized to receive a coil spring 3052. Coil spring 3052 is positioned to bias binding members toward the bound position as shown in FIG. 83.

A guide pin 3054 is supported by spring support 3048. Member mover 3046 includes an aperture 3054 sized to receive pin 3056 to guide member mover 3046 between first and second positions as shown in FIGS. 83 and 84. As shown in FIG. 82, member mover 3046 includes a channel 3058 sized to receive another coil spring 3060 that biases member mover 3046 to the first position. Coil spring 3060 is trapped between a first closed end 3062 of channel 3058 and a post 3064 coupled to link 3022. Thus, as member mover 3046 is moved to the second position, spring 3060 is compressed between closed end 3062 and post 3064 and urges member mover 3046 back to the first position.

Member mover 3046 includes a pair of ramps or cams 3066 that contact binding members 3036. When member mover 3046 is moved to the second position, ramps 3066 urge distal ends 3068 inward to unbind bound member 3038 permitting relative movement.

Figure 85:
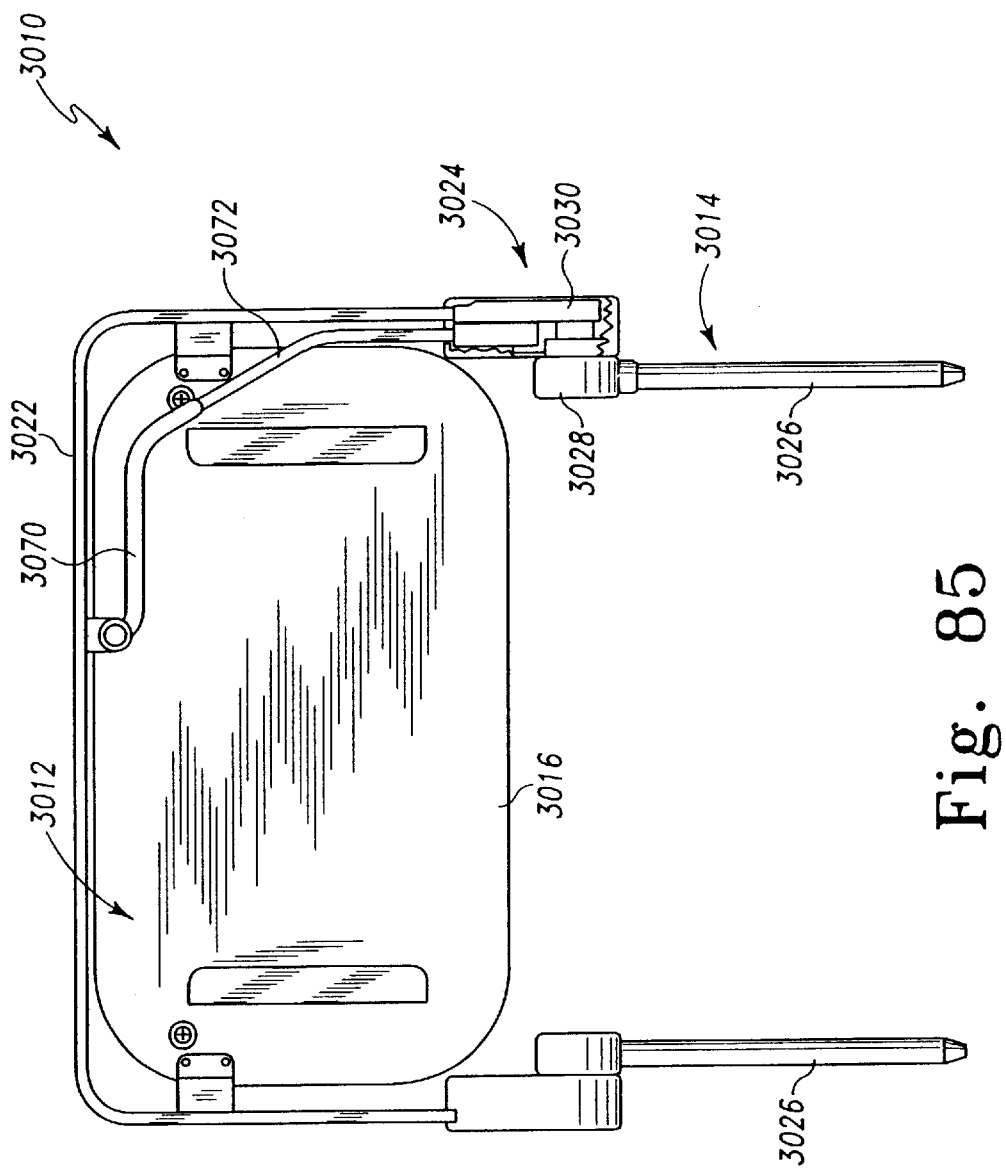
FIG. 85 is a bottom view of the head support section of FIG. 81 showing the head support section including a handle configured to move the position holder between the first and second positions.

As shown in FIG. 85, position holder 3024 further includes a handle 3070 pivotably coupled to link 3022 and a transfer link 3072 coupled to handle 3070 and member mover 3046 by a pin 3074. A user squeezes handle 3070 to move member mover 3046 between the first and second positions. When released, spring 3060 urges member mover 3046 back to the first position. Additional detail and description of suitable position holders is provided in U.S. Pat. No. 6,244,779, entitled "Angularly Adjustable Coupling," to Slasinski, filed Jun. 3, 1999, the disclosure of which is expressly incorporated by reference herein.

According to alternative embodiments of the present disclosure, the disclosed head support sections are positioned at other locations on the patient support, such as the sides or the foot ends of surgical table apparatus, to provide support for the arms or lower legs or feet of a patient. Similarly, according to other alternative embodiments, the disclosed lower leg sections are positioned at other locations on the patient support, such as the sides or head ends of surgical table apparatus, to provide support for the arms or head of a patient. According to other alternative embodiments of the present disclosure, the couplers or position holders of the various disclosed embodiment head section supports and foot section supports replace the other respective couplers or positions provided on the same or other disclosed embodiment head section supports and foot section supports.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention are desired to be protected.

What is claimed is:

1. A surgical table apparatus configured to support the head and body of a patient, the surgical table apparatus comprising a base, a body support section adapted to support the body of the patient, and a head support section including a head support member defining a head support surface configured to support the head of the patient and a first pair of parallel links configured to support the head support member, the head support member including first and second spaced-apart ends, the first end being positioned adjacent the body support section, the links including first and second ends, the first ends being pivotally supported to permit movement of the head support section relative to the body support section, the head support member being pivotally supported proximate the second end by the second ends of the links to permit movement of the head support member relative to the links, the head support member extending from the second ends of the links toward the body support section.

2. The surgical table apparatus of claim 1, wherein the head support section is removably coupled to the body support section.

3. The surgical table apparatus of claim 1, wherein the body support section includes a body support surface configured to support the body of the patient and the links are configured to permit lowering of the head support surface below the level of the body support surface.

4. The surgical table apparatus of claim 1, wherein the head support member is cantilevered from the links.

5. The surgical table apparatus of claim 1, wherein the head support section further includes a second pair of parallel links configured to support the head support member.

6. The surgical table apparatus of claim 1, wherein the head support section includes a first position holder movable between a first position permitting movement of the links and a second position blocking movement of the links.

7. The surgical table apparatus of claim 6, wherein the head support section further includes a second position holder movable between a first position permitting movement of the head support member relative to the links and a second position blocking movement of the head support member relative to the links.

8. A surgical table apparatus configured to support the head and body of a patient, the surgical table apparatus comprising
    a base,
    a body support section adapted to support the body of the patient, the body support section having a longitudinal axis, and
    a head support section including a head support member defining a head support surface configured to support the head of the patient and a first link extending away from the body support section, the link including a link body and first and second ends and defining a space lateral of the link body, the head support member being movably coupled to the second end of the link to permit movement of the head support member in the space lateral of the link body.

9. The surgical table apparatus of claim 8, wherein the head support section includes a second link, the first and second links are laterally spaced apart and cooperate to define the space therebetween.

10. The surgical table apparatus of claim 9, wherein the first and second links are parallel.

11. The surgical table apparatus of claim 8, wherein the body support section defines a body support surface and the links are configured to permit lowering of the head support surface of the head support member below the level of the body support surface.

12. The surgical table apparatus of claim 8, wherein the link is configured to permit lowering of the head support surface below the first end of the link.

13. The surgical table apparatus of claim 8, wherein the head support section further includes a first position holder movable between a first position permitting movement of the link and a second position blocking movement of the link.

14. The surgical table apparatus of claim 12, wherein the head support section further includes a second position holder movable between a first position permitting movement of the head support member relative to the link and a second position blocking movement of the head support member relative to the link.

15. The surgical table apparatus of claim 8, wherein the link is a component of a four-bar linkage configured to maintain the head support surface of the head support member is a generally horizontal orientation during movement of the head support member.

16. A surgical table apparatus configured to support the head and body of a patient, the surgical table apparatus comprising
    a base,
    a body support section including a body support surface adapted to support the body of the patient, and
    a head support section including a head support surface and a first four-bar linkage configured to permit lowering of the head support surface below the level of the body support surface, the first four-bar linkage being configured to permit the head support surface to tilt relative to the body support section, the head support surface being coplanar with the body support surface in a first position and parallel with body support surface in a second position below the body support surface.

17. The surgical table apparatus of claim 16, wherein the head support section further includes a second four-bar linkage that is parallel with the first four-bar linkage and configured to permit lowering of the head support surface below the level of the body support surface.

18. The surgical table apparatus of claim 17, wherein the head support member is positioned between the first and second four-bar linkages.

19. The surgical table apparatus of claim 16, wherein the first four-bar linkage is configured to maintain the head support surface of the head support member in a generally horizontal orientation during movement of the head support member.

20. The surgical table apparatus of claim 16, wherein the head support section further includes a first position holder movable between a bound position blocking movement of the first four-bar linkage and an unbound position permitting movement of the first four-bar linkage.

21. A surgical table apparatus configured to support the head and body of a patient, the surgical table apparatus comprising
    a base,
    a body support section including a body support section adapted to support the body of the patient,
    a head support section including a head support surface, a first four-bar linkage configured to permit lowering of the head support surface below the level of the body support surface, a first position holder movable between a bound position blocking movement of the first four-bar linkage and an unbound position permitting movement of the first four-bar linkage, and a second position holder movable between a first position permitting movement of the head support member relative to the first four-bar linkage and a second position blocking movement of the head support member relative to the first four-bar linkage.

22. A surgical table apparatus configured to support the head and body of a patient, the surgical table apparatus comprising
- a base,
- a body support section including a body support section adapted to support the body of the patient,
- a head support section including a head support surface and a first four-bar linkage configured to permit lowering of the head support surface below the level of the body support surface, and the first four-bar linkage including a first link, a second link pivotably coupled to the first link at a first pivot location, a third link pivotably coupled to the second link at a second pivot location, and a fourth link pivotably coupled to the third link at a third pivot location and pivotably coupled to the first link at a fourth pivot location.

23. The surgical table apparatus of claim 22, wherein the first link is removably coupled to the body support section.

24. The surgical table apparatus of claim 22, wherein the first link is coupled to the body support section and the head section support further includes a position holder positioned to block pivotably movement of the second link relative to the first link at the first pivot location.

25. The surgical table apparatus of claim 24, wherein the head section support further includes a second position holder movable between a first position permitting movement of the head support member relative to the first four-bar linkage and a second position blocking movement of the head support member relative to the first four-bar linkage.

26. The surgical table apparatus of claim 22, wherein the head support member is coupled to the third link.

27. The surgical table apparatus of claim 22, wherein the first and second pivot locations are spaced apart by a first distance and the third and fourth pivot locations are spaced apart by a second distance that is greater than the first distance.

28. The surgical table apparatus of claim 22, wherein the first and third links are non-parallel.

29. The surgical table apparatus of claim 28, wherein the second and fourth links are non-parallel.

30. A surgical table apparatus configured to support the head and body of a patient, the surgical table apparatus comprising
- a base,
- a body support section including a body support section adapted to support the body of the patient, and
- a head support section including a head support surface, a first four-bar linkage configured to permit lowering of the head support surface below the level of the body support surface, and a notched portion defining a clearance space through which at least a portion of the first four-bar linkage passes during lowering of the head support surface below the level of the body support surface.

31. A surgical table apparatus configured to support the appendages and body of a patient, the surgical table apparatus comprising
- a base,
- a body support section adapted to support the body of the patient, and
- an appendage support section coupled to the body support section, the appendage support section including an appendage support surface and a linkage configured to permit movement of the appendage support surface through first and second ranges of elevations relative to the body support section, the appendage support surface being substantially parallel to the body support section though the first range of elevations and substantially non-parallel to the body support section through the second range of elevations.

32. The surgical table apparatus of claim 31, wherein the linkage is a four-bar linkage.

33. The surgical table apparatus of claim 32, wherein the linkage includes a first link, a second link pivotably coupled to the first link at a first pivot location, a third link pivotably coupled to the second link at a second pivot location, and a fourth link pivotably coupled to the third link at a third pivot location and pivotably coupled to the first link at a fourth pivot location.

34. The surgical table apparatus of claim 33, wherein the first link is removably coupled to the body support section.

35. The surgical table apparatus of claim 33, wherein the first link is coupled to the body support section and the appendage support section further includes a position holder positioned to block pivotably movement of the second link relative to the first link at the first pivot location.

36. The surgical table apparatus of claim 33, wherein the appendage support surface is coupled to the third link.

37. The surgical table apparatus of claim 33, wherein the first and second pivot locations are spaced apart by a first distance and the third and fourth pivot locations are spaced apart by a second distance that is greater than the first distance.

38. The surgical table apparatus of claim 33, wherein the first and third links are non-parallel.

39. The surgical table apparatus of claim 38, wherein the second and fourth links are non-parallel.

40. The surgical table apparatus of claim 31, wherein the appendage support section includes a notched portion defining a clearance space through which at least a portion of the linkage passes during lowering of the appendage support surface below the level of the body support section.

41. The surgical table apparatus of claim 31, wherein the linkage is configured to rotate relative to the body support section about a first pivot axis in a clockwise direction and an opposite counterclockwise direction, the head support member is configured to rotate relative to the linkage about a second pivot axis in the clockwise direction and an opposite counter clockwise direction, the linkage is configured to automatically rotate the head section member in the clockwise direction when the linkage is rotating in the counterclockwise direction.

42. The surgical table apparatus of claim 31, wherein the appendage section support includes a position holder movable between a first position permitting movement of the linkage relative to the body support section and a second position blocking movement of the linkage relative to the body support section.

43. The surgical table apparatus of claim 31, wherein the appendage section support includes a position holder movable between a first position permitting movement of the head support member relative to the linkage and a second position blocking movement of the head support member relative to the linkage.

44. A surgical table apparatus configured to support the head and body of a patient, the surgical table apparatus comprising
- a base,
- a body support section including a body support surface adapted to support the body of a patient,
- a head support section including a head support member defining a head support surface adapted to support the head of a patient and a member support configured to support the head support member, the member support being configured to permit movement of the head support surface of the head support member between a first use position and a storage position with the head support surface and the body support surface cooperating to define an angle of greater than 270° therebetween, the member support being configured to permit movement of the head support surface to a second use position elevated above the body support surface, the head support surface facing toward the floor when in the storage position.

45. A surgical table apparatus configured to support the head and body of a patient, the surgical table apparatus comprising
    a base,
    a body support section including a body support surface adapted to support the body of a patient, and
    a head support section including a head support member defining a head support surface adapted to support the head of a patient and a member support including a four-bar linkage and configured to support the head support member, the member support being configured to permit movement of the head support surface of the head support member between a first use position and a storage position with the head support surface and the body support surface cooperating to define an angle of greater than 270° therebetween, the member support being configured to permit movement of the head support surface to a second use position elevated above the body support surface.

46. A surgical table apparatus configured to support the head and body of a patient, the surgical table apparatus comprising
    a base,
    a body support section including a body support surface adapted to support the body of a patient, and
    a head support section including a head support member including a head support surface adapted to support the head of a patient, the head support surface and the body support surface cooperating to define an angle therebetween, the head support section further including a first position holder configured to permit adjustment of the angle, the head support member including a first end and a second end opposite the first end, the second end being positioned between the first end and the body support section, the position holder being positioned adjacent to the first end of the head support member.

47. The surgical table apparatus of claim 46, wherein the head support section further includes a second position holder configured to move between a first position permitting movement of the head support member relative to the body support section.

48. The surgical table apparatus of claim 46, wherein the first position holder includes a worm gear mechanism having first and second gears that mate.

49. The surgical table apparatus of claim 46, wherein the head section support further includes a member support positioned to support the head support member relative to the body support section and the first position holder is configured to permit movement of the head support member relative to the member support.

50. The surgical table apparatus of claim 49, wherein the member support includes a first end pivotably supported by the body support section and a second end spaced apart from the first end, and the first position holder is positioned adjacent to the second end of the member support.

51. The surgical table apparatus of claim 49, wherein the first position holder is configured to permit movement of the second end of the head support member to elevations above and below the first end of the head support member.

52. The surgical table apparatus of claim 46, wherein the first position holder is movable between a first position blocking movement of the head support member relative to the body support section and a second position permitting movement of the head support member relative to the body support section.

53. A surgical table apparatus configured to support the head and body of a patient, the surgical table apparatus comprising
    a base,
    a body support section adapted to support the body of a patient, and
    a head support section including a head support member adapted to support a patient's head and a position holder configured to permit movement of the head support member relative to the body support section, the position holder including a binding member and a bound member, the binding member including an edge defining a void sized to receive a portion of the bound member, the binding member being movable relative to the portion of the bound member between a bound position in which a projection of the void relative to the portion of the bound member has a first area and an unbound position in which the projection of the void relative to the portion of the bound member has a second area that is greater than the first area.

54. The surgical table apparatus of claim 53, wherein the position holder further includes a member mover configured to move the binding member between first and second positions moving the binding member between the bound and unbound positions.

55. The surgical table apparatus of claim 54, wherein the member mover slides relative to the binding member between the first and second positions.

56. The surgical table apparatus of claim 54, wherein the member mover includes a cam positioned to engage the binding member to move the binding member between the first and second positions.

57. The surgical table apparatus of claim 54, wherein the member mover is biased toward the first position.

58. A surgical table apparatus configured to support the head and body of a patient, the surgical table apparatus comprising,
    a base,
    a body support section including a body support surface adapted to support the body of a patient, and
    a head support section including a head support member defining a head support surface adapted to support the head of a patient and a four-bar linkage configured to support the head support member and to permit movement of the head support surface between a first use position and a storage position, the four-bar linkage including a first link and a second link, the first and second links including a first end and second end, the first end of the first link being pivotally coupled to a first pivot point on the head support surface, the first end of the second link being pivotally coupled to a second pivot point on the head support surface, the second end of the first link being pivotally coupled to a third pivot point on the body support section, the second end of the second link being pivotally coupled to a fourth pivot point on the body support section, the first and second pivot points being spaced apart by a first distance, the third and fourth pivot points being spaced apart by a second distance, the first distance being unequal to the second distance.

59. The surgical table apparatus of claim 58, wherein the first link is non-linear.

60. The surgical table apparatus of claim 58, wherein the first link is curved.

61. The surgical table apparatus of claim 58, wherein the first link is longer than the second link.

62. A surgical table apparatus configured to support the head and body of a patient, the surgical table apparatus comprising, a base, a body support section including a body support surface adapted to support the body of a patient, and a head support section including a head support member defining a head support surface adapted to support the head of a patient, a four-bar linkage configured to support the head support member, and an independent adjuster coupled between the four-bar linkage and the head support surface and configured to permit adjustment of the head support surface relative to the four-bar linkage, the four-bar linkage including a first link and a second link, the first and second links including a first end and second end, the first end of the first link being pivotally coupled to a first pivot point on the head support surface, the first end of the second link being pivotally coupled to a second pivot point on the head support surface, the second end of the first link being pivotally coupled to a third pivot point on the body support section, the second end of the second link being pivotally coupled to a fourth pivot point on the body support section, the first and second pivot points defining a first axis, the third and fourth pivot points defining a second axis, the first axis being non-parallel to the second axis.

63. The surgical table apparatus of claim 62, wherein the first link is non-linear.

64. The surgical table apparatus of claim 62, wherein the first link is curved.

65. The surgical table apparatus of claim 62, wherein the first link is longer than the second link.

66. A surgical table apparatus configured to support the head and body of a patient, the surgical table apparatus comprising, a base, a body support section including a body support surface adapted to support the body of a patient, and a head support section including a head support member defining a head support surface adapted to support the head of a patient and a four-bar linkage configured to support the head support member and to permit movement of the head support surface between a first upwardly facing position and a second downwardly facing position, the four-bar linkage including a first link and a second link, the first and second links including a first end and second end, the first end of the first link being pivotally coupled to a first pivot point on the head support surface, the first end of the second link being pivotally coupled to a second pivot point on the head support surface, the second end of the first link being pivotally coupled to a third pivot point on the body support section, the second end of the second link being pivotally coupled to a fourth pivot point on the body support section, the first link having a first length defined between the first and third pivot points, the second link having a second length defined between the second and fourth pivot points, the first length being greater than the second length.

67. The surgical table apparatus of claim 66, wherein the first link is non-linear.

68. The surgical table apparatus of claim 66, wherein the first link is curved.

69. The surgical table apparatus of claim 66, wherein the second link is non-linear.

70. The surgical table apparatus of claim 66, wherein the second link is curved.

* * * * *